(12) United States Patent
Geromanos et al.

(10) Patent No.: US 10,573,501 B2
(45) Date of Patent: Feb. 25, 2020

(54) TECHNIQUES FOR PROCESSING OF MASS SPECTRAL DATA

(71) Applicant: WATERS TECHNOLOGIES CORPORATION, Milford, MA (US)

(72) Inventors: Scott J. Geromanos, Middletown, NJ (US); Steven J. Ciavarini, Natick, MA (US); Curt Devlin, Fairhaven, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 238 days.

(21) Appl. No.: 15/578,148

(22) PCT Filed: May 31, 2016

(86) PCT No.: PCT/US2016/034959
§ 371 (c)(1),
(2) Date: Nov. 29, 2017

(87) PCT Pub. No.: WO2016/196432
PCT Pub. Date: Dec. 8, 2016

(65) Prior Publication Data
US 2018/0166265 A1      Jun. 14, 2018

Related U.S. Application Data

(60) Provisional application No. 62/168,123, filed on May 29, 2015.

(51) Int. Cl.
*H01J 49/00*       (2006.01)
*G01N 30/72*       (2006.01)
(Continued)

(52) U.S. Cl.
CPC .......... *H01J 49/0036* (2013.01); *G01N 30/72* (2013.01); *G01N 30/8675* (2013.01);
(Continued)

(58) Field of Classification Search
CPC .. H01J 49/0036; H01J 49/0031; G16C 20/70; G01N 30/72; G01N 30/8675; G01N 33/6854
(Continued)

(56) References Cited

U.S. PATENT DOCUMENTS

2004/0222389 A1*  11/2004  Swenson ............... C23C 14/221
                                                         250/492.21
2005/0061967 A1*   3/2005  Shvartsburg ............ H01J 49/04
                                                           250/288
(Continued)

FOREIGN PATENT DOCUMENTS

GB           2408574 A       6/2005

OTHER PUBLICATIONS

International Search Report and Written Opinion in PCT/US2016/034959 dated Oct. 7, 2016.
(Continued)

*Primary Examiner* — Nicole M Ippolito

(57) ABSTRACT

Techniques for performing data acquisition and analysis are described. A multi-mode acquisition strategy may be performed which iteratively selects mass isolation windows of different sizes in different scan cycles to acquire experimental data. The mass isolation windows selected may provide for acquiring elevated energy scan data for a defined set of m/z values. Single scan data analysis may be performed. Data analysis may include forming precursor charge clusters, chaining precursor charge clusters having the same mass to charge ratio to form peaks profiles, and using criteria to align precursor and product ions of the experimental data. Unsupervised and supervised clustering may be performed using a database and composite ion spectra formed from experimental data. Also described are a small molecule
(Continued)

acquisition enhancement and additional techniques applicable for biopharmaceutical and other applications.

20 Claims, 51 Drawing Sheets

(51) Int. Cl.
  *G01N 30/86* (2006.01)
  *G01N 33/68* (2006.01)
  *G06F 19/00* (2018.01)
  *G16C 20/70* (2019.01)

(52) U.S. Cl.
  CPC ......... *G01N 33/6854* (2013.01); *G16C 20/70* (2019.02); *H01J 49/0031* (2013.01)

(58) Field of Classification Search
  USPC .................. 250/281, 282, 283, 287, 288
  See application file for complete search history.

(56) References Cited

U.S. PATENT DOCUMENTS

| | | | |
|---|---|---|---|
| 2006/0085142 A1* | 4/2006 | Mistrik | G01N 27/62 702/27 |
| 2008/0164409 A1* | 7/2008 | Schultz | G01N 27/622 250/282 |
| 2010/0286927 A1 | 11/2010 | Horn et al. | |
| 2012/0156707 A1 | 6/2012 | Hartmer et al. | |
| 2012/0253684 A1 | 10/2012 | Gorenstein et al. | |
| 2012/0326023 A1 | 12/2012 | Kozole | |
| 2017/0108508 A1* | 4/2017 | Geromanos | H01J 49/421 |

OTHER PUBLICATIONS

Kuhl, C., et. al., "CAMERA: An Integrated Strategy for Compound Spectra Extraction and Annotation of Liquid Chromatography/Mass Spectrometry Data Sets," Analytical Chemistry, 84:283-289 (2012).

Broeckling, C. D., et. al., "RAMClust: A Novel Feature Clustering Method Enables Spectral-Matching-Based Annotation for Metabolomics Data," Analytical Chemistry, 86:6812-6817 (2014).

Frank, A. M., et. al., "Clustering Millions of Tandem Mass Spectra," Journal of Proteome Research, 7:113-122 (2008).

Lam, H., et. al., "Building Consensus Spectral Libraries for Peptide Identification in Proteomics," Nature Methods, 5 (10): 873-875 (Oct. 2018).

International Preliminary Report on Patentability for International Application No. PCT/US2016/034959 dated Dec. 14, 2017.

Partial Supplementary European Search Report for EP Patent Application No. 16804202.6, dated Mar. 4, 2019.

Extended European Search Report for EP Patent Application No. 16804202.6, dated Jun. 17, 2019.

\* cited by examiner

Precursor Delta-Mass Modifications

| Modification | Description | UNIMOD | Site | Mass Difference |
|---|---|---|---|---|
| Neutral Losses | Loss of H₂O | | H2O | -18.010565 |
| | Loss of NH₃ | [385] Loss of NH₃ | N-term | -17.026549 |
| Carbamidomethyl | Reagent Iodoacetamide | [4] Iodoacetamide | C | 57.021464 |
| Oxidation | | [35] Oxidation | M | 15.994915 |
| Phosphorylation | Neutral loss of HPO₃ (79.966331) | [21] Phosphorylation | S,T | -97.976896 |
| Glycosylation | N-Acetylhexosamine | [43] HexNAc | S,T,N | 203.079373 |
| | | [793] Hex1HexNAc1 | S,T,N | 365.132196 |
| | O-glycosylated | [149] Hex1HexNAc1NeuAc1 | | 656.227613 |

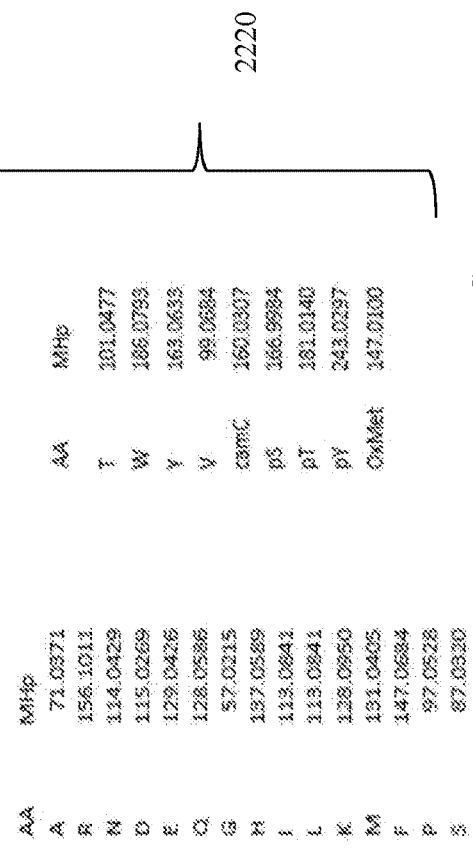

FIG. 23

TECHNIQUES FOR PROCESSING OF MASS SPECTRAL DATA

RELATED APPLICATIONS

This application is a national phase filing claiming the benefit of and priority to International Patent Application No. PCT/US2016/196432, filed on May 31, 2016, which claims priority to U.S. Provisional Patent Application No. 62/168,123, filed on May 29, 2015, TECHNIQUES FOR PROCESSING OF MASS SPECTRAL DATA, which is incorporated by reference herein.

TECHNICAL FIELD

This application generally relates to techniques for processing of data obtained from performing mass spectral analysis of a sample.

BACKGROUND INFORMATION

Mass spectrometry (MS) is used widely for identifying and quantifying molecular species in a sample. During analysis, molecules from the sample are introduced into the mass analyzer and are ionized to acquire a charge, thus forming ions. The analyzer responds to each of the molecule's ions by the ratio of their mass to the charge that they have acquired; hence mass-to-charge ratio m/z. A detector produces a signal relating to the intensity of the ions at their particular m/z.

A chromatographic separation technique may be performed prior to injecting the sample into a mass spectrometer. Chromatography is a technique for separating compounds, such as those held in solution, where the compounds will exhibit different affinity for a separation medium in contact with the solution. As the solution flows through such an immobile medium, the compounds separate from one another. Common chromatographic separation instruments include gas chromatographs (GC) and liquid chromatographs (LC). When coupled to a mass spectrometer, the resulting systems are referred to as GC/MS or LC/MS systems. GC/MS or LC/MS systems are typically on-line systems in which the output of the GC or LC is coupled directly to the MS.

In an LC/MS system, a sample is injected into the liquid chromatography system at a particular time, which triggers the system to acquire data. The liquid chromatography causes the sample to elute over time resulting in a separated analyte that exits the column. The time at which a particular analyte exits the column is called its retention time. The eluent exiting the liquid chromatograph is continuously introduced into the ionization source of the mass spectrometer. As the separation progresses, the composition of the mass spectrum generated by the MS evolves and reflects the changing composition of the eluent.

Typically, at regularly spaced time intervals, a computer-based system samples and records the spectrum. The intensity response of an ion is the height or area of the peak as seen in its spectrum. The spectra generated by conventional LC/MS systems may be further analyzed. Mass or mass-to-charge ratio measurement of an ion are derived through examination of a spectrum peak (intensity vs. m/z) that contains the ion. Retention time measurement of an ion are derived by examination of a chromatogram peak (intensity vs. time) that contains the ion.

Two stages of mass analysis (MS/MS also referred to as tandem mass spectrometry) may also be performed. One particular mode of MS/MS is known as product ion scanning where parent precursor ions of a particular m/z value are selected in the first stage of mass analysis by a first mass filter/analyzer. The selected precursor ions are then passed to a collision cell where they are fragmented to produce product fragment ions. The product fragment ions are then analyzed by a second mass filter/analyzer.

SUMMARY OF THE INVENTION

In accordance with one aspect of the techniques herein is a method of performing sample analysis comprising: analyzing a sample using one or more instruments including a mass spectrometer that performs mass spectrometry, wherein said mass spectrometer operates in said analyzing in accordance with a schedule, said schedule including mass isolation windows used for a plurality of cycles each including a plurality of scans, wherein said analyzing includes: performing a first low energy scan at the beginning of each cycle of the plurality of cycles, said first low energy scan having an associated m/z range denoting an m/z range of precursor ions; and iteratively using different mass isolation windows in elevated energy scans until fragmentation has been performed for the associated m/z range of the first low energy scan; obtaining experimental data as a result of said analyzing, said experimental data including low energy scan data obtained when performing one or more low energy data acquisitions using the mass spectrometer; determining precursor charge clusters using the low energy scan data; and determining a peak profile for a first precursor ion by chaining together a portion of the precursor charge clusters that identify the first precursor ion, each of said precursor charge clusters in the portion being from a different low energy scan. The method may include determining a bounded region having a plurality of dimensions including m/z and retention time; and iteratively using different mass isolation windows in elevated energy scans until fragmentation has been performed for the bounded region. Said analyzing may include performing ion mobility spectrometry and the plurality of dimensions of the bounded region includes drift time. A scheduler may track whether an elevated energy data acquisition has been performed for the associated m/z range of the first low energy scan. At least a first portion of the mass isolation windows may have sizes and associated m/z ranges determined in accordance with selecting approximately a same number of precursor ions for fragmentation, and said analyzing may include performing an elevated energy data acquisition for each mass isolation window in said first portion whereby ions of a companion low energy scan having m/z values within said each mass isolation window are fragmented in said elevated energy data acquisition. The schedule may include a cycle time for each of the plurality of cycles determined in accordance with any of a median and mean chromatographic peak width and a minimum number of scans performed in each of the plurality of cycles. The mass isolation windows of the schedule may include narrow band mass isolation windows and wide band mass isolation windows. Each of the narrow band isolation windows may have a corresponding size ranging from a first minimum to a first maximum, and each of said wide band isolation windows may have a corresponding size ranging from a second minimum to a second maximum, wherein said first maximum may be less than said second minimum. A center m/z value for each of the narrow band mass isolation windows and wide band mass isolation windows may change with scan cycle. The method may include performing first processing to construct a first precursor charge cluster of a first low energy scan, said first processing including: selecting a first ion in the first low energy scan, the first ion having a first m/z that is lowest m/z value of all ions in the first low energy scan; receiving a plurality of delta m/z values, each of the plurality of delta m/z values being associated with a different one of a plurality of charge states wherein said each delta m/z value denotes a theoretical m/z distance between any two consecutive isotopes of an isotope cluster having the associated different one of the plurality of charge states; traversing the plurality of delta m/z values in accordance with a decreased ordering of the plurality of charge states to determine whether there is a second ion in the first low energy scan having an associated m/z value equal to the sum of one of the plurality of delta m/z values and the first m/z for the first ion, wherein said traversing step terminates after locating a single ion qualifying as the second ion; and responsive to determining there is the second ion in the first low energy scan having an associated m/z value equal to the sum of one of the plurality of delta m/z values and the first m/z for the first ion, determining that the second ion is a next isotope in a chain subsequent to the first ion. The method may include adding additional ions from the first low energy scan to the chain, wherein each of the additional ions has an associated m/z that is equal to a sum of the first m/z and a multiple of said one of the plurality of delta m/z values. The chain of ions in the first low energy scan may be a candidate precursor charge cluster and the method may include performing processing using an isotopic model to validate the candidate precursor charge cluster. Processing may include revising an attribute of an ion included in the candidate precursor charge cluster in accordance with the isotopic model. A first precursor charge cluster for the first precursor ion may be included in a first low energy scan, and the method may include determining, based on mass error, whether there is interference for the first precursor ion in the first low energy scan whereby another ion co-elutes for at least a portion of a same time as the first precursor ion; determining whether a first mass error for the first precursor ion in the first low energy scan is not within a defined acceptable mass error range; responsive to determining the first mass error is not within the defined acceptable mass error range, determining there is interference for the first precursor ion; determining there is interference for the first precursor ion for multiple scans subsequent to the first low energy scan, wherein mass errors for the multiple scans are within the defined acceptable mass error range; determining whether a second mass error for the precursor ion in a second low energy scan, that is subsequent to the multiple scans, is within the defined acceptable mass error range and whether the second mass error is a complementary mass error value with respect to the first mass error; and responsive to determining the second mass error is not within the defined acceptable mass error range and is not a complementary mass error value with respect to the first mass error, determining that interference for the first precursor ion ends and the second mass error is a complementary mass error value for the first mass error. The experimental data may include elevated energy scan data obtained when performing elevated energy data acquisitions using the mass spectrometer. The portion of precursor charge clusters may be included in a first set of low energy scans having corresponding elevated energy scans including fragment ions generated as a result of fragmenting precursor charge clusters in the first set of low energy scans. The method may include selecting a first precursor charge cluster from the portion of precursor charge clusters, said first precursor charge cluster being included in a first low energy scan having a corresponding first elevated energy scan; and determining a fragment set of one or more fragment ions from the first elevated energy scan originating from fragmentation of the first precursor charge cluster. The method may include constructing a composite precursor product ion spectrum including the first precursor charge cluster and the fragment set; and storing the composite precursor product ion spectrum in a database. Each of the precursor charge clusters in the portion of precursor charge clusters chained together to form the peak profile may be in a different low energy scan and each precursor charge cluster may have an associated ion current denoting a ratio of an intensity of said each precursor charge cluster relative to a total ion intensity in said different low energy scan. The first precursor charge cluster in the first low energy scan may have a maximum ion current of all ion currents for the precursor charge clusters in the portion. The sample may include one or more proteins. A minimum number of five points may be used to form the peak. The method may include performing a plurality of injections of a plurality of samples including the sample; and analyzing each of the plurality of samples using the one or more instruments, said analyzing each of the plurality of samples including: iteratively using different mass isolation windows in elevated energy scans until fragmentation has been performed for a second bounded region having a second plurality of dimensions including m/z and retention time, wherein the second bounded region is completely sampled a first time as a result of sample analysis spanning at least two consective injections of the plurality of injections whereby first experimental data, obtained as a result of analyzing a first of the plurality of samples in a first injection of the two consecutive injections, is provided as an input to a scheduler that automatically determines a second schedule for a second injection of the two consecutive injections, wherein the scheduler uses the first experimental data to determine a first portion of the second bounded region that has not yet been sampled and schedules sampling of the first portion in connection with sample analysis performed for the second injection. The second plurality of dimensions of the second bounded region may include drift time and completely sampling the second bounded region may include completely sampling ranges associated with each of the second plurality of dimensions of the second bounded region. The first experimental data, used by the scheduler to determine the second schedule, may include any one or more of information on ion flux denoting a frequency of detected ions in each of a plurality of different m/z range bins, a distribution of retention time vs m/z sampled, a distribution of drift time vs. m/z sampled, and a distribution of drift time vs retention time sampled.

In accordance with another aspect of techniques herein is a system comprising: one or more instruments including a mass spectrometer that performs mass spectrometry; a processor that executes code; and a memory comprising code stored thereon that, when executed, performs a method of sample analysis comprising: analyzing a sample using the one or more instruments, wherein said mass spectrometer operates in said analyzing in accordance with a schedule, said schedule including mass isolation windows used for a plurality of cycles each including a plurality of scans, wherein said analyzing includes: performing a first low energy scan at the beginning of each cycle of the plurality of cycles, said first low energy scan having an associated m/z range denoting an m/z range of precursor ions; and iteratively using different mass isolation windows in elevated energy scans until fragmentation has been performed for the associated m/z range of the first low energy scan; obtaining experimental data as a result of said analyzing, said experimental data including low energy scan data obtained when performing one or more low energy data acquisitions using the mass spectrometer; determining precursor charge clusters using the low energy scan data; and determining a peak profile for a first precursor ion by chaining together a portion of the precursor charge clusters that identify the first precursor ion, each of said precursor charge clusters in the portion being from a different low energy scan.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the techniques described herein.

FIG. 23 is an example of a table of precursor delta mass modifications and associated monoisotopic masses that may be used in an embodiment in accordance with techniques herein;

DESCRIPTION

Figure 1:
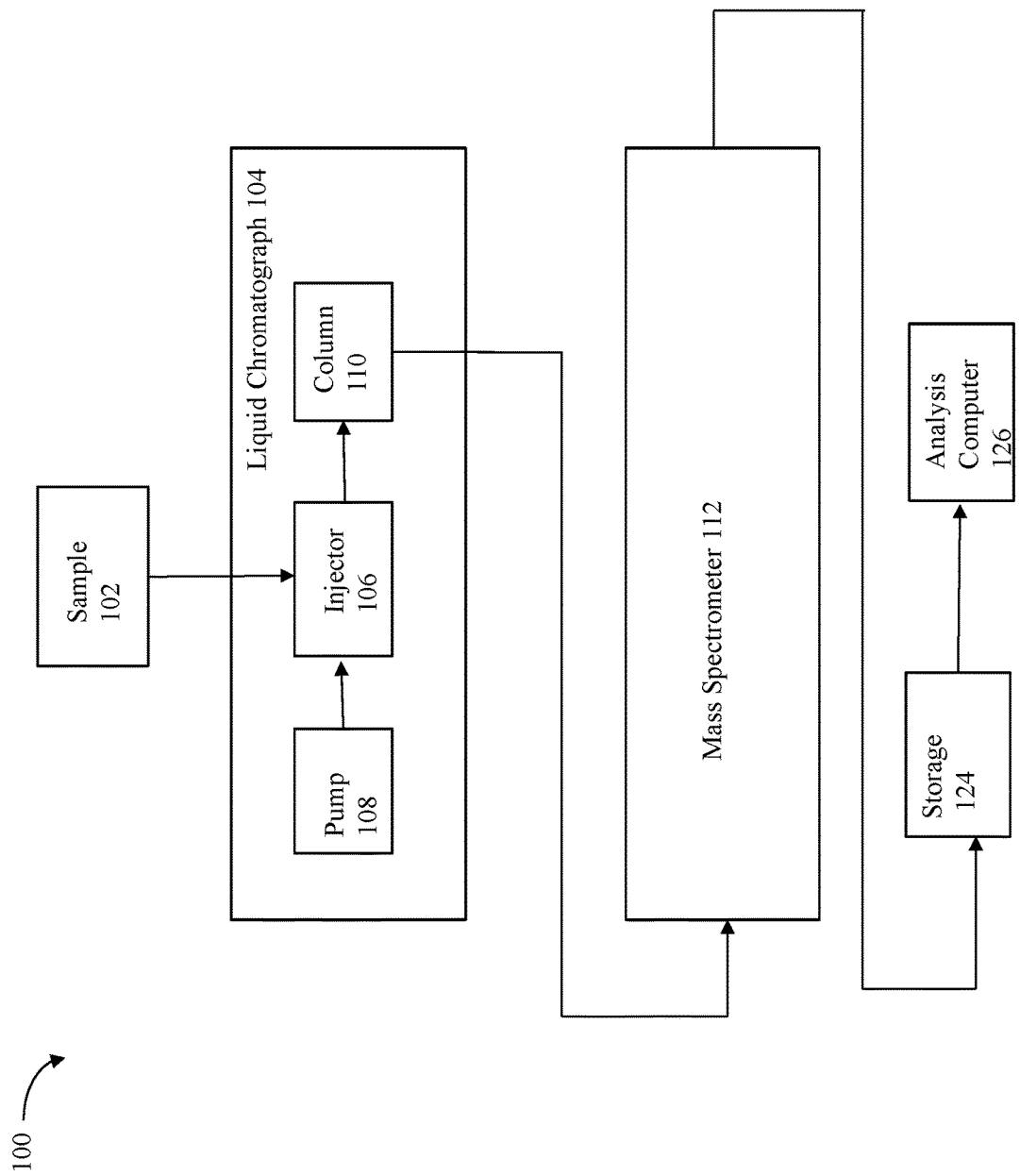
FIG. 1 is a block diagram of a system in accordance with one embodiment of the techniques herein.

As used herein, the following terms generally refer to the indicated meanings:

"Chromatography"—refers to equipment and/or methods used in the separation of chemical compounds. Chromatographic equipment typically moves fluids and sample analytes under pressure and/or electrical and/or magnetic forces. The word "chromatogram," depending on context, herein refers to data or a representation of data derived by chromatographic means. A chromatogram can include a set of data points, each of which is composed of two or more values; one of these values may be a scan time or corresponding chromatographic retention time value, and the remaining value(s) are typically associated with values of intensity or magnitude, which in turn correspond to quantities or concentrations of eluting components of a sample. In connection with techniques herein, the sample analyte may contain one or more compounds, molecules or components of interest.

A sample analyte may refer to the composition, mixture, solution, material, solid, tissue, or more generally, any substance that is to be analyzed. In connection with techniques herein, the sample may contain one or more compounds, molecules or components of interest. A sample or compound of interest may generally be, or include, any molecule, including, for example, a small molecule, such as an organic compound, metabolite, and organic compounds, as well as a larger molecule such as a protein or peptide.

Retention time—in context, refers to the time in a chromatographic profile at which an eluting component reaches its maximum intensity.

Ions—in context, is an ionized molecule of the sample analyte that is detected using a mass spectrometer (MS) and generated as a result of performing an experiment in an LC/MS system. As such, an ion is characterized by its retention time, m/z (mass to charge ratio), and intensity measured values.

LE—(low energy state of collision cell) refers to precursor ion data and is independent of acquisition method. LE data can be acquired utilizing both Data Dependent and Independent modes of acquisition.

HE—(high energy state of collision cell) refers to product/fragment ion data and is independent of acquisition method. HE data can be acquired utilizing both Data Dependent and Independent modes of acquisition. High-energy mode may also be referred to as elevated-energy (EE) mode.

Drift—in context, refers to the measurement of an ion's mobility in the gas phase. An additional experiment cell built into the mass spectrometer separates gas phase ions according to their mobilities, thus providing for an additionl dimension of ion separation; by drift as well as m/z. Ion mobility relates to the structural size of the ionized molecule expressed as collisional cross-sectional area (CCSA) by appropriate calibration and conversion of drift time. This technique is referred to as Ion Mobility Spectrometry (IMS).

Ion fingerprint—refers to the validated product ion spectrum of a molecular entity, including a measure of variation in each product ion's relative intensity across all the experimental data used in its validation.

In an embodiment in accordance with techniques herein, the intensity value of an ion may be based on its area under the curve (AUC), denoting the peak corresponding to its measured intensity. Each intensity value may be determined as an area under a curve such as formed by a Gaussian distribution of recorded pulses. Thus, various ratios of intensities as described herein may be characterized as area ratios.

Generally, an LC/MS system may be used to perform sample analysis and may provide an empirical description of, for example, a protein or peptide as well as a small molecule such as a pharmaceutical or herbicide in terms of its mass, charge, retention (elution) time, and intensity. When a molecule elutes from a chromatographic column, its intensity profile or peak shape appears over a specific time period and reaches its maximum or peak signal at its retention time. After ionization and (possible) fragmentation such as in connection with mass spectrometry, the compound appears as a related set of ions.

In an LC/MS separation, an ionized molecule may exist at a single or multiple charged states. MS/MS may also be referred to as tandem mass spectrometry, which can be performed in combination with LC separation (e.g., denoted LC/MS/MS).

Techniques and embodiments will now be described with reference to exemplary methods and apparatus for analyzing samples, such as may be for sample analyses in a system analyzing a sample by performing an LC/MS experiment. It will be appreciated that the techniques described herein may be used in connection with other embodiments and have broader application than those that may be provided and listed herein for purposes of illustration and example.

FIG. 1 is a schematic diagram of a system that may be used in connection with techniques herein. A sample 102 is injected into the fluid stream of liquid chromatography system 104 through an injector 106. A pump 108 supplies mobile phase solvent to the injector and pumps the sample through a column 110 to separate the sample analyte mixture into eluting components exiting the column and observed by their retention times.

The output from the column is introduced into a mass spectrometer 112 for analysis. It should be noted that the particular components included in a mass spectrometer 112 used in an embodiment may vary with the particular types of mass spectrometer utilized. Following the description of element 112, some components that may be included in the mass spectrometer 112 and are not illustrated in FIG. 1 for simplicity. Initially, the sample is desolvated and ionized by a desolvation/ionization device of the mass spectromter. Desolvation can be any technique including, for example, a heater, a gas, a heater in combination with a gas or other desolvation technique. Ionization can be by any ionization techniques, including for example, electrospray ionization (ESI), atmospheric pressure chemical ionization (APCI), matrix assisted laser desorption (MALDI) or other ionization techniques. Ions resulting from the ionization are fed to a collision cell of the mass spectrometer with a voltage gradient being applied to an ion guide. The collision cell can be used to pass the precursor ions (in low-energy mode) or to fragment the precursor ions (in high-energy mode).

As described in more detail, elsewhere herein, different techniques, including one described in U.S. Pat. No. 6,717,130, to Bateman et al. ("Bateman"), which is incorporated by reference herein, may be used in which an alternating voltage can be applied across the collision cell to cause fragmentation. Spectra are collected for the precursors at low-energy (no collisions) and fragments at high-energy (results of collisions).

A separate technique includes the serial application of a mass selection window, where precursor ions are selected by such criteria such as m/z, m/z and intensity, m/z, intensity and ion mobility drift, or by inclusion or exclusion of a list of target compounds, including either: m/z, m/z and intensity, m/z, intensity and drift. Here a m/z value is selected, the first mass analyzer, typically a quadrupole, is set to a mass isolation window and only those precursor ions within the mass isolation window are transferred to the collision cell to cause fragmentation. Spectra are collected for the selected precursors (no collisions) and their fragments (results of collisions).

In the mass spectrometer 112, the output of collision cell is directed to a mass analyzer. The mass analyzer can be any mass analyzer, including quadrupole, time-of-flight (TOF), ion trap, magnetic sector mass analyzers as well as combinations thereof. A detector of the mass spectrometer detects ions emanating from the mass analyzer. The detector can be integral with mass analyzer. For example, in the case of a TOF mass analyzer, the detector can be a microchannel plate detector that counts intensity of ions, i.e., counts numbers of ions impinging it.

A storage medium 124 may provide permanent storage for storing the ion detections (m/z, retention time, mobility drift, intensity counts, etc.) for analysis. For example, storage medium 124 can be an internal or external computer data storage device such as a disk, flash-based storage, and the like. An analysis computer 126 analyzes the stored data.

Data can also be analyzed in real time without requiring storage in a storage medium 124. In real time analysis, the detector of the mass spectrometer passes data to be analyzed directly to computer 126 without first storing it to permanent storage.

The collision cell of the mass spectrometer 112 performs fragmentation of the precursor ions. Fragmentation can be used to determine the primary sequence of a peptide and subsequently lead to the identity of the originating protein. The collision cell includes a gas such as helium, argon, nitrogen, air, or methane. When a charged precursor interacts with gas atoms, the resulting collisions can fragment the precursor by breaking it up into resulting fragment or product ions. Such fragmentation can be accomplished as using techniques described in Bateman by switching the voltage in a collision cell between a low voltage state (e.g., low energy, <5 V) that obtains MS spectra of the peptide precursor, and with a high voltage state (e.g., high or elevated energy, >15V) that obtains MS spectra of the collisionally induced fragments of the precursors. High and low voltage may be referred to as high and low energy, since a high or low voltage, respectively, is used to impart kinetic energy to an ion.

Various protocols can be used to determine when and how to switch the voltage for such an MS/MS acquisition. For example, conventional methods trigger the voltage in either a targeted or data dependent mode (data-dependent acquisition, DDA). These methods also include a coupled, gas-phase isolation (or pre-selection) of the targeted precursor. The low-energy spectra are obtained and examined by the software in real-time. When a desired mass reaches a specified intensity value in the low-energy spectrum, the voltage in the collision cell is switched to the high-energy state. The high-energy spectra are then obtained for the pre-selected precursor ion. These spectra contain fragments of the precursor peptide seen at low energy. After sufficient high-energy spectra are collected, the data acquisition reverts to low-energy in a continued search for other precursor masses of suitable intensities for high-energy collisional analysis.

It should be noted that different suitable methods may be used with a system as described herein to obtain ion information such as for precursor and product ions in connection with mass spectrometry for an analyzed sample. Although conventional switching techniques can be employed, embodiments may also use techniques described in Bateman that may be characterized as a fragmentation protocol in which the voltage is switched in a simple alternating cycle. This switching is done at high enough frequency so that multiple high- and low-energy spectra are obtained within a single chromatographic peak. Unlike conventional switching protocols, the cycle is independent of the content (m/z) of the data. Such switching techniques described in Bateman provide effectively simultaneous mass analysis of both precursor and product ions. In Bateman, a high- and low-energy switching protocol may be applied as part of an LC/MS analysis of a single injection of a peptide mixture. In data acquired from the single injection or experimental run, the low-energy spectra contains ions primarily from unfragmented precursors, whereas the high-energy spectra contain ions primarily from fragmented precursors (e.g., product fragment ions). For example, a portion of a precursor ion may be fragmented to form product ions, and the precursor and product ions are analyzed simultaneously, either at the same time or, for example, in rapid succession through application of rapidly switching or alternating voltage to a collision cell of an MS module between a low voltage (e.g., pass primarily the precursors) and a high or elevated voltage (e.g. generate primarily precursor fragments) to regulate fragmentation. Operation of the MS in accordance with the foregoing techniques of Bateman by rapid succession of alternating between high (or elevated) and low energy may also be referred to herein as the Bateman technique and the high-low protocol.

In summary, such as when operating the system using the Bateman technique, a sample 102 is injected into the LC/MS system. The LC/MS system produces two sets of spectra: a set of low-energy spectra and a set of high-energy spectra. The set of low-energy spectra contain ions primarily associated with precursors. The set of high-energy spectra contain ions primarily associated with precursor fragments. These spectra are stored in a storage medium 124. After data acquisition, these spectra can be extracted from the storage medium and displayed and processed, post acquisition, by algorithms in the analysis computer 126.

The data acquired by the high-low protocol allows for the accurate determination of the retention times, mass-to-charge ratios, and intensities of all ions collected in both low- and high-energy modes. In general, different ions are seen in the two different modes, and the spectra acquired in each mode may then be further analyzed separately or in combination.

The ions from a common precursor as seen in one or both modes will essentially share the same retention time (and thus have substantially the same scan times) and LC peak shapes. The high-low protocol allows the meaningful comparison of different characteristics of the ions within a single mode and between modes. This comparison can then be used to group ions seen in both low-energy and high-energy spectra. Various techniques are described herein for grouping or associating a precursor ion of the low-energy spectra with fragment ions of the high-energy spectra originating from the precursor ion.

Figure 2:
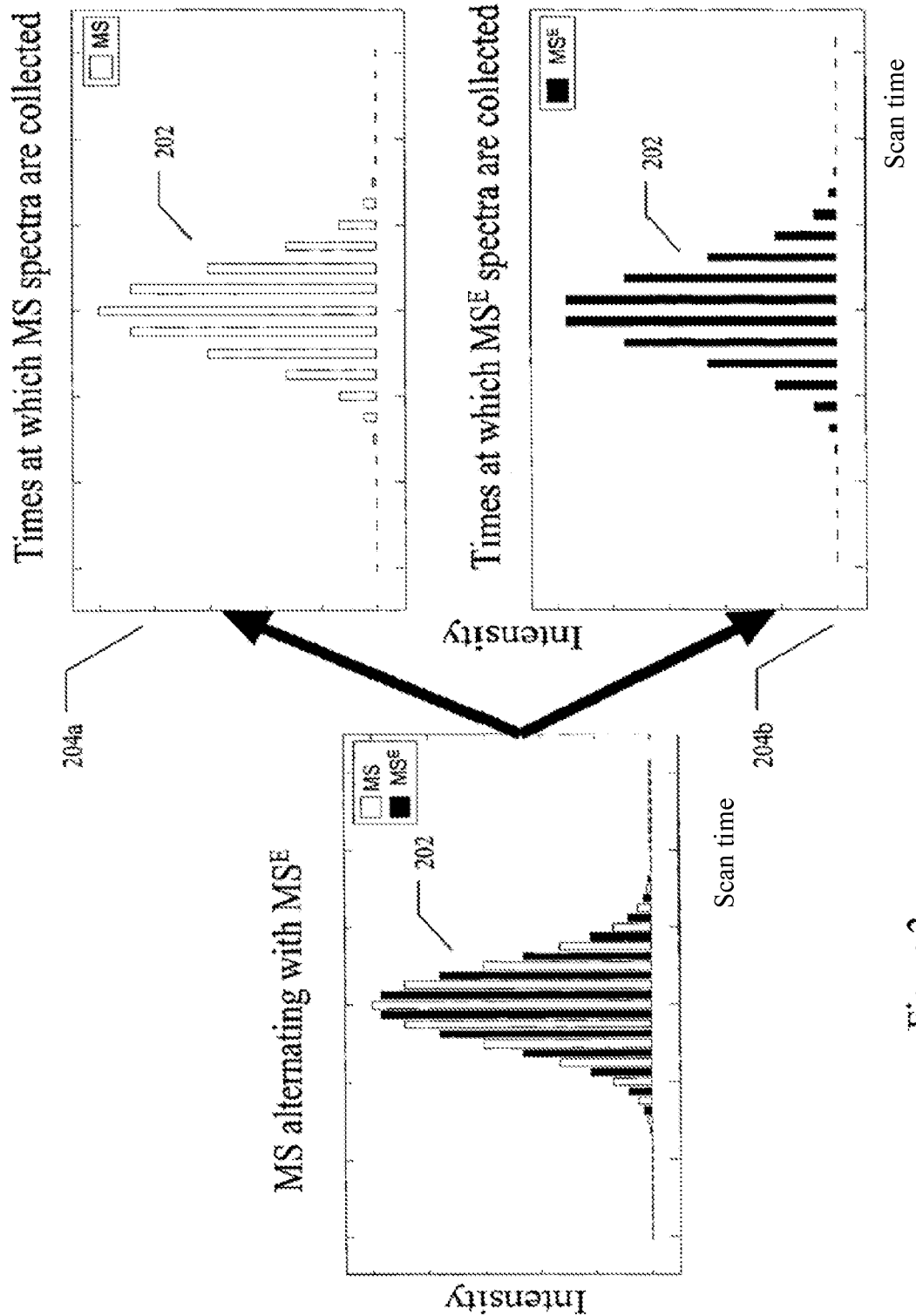
FIG. 2 shows three related graphs that illustrate the collection of mass spectra in accordance with one embodiment of the techniques herein.

FIG. 2 illustrates the times at which spectra are obtained during the elution of a peak resulting from application of the alternating low- and high-energy modes, according to an embodiment with the techniques herein. FIG. 2 shows that the chromatographic profile associated with an eluting precursor can be reconstructed from both its high- and low-energy spectral data across multiple spectrum scans.

Peak 202 represents the LC elution peak profile of a single precursor. The horizontal axis is time, for example, such as the different MS scan times or corresponding retention times during sample elution. The vertical axis is an arbitrary representation of the time-varying concentration of the chromatographic profile of the precursor as it elutes from the chromatographic column.

Thus the first graph of LC peak 202 illustrates the alternating collection over time of low-energy spectra (i.e., spectra from unfragmented precursors, labeled "MS") and elevated-energy spectra (i.e., spectra from fragmented precursors, that is, product ions, labeled "$MS^E$"). Second and third graphs, 204a and 204b, respectively, illustrate the MS and $MS^E$ spectral collection scans and the reconstruction of the peak 202 associated with the precursor as may be generated using the Bateman technique. Plots 204a (low-energy) and 204b (high-energy) in FIG. 2 depict the same chromatographic peak 202, wherein the horizontal axis represents time and the vertical axis represents intensity of an ion.

Due to the high mass resolution of a mass spectrometer and the ubiquitous presence of isotopes occurring in nature, the molecules entering the mass spectrometer group into a series of isotopic mass peaks we refer to herein as an isotope cluster. The presence of these peaks and their differing intensities are characteristics of the elemental composition of a particular molecule. A molecule ionized by the mass spectrometer thus produces a series of isotopic charge clusters, whereby the intrinsic isotopic cluster representing the molecule takes on a distribution of charge states. Thus, an ionized molecule with a particular isotopic distribution and charge state z is observed in the mass spectrum as a series of m/z peaks, each separated by the inverse of its charge state (1/z). Also, depending on the charge distribution of an ionized molecule, each isotope cluster will be observed at a particular m/z space; the higher the charge, the lower the m/z, and the smaller the peak spacing.

Since the ions produced in the low-energy mode are primarily those of the precursor ions, their mass spectrum will appear (as just described) as isotopic charge clusters. In high-energy mode, the ions are primarily product fragment ions of the precursor. As such, the fragment ion isotopic charge cluster distribution will depend on the resultant fragment mass and reduced charge state from the precursor.

In the plot of peak 202, the alternating bars of different density represent the times at which spectra were collected with low- and high-energy voltages during the elution of the depicted LC peak. The bars alternate uniformly in time. Plot 204a illustrates exemplary the times at which low-energy voltage was applied in the collision cell, resulting in low-energy spectra. Plot 204b illustrates times at which high-energy voltage was applied in the collision cell, resulting in high-energy spectra. As shown in 204a and 204b, the chromatographic peak is sampled multiple times by the high- and low-energy modes. A sample thus produces isotopic charge clusters in both low- and elevated-energy modes.

Thus, when operating the MS instrument using the high-low protocol as described in Bateman, for a single experimental run or sample injection, analysis may result in obtaining a first set of low energy mass spectral data represented by 204a containing primarily precursor ion data and a second set of high or elevated energy mass spectral data represented by 204b containing primarily fragment ion data.

As described in more detail below, such data generated as a result of mass spectral analysis generally includes scan or acquisition times.

In some embodiments, the system of FIG. 1 may further include components in the mass analyzer (or as a separate component or instrument) to additionally perform ion mobility spectrometry (IMS) as an additional dimension of separation. In such embodiments, further processing of the mass spectral data may convert the resulting mass spectral data scan times of the first form to corresponding retention times and also corresponding ion mobility drift times. As described in more detail elsewhere herein, techniques herein may perform processing on the first form of mass spectral analysis data with scan times.

With reference back to FIG. 1, in operation, the sample 102 is injected into the LC 104 via the injector 106. The pump 108 pumps the sample through the column 110 and the sample is separated into eluting components characterized by their retention times exiting the column 110. A high-pressure solvent stream provided by pump 108 through the injector 106 forces sample 102 to migrate through a chromatographic column 110 in liquid chromatography system 104. Column 110 typically comprises a packing of silica beads whose surface comprises bonded molecules. The output fluid stream from the column 110 is directed to MS 112 for analysis. In one embodiment, the LC 104 may be an ultra performance liquid chromatography (UPLC) system such as the ACQUITY UPLC® System from Waters Corporation of Milford, Mass.

Mass analyzers of the MS 112 can be placed in tandem in a variety of configurations, including, e.g., quadrupole time-of-flight (Q-TOF) mass analyzers. A tandem configuration enables on-line collision modification and analysis of an already mass-analyzed molecule. For example, in triple quadrupole based massed analyzers (such as Q1-Q2-Q3 or Q1-Q2-TOF mass analyzers), the second quadrupole (Q2), imparts accelerating voltages to the ions separated by the first quadrupole (Q1). These ions, collide with a gas expressly introduced into Q2. The ions fragment as a result of these collisions. These fragments are further analyzed by the third quadrupole (Q3) or by the TOF. In one embodiment, the MS 112 may be a QTOF mass spectrometer such as, for example, the SYNAPT G2™ Mass Spectrometer from Waters Corporation of Milford, Mass.

As an output, the MS 112 generates a series of spectra or scans collected over time. A mass-to-charge spectrum is intensity plotted as a function of m/z. Each element, a single mass-to-charge ratio of a spectrum may be referred to as a channel. Viewing a single mass channel over time provides a chromatogram for the corresponding mass-to-charge ratio. The acquired mass-to-charge spectra or scans can be recorded on a storage medium such as a hard-disk drive or other storage media represented by element 124 that is accessible to computer 126. Typically, a spectrum or chromatogram is recorded as an array of values and stored on storage 124. The spectra stored on 124 may be accessed using the computer 126 such as for display, subsequent analysis, and the like. A control means (not shown) provides control signals for the various power supplies (not shown) which respectively provide the necessary operating potentials for the components of the system 100 such as the MS 112. These control signals determine the operating parameters of the instrument. The control means is typically controlled by signals from a computer or processor, such as the computer 126.

Once the molecule elutes from column 106, it can be conveyed to the MS 112. A retention time is a characteristic time. That is, a molecule that elutes from a column at retention time t in reality elutes over a period of time that is essentially centered at time t. The elution profile over the time period is referred to as a chromatographic or LC peak. The elution profile of a chromatographic peak is typically characterized by a bell-shaped or Gaussian curve. The peak's bell shape has a width that typically is described by its full width at half maximum height (FWHM). The molecule's retention time is the time of the apex of the peak's elution profile. Spectral peaks appearing in spectra generated by mass spectrometers have a similar shape and can be characterized in a similar manner.

The storage 124 may be any one or more different types of computer storage media and/or devices. As will be appreciated by those skilled in the art, the storage 124 may be any type of computer-readable medium having any one of a variety of different forms including volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, (DVD) or other optical storage, magnetic cassettes, magnetic tape, magnetic disk storage or other magnetic storage devices, or any other medium which can be used to store the desired code, data, and the like, which can be accessed by a computer processor, or more generally any processor of a computer or other component.

The computer 126 may be any commercially available or proprietary computer system, processor board, ASIC (application specific integrated circuit), or other component that includes a computer processor configured to execute code stored on a computer readable medium. The processor, when executing the code, may cause the computer system 126 to perform processing steps such as to access and analyze the data stored on storage 124. The computer system, processor board, and the like, may be more generally referred to as a computing device. The computing device may also include, or otherwise be configured to access, a computer readable medium, such as represented by 124, comprising executable code stored thereon which cause a computer processor to perform processing steps.

The system 100 may be used to perform an LC/MS experiment to analyze a sample and generate mass spectra for precursor and product or fragment ions of at least one compound or molecule in the sample. The generated mass spectra may be further analyzed and/or processed for use in connection with any of a variety of techniques for different applications. In connection with the techniques herein, the mass spectra data may be analyzed to identify and quantitate a precursor molecule with its associated product ions.

Any suitable method using the system 100 may be used to obtain both precursor and product ions from a sample injection. Some methods, such as operating the MS instrument in accordance with the high-low protocol as described in Bateman, provide effectively simultaneous mass analysis of both precursor and product ions. For example, a portion in time of an eluted precursor is fragmented to form product ions, and the precursor and product ions are substantially analyzed simultaneously, either at the same time or, for example, in rapid succession. Thus, an embodiment may use the technique described in Bateman or other suitable technique to operate the MS instrument. An embodiment may use techniques described elsewhere herein to determine which product ions are derived from a particular precursor whereby such product ions may be characterized as associated with, or related to, multiply eluting precursors.

In accordance with techniques described elsewhere herein, peak shape, width, and scan times of the peaks associated with precursor ions and with product ions may be compared to determine which product ions are associated with a particular precursor ion. Ions (precursors and fragments) derived from a common originating molecule have similar characteristics, such as their relative intensities. As a molecules elutes from an LC, it increases in its intensity to a maximum, then decreases in intensity untill below the limit of detection (LOD). Product ions of that precursor will behave identically in that the ratio of the intensities of the product ions to their parent precursor remains constant, though each are constantly changing in absolute intensity. Thus the relative intensities within and between scans of precursor ions and their associated products have to be consistent, illustrating a common peak shape or profile and the like, as described elsewhere herein.

In an LC/MS experiment as mentioned above, an ion can be described and/or referred to by its scan time, mass-to-charge ratio or mass, charge state, and intensity. An originating molecule can give rise to multiple ions whereby each such ion is either a precursor or a fragment. These fragments arise from processes that break up the originating molecule. These processes can occur in the ionization source or in a collision cell of the MS 112. Because fragment ions derive from a common eluting, originating molecule, they are, by definition, present at an intensity ratio reflective of the fragmentation efficiency (product ion area/precursor ion area) for each scan across its chromatographic peak profile. The time of ion formation, fragmentation, and ion detection is generally much shorter than the peak width of the originating molecule. For example, a typical chromatographic peak width, measured at full-width at half-maximum (FWHM) is 5 to 30 seconds. The time of ion formation, fragmentation, and detection is typically sub milliseconds.

In an embodiment using the Bateman technique or high-low protocol for data acquisition that obtains alternating LE and HE scans such as illustrated in FIG. 2, on a chromatographic time scale, the time of ion formation, fragmentation and detection may be characterized in one aspect as essentially an instantaneous process. It follows that differences in observed scan times of the ions in such an embodiment that derive from an originating molecule is effectively zero. That is, sub-millisecond retention time differences between ions that derived from an originating molecule are small compared to the chromatographic peak width.

With respect to ions that are generated from collision-induced disassociation of intact precursor ions, the fragment or product ions are associated with their parent precursor ion. By using the mass spectrometer in a high-low data acquisition mode (also referred to herein as an elevated-low-data acquisition mode) as described in the Bateman '130 patent, this association is accomplished without requiring the instrument to pre-select a single precursor for subsequent fragmentation. More specifically, associated ions are appropriately grouped when multiple precursors are fragmenting simultaneously at essentially the same scan time.

With respect to data acquired by serial mass isolations, the time at which an ion is selected for fragmentation and when it is fragmented can be substantially different, as such, in order to calculate the correct intensity ratios, product ion/precursor ion, it is necessary to extrapolate a precursor ion's intensity at its actual time of fragmentation. This is accomplished by generating a linear regression between the intensity values of the precursor ion from the subsequent and prior LE scans, and applying the associated time interval.

The elution time and chromatographic peak profile of a molecule eluting from a chromatographic support matrix, such as column 110, is a function of the physical interaction of that molecule between the support matrix and mobile phase. The degree of interaction that a molecule has between the support matrix and the mobile phase dictates the chromatographic profile and elution time for that molecule. In a complex mixture, each molecule is chemically different. As a result, each molecule can have a different affinity for the chromatographic matrix and the mobile phase. Consequently, each molecule can exhibit a unique chromatographic profile.

Generally, a chromatographic profile for a specific molecule is unique and describes the physicochemical properties of that molecule. Parameters optionally used to characterize the chromatographic peak profile of a given molecule include the time of initial detection (lift off), normalized slope, the time of inflection points relative to the time of the peak apex, the time of maximum response (peak apex), the peak width at inflection points, the full-width-at-half-maximum (FWHM), peak shape asymmetry, and the time of the final detection (touch down), to name only a few.

As described in more detail below, more generally, techniques herein may be used in connection with processing one or more MS data sets in the first form as described elsewhere herein obtained from the same or different experiments. The MS data sets may be obtained by operating the MS instrument in accordance with the high-low protocol described in Bateman or any other suitable manner.

Figure 3:
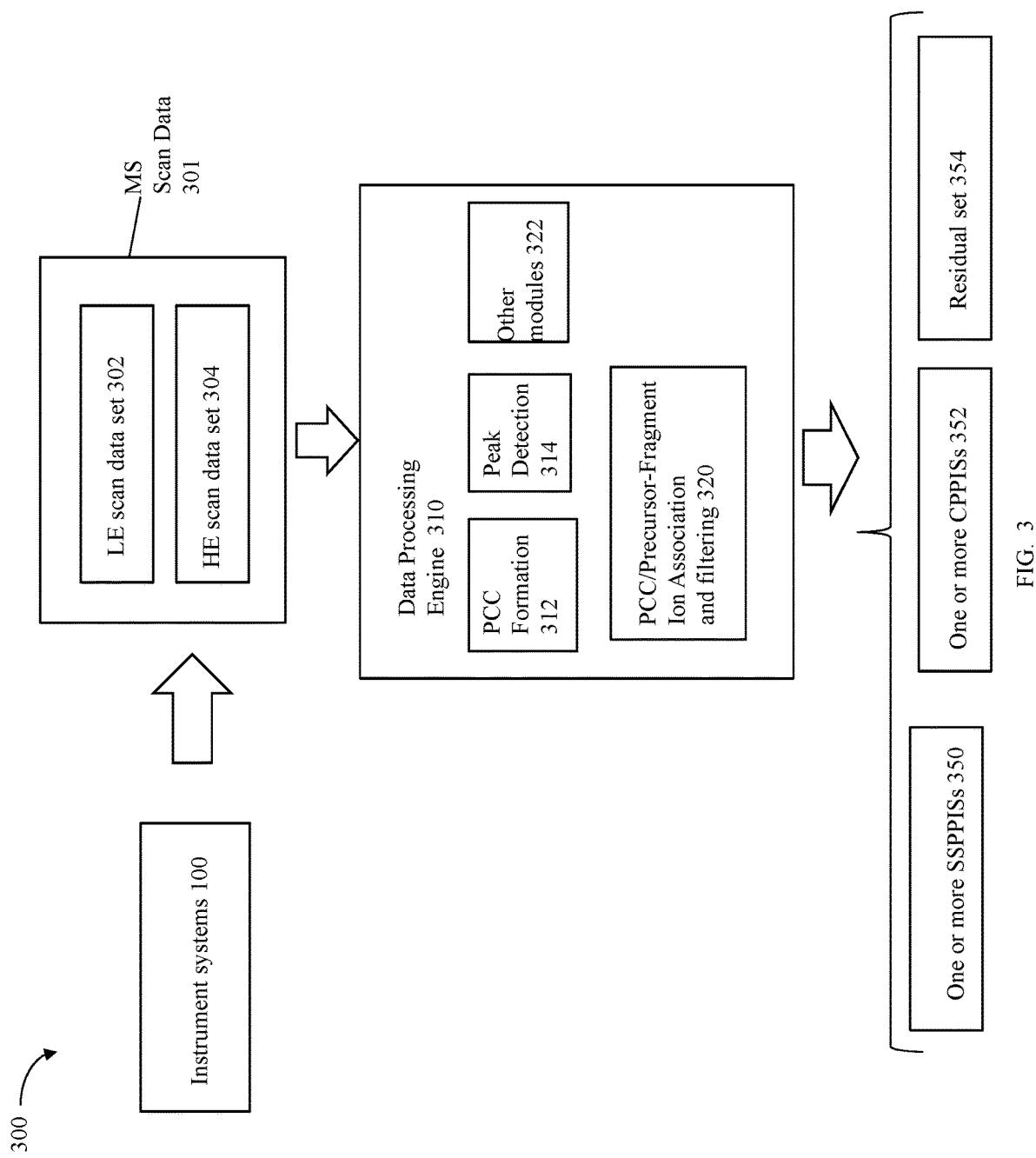
FIG. 3 is an example of components and data that may be used in an embodiment in accordance with techniques herein.

Referring to FIG. 3, shown is an example illustrating components that may be used in an embodiment in accordance with techniques herein. The example 300 includes instrument systems 100 denoting the instruments, such as the LC and MS instruments, performing sample analysis such as illustrated in the system 100 of FIG. 1. In this example, an experiment may be performed to analyze a sample where MS (LE) and MS/MS (HE) data is acquired for a single precursor, m/z range of precursors, or the entire m/z scale of precursors within a very narrow time window between a collection of the LE and HE data sets. As an example, LE and HE data is acquired in accordance with the high-low protocol of Bateman to generate the MS scan data 301 for a single sample analysis. As noted above and elsewhere herein, such a set of MS scan data 301 for the single experimental run or injection may include two data sets—the low energy (LE) scan data set 302 and the high energy (HE) scan data set 304. Element 302 may denote the MS scan data acquired when operating the MS instrument in low energy mode and element 304 may denote the MS scan data acquired when operating the MS instrument in high energy mode. In this example, the data sets 302 and 304 may include the full scan data for all detected ions with no mass filtering.

The MS scan data 301 may be provided as an input to the data processing (DP) engine 310. The DP engine 310 may be embodied as one or more software modules that process the MS scan data 301, whereby such processing includes performing precursor charge cluster (PCC) formation 312, peak detection 314 on a per-scan basis with respect to each PCC, and PCC or precursor-fragment ion association and filtering 320. The DP Engine 310 may also include one or more other modules 322. As an output, the DP engine 310 may generate one or more SSPPISs (Single-Scan Precursor-Product Ion Spectrum) 350. An SSPPIS represents a single PCC and its associated product or fragment ions reflecting a single scan. Processing performed by each of the foregoing modules of the DP Engine 310, along with PCCs, SSPPISs and the like are described in more detail elsewhere herein. As also described in more detail in following paragraphs, one or more SSPPISs may be used in obtaining a mass fingerprint to uniquely identify a particular molecule. In some embodiments, associated or related SSPPISs may be further combined into one or more CPPISs (Composite Precursor-Product Ion Spectrum) 352 as described in more detail elsewhere herein.

Additionally, the DP engine 310 may also output a residual set 354 of unmatched ions. As described in more detail elsewhere herein, the residual set 354 may include any unmatched PCCs and/or unmatched fragment ions.

The DP engine 310 may operate in a first processing mode referred to herein as non-supervised or unsupervised clustering whereby the formation of a CPPIS is made from a series of SSPPISs by tracking the intensities of a single PCC and that of its product ions contained in each surrounding SSPPIS across the LC peak elution profile. Only the product ions of each SSPPIS that follow specific algorithmically-determined intensity ratio relations to the tracked precursor charge cluster or one or more of its isotopes are retained.

In typical situations in which an LC peak may exhibit more than one overlapping eluting component, the creation of SSPPISs will assign the same high energy product ion spectrum to multiple precursor charge clusters (PCCs) if they are found in the same mass isolation window in which the product ion spectrum was acquired. This is always the case with the high-low protocol of Bateman to generate the MS scan data. The product ions of a single scan acquisition thus generally have a one-to-many relationship to their assigned PCCs. Thus the discarded product ions of one particular SSPPIS become the filtered ions retained in a different SSPPIS belonging to a different PCC. The culmination of this process results in the creation of CPPISs in which the product ions retained in their associated SSPPISs are most likely the rightful ones belonging to a particular precursor charge cluster.

The DP engine 310 may also operate in a second processing mode referred to herein as supervised clustering whereby the formation of a CPPIS is made from a series of one or more SSPPISs by matching the precursor-product ions of a known fingerprint or target molecule or compound, such as may be stored in a database or library, to all SSPPISs within a user- or algorithm-defined set of matching criteria.

As described elsewhere herein, the modules 312, 314 and 320 may perform processing for both the supervised and non-supervised clustering modes. In one embodiment, the modules 312 and 314 may perform the same processing of the MS Scan data 301 for both the supervised and non-supervised clustering modes. The processing performed by the module 320 may vary depending on whether the DP engine 310 is operating in the non-supervised clustering mode or supervised clustering mode.

Figure 4:
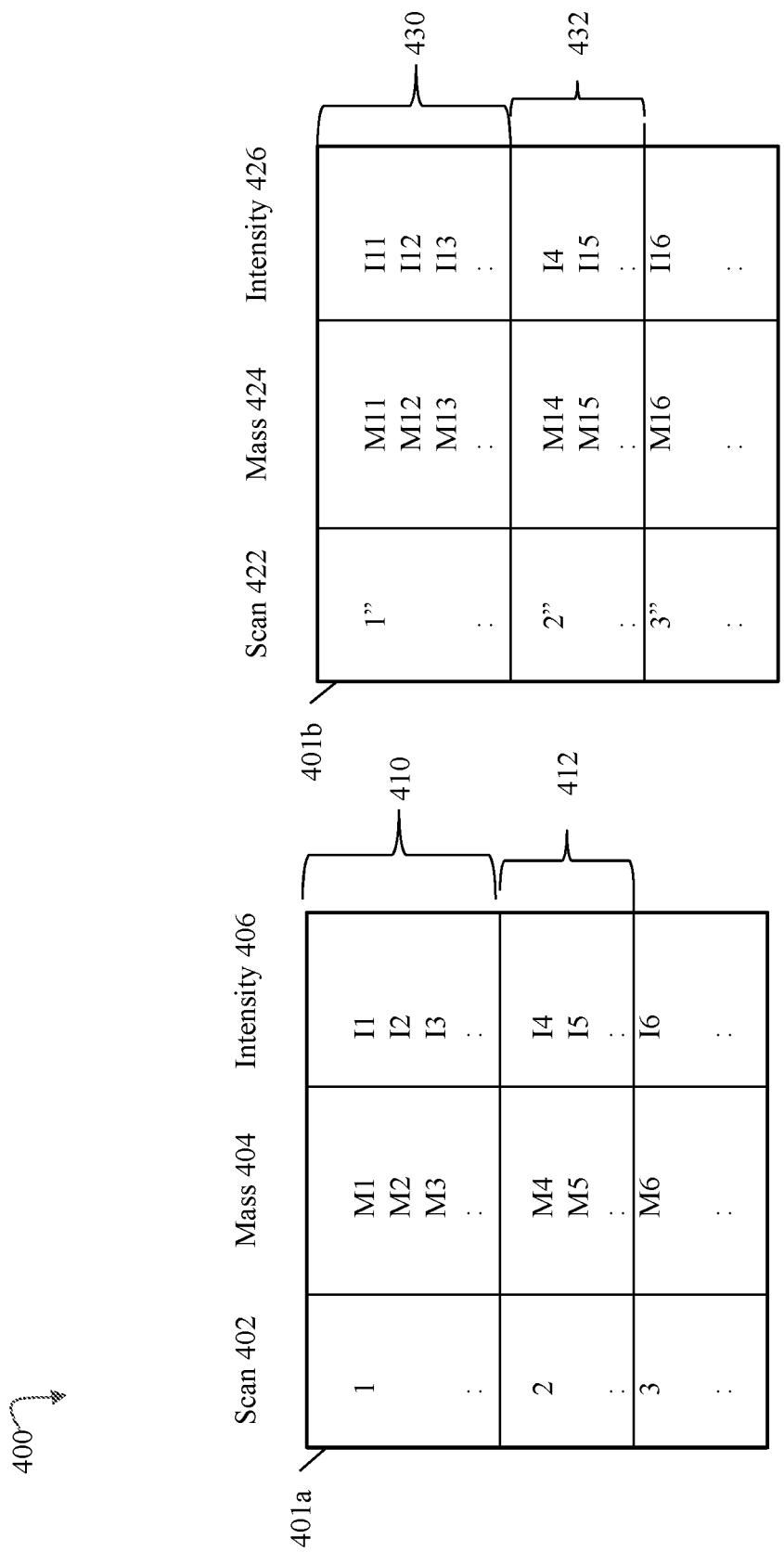
FIGS. 4 and 5 are examples of MS scan data that may be used in an embodiment in accordance with techniques herein.

Referring to FIG. 4, shown is an example of information that may be included in the mass spectral data that is processed in an embodiment in accordance with techniques herein. The example 300 illustrates information that may be included in the first form of MS scan data 301. Element 401a may represent the precursor ion spectral data, (denoted as the LE scan data set 302 in FIG. 3) obtained as a result of performing an experiment described above in connection with FIG. 3 when operating the MS instrument in accordance with the high-low protocol of Bateman. Element 401b may represent the product or fragment ion spectral data obtained as a result of performing an experiment described above in connection with FIG. 3 when operating the MS instrument in accordance with the high-low protocol of Bateman. In particular, in an embodiment utilizing an MS instrument operating in accordance with the high-low protocol of Bateman, data of 401a and 401b may be acquired in a single experiment or run whereby alternating scans are associated with precursor and product ion spectra. In the example 400, scan I of table 401a and a corresponding scan I" of table 401b represent data acquired for substantially the same $I^{th}$ scan time and thus represent corresponding scans, where I represents a scan number that is an integer greater than 0 in this example. For a corresponding scan number I, information of table 401a is denoted by I in the scan number column 402 and information of table 401b for the same scan number is denoted by I" in the scan number column 422 pair. In the example 300, a pair of corresponding scans, I and I", have substantially the same scan time, whereby scan I of the pair has data in the table 401a or low energy scan data, and scan I" of the same pair has data in the table 401b or high energy scan data.

As illustrated by tables 401a and 401b, each of the data sets 401a, 401b may include information for multiple scan times for the different mass spectral scans. For each scan, a list of one or more detected masses and associated intensities may be obtained by performing mass spectrometry. For example with reference to the table 401a, column 402 represents the list of the scans, column 404 represents the detected masses at the scan, and column 406 represents the intensities of the detected masses in column 304. For scan 1, the rows of the table 401*a* denoted by cell or entry 410 list the masses and associated intensities detected. For scan 2, the rows of the table 401*a* denoted by the cell or entry 412 list the masses and associated intensities detected. Each row of the table 401*a* includes a mass and an intensity denoting the intensity of the detected mass in that row. For example, i1 is the intensity of mass m1 detected in scan 1, and i2 is the intensity of mass m2 detected in scan 1. Table 401*b* may include information similar to that as described in connection with table 401*b* but for alternating corresponding scans associated with fragment ion data. With reference to the example 300, 410 and 430 denote corresponding low and high energy scan data for corresponding scans 1 and 1", 412 and 432 denote corresponding low and high energy scan data for corresponding scans 2 and 2".

Figure 5:
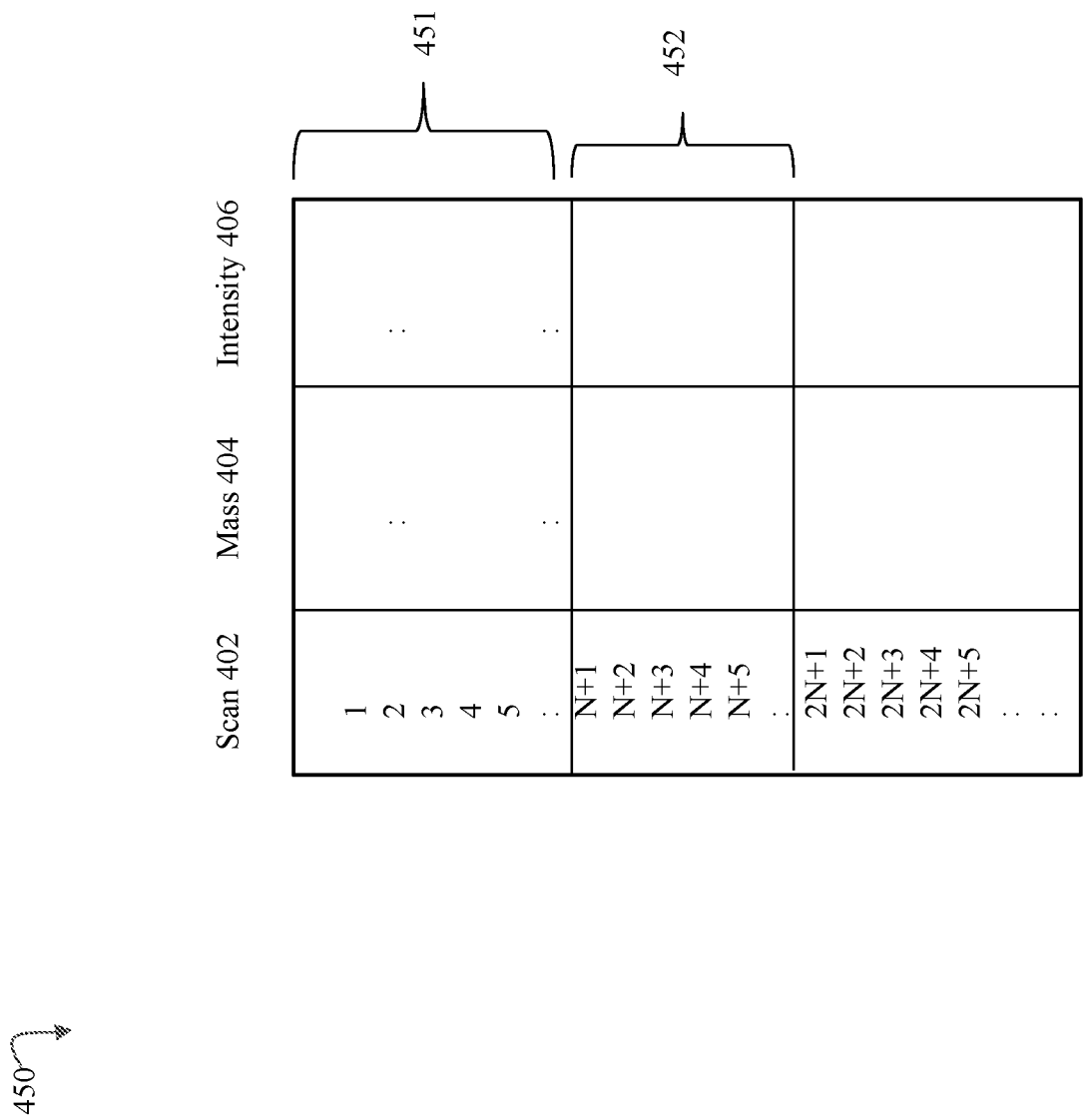

It should be noted that a pair of corresponding scans (one from table 401*a* and a second from table 401*b*) having substantially the same scan time may denote a retention time or drift time, depending on the particular experiment. For example, if the separation processing performed prior to mass spectrometry includes chromatographic separation, such as for LC or GC, without ion mobility spectrometry, the scan times denote retention time. If the separation processing performed prior to mass spectrometry includes ion mobility spectrometry but no chromatographic separation, the scan times denote drift times. If both chromatography and ion mobility spectrometry are performed prior to mass spectrometry, a scan time may denote either a retention time or a drift time. For example, with LC/IMS/MS, a set of consecutive scan times may form a scan group representing a group of multiple drift times associated with a single retention time whereby a scan group (of the scan times corresponding to drift times) may be characterized as nested within or between two scan times corresponding to chromatographic retention times. For example, with reference to FIG. 5, shown is an example of scan groups 451 and 452 each including N scans. In an LC/IMS/MS experiment, each scan group 451, 452 may be associated with a different retention time. Within a single scan group, such as 451, each individual scan time may correspond to a different drift time.

The mass spectral data may have alternative forms than that as described herein, for illustration. The precursor and product ion mass spectral data operated upon using techniques herein and such as illustrated in FIGS. 4 and 5 may be characterized in one aspect as mass spectral data in a first form that has not yet been processed by other software that performs peak detection, maps or translates scans and scan times to corresponding retention times and/or drift times, and the like.

It should be noted that mass spectral data including information similar to that as described in connection with FIGS. 4 and 5 may be obtained when operating the MS instrument for an experiment in a manner different than as noted above in accordance with the high-low protocol of Bateman.

Figure 6:
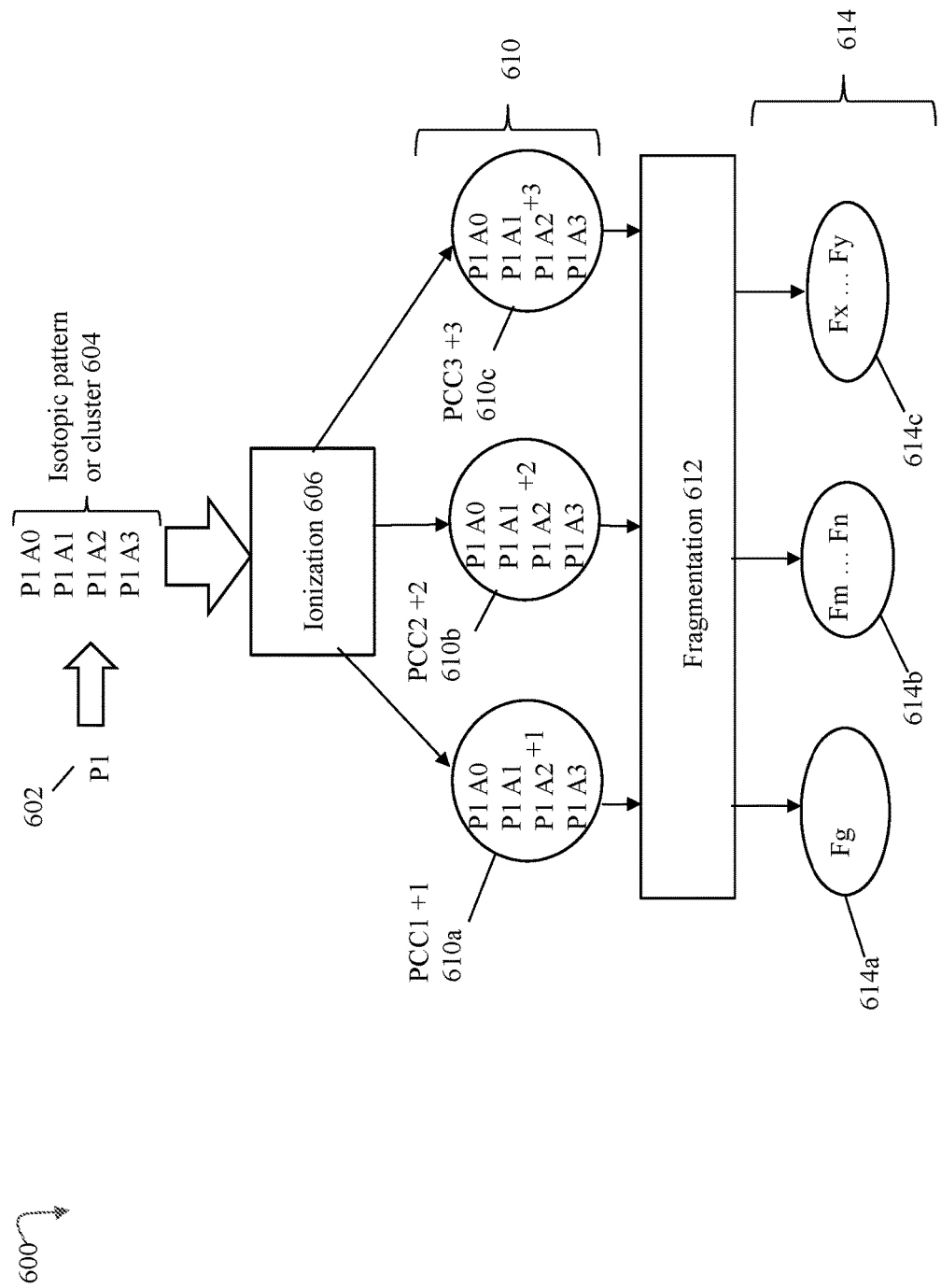
FIGS. 6 and 6a are examples illustrating processing that may be performed in an embodiment in accordance with techniques herein to generate information included in a fingerprint or pattern for a molecule.

Referring to FIG. 6, shown is an example illustrating processing that may be performed in an embodiment in accordance with techniques herein to generate information included in a fingerprint or pattern for a molecule. In the example 600, P1 602 may denote a parent precursor that is a single molecule or eluting component of a sample. The parent precursor or single molecule has an isotopic pattern or cluster 604, which in the example is P1 A0, P1 A1, P1 A2, and P1 A3. Each P1 Ai, where "i" is a value in the inclusive range 0 . . . 3 in this example 604 denotes the isotopic distribution of the precursor P1. In connection with description herein, the isotopic pattern or cluster 604 may also be referred to simply as the precursor. When the precursor having isotopic pattern 604 is subjected to ionization 606, such as in connection with an MS instrument, the precursor is ionized thereby resulting in a series of PCCs, each of different charge states 610. Each precursor charge cluster or PCC 610*a*-610*c* has the identical isotopic distribution. The delta m/z spacing between isotopes varies with charge, albeit the intensity ratio within and between Ai is constant. In this example, ionization of the eluting component P1 602 results in 3 precursor charge clusters or PCCs 610*a*-*c*. PCC1 610*a* has a charge of +1, PCC2 610*b* has a charge of +2 and PCC3 610*c* has a charge of +3. Each of the foregoing precursor ions or PCCs 610*a*-*c* may be further fragmented as a result of fragmentation processing 612, such as in connection with processing by the MS instrument, thereby resulting in a series of fragmentation sets 614. More specifically in this example, each of the PCCs 610*a*-*c* is subjected to fragmentation 612 resulting in an associated sets of the fragmentation ions 614*a*-*c*. In the example 600, a product or fragment ion generated as a result of fragmenting a precursor ion or PCC may be denoted by each F included in 614*a*-*c*. PCC1 610*a* may be fragmented resulting in fragmentation set 614*a* including fragment or product ions originating from PCC1. PCC2 610*b* may be fragmented resulting in fragmentation set 614*b* including fragment or product ions originating from PCC2. PCC3 610*c* may be fragmented resulting in fragmentation set 614*a* including fragment or product ions originating from PCC3.

In an embodiment where the ion fingerprint of a molecule is to be determined by comparing SSPPISs of a precursor ion's charge state requires the data include drift or CCSA. Ion mobility separates precursor ions by charge. Charge state has no influence on chromatographic elution; as such, all charge states of a precursor track identically with time. Ion mobility separates the different charge states providing the means for the DP to calculate the necessary intensity ratios within and between precursors and products by their charge states. The results can then be compared and collapsed into a single ion fingerprint or Composite Precursor Product Ion Spectrum or CPPIS.

In an embodiment in accordance with techniques herein, the fingerprint of the molecule denoted by P1 602 consists of three identified and validated fragment ion patterns denoted in 614*a*-*c* for each of the three PCCs denoted in 610*a*-*c*. As described herein, an embodiment in accordance with techniques herein may also store error indicators or consistency indicators associated with the area ratios (e.g., various AR values described elsewhere herein) of precursor and product ions for each product ion contained in the ion fingerprint.

In one embodiment in accordance with techniques herein, attributes associated with each PCC may include m/z, m/z and retention time, m/z, retention and drift time, or any and all pre-ion detection separation measurements or combinations thereof. The m/z or record of a PCC or precursor's ion m/z is the $A_0$ isotope or monoisotope. The intensity of the PCC or precursor ion, such as denoted by each of 610*a*-*c*, in a single scan may be the sum of the intensities of all its isotopes in the single PCC for that single scan. For example, the intensity of the precursor ion denoted by PCC1 610*a* in a scan S1 is the sum of the intensities of P1 $A_0$, P1 $A_1$, P1 $A_2$ and P1 $A_3$, as occurring in PCC1 610*a* for the scan S1.

It should also be noted that the intensity or concentration of the parent precursor P1 is equal to the sum of the intensity or concentrations of each of the PCCs 610*a*-*c*. Additionally, the number of isotopes 604 of the precursor is a function of its elemental composition and concentration as are each of its charge-states reflective in 610. Though the intensity distribution is constant for all charge states, given elemental composition is charge state independent, the number of isotopes per charge state is a function of P1's molar distribution by charge state. The number of observable isotopes of a particular PCC is determined by the mass analyzer's dynamic range an limit of detection.

As noted elsewhere herein, an SSPPIS as generated by the DP engine 310 of FIG. 3 represents a single PCC and its associated product ions. An SSPPIS may be created for each precursor charge cluster in each low energy single scan. The product ions from the companion elevated energy scan are shared or associated with each PCC in the same scan after filtering, e.g., by intensity and m/z relative to their parent precursor or by comparison to a target set of product ions, creating a unique SSPPIS.

With reference to the example of FIG. 6, parent molecule P1 results in 3 PCCs or precursor ions all having the same retention time but different intensities or concentrations, different masses, different charges, different m/z values and different drift times. As also illustrated each of the 3 PCCs may be further subject to disassociation producing their own product or fragment ion pattern 614.

In one embodiment in which a collision cell of an MS instrument is used to perform disassociation or fragmentation of the precursor ions or PCCs, the following may be the product/fragment ion patterns resulting, whereby charge is conserved. In other words, the charge of a fragment ion cannot exceed that of its parent. Generally, precursor ions disassociate into fragment ions of charge-state not exceeding the charge state of the parent precursor, minus one, given that a product ion has to be charged in order to be detected. In general charge is conserved in that a precursor that fragments generating two complement ions where F1+F2=the precursors elemental mass+ its charge state times 1.007 (mass of a proton). For example, PCC2+2 610b may be fragmented into two fragments Fm and Fn of 614b, where each such fragment has a charge of 1+. PCC3+3 610c may be fragmented into 2 fragments Fx and Fy, where Fx has a charge of 1+ and Fy has a charge of 2+. As described elsewhere herein, each fragment or product ion may also have an associated intensity, charge state, mass m/z and the like.

A first SSPPIS for PCC1 610a may be generated that includes the fragment ions of 614a, thereby denoting that fragment ions 614a are associated with or generated by fragmentation of the PCC1 610a. A second SSPPIS for PCC2 610b may be generated that includes the fragment ions of 614b, thereby denoting that fragment ions 614b are associated with or generated by fragmentation of the PCC2 610b. A third SSPPIS for PCC3 610c may be generated that includes the fragment ions of 614c, thereby denoting that fragment ions 614c are associated with or generated by fragmentation of the PCC3 610c.

In an embodiment performing an LC/MS/IMS analysis, PCCs, such as PCC 610a-c, originating from the same precursor such as P1, may be differentiated in the time dimension in terms of their associated drift time. In such an embodiment, the various fragment ions originating from each of the PCCs may also be determined based on the differences in drift times of the various fragment ions, such as illustrated by 614. In an embodiment performing an LC/MS analysis, thereby omitting IMS, such drift time differentiation is not available, and thus all PCCs may be observed as eluting in the same scan. In such an embodiment, it is not possible to therefore use drift time as a dimension to separate or associate the various fragment ions originating from each of the PCCs. Thus, in such an embodiment using LC/MS and omitting IMS, some of the same fragment ions may be included in multiple sets of the fragment ion sets 614a-c if it is possible for the fragment ion to originate from multiple ones of PCCs 610a-c. For example, consider an embodiment using LC/MS (no IMS) where a fragment Fk may have a charge state of +1 and may therefore possibly originate from any of PCCs 610a-c and may be included in each of 614a-c, since drift time is not available for use as a separating dimension to further associate a fragment ion with its originating PCC.

Figure 6A:
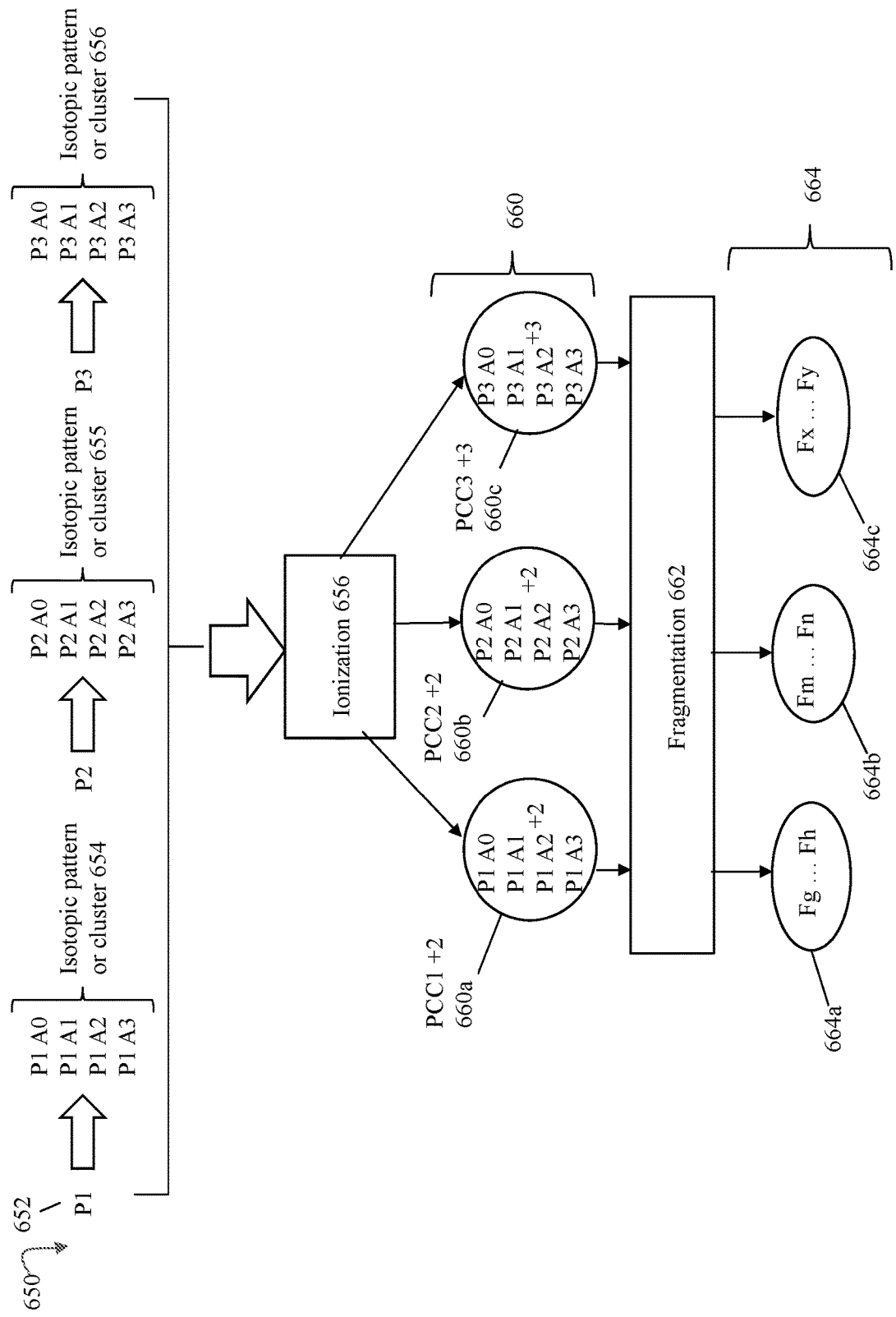

With reference to FIG. 6a, shown is an example illustrating 3 different precursors P1, P2 and P3, where P1, P2 and P3 each, respectively, have isotopic pattern or cluster 654, 655 and 656. In this example, P1-P3 illustrate 3 precursors eluting in the same scan. P1 may be ionized, resulting in PCC1 660a. P2 may be ionized, resulting in PCC2 660b. P3 may be ionized, resulting in PCC3 660c. PCCs 660a-c appear in the same LE scan. PCCs 660a-c may be fragmented 662, resulting in generating fragment ions included in fragment ion sets 664a-c, whereby all fragment ions of 664a-c may be included in the same single fragment ion scan (e.g., same HE scan).

Using techniques described in following paragraphs, a first SSPPIS for PCC1 660a may be generated that includes the fragment ions of 664a, thereby denoting that fragment ions 664a are associated with or generated by fragmentation of PCC1 660a. A second SSPPIS for PCC2 660b may be generated that includes the fragment ions of 664b, thereby denoting that fragment ions 664b are associated with or generated by fragmentation of PCC2 660b. A third SSPPIS for PCC3 660c may be generated that includes the fragment ions of 664c, thereby denoting that fragment ions 664c are associated with or generated by fragmentation of PCC3 660c.

Thus, a fingerprint for P1 precursor denoting a single molecule or single eluting component may include information from its associated first SSPPIS for PCC1 660a along with additional information, such as attribute information for the PCC and each fragment ion related to the physical or chemical properties of the PCC and/or ion, as well as attribute information such as one or more metrics and associate error indicators described elsewhere herein. In a similar manner, a fingerprint for P2 precursor denoting a single molecule or single eluting component may include information from its associated first SSPPIS for PCC2 660b, and a fingerprint for P3 precursor denoting a single molecule or single eluting component may include information from its associated first SSPPIS for PCC3 660c.

As described in FIG. 6, each of the PCCs 660a-c in FIG. 6a may exist at multiple charge states and if ion mobility was part of the acquisition workflow, as a first instance, the fragment ion fingerprint is generated by application of the described process on the different charge-states. In the absence of ion mobility, the ion fingerprint is generated by comparing the area ratios of PCCs or precursor ions 660a-c and product ions 664a-c, first identifying the product ions that are behaving similarly to their parent and then comparing those area ratios across the scan reflecting the parent molecule's chromatographic elution.

As described herein in more detail below, the acquired scan data may be processed on a per single-scan basis. The fragmentation pattern of a product or fragment ion and its relation to its parent ion, such as a PCC, may be defined as the intensity relationship between the product ion and its parent, such as its associated SSPPIS, such that the area ratio or intensity ratio between the two has to be consistent (within some experimental variance) within and between the scans defining its chromatographic profile. Techniques herein utilize such principles and relationships between a parent ion, such as a PCC, and its fragments, as recognized by the inventors. To elaborate, the fragmentation pattern of a precursor is consistent across its elution. To that end, the intensity relationship between a precursor ion and its constituent product ions should remain constant in the absence of interference. The number of product ions a precursor ion or PCC will generate during fragmentation is a function of its length/mass and concentration. The rate at which a PCC's intensity varies (e.g., increases and/or decreases) across the scans defining its elution profile is the same for the product ions emanating from that precursor. Similarly, given a consistent applied collision energy (eV), the fragmentation efficiency (ratio of product ion intensity/precursor ion intensity) also remains constant (within some experimental variance) across all the scans defining its elution profile as will the intensity of a product ion divided by the intensity of all product ions known to be part of that eluting component.

Techniques herein use validating heuristics utilizing a single-scan and scan-by-scan basis to track and validate product ion alignment to a parent precursor ion or PCC. As described in more detail below, a metric AR1 (area ratio 1) is defined as the intensity or area ratio of a product ion to its PCC in a single (same) scan time. Given the single-scan schema that may be used in an embodiment in accordance with techniques herein, each PCC has its intensity tracked across the elution peak. The scan in which the PCC is the highest is termed the Pivot Point (PP) or apex. The AR1 metric for a PCC and an associated or matching fragment ion should be the same (within some specified tolerance) across all scans/scan times of the elution peak. Additionally, as another validating technique, all neighboring scans in the peak are compared to the pivot scan using another metric, AR2 (area ratio 2, described below in more detail). Briefly, AR2 values may be determined for both the PCC and a matched (potentially) product ion. AR2 for a PCC may be defined as the intensity or area ratio of the PCC in any neighboring scan of the peak to that of the PCC in the PP or apex scan. Likewise, AR2 for a product or fragment ion may be defined as the intensity or area ratio of the fragment ion in any neighboring scan of the peak to that of the same ion in the PP or apex scan. The intensity or area ratio of a PCC and its product ions matched within a scan (AR1) and between scans (AR2) should be consistent within a statistical variance. Quantitative accuracy and precision by Area Under the Curve (AUC) dictates that there be a minimum number of scans across a peak. This ensures there are enough single scans across the peak to provide the necessary statistics to determine which ions are behaving similarly.

What will now be described is processing that may be performed in an embodiment for non-supervised clustering. It is used to determine a fingerprint of an eluting component or molecule without a priori knowledge that the particular molecule is included in the sample for which experimentation and data analysis are being performed. In connection with performing an experiment of a sample such as LC/MS or LC/IMS/MS, there may be multiple molecules eluting at the same time (e.g., having nearly the same retention time). Non-supervised clustering in an embodiment in accordance with techniques herein may be used to generally determine a fingerprint for an eluting component and may further facilitate generating such fingerprints for two overlapping or interfering components having the same or similar elution times. Thus, non-supervised clustering may be used to correctly associate or match fragment ions with their originating molecule or component and correctly associate or match fragment ions with their originating PCC. As described below and elsewhere herein in an embodiment in accordance with techniques herein, information regarding each PCC and associated fragment ions may be stored and maintained as a unit as may be represented by a single SSPPIS. Thus as illustrated in the examples of FIGS. 6 and 6a, a single fingerprint of a molecule or eluting component may comprise information from multiple PCCs and thus multiple SSPPISs. As described in more detail below, for a data set generated as a result of an LC/MS experiment on a sample, processing for non-supervised clustering may determine which fragment ions are associated with their rightful PCCs. Subsequently, processing may be performed to determine group or associate PCCs (and their matched fragment ions) with particular eluting components or molecules (e.g., determine which one or more of the PCCs should be grouped together and associated with a single eluting component or molecule).

Figure 7:
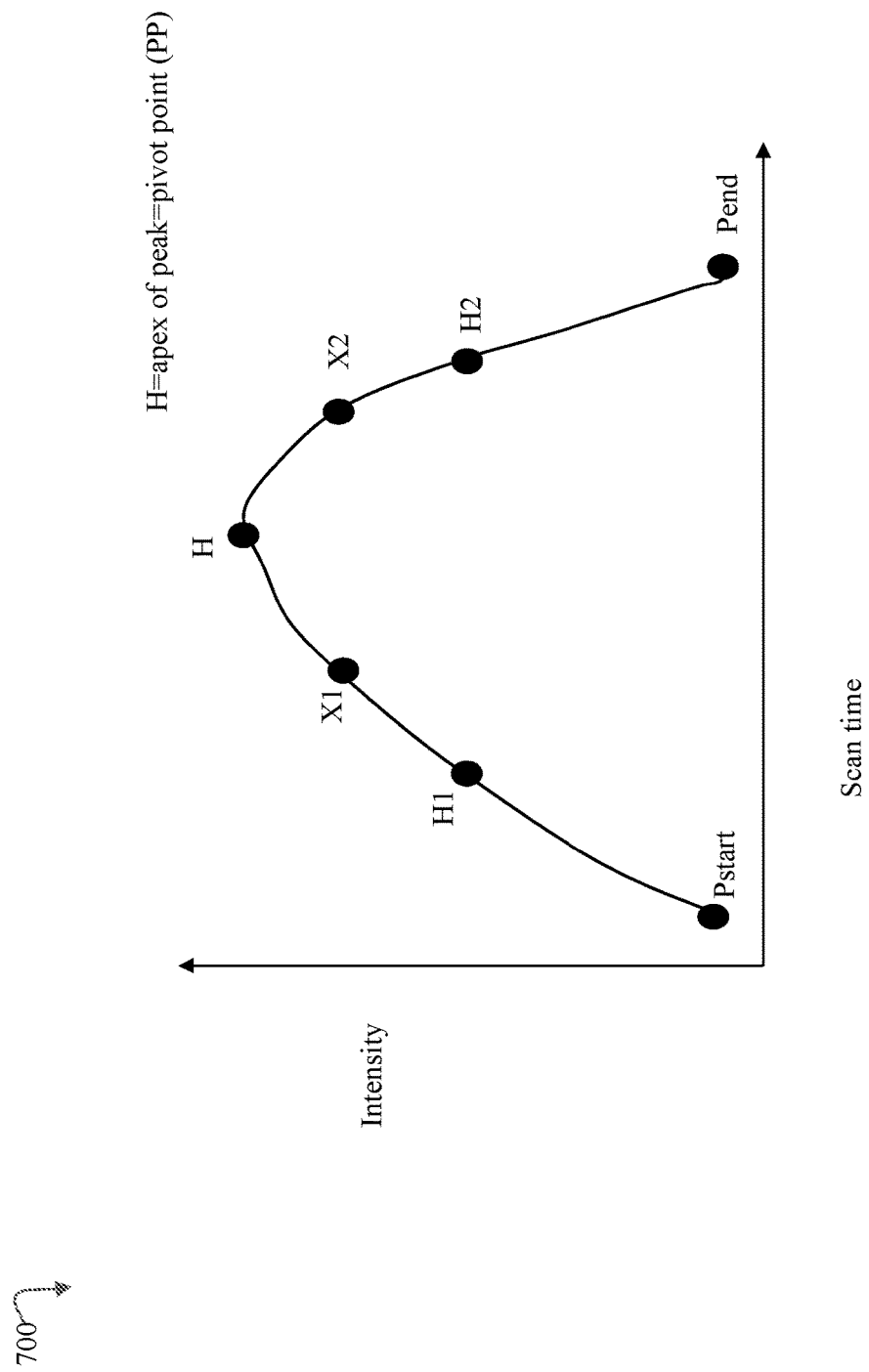
FIG. 7 is an example of an eluting peak of a PCC (precursor charge cluster) that may be detected on a scan-by-scan basis in an embodiment in accordance with techniques herein.

With reference back to FIG. 3, the PCC formation module 312 of the DP Engine 310 may perform processing of the LE scan data set 302 on a scan by scan basis to determine a set of PCCs for each scan time. Each PCC in a single scan has an associated m/z (typically $A_0$ monoisotope), charge state z and intensity as described elsewhere herein. The same PCC, as identified using its associated m/z, is then tracked by the LC peak detection module 314 through a series of successive scans. For each scan, the intensity of the PCC is also tracked. The result of the foregoing tracking should form a peak response of intensity values in different successive scans for the PCC, thereby denoting an intensity envelope of an eluting chromatographic peak for the single PCC. Thus, a single PCC is tracked across successive scans to determine the elution peak from the PCC such as illustrated in FIG. 7. It should be noted that the resulting tracking for a single PCC such as illustrated by FIG. 7 may be performed for each tracked PCC.

Referring to FIG. 7, shown is a graphical illustration of an LC peak determined for a single PCC in an embodiment in accordance with techniques herein. As part of peak detection, processing is performed to ensure that the intensity increases in successive scans from points Pstart to H and then decreases in successive scans from points H to Pend. Pstart denotes the first scan of the peak or when the m/z of the PCC may be initially detected. H denotes the apex of the peak where the detected intensity associated with the m/z of the PCC is at a maximum. H may also be referred to as the pivot point (PP). Pend denotes the last or ending scan of the peak or when the m/z of the PCC is no longer detected.

Within a single scan there is a relationship between the intensity of a precursor ion and its product ions where such a relationship is part of the fragmentation pattern of the precursor and its product ions. In an embodiment in accordance with techniques herein, an AR2 (area ratio 2) metric denoting a PCC or precursor ion ratio of the same precursor ion or PCC in different scans may be determined and used in connection with determining matching or associated fragment ions generated from the PCC. When an SSPPIS is initially formed, each product ion is assigned an AR1 value, where AR1 (area ratio 1) is equal to the intensity of the product ion divided by the intensity of the precursor. Provided a consistent collision energy is applied across the scans during the precursor's elution, the AR1 values for each scan member of the elution profile should be consistent within some experimental error.

Between scans, the intensity ratio of a particular PCC from scan t1=X intensity and scan t2=Y intensity results in a ratio X/Y. Fragments associated with the same PCC in the same scans t1 and t2 must behave the same way by having similar intensity ratios within some specified tolerance. If the PCC's intensity increases between scans t1 and t2, so must its associated fragment ions. If the PCC's intensity decreases between scans t1 and t2, so must its associated fragment ions. Thus, the foregoing intensity ratios of a PCC may be used to differentiate or distinguish and properly associate fragments from different PCCs or precursor ions.

In an embodiment in accordance with techniques herein, an AR2 (area ratio 2) metric denoting a PCC or precursor ion ratio of the same precursor ion or PCC between any scan and its corresponding apex scan may be determined and used in connection with determining matching or associated fragment ions generated from the same PCC. The product ions of any scan must reflect an AR2 ratio with their corresponding ions from the apex scan as that of their PCC AR2 ratio, if they are related to the same PCC. As described below, AR2 ratios or metrics for a PCC and each of its product ions may be determined generally for each scan or points on the LC peak curve. The FWHM points at scans H1 and H2 of FIG. 7 are two such points.

To summarize, for a single PCC, processing may be performed in a first step to track a particular PCC through different scans in order to perform peak determination such as illustrated in FIG. 7. As a second step, the scan of the detected peak with the largest or maximum intensity for a particular PCC may be identified and denoted as the apex or pivot point scan from which the AR2 metric is calculated.

As a third step, the two FWHM points, H1 and H2, may be determined. In the third step, points or scans corresponding to half the height of the maximum intensity (e.g., intensity of the apex point H) on both the left hand side (LHS or up slope) of the peak and right hand side (RHS or down slope) of the peak are identified. For example, such processing determines point H1 to the left of H and point H2 to the right of H at which the intensity is ½ the maximum (or ½ the intensity at PP or point H). For example, the peak or maximum intensity IMAX may be at scan 1008 and the intensity may be IMAX/2 at scans 1004 H1 (to left of PP) and H2 1012 (to right of PP). Thus, H1 denotes scan of half height on LHS of the peak, and H2 denotes the scan of half height on the RHS of the peak.

Define the upslope ratio U and downslope ratio D for the PCC illustrated in FIG. 7 as follows:

Upslope ratio $U = H1$ intensity/$H$ intensity    EQUATION 1 and

Downslope ratio $D = H2$ intensity/$H$ intensity    EQUATION 2 where
H is the maximum intensity of the PCC at the identified peak pivot scan;
H1 is the intensity of the PCC in the identified scan denoted by point H1; and
H2 is the intensity of the PCC in the identified scan denoted by point H2.

It should be noted that both the upslope ratio U and downslope ratio D for the two FWHM points H1 and H2 will always result in a PCC intensity ratio of approximately ½ via the definition of FWHM. EQUATIONS 1 and 2 above represent a customized form of the AR2 ratio for the particular points or scans, respectively, H1 and H2.

Generally, an AR2 ratio for a PCC and each of its product ions may be determined for each scan or point on the peak or curve. The FWHM points for scans H1 and H2 are examples of two such points. Thus, the AR2 ratio may be determined for both a PCC and its product ion intensities from the scan at point H (e.g., the PP or apex) and generally between any other scan $S_x$ on the peak or curve:

$AR2_P = \text{Int}(\text{scan } S_x, PCC)/\text{Int}(\text{scan } PP, PCC)$    EQUATION 3a $AR2_F = \text{Int}(\text{scan } S_x, F_x)/\text{Int}(\text{scan } PP, F_x)$    EQUATION 3b for AR2
where
Int (scan $S_x$, PCC) is the intensity of the PCC in some scan $S_x$ denoting another scan besides the PP or H scan; and
Int (scan PP, PCC) is the intensity of the precursor ion in scan H (e.g., at the PP or apex of the peak) where the PCC's intensity is at its maximum or apex in the detected peak; and
Int (scan $S_x$, $F_x$) is the intensity of a particular fragment ion $F_x$ with m/$z_x$ belonging to PCC in scan $S_x$; and
Int (scan PP, $F_x$) is the intensity of a particular fragment ion $F_x$ with m/$z_x$ belonging to PCC in scan H or at the PP; and
the value of $AR2_F$ reflects a similar value of $AR2_P$ in the same scan Sx within a given tolerance if the fragment ion $F_x$ is truly related to PCC.

In an embodiment described herein, the AR2 values for the PCC (based on EQUATION 3a) may be determined first for the FWHM points in scans H1 and H2 as follows:

$$AR2 = \text{UPSLOPE RATIO } U = \text{DOWNSLOPE RATIO } D$$
$$= \text{Int}(H1, PCC)/\text{Int}(H, PCC) = \text{Int}(H2, PCC)/\text{Int}(H, PCC)$$

where
Int (H, PCC) is the intensity of PCC in scan H where the precursor's intensity is at its maximum or apex in the detected peak;
Int (H1, PCC) is the intensity of PCC in scan H1 where the PCC's intensity is at FWHM on the upslope or LHS of the peak; and
Int (H2, PCC) is the intensity of PCC in scan H2 where the PCC's intensity is at FWHM on the downslope or RHS of the peak.

By the definition of FWHM, AR2 for the PCC for the FWHM scans will always be ½, within some expected tolerance.

In a fourth step, processing may be performed to examine the fragment or elevated energy scan data for scans H, H1 and H2 and determine matching fragment ions for the PCC between scans by matching mass or m/z for a particular fragment between scans and matching an intensity ratio (IR) for the fragment with that of the AR2 value of the PCC (as determined using EQUATION 3a). It should be noted that the IR for the fragment in the following is the AR2 value for the fragment ion $AR_F$ as denoted by EQUATION 3b.

To further illustrate, processing may be performed to determine a first set of matching fragments between scans H and H1 and also determine a second set of matching fragments between scans H and H2. For example, fragment F1 in scan H is determined to match fragment F1" in scan H1 if:

mass or m/z of F1 matches mass or m/z of F1" within some specified mass tolerance; and
the intensity ratio IR calculated as:

$$IR = \text{intensity of } F1" \text{ in scan } H1/\text{intensity of } F1 \text{ in scan } H$$

matches AR2 (of the associated PCC with respect to the same scans H and H1) within some specified tolerance. For example, assume scan H1 is at scan time 1004 where fragment ion F1 exists with mass m1 and intensity 5,000, and where fragment ion F2 exists with mass m2 with intensity 5,000. Assume scan H is at scan time 1008 where fragment ion F1 exists with mass m1 and intensity 10,000, and where fragment ion F2 exists with mass m2 and intensity 6,000. Assume further for this example that scan H2 is at scan time 1012 where fragment ion F2 exists with mass m2 and intensity 3,000.

Then, based on the foregoing, for fragment ion F1 in scans H and H1, IR=5,000/10,000=½, which matches the AR2 value of ½ for the PCC. Thus, F1 is included in the first set of matching fragments for the PCC.

For F2 in scans H and H1, IR=5,000/6,000=0.83 which does not match the AR2 value of ½ for the PCC. Thus, F2 is not included in the first set of matching fragments for the PCC.

For F2 in scans H and H2, IR=3,000/6,000=½, which does match the AR2 value of ½ for the PCC. Thus, F2 is included in the second set of matching fragments for the PCC.

Thus, an AR2 value may be determined for each scan in the detected peak for the PCC (e.g., each scan other than scan H) and included in validation criteria used in filtering or validation to determine a set of matching or associated fragment ions for the PCC. Thus, there is an AR2 value for the PCC for each scan point relative to the peak. For example, if there are 12 points or scans in the detected peak for the PCC, then there will be 11 AR2 values for the PCC (since 1 of the 12 points is the apex of the peak or PP).

It should be noted that the metric denoted as IR above may be more generally characterized as in EQUATION 3b and referred to herein as another AR2 value determined with respect to the intensity or area ratio of the fragment ion (rather than the PCC) in the same two scans as the PCC. As noted above and elsewhere herein, the AR2 value determined for the PCC with respect to two different scan times and the AR2 value determined for a fragment ion F in the same two scan times as the PCC should be the same, within some specified tolerance, if F is associated with or produced via fragmentation of the PCC.

In instances where a PCC is interfered in a given scan such that its intensity is not following the LC peak, the intensity of the near-neighboring scan is a linear regression interpolation, and if the intensity of the PCC at the outlying scan is higher when the upslope and down slope is compared with the apex scan, the two AR1 and AR2 values should be consistent, given a Gaussian peak shape. As such, when comparing any near-neighbor scans, when calculating the AR2 values between the apex and any other scan, the intensity of the PCC is validated in a first instance by performing a linear regression and interpolation about the near neighboring scans.

In one embodiment, processing may be performed to determine the number of matching fragments for scans H1 and H2 in accordance with AR2 values for such scans as described above. Then validation processing may be performed for the first matching fragment set determined for scan H1 and the second matching fragment set determined for scan H2. Such validation processing may include using one or more additional validation criteria such as using other criteria including other metrics (such as the AR1 (area ratio 1) metric, and other criteria described in more detail below. For example, such validation processing may include determining whether the number of matching fragments in the set is at least a specified minimum number (e.g., see FIG. 8 and associated processing described elsewhere herein). If validation processing is successful in validating the matching fragment sets determined for points or scans H1 and H2, then processing may continue for other scans or points on the curve. Otherwise, if validation processing fails for H1 and/or H2, then an alternative technique may be used to determine fragment ions associated with a particular PCC.

In one embodiment, processing may further proceed with determining a number of matching fragments for scans at midway points between H1 and H (as denoted by point X1 on FIG. 7) and then midway between scans H and H2 (as denoted by point X2 of FIG. 7). For each scan at points X1 and X2, processing may be performed similar to that as described above and elsewhere herein in connection with each scan at points H1 and H2. For, example, for each scan denoted by X1 and X2, determine an AR2 (area ratio 2) value, determine a matching fragment set for the scan, and then determine whether the matching fragment set passes any further validation criteria (e.g., AR1, and other criteria described herein). Such validation criteria may include having the matching fragment set include a minimum number of fragments. Additionally, the criteria may also include comparing the number of detected fragments for the scan relative to one or more other scans. For example, it is expected that as the intensity of the PCC increases from scan S1 to scan S2, the number of detected fragments similarly increases whereby the number of detected fragments in scan S1<number of detected fragments in scan S2. Such criteria may also include examining the intensity of a fragment in the scans S1 and S2 whereby the intensity of fragment F1 in scan S1 should similarly be less than F1's intensity in scan F2.

Such processing may be iterated by repeatedly determining a next scan point located between two other consecutive scan points that have been processed until all such points of the peak of the PCC have been processed. Thus it should be noted that the repeated processing of midway scan points are performed for scans in the upper portion of the peak or curve for the PCC (e.g., upper portion including scan points from H1 to H2, inclusively) and also for scans in the lower portions of the peak or curve for the PCC (e.g., scans from points Pstart to H1 and scans from H2 to Pend). In one embodiment, if validation processing fails to validate a set of fragments determined for a scan in the lower portions of the peak below the FWHM points H1 and H2, the set of fragments of the scan failing validation processing may be excluded and processing may continue with any remaining scans in the lower portions of the peak for the PCC.

What will now be described is another metric, the AR1 (area ratio 1) metric that may also be included in validation criteria used in validating or filtering fragment ions in connection with determining what fragment ions are associated with each PCC.

For each scan Sj, each product or fragment ion Fi in scan Sj has an AR1 (Area ratio 1) value that may be expressed as:

$$AR1 = \text{intensity of } Fi \text{ in scan } Sj/\text{intensity of PCC in scan } Sj$$

For example, in scan S1, suppose there are fragments F1 with intensity X, F2 with intensity Y, and PCC P1 with intensity Z. There are 2 AR1 values for scan S1 where a first AR1 value is X/Z and second AR1 value is Y/Z.

Processing in an embodiment in accordance with techniques herein may validate AR2 values using AR1 values. For each matched fragment Fi determined using AR2 and which passes validation processing as described above, further validation processing may now be performed using AR1 values for the particular fragment Fi. Such further validation processing performed using AR1 for Fi may compare AR1 values for scans 1 through N (in the peak) for a fragment F1. If all such AR1 values are not the same, within some tolerance, then fragment F1 is not matched with PCC P1 (whose intensity is used in computing the foregoing AR1 and AR2 values).

Validation criteria used to validate scan data and associated fragment ions for a particular PCC may further include another metric based on fragmentation efficiency that will now be described.

Generally, in a well performed experiment, it is desirable to not over fragment precursor ions by operating with excessive collision energy. This results in a portion of the unfragmented PCC or precursor ion P1 having mass M1 appear in the elevated energy or fragment ion spectra for each scan. Techniques herein may determine:
1. whether P1 appears in the fragment ion or EE scan data of a scan S1 and, if so,
2. determining the intensity of P1 in the EE scan data for scan S1.

Assume it has been determined that PCC or precursor P1 is associated with product or fragment ions F1 and F2 for scan S1. For scan S1, P1 has intensity X1 in the LE or precursor scan and intensity X2 in the EE fragment ion scan. The following relationship R1 may be included in the validation criteria and must evaluate to true in order for data of a particular scan S1 to be valid.

Relationship R1: The intensity difference $X1-X2$>sum of the intensities of all fragment or product ions in the EE scan data for scan $S1$ The foregoing relationship R1 includes "X1-X2" on the left hand side (LHS). If X1 denotes the starting intensity or amount of P1 in the LE data prior to fragmentation and X2 denotes the remaining intensity or amount of P1 after fragmentation, then the expression X1-X2 represents the maximum or an upper bound on the total intensity or amount of P1 that may appear as fragmented ions in the EE scan data. The right hand side (RHS) of R1 is the actual calculated sum of the intensities of all fragment or product ions in the EE scan data for scan S1, thereby denoted the sum of intensities of all observable fragment ions in the EE scan data. The RHS of R1 should be less than the maximum or upper bound denoted by the LHS of R1.

In an embodiment in accordance with techniques herein, validation criteria may also include examining the number of fragment ions determined for each scan as matching or being associated with a PCC. With reference to FIG. 7, it may be generally expected that the number of fragment ions that should be matched increases as the scan time for points between Pstart and H increases (e.g., moves upward from Pstart to the apex of the peak). Additionally, for points P1 and P2 in the inclusive range of Pstart and H, where P1 has a scan time<another scan time associated with point P2, it is expected that one or more fragment ions included in a first set determined for the point P1 are also included in a second set of one or more fragments determined for point P2. In a similar manner, it may be generally expected that the number of fragment ions that should be matched decreases as the scan time for points between H and Pend increases (e.g., moves downward from the apex of the peak to Pend). Additionally, for points P3 and P4 in the inclusive range of H and Pend, where P3 has a scan time<another scan time associated with point P4, it is expected that one or more fragment ions included in a first set determined for the point P4 are also included in a second set of one or more fragments determined for point P3.

As noted above, the expected number of fragments obtained as a result of fragmentation for a particular PCC may vary with the particular PCC and may depend on the complexity and intensity of the PCC. Similarly, the number of matched fragments or fragments in the scan determined as being associated with the PCC or precursor ion may depend on the complexity and intensity of the PCC or precursor ion. In one embodiment, the minimum number of matched fragments for a particular PCC expected in a scan may be determined based on criteria including the intensity of the PCC in the LE scan and also an attribute of the PCC related to (e.g., denoting) the complexity of the PCC. In one embodiment the attribute denoting the PCC complexity in a scan may be the molecular weight Mr (chargeless mass based on elemental composition of molecule). As a variation, an embodiment may vary the attribute used denoting the PCC complexity with the molecule. For example, for simple or small molecules, the molecular weight Mr (chargeless mass based on elemental composition of molecule) may be used. For peptides, or more complex molecules, rather than Mr, the length of the PCC may be estimated. The length of the PCC or precursor ion may vary with its complexity. For example, for complex molecules such as for peptides, the PCC in a scan T1 is a chain of amino acids and the length determined may be the length of the amino acid chain.

Figure 8:
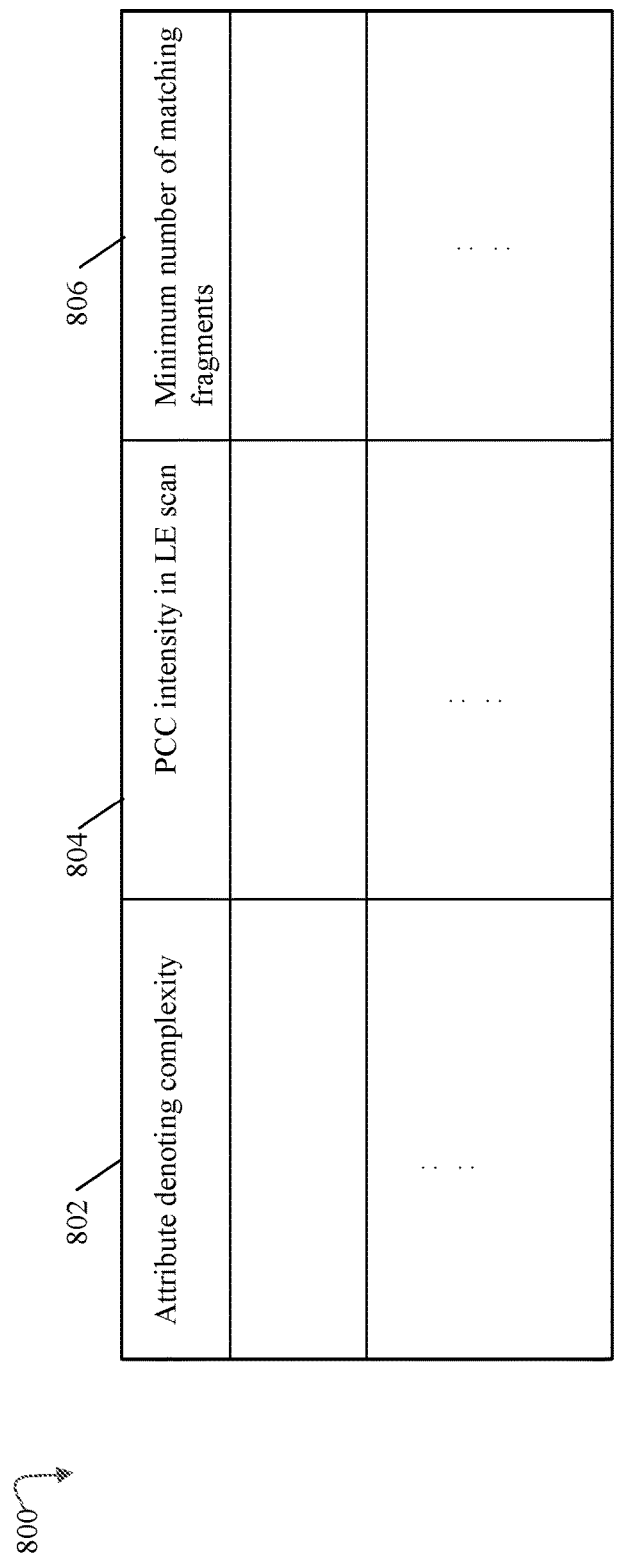
FIG. 8 is a table of information that may be used in an embodiment in accordance with techniques herein.

Thus generally, the minimum number of fragment ions that need to be matched or associated with a PCC in a scan S1 may be expressed as a function G having a value determined in accordance with the complexity C of the PCC and the intensity I of the PCC in the LE scan data of that scan S1 (e.g., for scan S1 and PCC or precursor ion P1, G(C, I)=minimum number of fragment ions to be matched or associated with P1 in scan S1). In one embodiment, the minimum number of fragments may be determined using a table of values, such as illustrated in FIG. 8, including information that may be predetermined based on expert knowledge and best practices of those skilled in the art. Such minimum values may be provided, for example, based on information supplied or determined by manufacturers of different MS instruments.

Referring to FIG. 8, shown is an example of a table that may be used in an embodiment in accordance with techniques herein to determine a minimum number of matching fragments expected for a PCC or precursor ion. The table 800 may include a column 802 of values of an attribute denoting complexity of the PCC or precursor ion, column 804 of values denoting different intensities of the PCC or precursor ion in the LE scan, and column 806 identifying minimum numbers of matching fragments. Thus a row of the table 800 identifies a minimum number of matching fragments expected for a particular combination of values in columns 802 and 804 in the same row. In one embodiment, the attribute denoting the complexity in column 802 may be any suitable attribute, some examples of which are noted above; for example, such as molecular weight Mr, the length of the amino acid chain such as for complex molecules, and the like.

A table as illustrated in FIG. 8 may be utilized to specify a minimum number of matching fragment ions expected for a PCC at a particular scan time to remove gross errors where there is a large amount of interference. In one embodiment, the minimum numbers specified in the table may be based, for example, on a fragmentation efficiency in the range of 50-60% (e.g., where fragmentation efficiency may be determined empirically based on the relationship R1 described elsewhere herein).

In one embodiment, use of the table such as illustrated in FIG. 8 may be performed as a last step in connection with validation criteria and validation processing with respect to a set of fragment ions determined as matching or being associated with a particular PCC for a particular scan in the curve or peak detected for the PCC (e.g., such as illustrated in FIG. 7).

In one embodiment in accordance with techniques herein, for a particular PCC for which matching fragment ions are being determined in the various scan times, if the validation criteria are not met for all scan times included in the top half of the peak for the PCC (e.g., from FWHM on LHS (H1 scan) to FWHM on RHS (H2 scan), then no further processing of other scan points on the curve or peak may be performed. For example, if validation criteria of AR1, AR2 and the minimum number of matching fragment ions are not met for a scan in the top half of the peak or curve for the PCC, then an embodiment may use an alternative technique. Such processing to determine matching fragments for scans in the top half of the peak or curve may be terminated upon the first occurrence of any scan point in the top half to fail validation processing (e.g., does not pass AR1, AR2, min number of matching fragments, and the like for validation criteria used in an embodiment). If validation failure occurs for any scan time in the top half of the curve or peak, then an alternative technique may be utilized to determine fragment ions matching a particular PCC. If validation failure occurs for a scan in the lower portions of the peak or curve for the PCC (e.g., scans from points Pstart to H1 and scans from H2 to Pend, processing may continue with other remaining scans in the lower portion whereby any data or fragments determined for the particular failed scan are excluded.

An embodiment in accordance with techniques herein may also use another metric AR3 (area ratio 3) that may be determined for each fragment or product ion associated with a particular molecule or component. AR3 for a fragment Fi may be expressed as:

AR3=fragment $Fi$(intensity)/SUM of the intensities of all fragments matched to the PCC where Fi (intensity) is the intensity of the fragment Fi associated with the PCC; and "SUM of the intensities of all fragments matched to the PCC" denotes the mathematical summation of the intensities of all fragments matched to the PCC.

In one embodiment, AR3 may be determined on a per scan or scan time basis (e.g., in a manner similar to that as described herein for AR1 values) for each fragment ion determined as matched or associated with a particular PCC. Validation processing performed using AR3 values for fragment ion F1 may compare AR3 values for scans 1 through N (across the peak for a particular PCC) for the fragment ion F i. If all such AR3 values are not the same, within some tolerance, then fragment F1 is not matched with that particular PCC (whereby the fragment ions summed as the denominator of A3 for a scan are all those determined as associated with or matched to the PCC in the scan).

Thus at this point in non-supervised clustering, for each PCC having a detected peak or curve such as illustrated in FIG. 7, a set of zero or more fragments may be determined for each scan across the PCC's peak. Using validation criteria such as described herein, each such set of fragment ions may be further filtered or refined. In some cases where the validation criteria and associated processing fails to be met for a particular fragment ion set at a particular scan time, the fragment ion set may be discarded or not further considered (e.g., such as where the scan time is in the lower portion of the peak as described elsewhere herein) and processing may continue with other fragment sets from other scan times. In some cases where the validation criteria and associated processing fails to be met for a particular fragment ion set at a particular scan time (e.g., such as where the scan time is in the upper portion of the peak between points H1 and H2 as described elsewhere herein), processing using the validation criteria may cease to evaluate other fragment sets from other scan times across the peak using the validation criteria and may use an alternative technique to determine which fragment ions are associated with the PCC.

Assume processing as described above using validation criteria results in determining multiple sets of fragments for the different scan times of the detected peak for a PCC. At this point, processing may be performed to form the SSPPIS for the PCC. Such processing may include combining the multiple sets of fragments across the scan times of the PCC's eluting peak into a single fragment set associated with the PCC, thereby denoting the sets of fragments associated with or generated by fragmentation or disassociation from the PCC. In one embodiment, the multiple sets of fragments for scan times of the detected peak of the PCC may be combined into a single set as a set union of all such multiple sets, whereby the combined single set of fragment ions and the PCC may form the SSPPIS for the PCC.

As part of combining multiple sets of fragments across the scan times of the detected peak of the PCC in forming the SSPPIS for the PCC, the values for the different metrics, such as AR1, AR2, AR3 and any others that may be used in an embodiment may be combined. In one embodiment, averages may be determined for AR1, AR2 and the like. For example, if there are 12 points or scan times across the peak for the PCC and 12 associated AR2 values (one for each of the 12 points), an average AR2 value may be determined for the PCC as an average of all such 12 AR2 values. A fragment ion F1 may appear in fragment ion sets of 8 of the 12 scan times, and this F1 has 8 AR1 values (one for each of the 8 scan times), and average AR1 value may be determined for F1 as an average of all such AR1 values. Similarly, averages may be determined for other area or intensity ratio metrics described herein (e.g., AR2 for a fragment ion). Averages may also be obtained with respect to one or more other attributes associated with the PCC and/or fragment ions associated with the PCC (e.g., included in the single fragment ion set matched to the PCC). For example, in one embodiment, the m/z of a fragment ion may be the average m/z value for the fragment ion (e.g., average m/z with respect to EE scan data for all scan times in which the fragment ion appears). As a variation, an embodiment may use the m/z value for the fragment ion as occurring at the scan time of the apex or point H of the peak.

At this point in the processing, a single set of fragments may be associated with or matched to each PCC whereby an SSPPIS has been created for each PCC. For example, with reference to FIG. 6, processing has determined that fragment set 614*a* is associated with PCC1 610, fragment set 614*b* is associated with PCC2, and that fragment set 614*c* is associated with PCC3. Processing may then be performed to further group or combine PCCs (and associated or matched fragment ions, and thus group such SSPPISs) which are associated with a particular eluting component or molecule. For example, processing may be performed to select and group the 3 SSPISs for the particular 3 PCCs 610*a-c* thereby denoting that these 3 PCCs originate from the same eluting component or molecule, such as P1 602. Thus, the aggregate result of grouping the 3 PCCs 610*a-c* and their associated fragment ion sets 614*a-c* (along with attributes associated with the foregoing) is information included in the fingerprint or pattern for the eluting component or molecule. The foregoing aggregate result including information of the fingerprint of a single eluting component or molecule may also be referred to herein as a CPPIS (Composite Precursor-Product Ion Spectrum).

The particular SSPPISs to be combined into a CPPIS may be determined as a matched set using any suitable technique. For example, an embodiment may determine the 3 SSPPISs for the 3 PCCs 610*a-c* as a matched set to be combined by matching the same relative molecular weight Mr of the PCC (within a specified tolerance) in each scan time of each detected peak of each of the SSPISs. Additionally, processing may ensure that each detected peak for the PCC in each SSPPIS of the matched set has a similar peak shape and profile where each peak appears in approximately the same scan time window (within some specified tolerance). Processing to validate which product ions of each SSPPIS in the matched set should be combined may further include using m/z, AR1, and AR2 within and between SSPPISs. Thus, the AR2 values for the precursors are expected to follow the Gaussian. Thus, SSPPISs may be excluded from the matched set if their m/z, AR1, and AR2 values are not consistent (within some tolerance).

In one embodiment, the fragment ion sets from each SSPPIS of the matched set may be combined, such as with a set union operation, to form the CPPIS fragment ion set for the eluting molecule or component. For example, with reference to FIG. 6, the CPPIS fragment ion set may be determined as the set union of fragments in 614*a-c*. As an alternative, processing may further include performing additional validation processing that may further filter or reduce the fragment ions included in the CPPIS fragment ion set determined as the set union of fragments in 614*a-c*.

In connection with performing such aggregation of SSPPISs for a single eluting component or molecule in the creation of a CPPIS, it should be noted that associated attributes (including metrics such as m/z, AR1, AR3 and the like) as well as a measurement for the PCC and its associated fragment ions may also be combined. In one embodiment, the error indicators for AR1 and AR3 may also be their associated CV.

As known in the art, the coefficient of variations or CV relating to a metric such as AR1 or AR3 may be defined as the ratio of the standard deviation $\sigma$ to the mean $\mu$ expressed as:

$$C_v = \frac{\sigma}{\mu} \qquad \text{CV Equation}$$

CV illustrates the extent of variability in relation to the mean of the population. Thus for example, CV with respect to AR1 for a fragment ion F1 may be used to denote the error or level of consistency associated with the intensity of F1 across the peak of a PCC, or with respect to all PCCs or SSPPISs associated with an eluting component or molecule.

Figure 9:
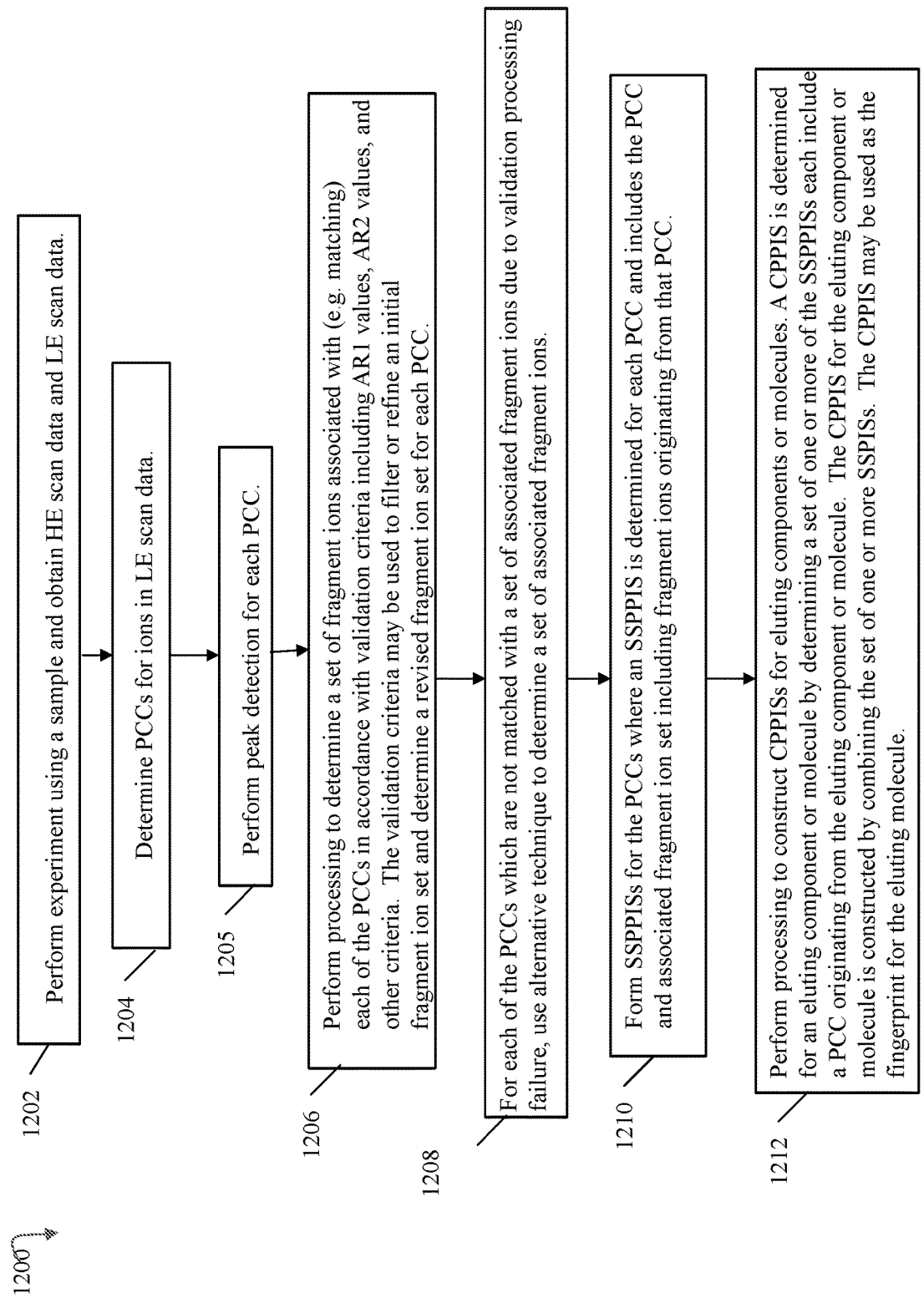
FIGS. 9, 10, 11, 13, 14, 14A, 17, 20, 24, 27, 28 and 33B are flowcharts of processing steps that may be performed in an embodiment in accordance with techniques herein.

Referring to FIG. 9, shown is a flowchart of processing, summarizing what may be performed in an embodiment in accordance with techniques herein for non-supervised clustering. The flowchart 1200 summarizes processing described above. At step 1202, an experiment may be performed using a sample to obtain HE scan data and LE scan data. The sample may include one or more eluting components or molecules. At step 1204, processing may be performed to determine PCCs for ions in the LE scan data. At step 1205, peak detection may be performed for each PCC. At step 1206, processing may be performed to determine, for each of the PCCs, a set of fragment ions associated with (e.g. matching) the PCC in accordance with validation criteria including AR1 values, AR2 values, and other criteria. The validation criteria may be used to filter or refine an initial fragment ion set and determine a revised fragment ion set for each PCC. At step 1208, for each of the PCCs that are not matched with a set of associated fragment ions due to validation processing failure, alternative techniques may be used to determine a set of associated fragment ions. At step 1210, processing may be performed to form SSPPISs for the PCCs where an SSPPIS is determined for each PCC and includes the PCC and associated fragment ion set of fragment ions originating from that PCC. At step 1212, processing may be performed to construct CPPISs for eluting components or molecules. A CPPIS is determined for each eluting component or molecule by determining a set of one or more of the SSPPISs, each includes a PCC originating from the eluting component or molecule. The CPPIS for the eluting component or molecule is constructed by combining the set of one or more SSPISs. The CPPIS may be used as the fingerprint for the eluting molecule.

In connection with FIG. 9, processing consistent with a description elsewhere herein, an SSPPIS may be created for each PCC in each LE single scan, with product ions obtained from the companion EE scan. The product ions in the companion EE scan are shared with each single PCC (though filtered by intensity and m/z relative to their parent precursor) creating a unique SSPPIS.

Figure 10:
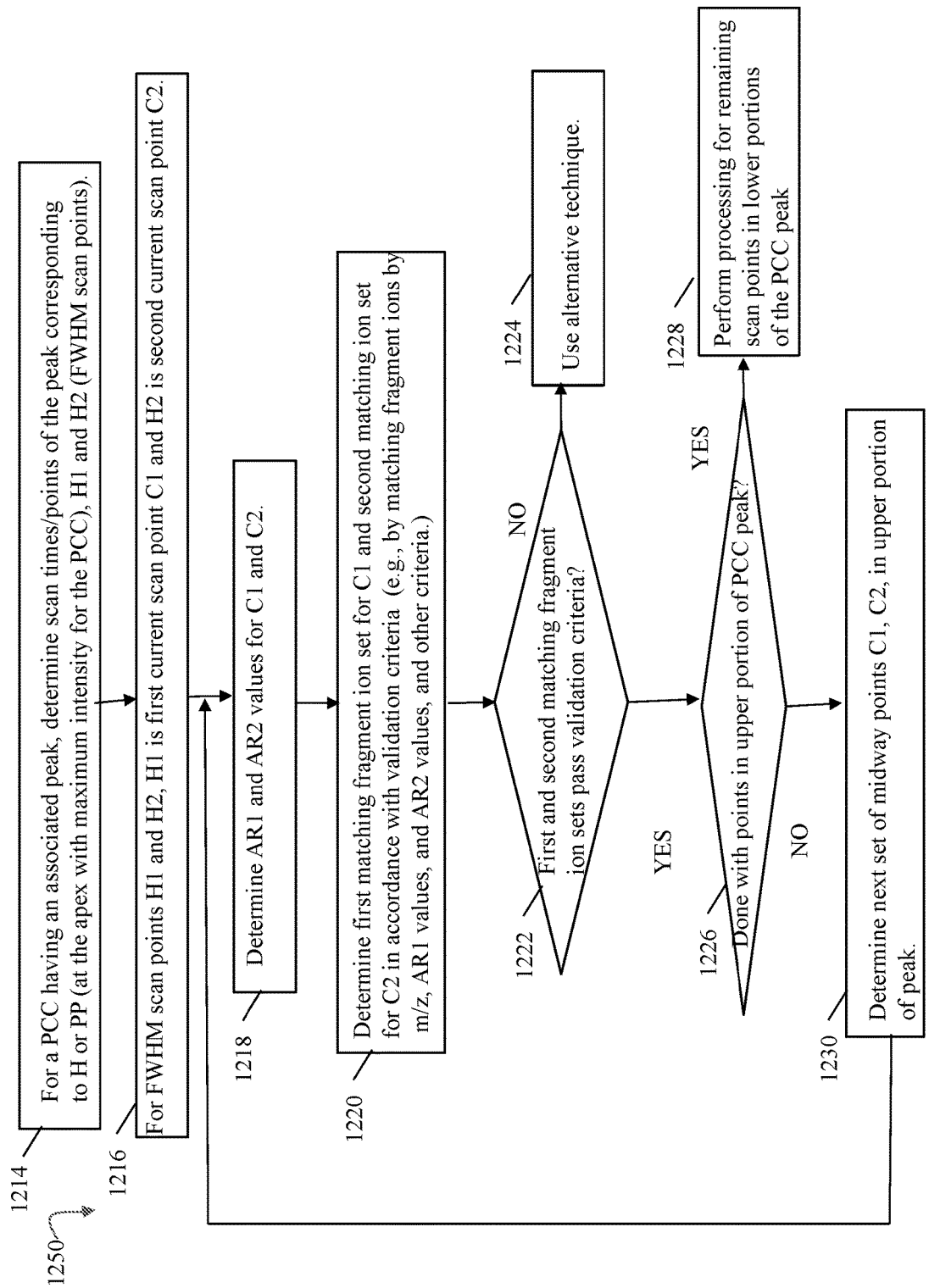

Referring to FIG. 10, shown is a flowchart 1250 providing additional detail of processing that may be performed in step 1206 (e.g., determine set of fragment ions associated with each of the PCCs) of FIG. 9 in an embodiment in accordance with techniques herein. The flowchart 1250 may be performed for each PCC. At step 1214, for a PCC having an associated peak, determine scan times/points of the peak corresponding to H or PP (at the apex with maximum intensity for the PCC), H1 and H2 (FWHM scan points). At step 1216, for the FWHM scan points H1 and H2, H1 is the first current scan point C1 and H2 is the second current scan point C2. At step 1218, AR1 and AR2 values are determined for C1 and C2. At step 1220, processing is performed to determine a first matching fragment ion set for C1 and a second matching fragment ion set for C2 in accordance with validation criteria (e.g., by matching fragment ions by m/z, AR1 values, and AR2 values, and other criteria). At step 1222, a determination is made as to whether the first and second matching fragment ion sets passed the validation criteria. If not, processing proceeds to step 1224 where an alternative technique may be used to determine fragment ion sets for the PCCs. If step 1222 evaluates to yes, control proceeds to step 1226 where a determination is made as to whether processing is complete for all points in the upper portion of the PCC peak. If step 1226 evaluates to yes, control proceeds to step 1228 to perform processing for remaining scan points in the lower portions of the PCC peak (e.g., scan points from Pstart to H1 and from H2 to Pend), with respect to matching SSPPISs in the lower portions H1 to pStart and H2 to Pend, a further filtering is accomplished in that only the more abundant matching product ions in SSPPIS from scan H will match with consistent AR1 and AR2 ratios.

If step 1226 evaluates to no, control proceeds to step 1230 to determine the next set of midway points C1 and C2 in the upper portion of the peak (e.g., next set of scan points in the upper portion from scans H1 to H2). As described herein, each next set of midway points may be determined by halving the scanning time or distance between H and the current points C1, C2 or between Pstart and C1 and C2 and Pend. From step 1230, control proceeds to 1218 to process the next set of scan points.

Figure 11:
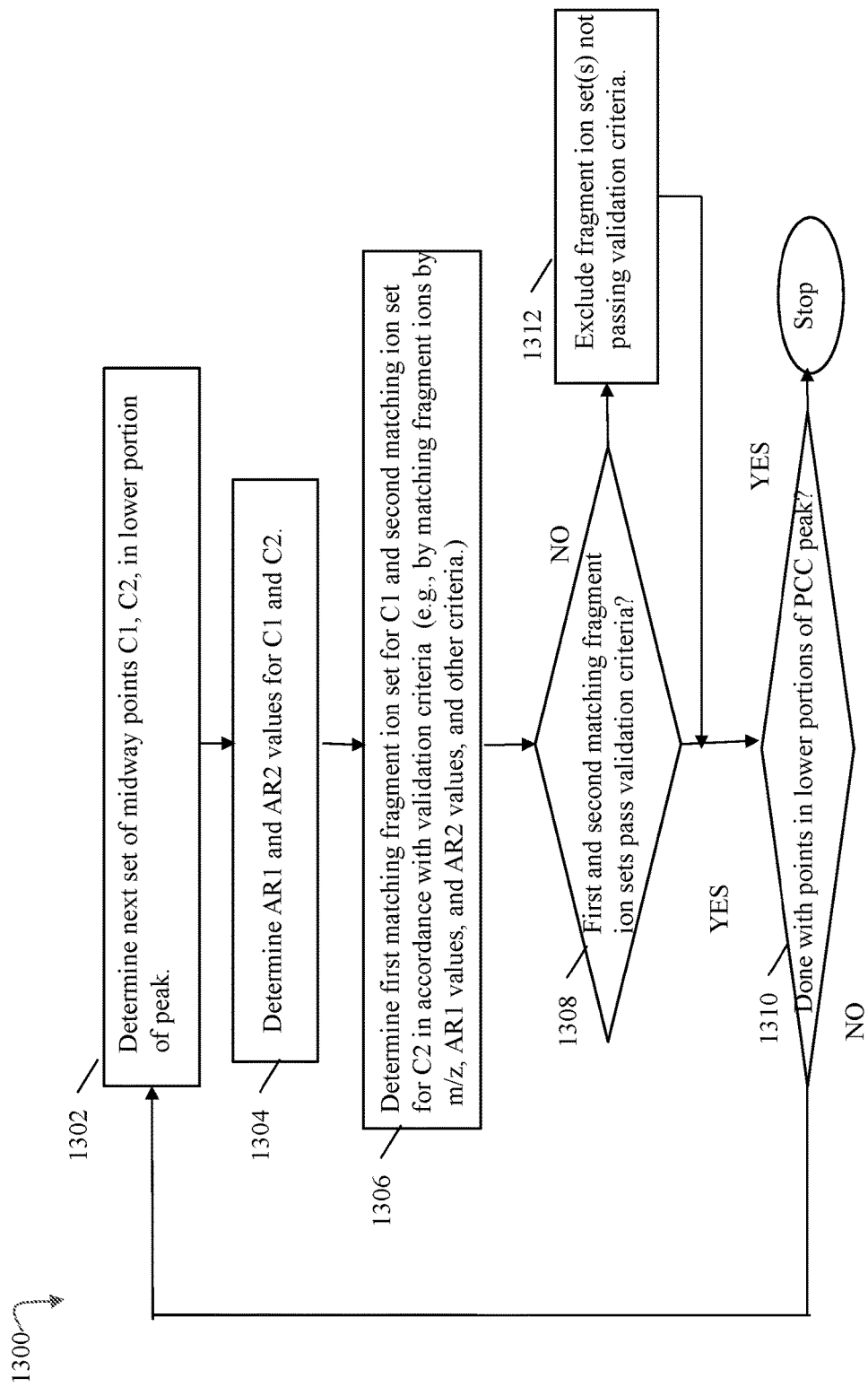

Referring to FIG. 11, shown is a flowchart of processing steps that may be performed in an embodiment in accordance with techniques herein to process the remaining scan points in the lower portions of the PCC peak. The flowchart 1300 provides additional detail of processing that may be performed in step 1228 of FIG. 9 At step 1302, processing may determine the next set of midway points C1, C2 in the lower portions of the peak. Step 1302 is similar to step 1230 of FIG. 10 with the difference that the midway points are located in the lower portions of the PCC peak. At step 1304, AR1 and AR2 values are determined for C1 and C2. Step 1304 is similar to step 1218 of FIG. 10. At step 1306, processing is performed to determine a first matching fragment ion set for C1 and a second matching fragment ion set for C2 in accordance with validation criteria. Step 1306 is similar to step 1220 of FIG. 10. At step 1308, a determination is made as to whether the first and second matching fragment ion sets pass the validation criteria. Step 1308 is similar to step 1222 of FIG. 10. If step 1308 evaluates to no, processing proceeds to step 1312 to exclude the fragment ion set(s) not passing the validation criteria. Control proceeds to step 1310. If step 1308 evaluates to yes, control proceeds directly to step 1310. In step 1310, a determination is made as to whether processing has been performed for all scan points in the lower portions of the PCC peak. If so, processing stops. Otherwise, if step 1310 evaluates to no, control proceeds to step 1302.

Figure 12:
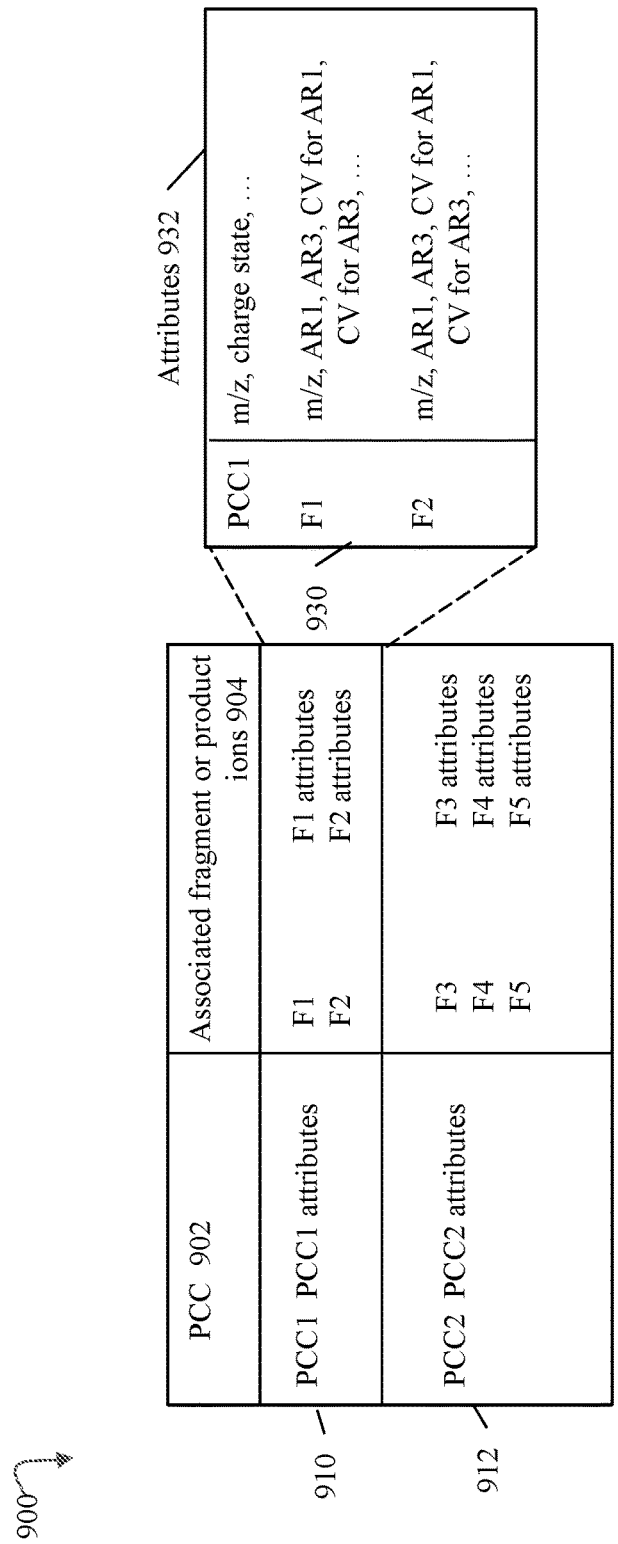
FIG. 12 is an example of information that may be included in a fingerprint of a molecule in an embodiment in accordance with techniques herein.

Referring to FIG. 12, shown is an example of information that may be included in a CPPIS for an eluting component or molecule and used as an identifying fingerprint for the eluting component or molecule in an embodiment in accordance with techniques herein. The example 900 includes a table with a first column PCC 902 and a second column associated fragment or product ions 904. Each row of the table denotes a PCC and its associated or matched fragment ions as may be determined using techniques herein. The example illustrates a molecule having two associated PCCs, PCC1 and PCC2 where PCC1 and its associated fragment ions are included in row 910 and PCC2 and its associated fragment ions are included in row 912. Generally, each row 910, 912 may include information, such as various attributes, for the PCC and its associated fragment ions. To further illustrate, element 930 provides further detail regarding information of row 910 as may be generated and used in an embodiment in accordance with techniques herein. Row 912 may include similar information to that of 930 although not illustrated in the example 900.

As illustrated in element 930, PCC1 may be associated with fragment ions F1 and F2. Attributes for PCC1 includes m/z, and charge state z. Attributes for each fragment F1, F2 may include m/z AR1, AR3, CVs for AR1 and AR3, as well as other attributes as described herein and known in the art. Other attributes as may be stored in an embodiment in accordance with techniques herein for PCCs and fragment ions may include, for example, hydrophobicity value, drift time or collisional cross section area (CCSA) if ion mobility is utilized, and the like.

With individual fragment ions and PCCs and also with each molecule's fingerprint, one or more error values such as CVs illustrated in FIG. 12 may be stored. Described herein, such error values may include CV as a measure of consistency or goodness of the fingerprint data. Generally, for a molecule identified using a pattern or fingerprint of data generated using non-supervised clustering having associated CVs, the greater the consistency such as indicated by one or more associated CVs, the better the resulting data. More generally, other error indicators besides CVs may be used in an embodiment in accordance with techniques herein. For example, rather than CVs, an embodiment may generally use any suitable error indicator or consistency indicator such as standard deviation, variance, and the like.

It should be noted that for each PCC included in FIG. 12, the isotopic pattern or cluster for the PCC may be stored (e.g., such as denoted by 604 of FIG. 6).

An embodiment in accordance with techniques herein may repeat non-supervised clustering multiple times (for same sample or different samples including the same components or molecules) and store collective results of data in a combined form in a library or database. Thus, non-supervised clustering may be performed in an iterative manner with each iteration updating the combined or collective fingerprint results for molecules obtained for all iterations to date. As additional iterations are performed, the CVs or other error indicators associated with the fingerprints of the molecules are also updated to reflect all such iterations performed.

In connection with combining fingerprint information from multiple instance of non-supervised clustering, it should be noted that first fingerprint information for a first molecule may be determined as a match for existing second fingerprint information currently in the library or database based on matching criteria. Such matching criteria may generally include determining matches (within specified tolerances) between one or more attributes including attributes such as m/z, scan/retention times, drift time, and the like, and metrics such as one or more area or intensity ratios (e.g., AR1, AR2, AR3) associated with the PCCs and/or fragments of fingerprints.

Such matching criteria may include, for example, determining whether there are statistically significant number of (relative number of matched product ions to all other CPPIS in the library) matching fragments that match (within tolerances) based on scan times, m/z and AR1, AR3 values, and the like). If such a match is determined, the first fingerprint information may be combined with the existing second fingerprint information. Such combining of CPPISs additionally filters the fingerprint by limiting the fingerprint to only repeating m/z values, updating any associated metrics (e.g., AR1 values, AR3 values, and the like), and error indicators such as CVs. The associated metrics, such as AR1 values maintained in the combined form may be, for example, an average value for the metric. The AR1 value can be utilized to estimate the PCC's intensity value, given the intensity of any matched and validated product ion in the fingerprint.

In connection with combining fingerprint information from multiple instances of non-supervised clustering, it should be noted that first fingerprint information for a new molecule may be added to the library or database as a new fingerprint if the first fingerprint information is determined not to be a match for an existing molecule's fingerprint in accordance with the matching criteria.

At a first point in time, such as after a particular number of non-supervised clustering iterations are performed, additional processing may be performed to evaluate the resulting collective fingerprint data obtained for all molecules. Such evaluation may include examining the CVs or other error indicators associated with the fingerprint data to determine which precursor and/or associated fragments are the "best" or most consistent in identifying a particular molecule.

For example, a first fragment compared between a first PCC and a second PCC may have an AR1 and or an AR2 value that when compared, have an associated CV that indicates a low error (e.g., such as lower than a specified threshold) or high consistency and a second fragment associated with an AR1 value and/or AR2 value with an associated CV that indicates a high error or low consistency (e.g., such as more than a specified threshold). Based on these error indicators, such as CVs of the AR1 and/or AR2 values (first PCC to a second PCC or first CPPIS to a second CPPIS) of the second fragment, it may be determined during the evaluation that the second fragment should be removed from the database and determined as not actually associated with the PCC's SSPPISs or CPPIS due to the high error or unacceptable inconsistency of observed results obtained using non-supervised clustering techniques. Based on the error indicator, such as the CV for the AR1 value of the first fragment such as may be included in a library or CPPIS, it may be determined during the evaluation that repeated performance of non-supervised clustering has confirmed that the first fragment is associated with the PCC due to the low error and consistency of observed results obtained using non-supervised clustering techniques. Thus, as a result of such evaluation, the combined or collective results may be revised or updated such as, for example, to remove and/or add one or more particular fragments of a fingerprint associated with a molecule based on the evaluation. Such evaluation may also determine whether a PCC of a fingerprint should remain or be removed from the fingerprint using an error indicator, such as the CV for the AR1 value associated with the precursor (e.g., remove or exclude the PCC if one or more associated error indicators such as its AR1 value does not meet a specified threshold level in a manner such as described for fragment ions above).

Figure 13:
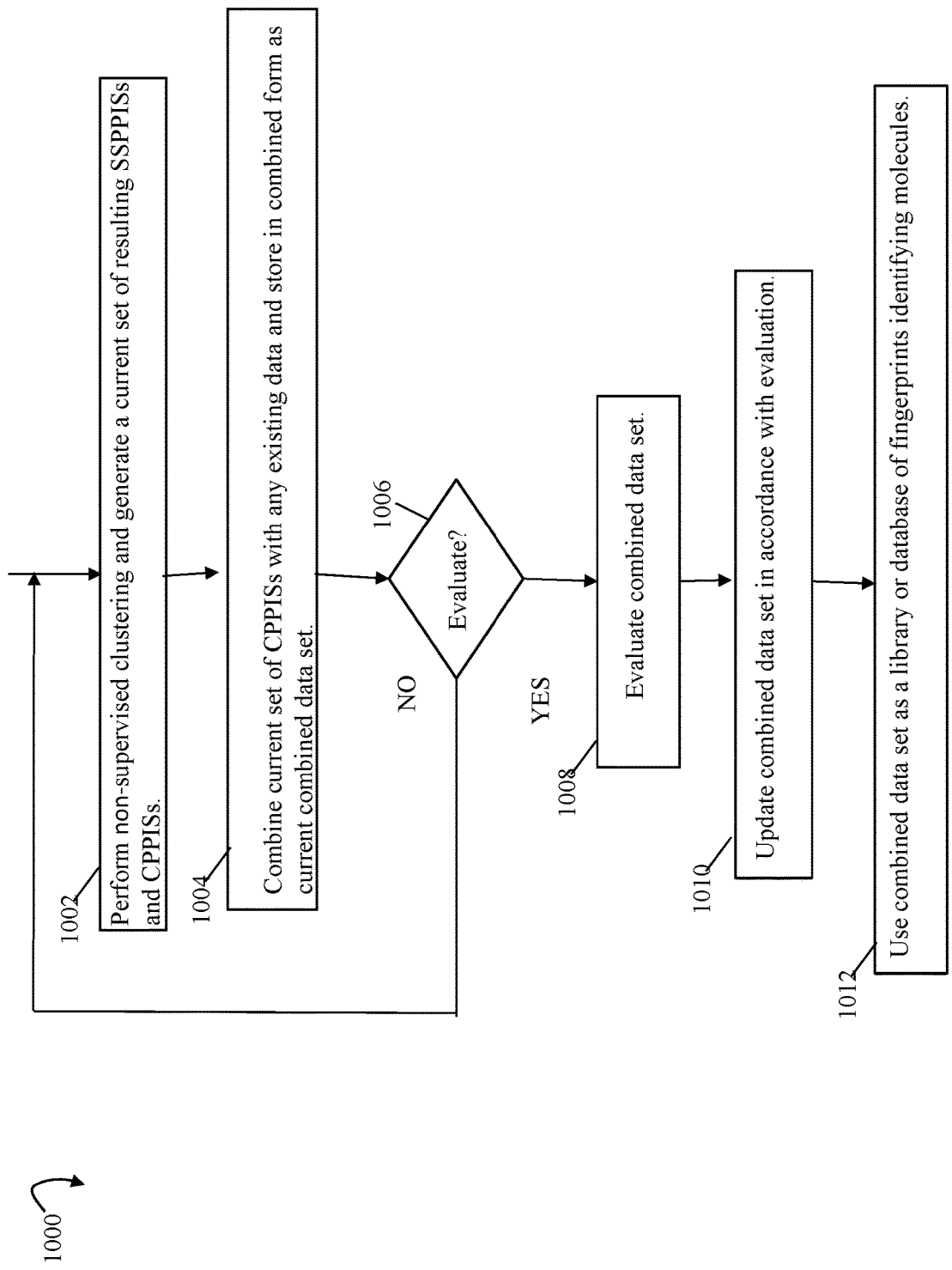

Referring to FIG. 13, shown is a flowchart of processing steps that may be performed in an embodiment in accordance with techniques herein. The flowchart 1000 summarizes processing described above. In step 1002, non-supervised clustering may be performed where a current set of resulting SSPISs are generated and then further grouped into one or more CPPISs. At step 1004, the current set of CPPISs may be combined with any existing data, such as an existing combined data set, including data from previous executions of the non-supervised clustering techniques. Step 1004 may result in a current combined data set incorporating results of precursor ions and associated fragment ions denoting fingerprints for molecules. Step 1004 may result in combining sets of data, such as in a set union, whereby no fragments or PCCs of a fingerprint are removed. The combined data set may be stored, for example, in a library or database.

At step 1006, a determination is made as to whether it is time to perform evaluation processing. As described above, step 1006 may include, for example, determining whether a specified number of non-supervised clustering iterations have been performed, whether a specified amount of time has elapsed, and the like. If step 1006 evaluates to no, control proceeds to step 1002. If step 1006 evaluates to yes, control proceeds to step 1008 to evaluate the current combined data set, such as the current version of the library or database including the combined information generated from the multiple executions of non-supervised clustering. At step 1008, evaluation processing is performed to evaluate the current combined data set. As described elsewhere herein, such evaluation may include examining error indicators associated with each fingerprint identifying a molecule, ions of a fingerprint, and the like, to determine whether any updates or revisions to the combined data set are needed. Such updates or revisions may be performed in step 1010 in accordance with the evaluation of step 1008. Steps 1008 and 1010 determine, for example, which one or more fragments associated with a precursor or PCC should remain in the fingerprint and which one or more fragments associated with a precursor or PCC should be removed from the fingerprint, which one or more precursors or PCCs of a fingerprint should remain, and which one or more PCCs (and associated fragments) of a fingerprint should be removed. Step 1010 may include, for example, determining, such as, using the CVs for AR1, AR2 and possibly AR3 value of a fragment ion, whether the fragment ion currently associated with a PCC should be removed from the fingerprint, thereby concluding that the fragment ion is not actually associated with the PCC or precursor for identification purposes. At step 1012, the updated combined data set generated as a result of step 1010 may be used as the library or database of fingerprints identifying molecules.

Thus, the flowchart 1000 describes a process that may be performed to incorporate results of multiple iterations of non-supervised clustering into a combined data set that has been revised or updated in accordance with error indicators or consistency indicators associated with each fingerprint used to identify a molecule. The output of flowchart 1000 may be, for example, a particular version of a library or database used to identify molecules. Flowchart 1000 processing may be repeated one or more times to determine a second and further subsequent versions of the library or database. Thus, flowchart 1000 processing may be performed to generate a validated and refined combined data set used as a library or database. The refined combined data set may be generated by performing repeated experimentation using samples containing known molecules having fingerprints determined by using non-supervised clustering.

In one embodiment, the processing of flowchart 1000 may be repeated until the error or consistency indicators associated with a fingerprint meet specified threshold levels thereby indicating that the fingerprint data is at a "steady state." For example, such processing may be performed until the fingerprints obtained using non-supervised clustering have associated error or consistency indicator(s) denoting that the resulting collective data used to determine the fingerprint is consistent within specified levels of consistency (e.g. have CV values below a specified threshold thereby denoting relative consistency among the collective data obtained through non-supervised clustering). Such consistency obtained for a fingerprint identifying a molecule denotes an associated high level of confidence in that the fingerprint correctly identifies the molecule and that the fingerprint has correctly associated a PCC of the fingerprint with its one or more fragment ions.

An embodiment in accordance with techniques herein may generate and/or utilize a different library or database for different instrument types, or more specifically, for each different technique used for disassociation or fragmentation of ions. For example, techniques herein may generate and/or utilize a first library or database for MS instruments using collision cells for fragmentation, a second library or database for MS instruments which are ion trap MS instruments, and the like.

Once a validated library having consistent data is generated using non-supervised clustering, comparisons may be made to the fingerprints of the library to identify whether a sample contains a particular molecule (where it is unknown whether the sample contains the particular molecule prior to the identification). For example, as described elsewhere herein, the validated library may be used in connection with supervised clustering. Additionally, the validated library may also be used with a sample known to include the particular molecule to further identify differences or anomalies with respect to the sample. For example, a sample may be known to include a first molecule, such as a first peptide, having a first fingerprint of the library. The sample may also include other molecules. Thus, processing of the sample, such as using supervised clustering described elsewhere herein, is expected to produce the first fingerprint. If there are additional unmatched ions also generated when processing the sample (e.g., PCCs and/or fragment ions not matched to any molecule in the validated library), it may be that those additional unmatched ions are generated as a result of interference due to another molecule or component also present in the sample.

Generally, it should be noted that SSPPISs from multiple experiments may be stored individually or may otherwise be stored in any suitable combined form such as also referred to herein as a CPPIS stored in a database. In one embodiment in accordance with techniques herein, techniques herein may operate on data in the form of SSPPISs and may generate SPPISs. The SPPISs may be stored in a combined form or combined data set such as a CPPIS. The CPPIS may be deconstructed into its associated SSPPISs for use with processing described herein.

What will now be described are techniques that may be used in connection with supervised clustering. Supervised clustering refers the creation of a supervised CPPIS by comparing the PCCs and associated fragment ions of a known target compound (such as from a fingerprint database or simulated database) to SSPPISs obtained from experimental results of a sample whereby such comparisons may use a defined set of matches and tolerances for retention time, drift, (if IMS was performed), m/z, AR1, AR2 and, given the matched product ions are known, AR3.

Generally with supervised clustering, there exists a target library with known fingerprints or patterns for molecules (e.g., library of what the fingerprint should be for a particular eluting component or molecule). For a given sample for which an experiment is performed (e.g., such as an LC/MS or LC/MS/IMS experiment), the experimental data may be processed using supervised clustering techniques described herein to determine whether the sample includes a known molecule or eluting component. Such a determination may be made by determining whether the sample's experimental data matches a known pattern or fingerprint of a known molecule as may be obtained from the library. The target library including fingerprint information for known molecules may be generated or obtained in any suitable manner. For example, the target library may be a version of a validated library generated using non-supervised clustering as described herein. Data for the target library may be, for example, generated using a simulator and the like. In accordance with supervised clustering, for example, a PCC may be obtained as a result of analyzing the sample's experimental data set. Processing may be performed to query the library to determine whether there is existing information in the library for the PCC. Such a determination may be made by matching attribute information of the PCC as obtained from the experimental data set with attribute information for PCCs in the library. Such attribute information for the PCC may include, for example, m/z, AR1, AR3 values and the like.

An embodiment in accordance with techniques herein may use a simulator or modeling software, for example, as described in Geromanos, S. J., Hughes, C., Golick, D., Ciavarini, S., Gorenstein, M. V., Richardson, K., Hoyes, J. B., Vissers, J. P. C. and Langridge, J. I. (2011), Simulating and validating proteomics data and search results. Proteomics, Volume 11, Issue 6: 1189-1211, which is incorporated by reference herein.

If a matching PCC entry is found in the target library, further processing may be performed using information for the PCC from the target library as described elsewhere herein for non-supervised clustering with the difference that, rather than use scan data for the apex or peak scan (e.g., PP or the H scan), processing is performed using the target fingerprint from the library for the PCC. For example, rather than use or compare fragments from the H scan, fragments from the library for the PCC are used. To further illustrate, rather than compare fragments of the H scan to fragments of the H1 and H2 scans, such as when performed non-supervised clustering, supervised clustering alternatively compares fragments of the H1 and H2 scans obtained from the experimental data to fragment ion information of the PCC obtained from library. In one embodiment, in a first instance, the fragments from the library are matched to the H scan by m/z. These matched product ions are then subjected to the identical processing as described for non-supervised clustering.

With supervised clustering, an experiment is performed using a sample as described above with non-supervised clustering to obtain scan data sets that are analyzed to determine the PCCs in the LE scan data. Further processing may then be performed for a particular PCC of the generated data that matches a PCC from library. For example, the generated data may include an eluting peak for PCC1 having a m/z matching that of the PCC1 in the library. As described elsewhere herein with non-supervised clustering, the detected peak for the PCC1 in the LE scan data may be examined to ensure it meets conditions characterizing an elution peak of a molecule. For example, the detected peak must have an appropriate distribution of intensities at the scan points of the peak (e.g., increasing from Pstart to the apex and decreasing from the apex to Pend).

Continuing with the example, the library indicates that PCC1 is associated with 15 fragment ions F1-F15. Rather than use EE scan data with fragments from scan H as in non-supervised clustering, processing of supervised clustering is performed using the fragment ions F1-F15 and associated attributes and information obtained from the library. As with non-supervised clustering, such processing may determine a first number of fragment matches between the F1-F15 in the library for PCC1 and fragments in the EE data for scan H1. Similarly, for scan H2, processing may be performed to determine a second number of fragment matches between the F1-F15 in the library for PCC1 and fragments in the EE data for scan H2. Such matching may be performed using the validation criteria and processing as described above in connection with non-supervised clustering with the difference of using the information for the PCC1 from the library rather than from the H scan. For example, the fragment ion sets for scans of the PCC's eluting peak may be matched against information for F1-F15 in the library in accordance with m/z matches and intensity ratio matches based on AR1, AR2 and AR3 values, or any combination thereof for the fragments. It should be noted that the AR values may be included in the library for comparison with experimental calculations.

Described below are additional details of differences with respect to the various metrics used in supervised clustering rather than those described elsewhere herein with non-supervised clustering.

One difference is the AR1, AR2 and AR3 metric calculations are only performed on those product ions matching the library fragments by m/z. Similar to non-supervised clustering, supervised clustering starts by matching the library fragment ions by m/z (within some tolerance) to the H scan with all subsequent processing identical to non-supervised clustering.

As in connection with non-supervised clustering, processing now examines the fragment ion data or the EE scan data for the H1 and H2 scans. For scan H1, examine the EE scan data and determine which fragment ions of the EE scan data from scan H1 that match any of the fragment ions F1-F15 of the PCC information in the library. As described in connection with non-supervised clustering, such fragment matches may be determined between scan H1 and the library by matching m/z AR1, AR2, and AR3 intensity ratio values (within specified tolerances).

Thus, processing is performed to determine a first set of matching fragments for PCC between fragment ions of the PCC as identified in the library and fragments in the EE scan data for scan H1. Processing also is similarly performed to determine a second set of matching fragments between fragment ions of the PCC as identified in the library and fragments in the EE scan data for scan H2. For example, fragment F1 in the library is determined to match fragment F1" in scan H1 if:

m/z of F1 in library matches m/z of F1" in scan H1, within some specified tolerance; and
the intensity ratio IR calculated as:

$$IR = \text{intensity of } F1\text{" in scan } H1/\text{intensity of } F1 \text{ from } H$$

matches the AR2 value for the PCC intensity with respect to the same two scans H1 and H, within some specified tolerance. As a second embodiment, the predicted intensity of a fragment ion such as F1 from the library may be obtained using F1's AR1 value. In particular, the estimated intensity for F1 may be obtained for the matched PCC whereby the AR1 value from the library may be multiplied by the intensity of the PCC in scan H1. Similarly, the AR1 value of any fragment ion obtained from the library may be used to determine the PCC's intensity in any scan of the eluting peak. As noted elsewhere herein, AR1=intensity of the product ion/intensity of the precursor ion or PCC. As such, given a PCC intensity, the intensity of the fragment ion is obtained by multiplying the fragment ion's AR1*the PCC intensity.

Validation processing of fragment ion sets at each scan time in the PCC's peak may be performed as described elsewhere herein with non-supervised clustering to determine matches between fragment ions in the library for the PCC and fragment ions included in EE scan data for those scan times of the PCC's peak. For example, as noted above, processing may determine the number of matching fragments F1-F15 in the library for scans H1 and H2 in accordance with AR2 values for such. Then validation processing is performed for the first matching fragment set determined for scan H1 and the second matching fragment set determined for scan H2. Such validation processing may include using one or more validation criteria as described elsewhere herein with non-supervised clustering. As with non-supervised clustering, such validation processing may include validating AR2 values using AR1 values and determining whether the relationship R1 is true (i.e., the intensity of a fragment ion must never be greater than that of its PCC). The AR1 metric may be determined in supervised clustering as described elsewhere herein for non-supervised clustering. Validation processing may compare AR1 values for scans in the PCC's peak for a fragment ion F1 denoted in the library. If all such AR1 values for all scans in the PCC's peak (as determined using the experimental data sets) do not match the AR1 value for F1 from the library, within some tolerance, then fragment F1 is not matched with the PCC, whose intensity is used in computing AR1 and AR2 values.

Such validation processing may include determining whether the number of matching fragments in each of the first matching set for H1 and the second matching set for H2 is at least a specified minimum number (e.g., such as may be determined using the table of FIG. 8 discussed elsewhere herein). Such processing performed for supervised clustering is similar to that as described above for non-supervised with respect to AR2 values and validation criteria of whether each scan has an associated number of matching fragments that meets the minimum number. For example, processing may be performed to traverse the scan points between the PCC's peak scans H1 and H2 and determine whether each scan point from H1 to H2, inclusively, has at least a minimum threshold number of fragments matching known fragments for the PCC from the library.

Determining matching fragment ion sets for all scan points in the PCC's peak may be performed in a manner similar to that as described elsewhere herein for non-supervised clustering.

It should be noted that described above is a process where the target library is queried to return a set of fragment ions, such as F1-15 for a specified PCC, and then processing may be performed to determine matching fragment ion sets for scans in the PCC's peak and whether each such scan has at least a required minimum number of fragment ion matches (between fragment ions in each EE scan data with F1-F15 from the library). For each scan point in a detected PCC's peak, criteria as described herein (e.g., using various ratios or AR values, minimum threshold number of fragment ion matches, and the like) may be applied and if such criteria is met for a scan point, then the SSPPIS for that scan is considered a match to the target PCC in the target library. In some instances, an identification that a detected PCC in the experimental data matches the target PCC of the library under consideration may be made with only a single scan match (e.g., such as with DDA obtained experimental data). For the detected PCC, an AR3 value may be calculated as described herein. As also described herein with non-supervised clustering, processing may be performed to group together multiple matched SSPPISs associated with the same eluting molecule. As with the AR1 values, AR3 values must be consistent across all SSPPISs (within a specified tolerance).

In one embodiment, the target library may be populated with theoretical data, such as generated using a simulator. Once a match is determined between a target PCC in the library and a PCC in the experimental data set for a sample, the information for the target PCC in the library may be replaced or supplemented using the information obtained from processing described herein from the experimental data set for the PCC. For example, the information for the SSPPIS for the PCC as determined from the experimental data may replace the theoretically generated information (e.g., retention time) for the target PCC in the library.

As described in more detail elsewhere herein, supervised clustering may be used in connection with many different applications and workflow processes. For example, a particular fragment ion set from a target library may be queried against all SSPPISs obtained from a set of experimental data to look for any modifications or variants of the target molecule. The input fragment ion set by definition is matched to a given PCC. Any variant of the molecule will produce a similar fragmentation spectrum (fragment ion list) to that of the no-variant form up to the point of the modification. As an output in response to locating such a matching fragment ion set, a PCC associated with the matched fragment ion set may be returned. The foregoing is another way in which supervised clustering may be used with a target library. Thus, in supervised SSPPIS identifications and subsequent CPPIS formation, the presence of the PCC in the SSPPIS is not a requirement. Though a valid identification of a target peptide demands the presence of its PCC, the supervised process affords an embodiment operating in accordance with techniques herein with the ability to identify any modification (sequence, chemical, post-translational), variant (point mutant) or missed cleaved form of the target peptide, provided a statistically significant number of product ions match. If a statistically significant number of product ions are matched, a delta m/z may be calculated between the target precursor m/z and that of the precursor present in all matched SSPPISs. This delta m/z may be compared to a lookup table of known delta m/z values in an attempt to identify the source of the modification. This is described in more detail in connection with other processing herein. Similarly, if the matched product ions reflect only a single fragmentation pathway (y" or b fragment ions) indicating a missed cleavage, the near neighboring peptide sequence may be retrieved for conformation by querying the residual (unmatched) product ions from each matched SSPPIS against that peptide's fragmentation pattern. This is described in more detail elsewhere herein in connection with precursor variants or modifications.

Thus, supervised clustering may be performed with respect to experimental scan data sets obtained for a sample as part of identifying that the sample includes particular known molecules having fingerprint information in the target library. For example, if all SSPPISs obtained from the experimental scan data match SSPPIS information of known molecules in the target library, then the resulting CPPIS for the sample has been confirmed as including only known molecules as identified in the target library. Alternatively, however, the supervised clustering of the sample may fail to match some PCCs and some fragment ions identified in the experimental scan data sets, which may also be referred to as residual, orphaned, or unmatched PCCs and fragment ions. For example, element 354 of FIG. 3 denotes such a residual set of data of unmatched ions. In this case, the CPPIS for the sample includes those matched PCC and fragment ions of known or target molecules as included in the target library. The residual set of unmatched PCCs and fragment ions not included in the identified CPPISs for the sample may denote some variant, unknown or unidentified molecule(s) not included in the library, and the like. As described elsewhere herein, the residual set may be further processed or analyzed.

As described above, supervised clustering performs the same processing as non-supervised clustering with the differences noted herein whereby the target or benchmark for comparison in non-supervised clustering is the scan H denoting the apex of an eluting peak for a tracked PCC across scans. In contrast, in supervised clustering, the target is specified as a known component or molecule having a known pattern or fingerprint (e.g., SSPPISs or CPPIS) from the library. In at least one embodiment, the target library used in supervised clustering may be initially generating by a simulator whereby the library contains theoretical data.

Supervised clustering as described herein may use the same AR (area ratio or intensity ratio) metrics with variations made to account for the different target (e.g., non-supervised uses information from the scan of the eluting PCC peak while supervised uses information from the library).

Generally, the target, such as the target library used in connection with supervised clustering, may be generated or more generally obtained in any suitable manner. For example, the target may be obtained from a library including information of known molecules or compounds, such as peptides, generated from any of previous experiments, simulation, non-supervised clustering, and the like.

Supervised clustering has many different applications and uses, some of which are described herein. For example, supervised clustering may be used with a target library of known molecules as described herein to identify whether a sample contains a known molecule having an associated fingerprint as included in the library. Thus, supervised clustering may be used to confirm the presence or absence of a known molecule in a sample under test. Additionally, supervised clustering may also be used in connection with determining whether the sample under test includes any residual or unmatched PCCs and/or fragment ions that may thereby denote that the sample may include one or more unidentified molecules, variants, and the like.

Figure 14:
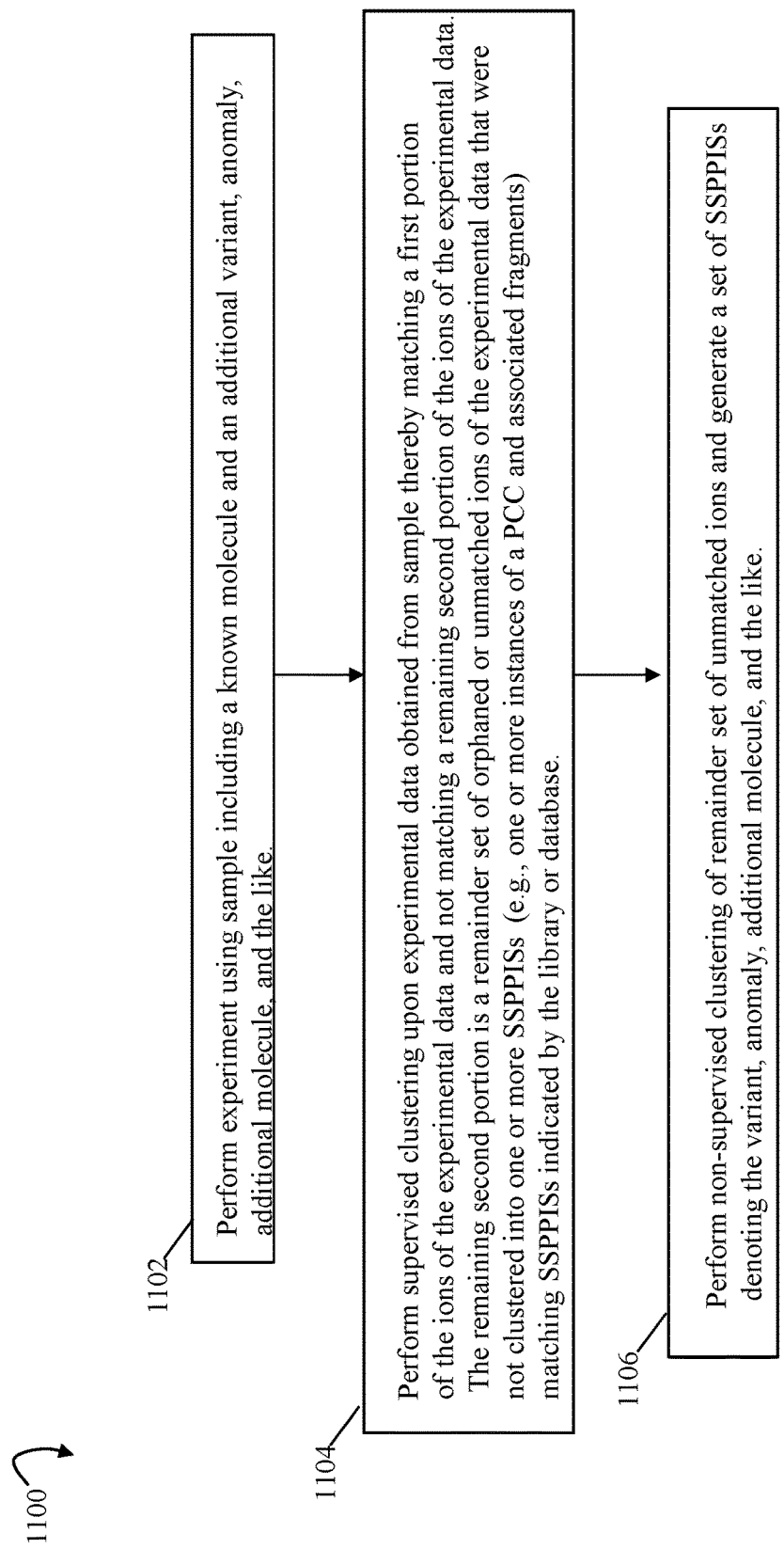

Referring to FIG. 14, shown is another flowchart 1100 of processing that may be performed in an embodiment in accordance with techniques herein. A sample may include a known first molecule and a known or unknown additional variant, anomaly, additional second molecule, and the like. At this point, assume there is a target library or database that has been validated such as described above to include consistent fingerprint data denoting the first molecule. Using such a library or database, processing of flowchart 1100 may be performed. At step 1102, an experiment is performed using the sample including the first known molecule and the additional variant, anomaly or second molecule. At step 1104, supervised clustering may be performed using the validated library or database and the experimental data obtained from step 1104 for the sample. As a result of the supervised clustering, a first portion of the ions of the experimental data were clustered into SSPPISs that also matched target SSPPISs of the library. Also as a result of step 1104, there is a remaining second portion of the ions of the experimental data that were not matched to the library or database. The remaining second portion of the experimental data is a remainder set of orphaned or unmatched ions of the experimental data that were not clustered into one or more SSPPISs (e.g., one or more instances of a PCC and associated fragments) thus not matching SSPPISs denoted by the library or database. Thus, the remaining second portion of ions includes ions characterizing the known additional variant, anomaly, or additional second molecule. In step 1106, non-supervised clustering of the remainder set of unmatched ions generates a resulting set of SSPPISs denoting the variant, anomaly, additional molecule, and the like. Thus, the resulting set of SSPPISs generated for non-supervised clustering of step 1106 may be used as a fingerprint denoting the variant, anomaly, additional molecule, and the like, and may be used to build a second database or library (e.g., such as using the processing described above in connection with FIG. 13). An embodiment may repeatedly perform flowchart 1100 processing for multiple experiments using the same sample or samples, including the same compounds or molecules. Such repeated processing may be used to obtain multiple sets of SSPPISs denoting the fingerprint of the additional variant, anomaly, additional molecule, and the like. The multiple sets of SSPPISs from step 1106 of the multiple experiments may be combined as described herein to form the collective data of the fingerprint for the additional variant, anomaly, additional molecule, and the like.

What will now be described is an additional embodiment or variation of supervised clustering techniques using a target library.

Figure 14A:
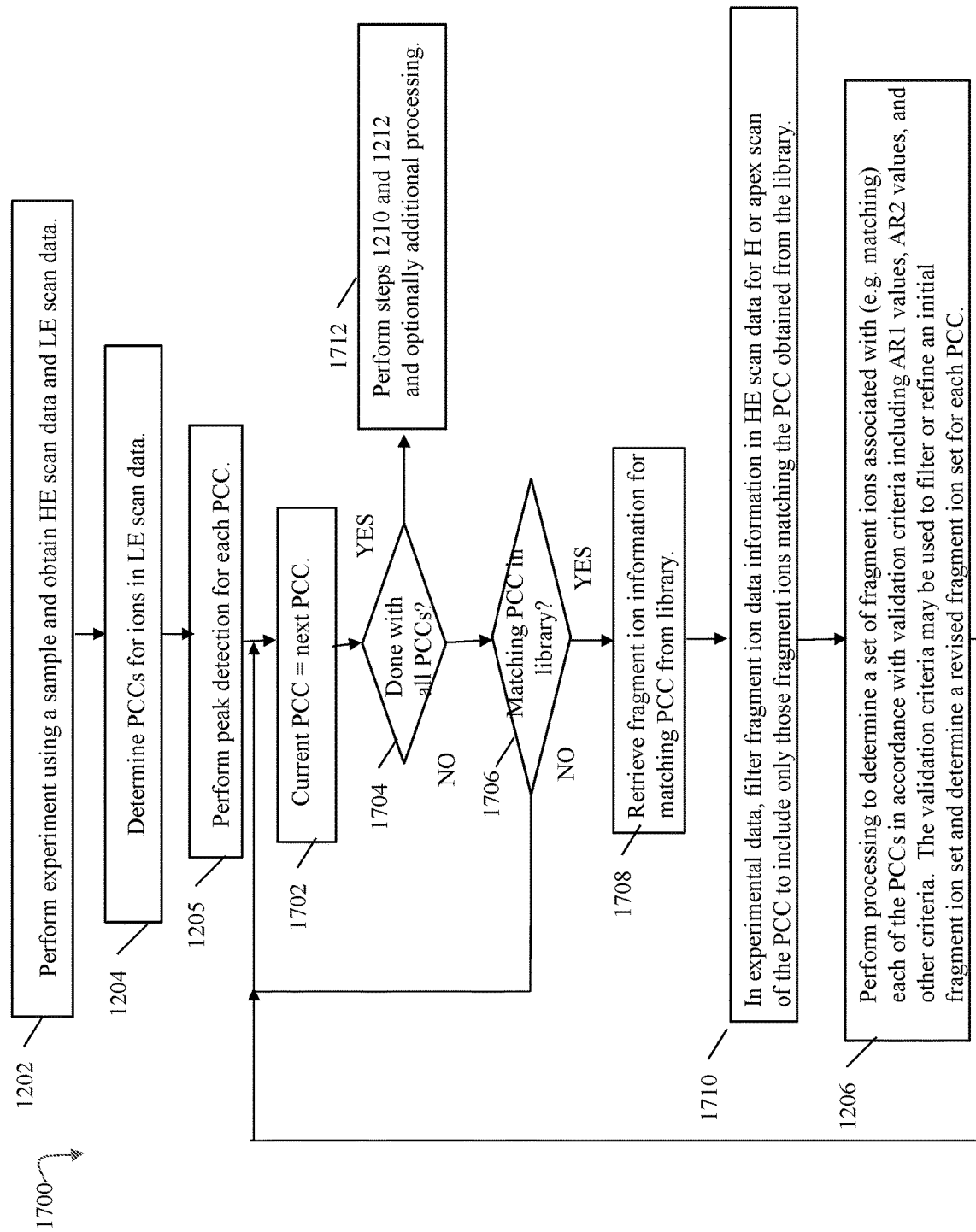

Referring to FIG. 14A, shown is a flowchart 1700 of processing steps that may be performed in an embodiment in accordance with techniques for supervised clustering. Processing may include performing steps 1202, 1204 and 1205 as described elsewhere herein such as in connection with FIG. 9. At step 1702, a variable current PCC may be assigned the next PCC to be processed. At step 1704, a determination is made as to whether all PCCs in the current set of experimental data have been processed. If step 1704, evaluates to yes, control proceeds to step 1712. Step 1712 processing may include performing steps 1210 and 1212, as described elsewhere herein, and optionally additional processing. Step 1712 additional processing may include, for example, replacing existing library information (e.g., regarding PCCs and associated fragments) with information obtained from current processing of the experimental data. For example, if the library contains theoretically generated information as obtained using a simulator, the library may be updated to replace such existing information using the PCC or precursor and associated fragment ion information obtained from experimental data as a result of flowchart 1700 processing.

If step 1704 evaluates to no, control proceeds to process the current PCC. At step 1706, it is determined whether a matching PCC is found in the library for the current PCC. As described elsewhere herein, such a matching PCC may be based on matching (within some specified tolerance) m/z, m/z and retention time, m/z, retention and drift time, or more generally any combination of pre-ion detection separation methodologies. If step 1706 evaluates to no, control proceeds to step 1702. If step 1706 evaluates to yes, control proceeds to step 1708 to retrieve fragment ion information (for one or more fragment ions) for the matching PCC from the library. At step 1710, the HE scan data of the experimental data for the H or apex scan of the PCC may be filtered to include only those fragment ions matching fragment ions of the PCC as obtained from the library. For example, assume the HE scan data for scan H or the apex scan of the PCC includes 15 fragment ions denoted F1-F15 and the library, for the same PCC, includes 5 fragment ions F1-F5. Such filtering in step 1710 filters the HE scan data to determine a first filtered fragment ion set including only the information for fragment ions F1-F5. The information of the first filtered fragment ion set will be used in subsequent processing and the remaining fragment ion information for fragments F6-F15 in the HE scan data for scan H or the apex scan may not be further utilized in subsequent processing steps. Processing proceeds to step 1206 to perform such processing as described elsewhere herein (such as in connection with FIG. 9). In this case, the fragment ion information used for the apex or H scan of the PCC is limited to fragment ion information in the HE scan data of the experimental data for only those fragment ions in the first filtered fragment ion set. From step 1206, processing proceeds to step 1702.

Unlike peptides or other complex molecules that produce many product ions during disassociation, small molecules often produce only a few. In addition, small molecules are often singly charged as are their fragments. Their intensity ratio (AR1) when compared to fragment ions from peptides are often quite lower. Being singly charged and lower in intensity does not provide for many isotopes. Here identifying and validating which product ions are associated with which precursor using precursor product ion area relationships alone require that a greater number of similar experiments be compared. However an embodiment in accordance with techniques herein may take advantage of the 50% survivor yield strategy (e.g., 50% PCC yield rule) employed by many small molecule laboratories provided the instrument control software could change the collision energy on a scan-by-scan basis. Here it is the variation in the fragmentation pattern throughout the molecule's elution that provides the additional orthogonality for identification and validation of alignment. The product ions of a co-eluting small molecule will have a different 50% survivor yield at a given collision energy, thus separating them from those emanating from the "true" parent precursor. As described in more detail in following paragraphs, an embodiment in accordance with techniques herein may incorporate the foregoing into experiments and data analysis performed for small molecule applications.

An embodiment in accordance with techniques herein may, for small molecules, change the fragmentation pattern across the eluting peak on a scan by scan basis by varying the collision energy throughout the elution peak. As described elsewhere herein, the fragmentation pattern may be characterized as the intensity relationship between a product ion and its parent precursor, such as its associated PCC. The fragmentation pattern is such that the area ratio or intensity between the two has to be consistent (within some experimental variance) across the chromatographic elution provided multiple cycles across the molecules elution fragmentation patterns can be compared within and between collision energy cycles. Techniques herein utilize such principles and relationships between a parent ion, such as a PCC, and its fragment. To elaborate, the fragmentation pattern of a precursor is consistent across its elution. To that end, the intensity relationship between a precursor ion and its constituent product ions at the same collision energies in the same as well as different collision energy cycles should remain constant in the absence of interference. The number of product ions a precursor ion or PCC will generate during fragmentation is a function of its length/mass and concentration. As a PCC's intensity varies (e.g., increases and/or decreases) across the detected peak, so does the intensity of its product ions.

In accordance with techniques herein, an embodiment may change the collision energy on a scan by scan basis in an experiment performed on a sample with small molecules. Assume that an experiment has been performed on a sample with small molecules resulting in obtaining LE scan data an EE scan data. The LE scan data as described herein includes primarily precursor or PCC scan data and the EE scan data includes primarily fragment ion scan data. Such LE and EE scan data sets may be examined to determine, for a particular PCC or precursor ion, what is the collision energy (CE) that results in the PCC or precursor ion appearing in the EE scan data with approximately ½ or 50% of the intensity (e.g. within some specified tolerance) of the PCC or precursor ion as in the LE scan data. As described elsewhere herein, the same ion may be located in different sets of scan data, such as the LE scan data and EE scan data, based on matching m/z in the different sets of scan data.

As a first step, the LE scan data may be examined to obtain the intensity of a PCC or parent precursor ion. For example, assume the intensity of the PCC or parent precursor ion in the LE scan data in scan S1 is 10e6. As a second step, the EE scan data is examined to locate the PCC in the EE scan data at scan S1 and obtain the PCC's intensity as it appears in the EE scan data at scan S1. For example, assume the intensity of the PCC or parent precursor ion in scan S1 of the LE scan data is 10e3 thereby denoting that 50% of the PCC has not been fragmented and 50% of the PCC has been fragmented. As a third step, the difference between the PCC or precursor ion's intensity in scan S1 of the LE scan and in scan S1 of the EE scan may be determined. The foregoing difference represents a maximum or upper bound on the expected total intensity of any fragment ions generated from the PCC or precursor ion in scan S1. Continuing with the example given the foregoing, it means that 10e6−10e3=10e3 denotes the maximum or upper bound on the expected total intensity of any fragment ions generated from the PCC or precursor ion in scan S1. Additionally, the difference 10e3 is also equal to 50% of the PCC or precursor ion's intensity of 10e6 as in the LE scan data for scan S1. Thus, an embodiment in accordance with techniques herein may note the particular CE used in connection with fragmentation of the PCC or precursor ion in the scan S1 where such CE results in fragmentation of approximately 50% of the PCC or precursor ion. In description herein, the foregoing may also be referred to as the 50% PCC yield rule.

An embodiment in accordance with techniques herein may perform an experiment where the CE energy is changed for each scan and the CE energy over time is varied to cycle through a series of CE values in subsequent scans that form a cycle or period. The CE cycle or period increases the CE, such as in CE intervals of steps, in a first portion of subsequent scans from a minimum CE value until the CE reaches a maximum or apex value and then the CE is subsequently decreased in CE intervals or steps until the minimum CE value is reached whereby the CE cycle or period is then repeated.

Figure 15:
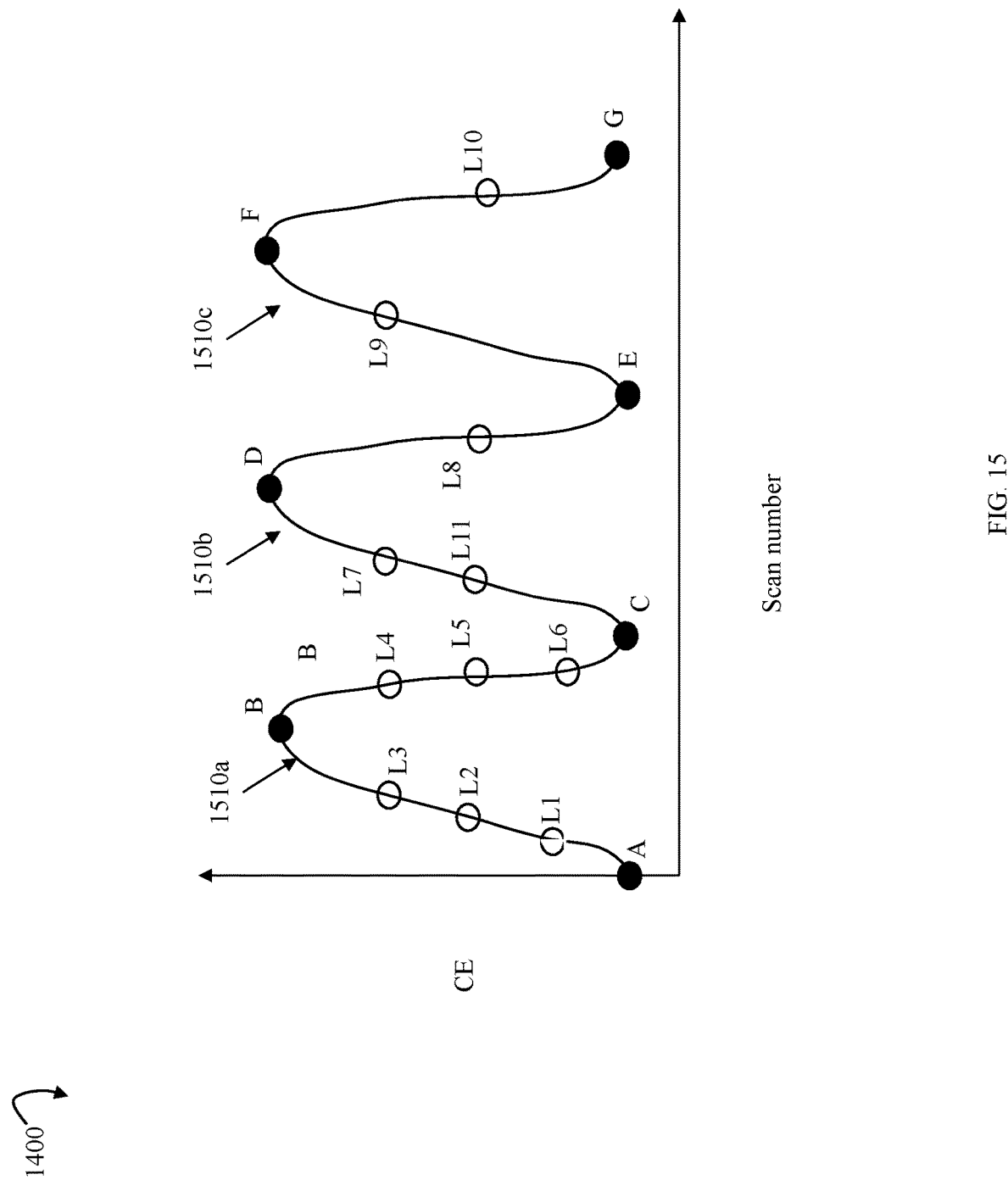
FIGS. 15 and 16 are graphical illustrations of different collision energy settings that may be used across elution time in an embodiment in accordance with techniques herein.

With reference to FIG. 15, shown is an example 1400 graphically illustrating how the CE may be varied per scan such that the CE values form a peak comprising the CE cycle or period. Points A, C, E and G may denote the CE minimum values in the CE cycle or period and points B, D and F may denote the CE maximum values in the CE cycle or period. A single CE cycle or period may be denoted between pairs of the same CE value in two successive CE periods or cycles. For example, a single CE cycle or period may be denoted between the points A and C whereby the CE is set to different CE values in each scan from point A to point C, which begins a new CE cycle or period. An embodiment may increment the CE value in each scan from the minimum to the maximum CE value on the upslope of the CE cycle or peak and also decrement the CE value in each scan from the maximum CE value to the minimum CE value on the downslope of the CE cycle or peak a predetermined amount each scan. Such CE values at each scan may be determined using any suitable technique such as in accordance with a mathematical function that controls the CE setting or selection per scan using software and/or hardware.

In one embodiment described herein such as illustrated in FIG. 15 and others, the CE cycle may be characterized as a Gaussian peak or curve such that CEs of the upslope are repeated in reverse order on the down slope of the same CE cycle. For example, L1, L2 and L3 denote points in CE cycle 1510*a*'s upslope and points L6, L5 and L4 denote points in CE cycle 1510*a*'s downslope where points or scans L1 and L6 have the same CE, points or scans L2 and L5 have the same CE, and points or scans L3 and L4 have the same CE. In a similar manner, CEs of each cycle are repeated so that, for example, L7 denotes a point or scan in CE cycle 1510*b* having the same CE as L3 and L4, L8 denotes a point or scan in CE cycle 1510*b* having the same CE as L5, and L11 denotes a scan in CE cycle 1510*b* having the same CE as points L2, L5 and L8. Similarly L9 denotes a point or scan in CE cycle 1510*c* having the same CE as L3, L4 and L7, and L10 denotes a point or scan in CE cycle 1510*b* having the same CE as L5 and L8. Thus, using a CE cycle comprised of CE values forming a Gaussian type peak or curve provides for having each CE value other than the apex or peak CE value occur twice within each CE curve. Further, if there are "n" CE cycles in one chromatographic peak as described in more detail below, then each such CE value (other than the peak CE value) occurs 2n times in the single chromatographic peak.

It should be noted that the number of scans or scan instances in each CE cycle or period at which the CE is varied is at least the median or average chromatographic peak width divided by two (2). More formally, assuming that the CE is varied each scan, the period T of the CE cycle denoting the number of scans in a CE cycle may be represented as:

$$T \leq \text{FWHM of elution or chromatographic peak} \quad \text{EQUATION CE CYCLE}$$

where

T is the period of the CE cycle denoting an integer number of scans in a single CE cycle where the CE is varied at each scan; and FWHM of elution or chromatographic peak denotes the FWHM of the median or average elution or chromatographic peak associated with an eluting component or molecule in the sample (e.g., FWHM=the average or median elution or chromatographic peak width/2).

Generally, EQUATION CE CYCLE more formally expresses the desire to perform an experiment in which at least one CE cycle occurs for scans in any eluting peak associated with a single molecule (e.g., any eluting peak of a single molecule or component will experience at least one CE cycle or experience each CE in the CE cycle at least once).

When varying the CE energy for a single eluting peak of a single PCC, the LE scan data and EE scan data may be examined to determine the scan at which the 50% PCC yield rule holds (e.g., scan in which the PCC or precursor ion has an intensity in the EE scan data that is approximately 50% of its intensity from the LE scan data).

It should be noted that the particular PCC may be tracked across different scans to determine its associated eluting peak as described elsewhere herein based on matching m/z for the PCC in the LE scan data in sequential subsequent scans. Additionally, the intensity associated with the PCC in the EE scan data of each scan of the detected peak should follow an expected relative intensity pattern between scans in accordance with the varying CE. For example, as the CE is increased from scan N to N+1, it is expected that the fragmentation experienced by the PCC or precursor ion also increases from scan N to N+1. Thus, from scan N to N+1, the intensity of the PCC in the EE scan decreases since the intensity associated with the generated fragment ions from fragmenting the PCC as represented in the EE scan data is increased. In other words, if the CE in scan N<CE in scan N+1, then the intensity of the PCC in the EE scan data for scan N>intensity of the PCC in the EE scan data for scan N+1 (since the intensity of the fragment ions generated from fragmentation of the PCC in scan N<intensity of fragment ions generated from fragmentation of the PCC in scan N+1).

In a similar manner, for scans in the detected peak for a PCC, the intensity of the PCC in the EE scan data between scans is expected to follow a relative intensity pattern between scans in accordance with varying the CE as the CE is decreased from the CE maximum at the apex to the CE minimum. For example, as the CE is decreased from scan N to N+1, it is expected that the fragmentation experienced by the PCC or precursor ion also decreases from scan N to N+1. Thus, from scan N to N+1, the intensity of the PCC in the EE scan increases since the intensity associated with the generated fragment ions from fragmenting the PCC as represented in the EE scan data is decreased. In other words, if the CE in scan N>CE in scan N+1, then the intensity of the PCC in the EE scan data for scan N<intensity of the PCC in the EE scan data for scan N+1. The foregoing expected relative intensity pattern between scans may be used in combination with matching m/z for the PCC to determine the peak for a PCC and track the PCC between scans.

In the scan of an eluting peak for a PCC where the 50% PCC yield rule holds, an AR2 ratio may be determined for the PCC in each scan of the tracked eluting peak and compared in a manner similar to that as described elsewhere herein as further validation criteria (in addition to the matching m/z and expected relative intensity pattern between scans of the peak) to ensure that the eluting peak is for the particular PCC (having the matching m/z and expected relative intensity pattern between scans of the peak). The AR2 ratio determined in this case is similar to as described elsewhere herein, such as in connection with EQUATION for AR2, with the difference that rather than use the intensity of the PCC in the apex or PP scan of the eluting peak based on the PCC intensity in LE scan data, the AR2 ratio uses the intensity of the PCC as in the EE scan data for scan M where the 50% PCC yield rule holds. It should be noted that changing the collision energy between any two neighboring scans will affect the fragmentation pattern. As such the AR2 ratio between scans unlike what was previously described will not be consistent between ion types but is rather reproducible between scan acquired at the same collision energy. It is the similarity of the pattern of fragmentation for scans or points having the same or similar collision energy that may be compared across the chromatographic elution. What may be performed using this particular version of the AR2 ratio is tracking the intensity of the residual unfragmented PCC or precursor ion as it appears in the EE scan data across different scans such as of the eluting peak for the PCC as the CE is varied.

Figure 16:
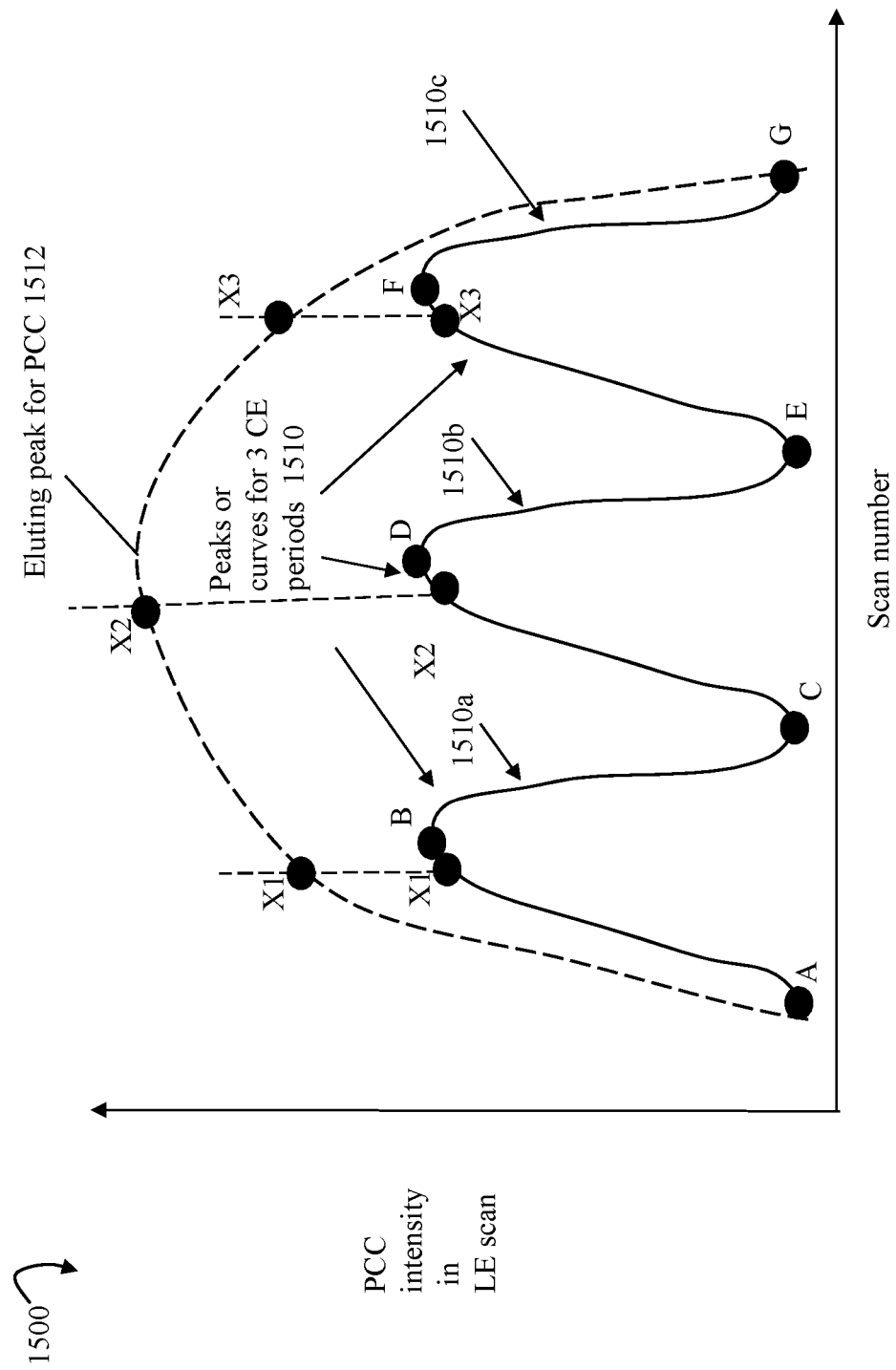

Referring to FIG. 16, shown is an example 1500 graphically illustrating an eluting peak 1512 for a PCC as may be determined based on the PCC's intensity in LE scan data of different scans. In this example 1500, there are 3 CE periods 1510 in a single eluting peak 1512 for the PCC. Thus, the CE is varied or cycles through the period of CEs 3 times during the single eluting peak 1512. The peaks or curves for the 3 CE periods 1510 are superimposed on this graph with the single eluting peak for purposes of illustration and description in following paragraphs.

As a first step, one or more scans in the eluting peak at which the 50% PCC yield rule holds may be determined. In this example, points X1, X2 and X3 may denote such points or scans at which the 50% PCC yield rule holds true for the PCC tracked having the peak 1512. As noted above, each of points X1, X2 and X3 denotes a scan in which the intensity of the PCC in the EE scan data is approximately 50% of the PCC's intensity in the LE scan data for the same scan (e.g., there is approximately 50% fragmentation efficiency for the PCC at the particular CE also denoted by each of point X1, X2 and X3).

As a second step, the associated CE peak or curve for a single CE period that includes each of the points X1, X2 and X3 may be determined. What will now be described is processing that may be performed with respect to a single CE peak or curve and scans in the CE peak but may be repeated with respect to each such CE peak or curve denoting a single CE period. For example, point X1 denotes a scan included in the scans associated with a first CE period 1510a illustrated by the curve formed by points A, B and C in the example 1500. Using the point X1 (denoting the scan at which the PCC's intensity in the EE scan data is approximately 50% of the PCC's intensity in the LE scan data) as the H scan (e.g., apex or PP scan), a series of AR2 ratios may be compared and used as validation criteria both within and between CE period(s) as will now be described. In other words, as described elsewhere herein, such as with non-supervised and supervised clustering, AR1 and AR2 values are utilized for determining which product ions are aligned to the PCC using the apex of the elution peak for the PCC (e.g., 1512) as the H scan. Rather than use the apex of the PCC elution peak as the PP in computing AR1 and AR2 values, the scan X1 may be used as the PP with points H1 and H2 (denoting the FWHM points on the upslope and downslope respectively) being determined with respect to the scan X now used as the PP. Given that fragmentation is a function of collision energy and in the described embodiment the collision energy is changing from scan-to-scan, comparison of AR1 and AR2 may be made both between scans of similar (or approximately the same within a specified tolerance) collision energy occurring in the same CE cycle as well as between scans having the same CE where such scans are in different collision energy cycles (e.g., as such the necessity for a minimum of two cycles per median chromatographic peak width (FWHM) in an embodiment in accordance with techniques herein).

As an example a typical small molecule has a 3 second wide chromatographic peak width (FWHM) with an acquisition speed of 100 milliseconds that's 3000 milliseconds/100 milliseconds or 30 scans. Requiring a minimum of two collision energy cycles would allow for 10 different collision energies, applying 5 different collision energies would allow for 6 collision energy cycles. The number of collision energy cycles is determined by acquisition speed the median chromatographic peak width (FWHM).

Thus, AR1 and AR2 ratios may be determined for each scan point within a collision energy cycle with:

$$AR1 = Int(F1 \ldots F_n)/Int(S1, PCC)$$

where
    n equals the number of fragment ions in the EE scan data of scan S1;
    Int (F1 ... $F_n$) denotes the intensity of any one of the "n" fragment ions in EE scan data of scan S1; and Int (scan S1, PCC) is the intensity, in the LE scan data of scan S1, of the PCC or precursor ion from which F1 through Fn originate (e.g., different AR1 value may be determined for each of the n fragments F1 through Fn based on a ratio to its parent precursor ion or PCC); and $$AR2 = Int(scan\ S1, PCC)/Int(scan\ M, PCC) \quad \text{EQUATION V3 for AR2 of PCC}$$

where

Int (scan M, PCC) is the intensity of PCC or precursor ion in the EE scan data for scan M of the CE period for the PCC where the 50% PCC yield rule holds for the PCC's intensity; and Int (scan S1, PCC) is the intensity of PCC or precursor ion in the EE scan data of some scan S1 denoting another scan of the CE period for the PCC besides scan M.

Similarly, we can determine AR2 values based on EQUATION V3 for fragment ions:

$$AR2 = Int(scan\ S1, F1)/Int(scan\ M, F1) \quad \text{EQUATION V3 for AR2 of Fragment ion}$$

where

Int (scan M, F1) is the intensity of fragment ion F1 in the EE scan data for scan M of the CE period for the PCC where the 50% PCC yield rule holds for the PCC's intensity; and Int (scan S1, F1) is the intensity of F1 in the EE scan data of some scan S1 denoting another scan of the CE period for the fragment ion F1 besides scan M.

Additionally, AR2 may be defined based on the above equation but with respect to two scans at corresponding points in two different CE cycles (e.g., where the same CE1 is applied in the two scans, such as L2 and L11 in two different CE cycles in 1510a and 1510b, and the same CE2 is applied in the scans L3, L7 and L9 respectively in CE cycles 1510a, 1510b and 1510c)

where

Int (scan M, PCC) is the intensity of PCC or precursor ion in the EE scan data for any scan M of the CE period for the PCC; and Int (scan S1, PCC) is the intensity of PCC or precursor ion in the EE scan data of scan M's companion or corresponding position in each subsequent collision energy cycle (e.g., S1 and M are corresponding scans at corresponding points in subsequent CE cycles where the same CE is applied); and also Int (scan M, F1) is the intensity of fragment ion F1 in the EE scan data for any scan M of the CE period; and Int (scan S1, F1) is the intensity of F1 in the EE scan data of some scan S1 denoting M's corresponding or companion scan in each subsequent CE cycle (e.g., S1 and M1 are corresponding scans in different CE cycles where the same CE is applied).

To further illustrate with reference to FIG. 15, AR1 values determined for a fragment F1 are expected to be the same in scans S1 and S2 of the same CE cycle if approximately the same CE is used in both S1 and S2 (e.g., AR1 is expected to be the same for F1 in the pair of scans L3 and L4. AR1 is expected to be the same for F1 in the pair of scans L2 and L5). AR1 values for F1 are expected to be the same in corresponding scans L3, L4, L7 and L9 of three different CE cycles where the same CE is used in all of L3, L4, L7 and L9 across multiple CE cycles. AR2 values determined for the PCC or precursor ion using EQUATION V3 above are expected to be the same in scans L3, L4 of the same CE cycle where the same CE is applied. Additionally, AR2 values for the same PCC using EQUATION V3 are expected to be the same in scans L3, L4, L7 and L9 within and across CE cycles where the same CE is applied.

Also, a first AR2 value determined for fragment F1 using EQUATION V3 above in scan L3 is expected to be the same as a second AR2 value determined for the PCC from which F1 originated using EQUATION V3 above in scan L3. Furthermore, the foregoing first and second AR2 values are also expected to be the same as AR2 values for the originating PCC and F1 using EQUATION V3 above in scans L4, L7 and L9. Still further, the foregoing first and second AR2 values (for the PCC and F1 in scan L3) are also expected to be the same as AR2 values determined for another fragment F2 also originating from the same PCC as F1 using EQUATION V3 above in scans L4, L7 and L9.

Thus, both the AR1 and AR2 ratios may be tracked and are expected to be approximately the same, within some specified tolerance, across similar scans (having about the same CE) of the CE period as the CE is varied. As described elsewhere herein where the AR2 ratios are determined and compared with respect to points H1 and H2 of the PCC eluting peak (as tracked based on LE scan data across scans), similar AR2 ratios may be determined for points H1 and H2 which are FWHM points determined with respect to the peak of the CE period rather than the PCC eluting peak. For example, the first CE period 1510a including X1 is a first peak or curve formed between points A, B and C. The FWHM points of the first CE period 1510a may be determined with respect to using scan X1 as the PP of the first CE period 1510a (such as illustrated in FIG. 16). These ratios too may be used as metrics for validating alignment of fragment ions.

For example, a first AR1 value may be determined for fragment ion F1 with respect to its parent precursor ion or PCC at a first scan S1 in a first CE cycle 1510a using a first collision energy CE1. A second AR1 value for F1 with respect to its parent ion or PCC may be determined in a corresponding scan S2 of the second CE cycle 1510b where scan S2 uses the same collision energy CE1 as in scan 1. It is expected that the both the foregoing AR1 values for F1 should be approximately.

Generally, the period of the CE cycle≤FWHM of PCC elution peak. In one embodiment in accordance with techniques herein, the H1 and H2 scan points used in determining AR2 ratios may be calculated based on the following interval:

$$\text{\# CEs or scans in a CE period}/3 = \text{interval} \quad \text{EQUATION INTERVAL}$$

where

"# CEs or scans in a CE period" is the number of CEs or EE scans in a single CE cycle or period.

For example, assume that scan X1 is scan 5 and that there are 10 CEs or 10 EE scans in each CE period (e.g., 10 CEs or scans in each of 1510a, 1510b and 1510c). Based on EQUATION INTERVAL above, the interval determined is 3⅓ which may be rounded to an integer value of 3. In this case, using scan 5 as the PP, the H1 and H2 points used for computing the AR2 values may be PP+3 scans (e.g., 5+3 denoting scan 8 as the point H2) and PP−3 scans (e.g., 5−3=2 denoting scan 2 as the point H1).

In an embodiment described herein, the AR2 values may be determined first between corresponding scans of two different CE cycles (e.g., scans from different collision energy cycles but both having the same collision energy) and also for the FWHM points in scans H1 and H2 of the CE period as follows:

$$\text{EQUATION B1}$$

$$AR2 = \text{UPSLOPE RATIO } U = \text{DOWNSLOPE RATIO } D$$
$$= Int(H1, \text{Precursor})/Int(H, \text{Precursor})$$
$$= Int(H2, \text{Precursor})/Int(H, \text{Precursor})$$

where
  Int (H, Precursor) is the intensity of PCC in the EE scan data of scan M where the PCC 50% yield rule holds in the CE peak;
  Int (H1, Precursor) is the intensity of PCC in the EE scan data of scan H1 on the upslope or LHS of the CE peak; and
  Int (H2, Precursor) is the intensity of PCC in the EE scan data of scan H2 on the downslope or RHS of the CE peak. It should be noted that the CE is approximately the same at both scans H1 and H2 of the same CE cycle.

As described elsewhere herein, processing may then examine the product or fragment ion scan data for scans H=M (=X1 in this example), and H1 and H2 determined with respect to M. Such processing includes matching fragment ions between cycles of similar collision energy and collision energy comparisons by m/z and intensity ratio.

A first set of matching fragment ions between scans H and H1 may be determined and a second set of matching fragment ions between scans H and H2. For example, fragment ion F1 in scan H is determined to match fragment ion F1" in scan H1 if:
  m/z of F1 matches m/z of F1", within some specified tolerance; and
  the intensity ratio IR calculated as:

IR=intensity of $F1''$ in scan $H1$/intensity of $F1$ in scan $H$ matches AR2 of its companion in the next collision energy cycle within some specified tolerance (e.g., matches AR2 as determined using EQUATION V3 for either fragment F1 or its originating PCC as determined with respect to scans of the next CE cycle corresponding to H and H1 (where a corresponding scan H" in the next CE cycle has the same CE as scan H and a corresponding scan H1" in the next CE cycle has the same CE as scan H1). It should be noted that the foregoing IR is another representation of the AR2 value and is also expected to be the same as the AR2 value as determined using EQUATION V3 for fragment F1's originating PCC with respect to scans H and H1.

In a similar manner, processing may be performed as described elsewhere herein to determine different AR2 values for different scan points of the curve or peak for each CE cycle using as the PP the scan at which the 50% PCC yield rule holds. Additionally, using as the PP the scan at which the 50% PCC yield rule holds, any other ratio described herein, such as the AR1 and AR3 ratios may be determined.

The foregoing additional AR1, AR2 and/or AR3 values may be used as additional validation criteria, along with other validation criteria as described herein, to validate the eluting PCC peak and also as validation criteria to filter or validate fragment ions associated with a particular PCC as also described herein.

As a variation to using the scan M at which the 50% PCC yield rule holds as the PP or H scan for determining various ratios, such as the AR1 and AR2 values, an embodiment may also use the scan of the CE cycle or peak in which the intensity of PCC in the EE scan data is at its minimum (with respect to all sets of EE scan data for all scans in the single CE period such as 1510a) thereby denoting the scan at which fragmentation of the PCC is maximum.

As a further variation to using the scan M at which the 50% PCC yield rule holds as the PP or H scan for determining AR2 values, an embodiment may more generally use the scan of the CE cycle or peak in which the intensity of PCC in the EE scan data is approximately 50% or less (with respect to all sets of EE scan data for all scans in the single CE period such as 1510a). More generally, an embodiment may select a threshold percentage which may be approximately 50% or less thereby denoting to select a scan for use as the H scan or PP in computing various ratios (e.g., AR1, AR2, etc. described herein) in which the intensity of the PCC in the EE scan data is approximately the threshold percentage or less (e.g., does not exceed the specified threshold percentage thereby denoting a threshold level or minimum level of fragmentation of the PCC).

An embodiment in accordance with techniques herein may also determine an ideal CE for the particular molecule having the eluting peak 1512. Such an ideal CE may be used to establish a CE for use in other experiments, such as for targeted data acquisitions to determine whether a sample includes the particular molecule having the eluting peak 1512. The following CE at which the 50% PCC yield rule holds may be used as the ideal CE for the particular PCC having eluting peak 1512. The ideal CE may be determined and stored as an average value across multiple experiments using non-supervised and/or supervised clustering. Similarly, an error indicator, such as CV, standard deviation, and the like, may be tracked for the ideal CE.

The foregoing may be characterized as a technique especially useful with small molecules. However, as will be appreciated by those skilled in the art, such techniques are not so restricted to use with small molecules but may generally be used with any molecule of any suitable size.

Figure 17:
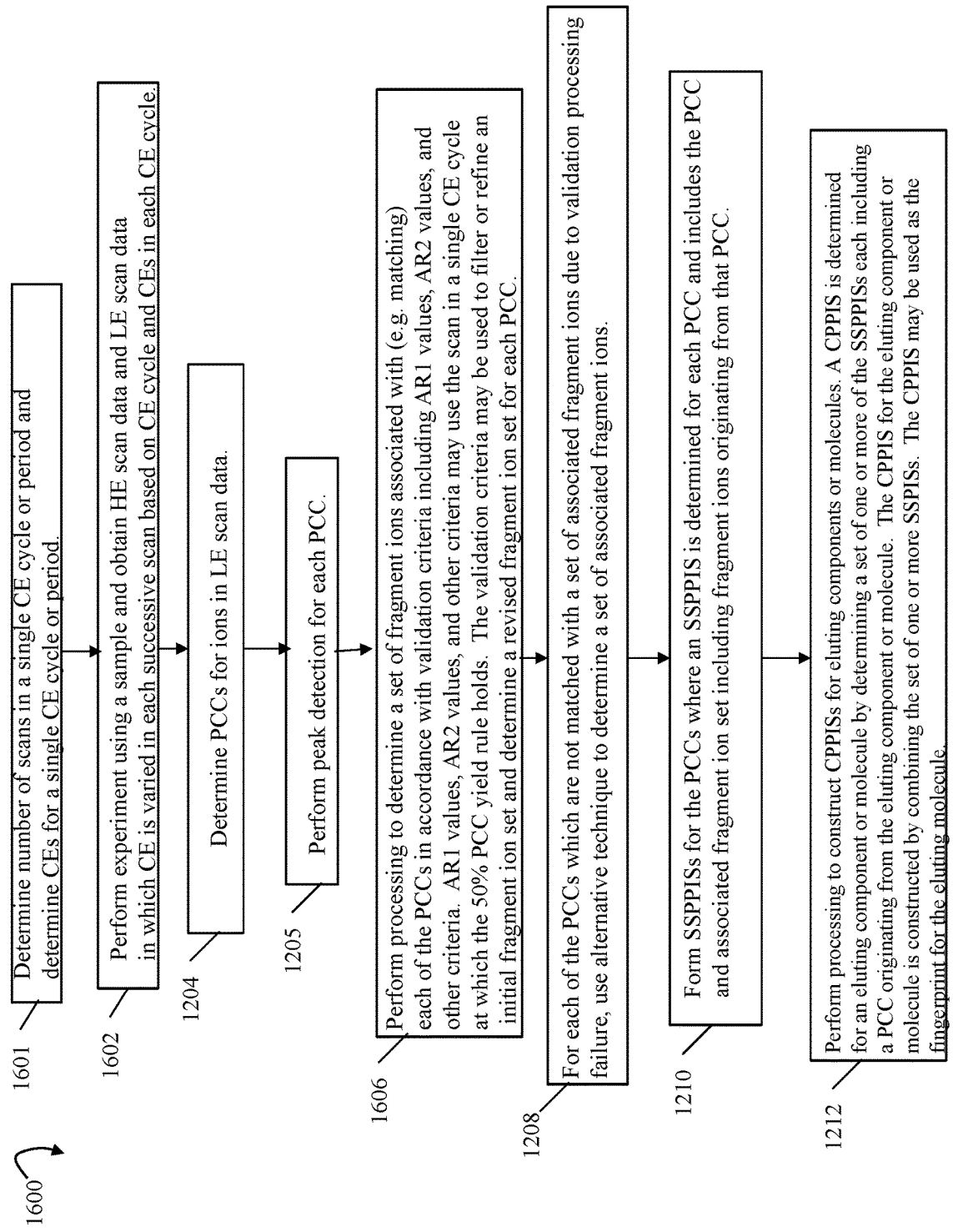

Referring to FIG. 17, shown is a flowchart 1600 summarizing processing described above that may be performed in an embodiment in accordance with techniques herein. In step 1601, the number of scans in a single CE cycle or period may be determined such as described elsewhere herein using EQUATION CE CYCLE. Additionally, the particular CE values or settings for each scan in a single CE cycle may be determined where, for each scan in the single CE cycle, the CE may be varied. The particular CEs included in a single CE cycle or period may be determined in any suitable manner some of which are described herein. For example, an embodiment may use a mathematical function to determine successive CE values in scans of the single CE period or cycle. Such CE values may, for example, form a wave or series of peaks denoting the different CE values cycled through over multiple CE cycles or periods. At step 1602, an experiment may be performed using a sample to obtain HE and LE scan data in which the CE is varied in each successive scan based on the CE cycle and CEs in each CE cycle. Processing may then be performed in step 1204 to determine PCCs for ions in the LE scan data and perform peak detection for each PCC in step 1205. Steps 1204 and 1205 of FIG. 17 are similar to those as described in connection with FIG. 9 for unsupervised clustering.

At step 1606, processing may be performed determine a set of fragment ions associated with (e.g. matching) each of the PCCs in accordance with validation criteria including AR1 values, AR2 values, and other criteria. The validation criteria may be used to filter or refine an initial fragment ion set and determine a revised fragment ion set for each PCC. Step 1606 processing is similar to step 1206 processing such as described in connection with FIGS. 9, 10 and 11 with the difference that such processing in step 1206 may be performed with respect to each CE scan cycle (rather than the PCC eluting peak). Additionally, the H scan or PP scan may differ and, rather than use the PCC eluting peak intensity apex as the H scan or PP (as in step 1206), step 1606 may use the scan in the single CE cycle or period at which the 50% PCC yield rule holds (or more generally where fragmentation of the PCC is at its maximum) as the alternate H scan or PP in computing AR2 and AR1 values. As also described herein, the 50% PC yield rule uses a 50% threshold level and step 1606 may be more generally performed using any suitable threshold level or threshold percentage. Steps 1208, 1210 and 1212 may then be performed and are similar to those described elsewhere herein such as in connection with FIG. 9.

Monoclonal antibodies are proteins that recognize foreign invaders, such as bacteria, in the body. Such monoclonal antibodies may be injected into the body, for example, for various therapeutic and medicinal purposes such as to cause the body's immune system to target a particular disease.

A source or host may manufacture or generate monoclonal antibodies that will recognize such foreign invaders. For example, a source or host may be an animal such as a rat, cow, and the like, which is used to generated the desired monoclonal antibodies. Processing may be performed to isolate or purify the monoclonal antibody and determine the fingerprint (e.g., precursor ions or PCCs and associated fragment ions for each) for the purified antibody (PA). Processing may be performed to verify or ensure that the PA as generated by the source or host is "pure" and does not include any other proteins (e.g., such as from the source or host), components or compounds other than the PA. Such processing may be performed to determine whether there are any host proteins in the PA. As known in the art, the FDA, for example, has restrictions and requirements on the PA in that the PA is "pure" and has been validated or verified as including only the PA and not including any host cell protein or other contaminants.

It should be noted that the amount or concentration of any contaminants, such as for the host cell protein, may be very small and thus the techniques utilized should be able to detect such very low concentration levels, such as at 0.1% concentration, of the contaminant proteins or other molecules besides the PA.

The PA may be a known protein for which a target library of peptides, associated fragment ions, and associated precursor and fragment ion information may be determined. In one embodiment, a simulator or modeling software may be used to predict, for the particular peptides of the protein, all the precursor ions and, for each precursor ion, associated fragment ions generated by fragmenting each such precursor ion. The foregoing is one way in which the target library for a protein, such as the PA, may be generated. More generally, an embodiment in accordance with techniques herein may use any suitable technique to obtain information used to populate the target library for the PA. In accordance with techniques herein, an embodiment may use the simulator to predict and generate the CCPISs for the PA used as targets for the supervised clustering.

Figure 18:
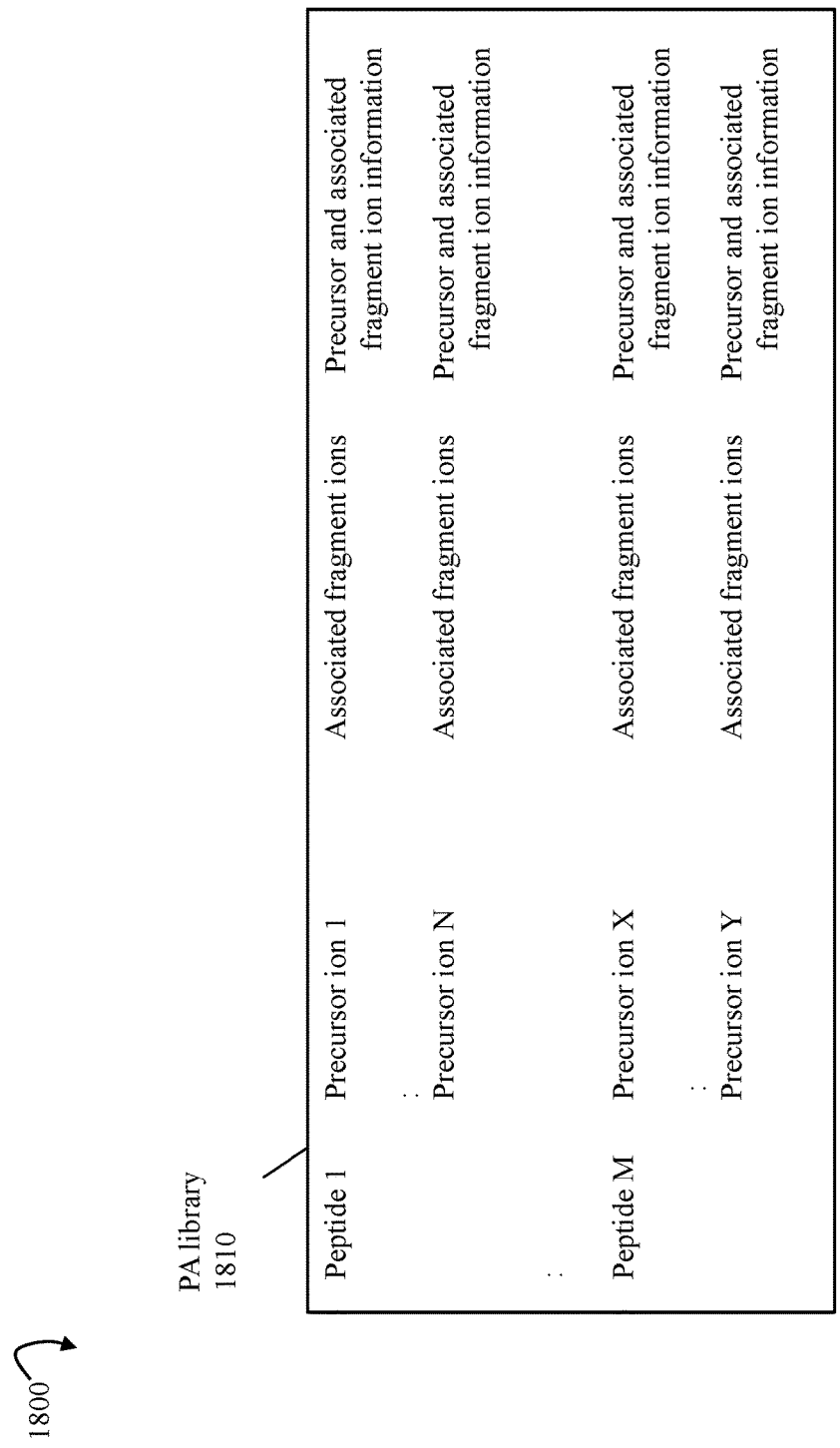
FIG. 18 is an example of information that may be included in a protein antibody (PA) used in an embodiment in accordance with techniques herein such as supervised clustering.

For example, as illustrated in FIG. 18, shown is an example representation of information that may be included in a library for a single PA which may include information, for example, for a hundred or more peptides denoted as peptide 1 through M. For each peptide, the library may identify a set of precursor ions and associated fragment ions. For example, for peptide 1, precursor ions 1 through N may be generated as a result of precursor ionization. Additionally, the library may identify, for each such precursor ion, the fragment ions generated as a result of fragmentation of such a precursor ion. For example, precursor ion 1 when fragmented generates a set of associated fragment ions. It should be noted that as described herein, each precursor ion in the library may correspond to a single PCC or may otherwise denote information for a single precursor as a combined set of one or more PCCs denoting different charge states for the same precursor ion. Additionally, the library may include ion information for the precursor and product ions, such as, for example, m/z of each ion, retention time, different intensity or area ratios for the ions (e.g., values for the AR1 and AR3 metrics), and the like.

Figure 19:
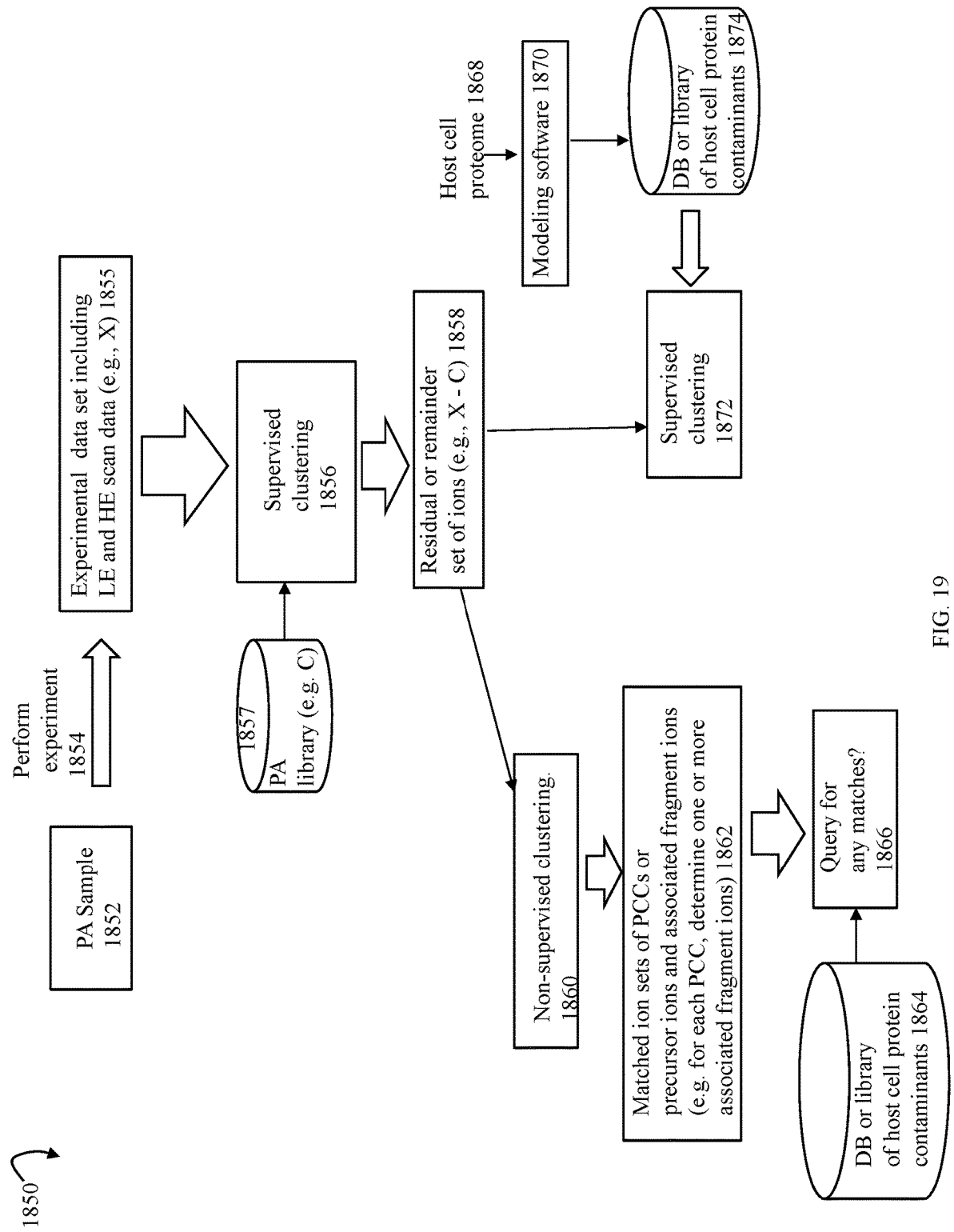
FIGS. 19, 21 22, and 26 are examples illustrating various workflows that may be performed in an embodiment in accordance with techniques herein.

With reference to FIG. 19, shown are example workflows that may be performed in an embodiment in accordance with techniques herein. An experiment 1854 may be performed on the sample 1852 including the PA to determine whether the PA is "pure" and includes only the PA. Such processing may determine whether the sample under analysis includes any host cell protein contaminant or other contaminants. As described herein and known in the art, the experiment 1854 may include performing protein digestion and LC/MS or LC/IMS/MS analysis. LE and HE scan data 1855 may be obtained for the experiment which may be further processed using the supervised clustering techniques 1856 described herein with the library for the PA protein 1857 used as the supervised clustering target library. For example, such processing denoted by 1856 may be performed using the supervised clustering as described in FIG. 14A where the matched ions are digitally removed from further consideration.

Such processing denoted by 1856 may including performing supervised clustering and generating a residual or remainder set of unmatched ions 1858. As described elsewhere herein, the residual or remainder set of unmatched ions 1858 may include unmatched precursor ions or PCCs and unmatched fragment ions that were determined not to be matched to information in the PA library 1857.

At this point, subsequent processing may use one of two alternative workflows. A first subsequent processing workflow includes processing denoted by 1860, 1862, 1864 and 1866 described in more detail below. A second subsequent processing workflow includes processing denoted by 1870, 1872 and 1874.

In connection with the first subsequent processing workflow, the residual or remainder set of unmatched ions 1858 may be input for processing by non-supervised clustering 1860. As an output, non-supervised clustering 1860 may determine output 1862 including matched ion sets of PCCs or precursor ions and associated fragment ions. For each PCC in 1858, non-supervised clustering 1860 may determine a set of one or more associated or matched fragment ions as included in the output 1862. The matched ion sets 1862 may then be queried 1866 against a third party DB or library of host cell protein contaminants 1864 (e.g., search the matched ion sets 1862 to determine whether any matched set of precursor ion and associated fragment ions match any of those in the DB or library 1864 to thereby identify that the matched ion sets 1862 include a host cell protein contaminant.

In connection with the second subsequent processing workflow, the host cell proteome 1868 may be input to modeling software 1870 in a manner as described elsewhere herein to generate a DB or library of host cell protein contaminants 1874 (e.g. including information such as in FIG. 18, FIG. 12, and the like). The residual or remainder set of unmatched ions 1858 may be input for processing by supervised clustering 1872 using the DB or library of host cell protein contaminants as the target library. In this manner, supervised clustering 1872 may be used to identify whether a sufficient number of matches are made between unmatched ions of the residual set 1858 and the DB or library of host cell protein contaminants to identify or confirm that the residual 1858 identifies any host cell protein contaminant.

Figure 20:
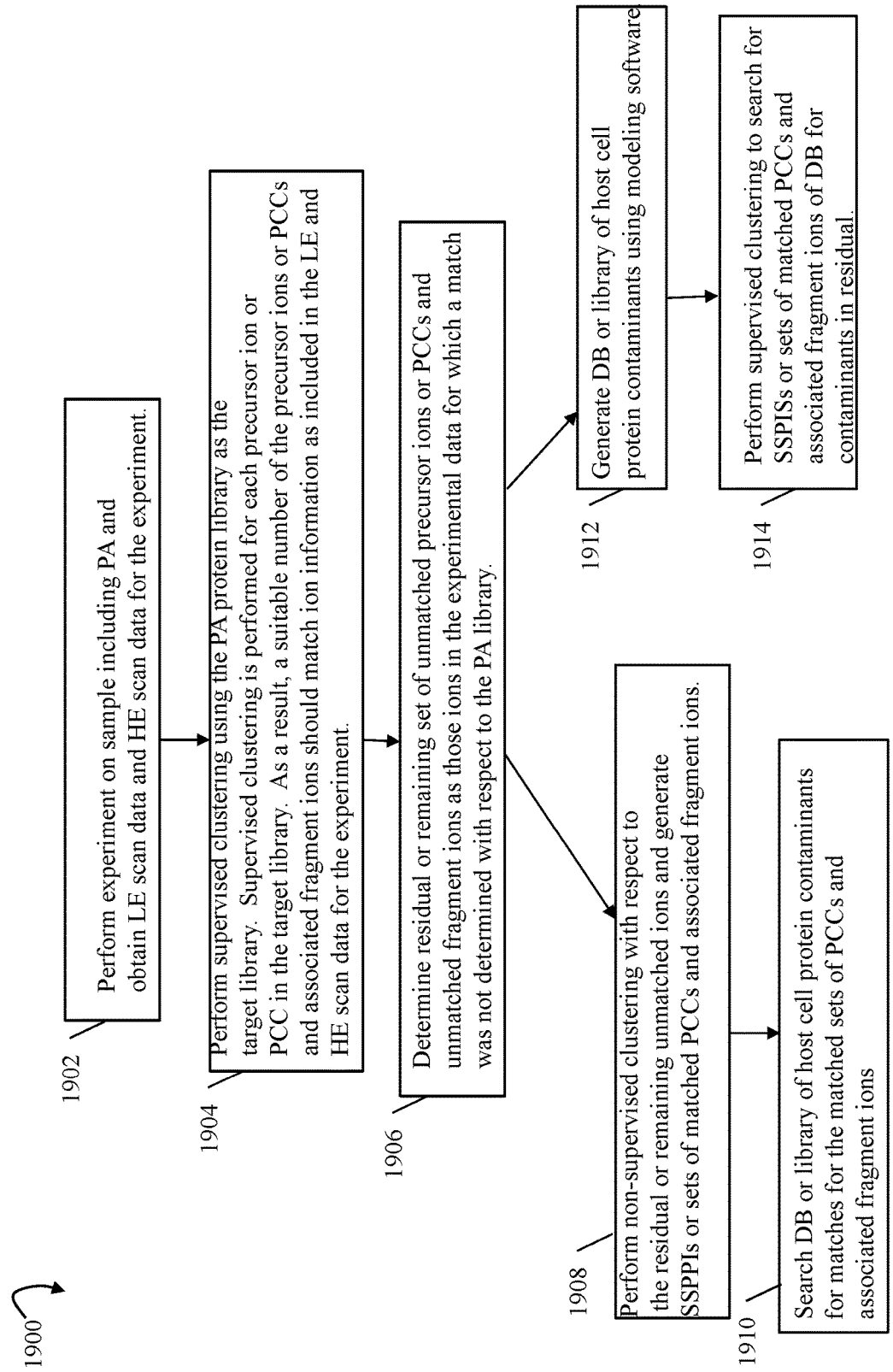

Referring to FIG. 20, shown is a flowchart of processing steps that may be performed in an embodiment in accordance with techniques herein. The flowchart 1900 summarizes processing as described above and in connection with FIG. 19. At step 1902, an experiment may be performed on the sample including the PA to obtain LE can data and HE scan data for the experiment. In step 1904, supervised clustering may be performed using the experimental data and using the PA protein library as the target library. Consistent with description elsewhere herein, the supervised clustering in step 1904 may be performed for each precursor ion or PCC in the target library to determine whether there is match in the LE scan data and, for each such matched PCC, whether the HE scan data includes any fragment ions for the PCC as identified in the target library. As a result, a suitable number of the precursor ions or PCCs and associated fragment ions for the PA of the library should match ion information as included in the LE and HE scan data for the experiment. At step 1906, processing may be performed to determine the residual or remaining set of unmatched precursor ions or PCC and unmatched fragment ions as those ions in the experimental data for which a matches was not determined in step 1904 with respect to the PA library. From step 1906, an embodiment may alternatively proceed to perform steps 1908 and 1910 forming the first subsequent workflow or may proceed to perform steps 1912 and 1914 forming the second subsequent workflow.

As a first alternative, processing may proceed from step 1906 to step 1908 to perform non-supervised clustering with respect to the residual or remaining unmatched ions from step 1906 to generate SSPPISs or sets of matched PCCs and associated fragment ions. Processing proceeds to step 1910 to search a DB or library of host cell protein contaminants for matches between the library and matched sets of PCCs and associated fragment ions (as determined by step 1908 processing). The DB or library used in step 1910 may be, for example, a third party provided library.

As a second alternative, processing may proceed from step 1906 to step 1912. In step 1912, processing may be performed to generate a DB or library of host cell protein contaminants such as using modeling software as described herein. In step 1914, supervised clustering may then be performed to search for SSPPISs or sets of matched PCCs and associated fragment ions of the DB or library (generated in step 1912) in the residual set (generated in step 1906).

Figure 21:
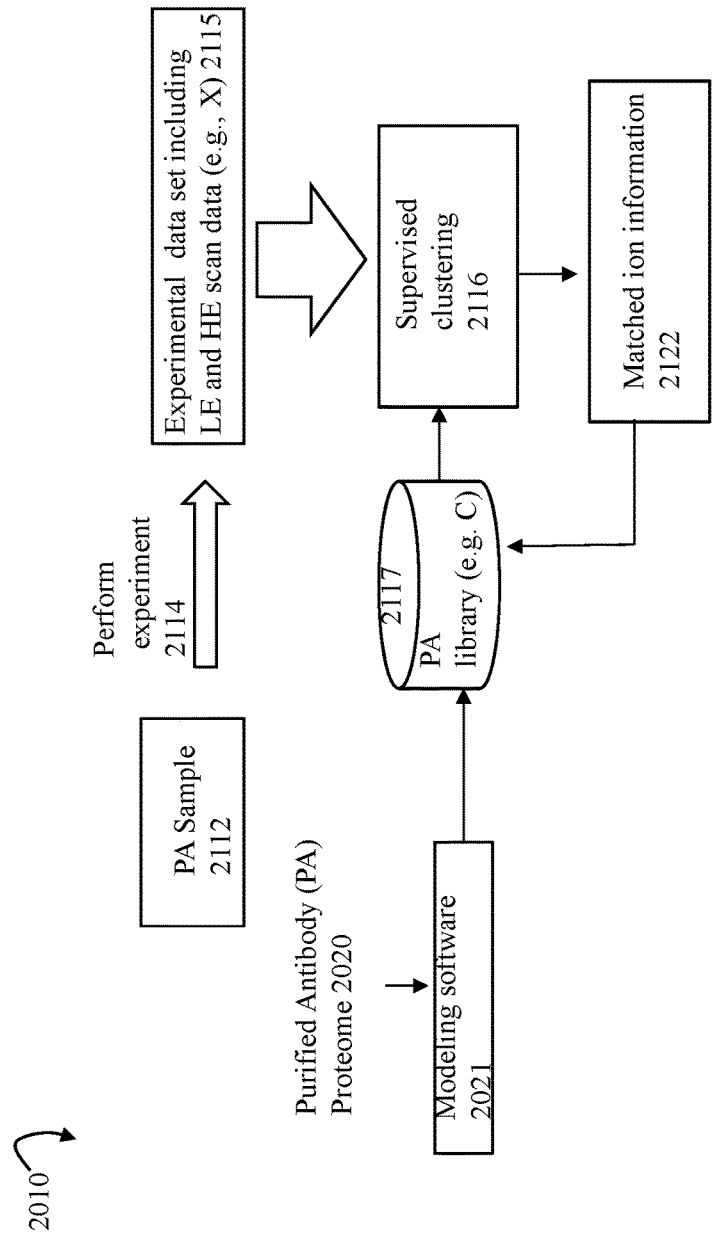

Referring to FIG. 21, shown is an example 2101 of processing that may be performed in an embodiment in accordance with techniques herein to generate a target library for a particular purified antibody (PA). The PA library 2117 may be used in connection with other techniques described herein, such as in connection with validating a sample for the presence of a particular protein or molecule. The PA library 2117 may also be used in connection with detecting and/or identifying variants, anomalies, contaminants, and the like in a sample. For example, as described herein, the PA library may be used in connection with analysis of a sample for detecting any of precursor variants or modifications, disulfide bonded peptides, antibody drug conjugates (ADCs) and host cell protein contaminants.

Thus, FIG. 21 illustrates one way in which a PA library may be generated for subsequent use as a target library in connection with performing supervised clustering in an embodiment in accordance with techniques herein.

As a first part of processing, the PA library 2117 may initially populated with theoretical data. In one embodiment, modeling software 2021, such as the simulator or simulation software mentioned elsewhere herein, may be provided with the PA proteome 2020 as an input. As an output, the modeling software 2021 generates a theoretical peptide map for the PA. The peptide map may include the peptides and associated ions for the PA. For example, the peptide map may include the precursor ions or PCCs and, for each such PCC, associated fragment ions generated through fragmentation of the PCC, and the like. The theoretically generated peptide map produced by the modeling software 2021 may be used to initially populate the PA library 2117 with peptide and fragment ion information of the PA. It should be noted that the peptide map used to populate the PA library 2117 includes ion information for the PA where all cysteines are modified so that there are no disulfides. The target PA library contains all theoretical "in-silico" CPPISs of all target peptides.

After initially populating the library 2117 with the theoretical peptide map, an experiment 2114 may be performed on the sample 2112 which is known to include the PA. As described herein and known in the art, the experiment 2114 may include performing protein digestion and LC/MS or LC/IMS/MS analysis. In this experiment, sample preparation includes performing reduction and alkylation whereby all cysteines in the sample are modified so that there are no disulfides (e.g. only tryptic peptides). LE and HE scan data 2115 may be obtained for the experiment 2114. The LE and HE scan data 2115 may be further processed using the supervised clustering techniques 2116 described herein with the library for the PA protein 2117 used as the supervised clustering target library. For example, such processing denoted by 2106 may be performed using the supervised clustering as described in FIG. 14A. As noted above, the information in the library 2117 includes ion information for the PA where all cysteines are modified so that there are no disulfides. If the sample is prepared as described in 2114 such that the cysteines are modified and there are no disulfides in the analyzed sample, then all peptides in the library 2117, including those that contain cysteine, should be matched to corresponding ion information in the experimental data set 2115. As an output, supervised clustering 2116 may generate matched ion information 2122 which may be used to update the PA library 2117. As described herein, the supervised clustering 2116 looks for the presence of each target precursor ion or PCC of the target PA library 2117 in the LE scan data of 2115. For each such matched target precursor ion or PCC, the associated target fragment ions for the matched target precursor are then retrieved from the library 2117 and used in connection with further processing to determine which of the target fragment ions of that precursor are present in the experimental data. Thus, at the end of supervised clustering 2116, the matched ion information 2112 may identify each target PCC or precursor ion of the library 2117 matched in the LE scan data of the experimental data set 2115, and, for each such matched PCC or precursor ion, an associated fragment ion set of fragment ions originating from the matched PCC or precursor ion. It should be noted that the associated fragment ion set generated as a result of supervised clustering identifies those fragment ions of the PA library 2117 determined by supervised clustering 2116 to be associated with the matched PCC or precursor ion in the experimental data set 2115. For example, the library 2117 may include 15 fragment ions for a matched target PCC or precursor ion. However, supervised clustering may determine that only 10 of those 15 fragment ions are associated with the matched target PCC or precursor ion in the actual experimental data set 2115.

Thus, after completing the supervised clustering 2116, the matched ion information 2112 may be used to update or repopulate the PA library 2117 (e.g., thereby replacing the theoretical or simulated ion information of 2117 with matched ion information 2112 based on actual real experimental data 2115). For example, reference is made back to FIG. 14A and associated description herein where the PA library 2117 may be initially populated with theoretical data and used in connection with supervised clustering 2116. For each PCC or precursor ion of the experimental data set 2115 matching a PCC or precursor ion in the library 2117, the theoretical ion information in the library 2117 for the PCC and its associated fragment ions may be replaced with, or updated to include, the ion information as obtained from the experimental data set. Additionally, for processing now being described, an embodiment may use the ion information as included in the experimental data set for the matched PCCs or precursors and associated fragment ions.

What will now be described are techniques that may be performed in connection with identification of precursor variants or modifications.

In the context of description here, a "variant" may be considered a single point mutation of a peptide associated with a purified antibody or therapeutic. In a broader sense techniques herein may be more generally applied and used with a "variant" that is any modified form of a peptide. Common modifications include but are not limited to oxidations (M, W), methylations (K, R), acetylations (K, R), labels (SILAC), linkers, likers with cytotoxic agents (e.g., ADC), glycans, phosphates, and the like. Keeping with the relationship between a precursor and its product ions, a peptide's fragmentation pattern up to the point of the variant/modification is nearly identical. The influence a variant/modification has on the physicochemical attributes of retention time and, if IMS is employed, drift time or cross sectional area (CCSA2) is a function of the length of the peptide. There are certain chemical modifications that are exceptions. For example, in connection with an ADC, the linker and its cytotoxic agent are very hydrophobic and have significant effect on the peptide's retention time.

Provided there are a statistically significant number of matched product ions in an initial validation or screening (the presence of a precursor ion match is not a necessity), a modified/variant form of the peptide can be accurately identified. Processing as described herein in more detail below recognizes the absence of the precursor ion in the matched SSPPIS and triggers additional processing whereby the Δ m/z between the precursor ion in the matched SSPPIS (there is only one) and the target m/z is computed and compared to a lookup table of known variants/modifications. If a match is found, the product ion spectra of the modified/variant is generated and compared to all SSPPISs within the precursor's peak envelope for validation of the identification and inclusion in the creation of a new CPPIS (variant). The success of this approach is a function of the position of the modification/variant in the peptide's linear string of amino acids and its fragmentation pattern. To clarify, if the Δ m/z is a modification or a point mutant (variant) of the second amino acid residue off the c-terminus, and 90% of the product ions generated by fragmentation (e.g. collision disassociation) are y" ions, then all of the y" ions from y"2 thru y" max of the modified/variant will carry the Δ m/z. As such these product ions cannot be matched in validation processing. On the other hand, if a sufficient number of b ions were generated during fragmentation and a statistically significant number of them matched, the modified/variant form of the peptide would have been identified.

If no variants are identified in a first pass based on Δ m/z with respect to precursor ions, processing may be further performed using a lookup table of Δm/z values reflecting the exact mass difference of all possible amino acid swaps (single point mutation). The Δm/z, Δ time and Δ drift time (if IMS is utilized) may be added to the extracted product ions. These product ions are then screened against all SSPPISs within the user-defined match tolerances in m/z, retention and drift times. A match is found if the Δm/z of the precursor is consistent with the Δm/z of the product ions and a variant CPPIS is created. When a variant is found the product ions identified may give insight into the position of the modified/variant in the sequence. As mentioned above, product ion m/z values are consistent up to the point of the modification. The product ion m/z value illustrating the first incorporation of the Δm/z tells the algorithm the general location of the variant amino acid. Once a tentative identification is made the product ions for all the possible sites of the variant are generated and compared to the other product ions residing in the matched SSPPISs. At this point, processing may attempt to identify the exact position of a modification or variant. Similar to the positional limitations previously described, Na+ and K+ adducts significantly alter the m/z values of either or both of the common fragment ion types (b, y"). If the sodiated or potassiated charge is localized at the c-terminus, fragmentation produced y" ions will include the Δm/z of the sodiation or potassiation (restricting them from matching to the unmodified peptide). The same is true for the n-terminus, replacing the y" ions with their complement b ions. Na+ and K+ adduct formation happens in the gas phase. As such the Na+ and K+ adducts of a peptide will have the identical retention time and drift time. With this being the case, processing searches for Na+ and K+ adducts, the Δm/z's may be added to the lookup table previously mentioned so that such modifications may be identified as one of the modified/variant forms of a target peptide. An embodiment in accordance with techniques herein may report any possible variant regardless of whether there is convincing product ion data to support its identification.

A distinct advantage of techniques herein is an indifference to the presence of the PCC in the screened SSPPIS. Though the identification of a primary peptide is enhanced by the presence of its parent molecule, it is not necessary. Processing described herein may be used to identify a modified/variant form of a precursor predicated solely on matching a statistically significant number of product ions, including their isotopes with their target CPPIS.

Figure 22:
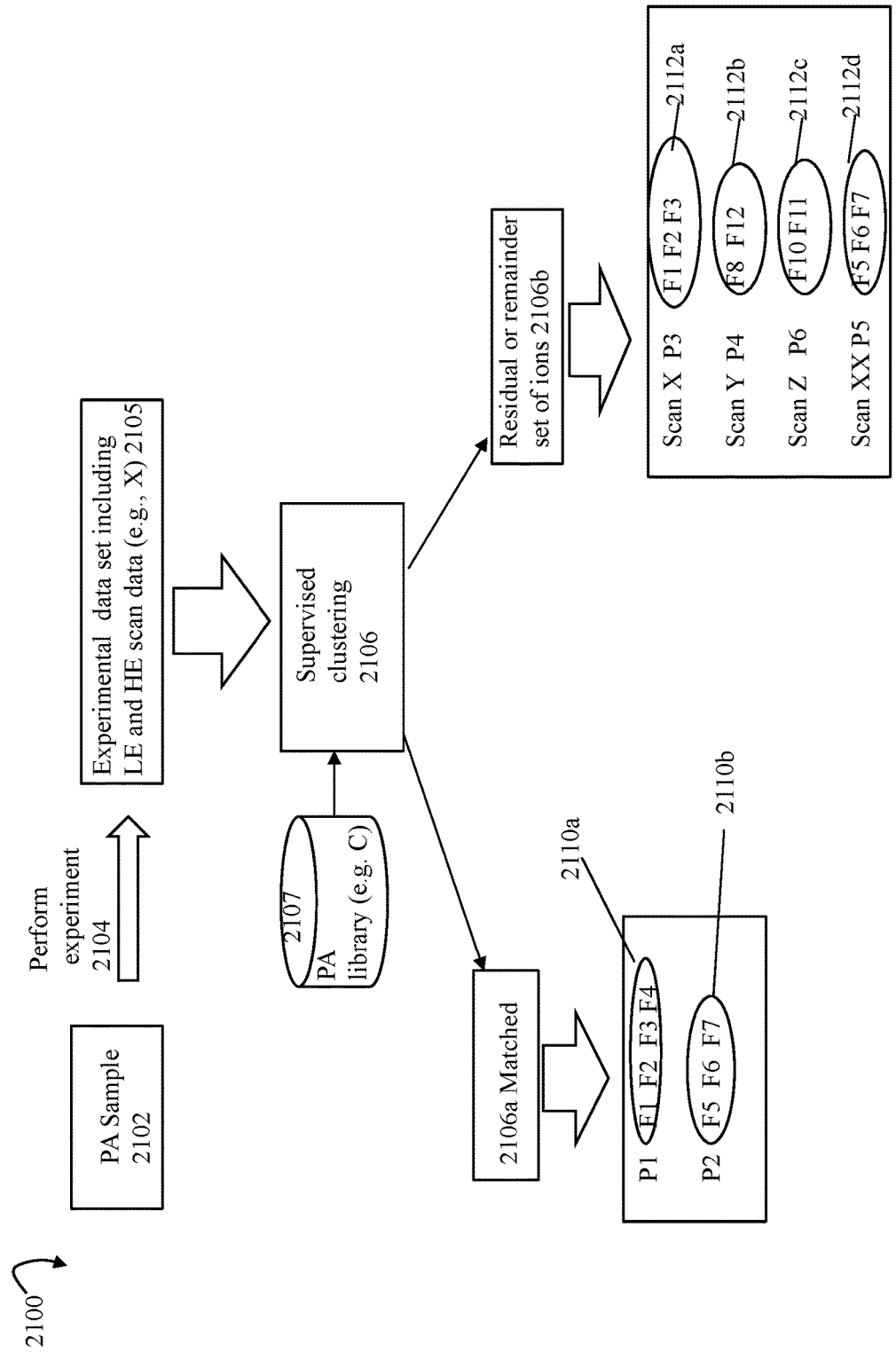

As a first part of processing in connection with techniques herein for detection and/or identification of a precursor variant or modification, steps may be performed to first validate the presence of the PA in the sample. With reference to FIG. 22, shown are example workflows that may be performed in an embodiment in accordance with techniques herein. An experiment 2104 may be performed on the sample 2102 including the PA to determine whether the sample 2102 does indeed include the PA. As described herein and known in the art, the experiment 2104 may include performing protein digestion and LC/MS or LC/IMS/MS analysis. In this experiment, sample preparation includes performing reduction and alkylation whereby all cysteines in the sample are modified so that there are no disulfides (e.g. only tryptic peptides). LE and HE scan data 2105 may be obtained for the experiment 2104. The LE and HE scan data 2105 may be further processed using the supervised clustering techniques 2106 described herein with the library for the PA protein 2107 used as the supervised clustering target library. For example, such processing denoted by 2106 may be performed using the supervised clustering as described in FIG. 14A. As described herein the PA library 2107 may be generated using any suitable technique and include the precursor ions or PCCs and, for each such PCC, associated fragment ions generated through fragmentation of the PCC (e.g., PA library 2107 includes CPPISs of precursor and related product ions for the PA). For example, the PA library 2107 may be generated to include information as described in connection with processing of FIG. 21. The information in the library 2107 includes ion information for the PA. If the sample is prepared as described in 2104, then all peptides in the library 2107 should be matched to corresponding ion information in the experimental data set 2105. Thus, in one embodiment, the presence of the PA in the sample 2102 may be validated by matching all peptides in the library 2107 to ion information in the experimental data set as a result of performing supervised clustering 2106. As an alternative the presence of the PA in the sample 2102 may be validated by matching at least a specified number of peptides in the library 2107 to ion information in the experimental data set as a result of performing supervised clustering 2106. The foregoing first part of processing may also be referred to as peptide mapping which is an identity test for proteins including the chemical or enzymatic treatment of a protein resulting in the formation of peptide fragments followed by separation and identification of the fragments in a reproducible manner.

As a result of performing supervised clustering in 2106, a first set of information 2106a may be obtained identifying those precursor ions or PCCs and associated fragment ions (e.g., CPPISs) of the library 2107 that were matched to corresponding ion information in the experimental data set 2105. Additionally, as a result of 2106 processing, a second set of information 2106b may be obtained denoting the residual or remainder set of unmatched ions (e.g., unmatched PCCs and unmatched fragment ions). The residual or remainder set of unmatched ions 2106b may include sets of ions in each scan not matched to a PCC or precursor of the library.

Thus, element 2106a denotes those peptides of the PA which were identified or matched to corresponding ion information in the experimental data set (e.g. element 2106a denotes the matched targets of the PA library (e.g. those PCCs or precursor ions of the library which were matched to ion information in the experimental data set)). From the matched PCC or precursor targets of the PA library as identified in 2106a, we now have the product ion spectra (e.g. CPPIS) of each such matched PCC or precursor ion whereby the product ion spectra denotes the fragment ions originating from the associated PCC or precursor ion. Additionally, ion information, such as AR1 values, AR2 values, and the like, for the matched PCC and associated fragment ions in 2106a may be as included in the experimental data set 2105.

At this point, processing may be performed to search the residual or remainder set of unmatched ions 2106b for the fragment ions of the matched PCC or precursor ion targets of 2106a. The fragment ion information for the fragment ions matched may be as included in the experimental data. For example, the library 2107 may include a PCC or precursor ion P1 and indicate that there are 20 fragment ions associated with (e.g., generated via fragmentation of) P1. When performing supervised clustering 2106, target P1 of the library may be matched to a corresponding P1 in the experimental data set. Additionally, the experimental data set 2105 may include only 5 fragments associated with P1. In one embodiment in accordance with techniques herein with supervised clustering, the library 2107 may be updated to replace the 20 fragment ions with the 5 fragment ions and corresponding fragment ion information of the experimental data set. Additionally, the information in the matched ion information 2106a for P1 may include the fragment ion set of 5 fragment ions and associated ion information as in the experimental data set.

With reference to FIG. 22, included in the matched ion set 2106a are rows of ion information. Each row of 2106a may identify a matched PCC or precursor ion that was matched in supervised clustering 2106 to a corresponding PCC or precursor ion of the library 2107. Each row of 2106a may include a fragment ion set of fragment ions which are identified in the experimental data set as being associated with a matched PCC or precursor ion included in the same row. Consistent with this example and others herein, a PCC or precursor ion may be denoted Pi, where "i" is an integer, and a product or fragment ion may be denoted Fi. For example, 2106a includes a first row with P1 that was matched to a corresponding PCC or precursor ion of the library 2107. In the experimental data set 2105, P1 has been determined (via supervised clustering 2106) to be associated with fragment ion set 2110a. 2106a includes a second row with P2 that was matched to a corresponding PCC or precursor ion of the library 2107. In the experimental data set 2105, P2 has been determined (via supervised clustering 2106) to be associated with fragment ion set 2110b.

For a fragment ion set in the matched ion information 2106a, the fragment ion set denotes a set of associated or related fragment ions that have been determined as all originating from the same precursor ion or PCC where the PCC or precursor ion has been matched to a corresponding PCC or precursor ion of the library 2107.

The residual or remainder set of ions 2106b in the example 2100 may include a row for ions of each scan not matched to a target of the library 2107 as part of supervised clustering 2106. For example, 2106b includes a first row for ions from scan X which includes P3 and F1-3, a second row of ions from scan Y which includes P4 and F8-12, a third row of ions from scan Z which includes P6 and F10-11 and a fourth row of ions from scan XX which includes P5 and F5-7. In one embodiment in accordance with techniques herein, each row of 2106b may correspond to an SSPPIS generated from supervised clustering but which has not been matched to a corresponding PCC or precursor ion of the library 2107.

An embodiment may further filter the fragment ion sets 2110a-b of 2106a. For example, in each fragment ion set 2110a-b processing may filter the fragment ions to only utilize those meeting a minimum intensity threshold. In one embodiment, for each fragment ion set 2110a-b, the threshold denoting the minimum intensity may be ⅓ the intensity of the fragment ion in the set having the maximum intensity. For example, assume F4 of 2110a has the maximum intensity MX of all fragment ions in 2110a. In this case, fragment ions of 2110a may be filtered to exclude from further processing any fragment ion of 2110a not having an intensity at least MX/3.

Similar filtering may be performed for each of the fragment ion sets of 2106a. In this example, assume that all illustrated fragment ions of 2110a and 2110b meeting such filtering criteria based on a minimum threshold intensity determined with respect to the maximum fragment ion intensity in each fragment ion set.

Processing may be performed to search sets of fragment ions 2112a-d of the residual 2106b to determine whether any fragment ion set of the residual 2106b includes a threshold number of fragment ions that match one of the fragment ion sets 2110a-b of 2106a. Generally, such matching between fragment ion sets of the matched ion information 2106a and the residual 2106b may be performed using matching criteria including matching fragment m/z (within a specified tolerance), matching fragment ion intensity ratios, and determining a minimum threshold number of fragment ion matches meeting the matching m/z and matching fragment ion intensity ratio criteria. This is explained in more detail below.

For example, a first fragment ion set 2110a of the matched ion information 2106a is retrieved and compared to each fragment ion set 2112a-d of the residual 2106b to determine whether there is at least a threshold number of matching fragments there between meeting the matching m/z and matching fragment ion intensity ratio criteria. The first fragment ion set 2110a is compared to fragment ion set 2112a to determine a number of matching fragments between the two sets. Such matching may look for matching fragments having the same m/z, within some specified tolerance. In this example with respect to 2110a and 2112a, assume that F1-F3 in both sets have matching m/z values.

Additionally, the fragment ion intensity ratio criteria must be met between the sets 2110a and 2112a. For a fragment ion set such as 2110a, a fragment ion intensity ratio (FII) may be determined for each fragment ion Fn thereof with respect to the maximum intensity of any fragment in the same fragment ion set. Formally, this may be represented as:

FII $Fn$=Intensity($Fn$)/MAX fragment intensity where
Fn denotes the fragment ion of a fragment ion set for which the FII is being determined; and
MAX fragment intensity denotes the maximum fragment ion intensity of all fragment ions in the same fragment ion set as Fn (e.g., where the fragment ion set is either from 2106a or 2106b).

To further illustrate, consider fragment ion set 2110a where it has been determined thus far that F1-F3 of 2110a having matching m/z values for F1-F3 of 2112a whereby the resulting fragment ion set thus far includes F1-F3 where F3 has the maximum intensity of F1-F3. Consistent with description elsewhere herein, processing may be performed to determine a first FII for F1 in 2110a and a second FII for F1 in 2112b and then compare the foregoing first FII and second FII to determine with the foregoing first FII and second FII match, within some specified tolerance. If not, then the fragment ion F1 is removed from the resulting ion fragment set and processing may continue. The foregoing processing of determining and comparing FIIs may be repeated for each Fi in the resulting fragment ion set.

At this point in processing, assume the resulting fragment ion set includes F1-F3 where it has been determined that F1-F3 in 2110a and 2112a have met the matching m/z and matching fragment ion intensity ratio criteria. Processing may now be performed to determine whether the resulting fragment ion set includes at least a minimum threshold number of fragment ions. For example, in one embodiment, the minimum threshold number of fragment ions may be expressed as N/2, rounded upward to the next integer value, where N may be the number of fragment ions in the set 2110a. If the resulting fragment ion set does include the minimum threshold number of fragment ions, then processing may determine that all matching criteria are met whereby 2110a and 2112a are determined as matching fragment ion sets in accordance with the matching criteria. Additionally, the resulting fragment ion set identifies the portion of the fragment ion set 2110a matching fragment ions from 2112a. Otherwise, if the resulting fragment ion set does not include the minimum threshold number of fragment ions, then processing may determine that 2110a and 2112a are not matching fragment ion sets.

Continuing with the above example, it may be determined that F1, F2 and F3 form the resulting matching fragment ion set denoting the fragment ions of 2112a that match fragment ions of 2110a. It should be noted that if comparison between 2110a and 2112a did not result in matching a threshold number of fragment ions meeting the matching criteria of matching m/z's and matching fragment ion intensity ratios, processing may continue by comparing fragment ions of 2110a to 2112b, 2110a to 2112c and 2110a to 2112d to determine whether any of 2212b-d is a matching for 2110a. Similar processing may also be performed with respect to each set of fragment ions of 2106a (e.g., compare 2110b to each of 2112a, 2112b, 2112c, and 2112d).

Continuing with the above example, it has been determined that F1, F2 and F3 form the resulting matching fragment ion set identifying the fragment ions of 2112a that match fragment ions of 2110a. Based on such a match, processing determines that there has been a modification or variant. Now processing may be performed to determine the particular modification or variant to an original molecule (e.g., original PCC or precursor). At this point processing may be performed to determine the delta mass (A mass) of the precursor or PCC modification by calculating the difference between m/z values of the two PCC or precursor ions associated with 2110a and 2112a. In connection with 2112a, it should be noted that P3 may appear in the same scan X as the fragment ion set 2112a in this example where the LE and HE scan data may be generated, for example using the Bateman technique and the high-low protocol (described elsewhere herein). More generally, depending on how the LE and HE scan data are obtained, the precursor P3 may be a precursor ion having its associated fragment ions in the scan denoted by scan X. It should also be noted that although only a single precursor ion P3 is illustrated as being unmatched and also having its fragment ions in scan X, more than one precursor ion may be so associated with the single scan X (e.g. multiple precursor ions may have their fragment ions in scan X).

In this example, a delta mass is determined as the absolute value of the difference between a first m/z of P1 (in 2110a) and a second m/z of P3 (in 2112a). More generally, the mass difference MD between a first ion IX and a second ion IY may be expressed as:

MD=ABS($Ix$ m/z-$Iy$ m/z)

where
Ix m/z denotes the m/z of Ix;
Iy m/z denotes the m/z of Iy; and
ABS denotes the mathematical absolute value of the difference.

The MD may be determined with respect to two precursor ions or PCCs such as P1 and P3 in this example (P1=Ix and P3=Iy) representing the m/z difference of the modification to the molecule or precursor. An embodiment in accordance with techniques herein may utilize a lookup table or structure indexed by different values for MDs each denoting a different precursor modification as indicated by the table. For example, an embodiment may use a table of modifications or variants known to molecules such as available through Unimod.org.

Reference is now made to FIG. 23 to further illustrate an example of a table 2210 that may be used in an embodiment in accordance with techniques herein. The table 2210 is an example of a precursor delta-mass modification table where column 2212 include the m/z differences of known modifications that may be of interest. A value for MD may be determined and used as an index into the table 2210 by searching for a matching value in column 2212 (matching within a specified tolerance). If a calculated MD value matches a value in column 2212, then the row of the table 2210 may be retrieved to obtain information regarding the corresponding precursor modification. Element 2220 may denote the monoisotopic masses utilized in determining the m/z differences in the last column of table 2210.

It should be noted that the table 2210 of precursor modification or variants may vary with those of interest in a particular embodiment in accordance with techniques herein.

If a match is found for a calculated MD value and an entry in the table, then it is determined that there has been a modification or variant of a precursor as denoted by the matched table entry.

Processing may be performed to determine the m/z values for the fragments of the modified precursor corresponding to the precursor modification or variant denoted by the matching table entry of 2210. An embodiment may use a simulator, for example, to compute the fragment masses or m/z values for the modification suggested by the matching entry of the table (e.g., suggested by the delta mass or MD match).

For example, with reference back to FIG. 22 and the above example, assume the match is made between 2112a and 2110a as described above and the MD calculated for such matching fragment ion sets matches an entry in the table 2210 thereby denoting that the MD corresponds to a precursor modification or variant. As noted above, the matched ion information 2106a indicates that P1 is the PCC or precursor ion matched to a corresponding precursor or PCC in the library 2107. In this example, P1 may be determined as the original PCC or precursor ion which is modified and the particular precursor modification or variant of P1 may be denoted by P3 (e.g., P3 is the modified version or variant of P1 denoted by the matching table entry of 2210 based on the calculated MD with respect to P3 and P1).

At this point, the simulator or modeling software may be used to determine, or calculate theoretically, the expected fragment ions and associated fragment ion m/z values for the particular precursor modification or variant suggested by the matching table entry. Assume the simulator determines that the set of fragment ions for the modification to P1 as denoted by the matching table entry or based on the calculated MD value is F1 F2" F3" F4 (where the simulator determines m/z values, along with possibly other information, for each of the fragment ions F1 F2" F3" and F4). Let F1 F2" F3" and F4 form the calculated fragment ion set of the precursor modification or variant for purposes of illustration in following paragraphs.

Processing may now be performed to validate the precursor modification or variant as suggested by the calculated MD value or mass difference. Such processing may include searching for the one or more of the fragment ions for the precursor variant in the residual 2106b. More specifically, such processing may search for one or more of the modified fragments (e.g., F2" F3" F4") of the calculated fragment ion set of the precursor modification in a scan of the eluting peak for the PCC of the precursor variant P3 (e.g., FIG. 7 illustrates scans of an eluting peak for a PCC).

For example, with reference back to FIG. 22, assume the residual 2106b also includes another row for scan YY as follows:

Scan YY P3 F1 F2" F3"

denoting another scan YY in which the precursor ion or PCC P3 appears with a different set of associated fragments F1 F2" and F3". Such processing to validate the precursor modification or variant may search the residual 2106b for another scan besides scan X in which the modified precursor ion or PCC, denoted by P3, appears. In this case, P3 appears in the additional scan YY where scan YY may denote a scan of the eluting peak for P3. For the matching scan YY where P3 appears, it is determined whether one or more of the modified fragments F2" F3" or F4" also appear. If so, then processing confirms the presence of the precursor modification or variant, otherwise validation does not confirm the presence of the precursor modification or variant. Continuing with this example, the modified fragments F2" and F3" both appear in scan YY thereby confirming or validating P3 as the particular precursor modification or variant as denoted by the calculated MD described above (e.g., entry in the table having a value in 2212 matching the calculated MD).

In accordance with techniques herein, an embodiment may further utilize other validation criteria to further validate the particular modification using, for example, values for AR1 and AR2 as described elsewhere herein. For example, using the ion information in the residual 2106b, P3 may be tracked across scans such as described herein and illustrated in connection with FIG. 7 and processing may be performed as also described herein to determine a set of related or associated fragment ions for P3 using validation criteria such as AR1 and AR2 values. In this case, the set of fragment ions associated with P3 should include one or more of the modified fragments F2" and F3". Additionally, consistent with discussion elsewhere herein using validation criteria such as AR1, AR1 as determined for F2" should be the same across scans of the eluting peak for P3 and AR1 as determined for F3" should be the same across scans of the eluting peak for P3. AR2 values determined for P3 and its fragments such as F2" and F3" should be the same across scans of the eluting peak for P3. For example, for scans H and M of P3's eluting peak, the following should hold true (within some specified tolerance):

intensity of $P3$ in scan $H$/intensity of $P3$ in scan $M=$ intensity of $F2"$ in scan $H$/intensity of $F2"$ in scan $M=$ intensity of $F3"$ in scan $H$/intensity of $F3"$ in scan $M$.

Described above is processing performed responsive to determining a match between fragment ion sets 2110a and 2112a for at least a threshold number of fragment ions. As an alternative, now consider the case where processing does not locate or determine a match between 2110a and 2112a for at least a threshold number of fragment ions. In this case, alternative processing may be performed if the number of fragment ions in 2110a is at least a minimum number, such as four (4). Such alternative processing may include determining an MD value (as described elsewhere herein) with the difference that this MD value denotes the mass or m/z difference with respect to a pair of "neighboring" fragments ions in 2110a. Such processing as described above for an MD with respect to two precursor ions or PCCs may be repeated for the MD value based on a pair of "neighboring" fragment ions (e.g., F1 and F2 of 2110*a*). In determining a pair of neighboring fragment ions with respect to a fragment ion set such as 2110*a* associated with a particular PCC or precursor ion, such as P1, the fragments in the set 2110*a* may be ordered in terms of increasing or decreasing m/z values of the fragments. Two fragment ions F1 and F2 may be neighboring in this context if F1 and F2 are next to each other in the ordered position in the m/z ranking.

It should be noted that if either the MD determined for the precursors or the MD for a pair of fragment ions as noted above does not match a mass delta or different entry of the table 2110, such an unmatched MD may denote a new or additional type or precursor modification not incorporated into the table.

Figure 24:
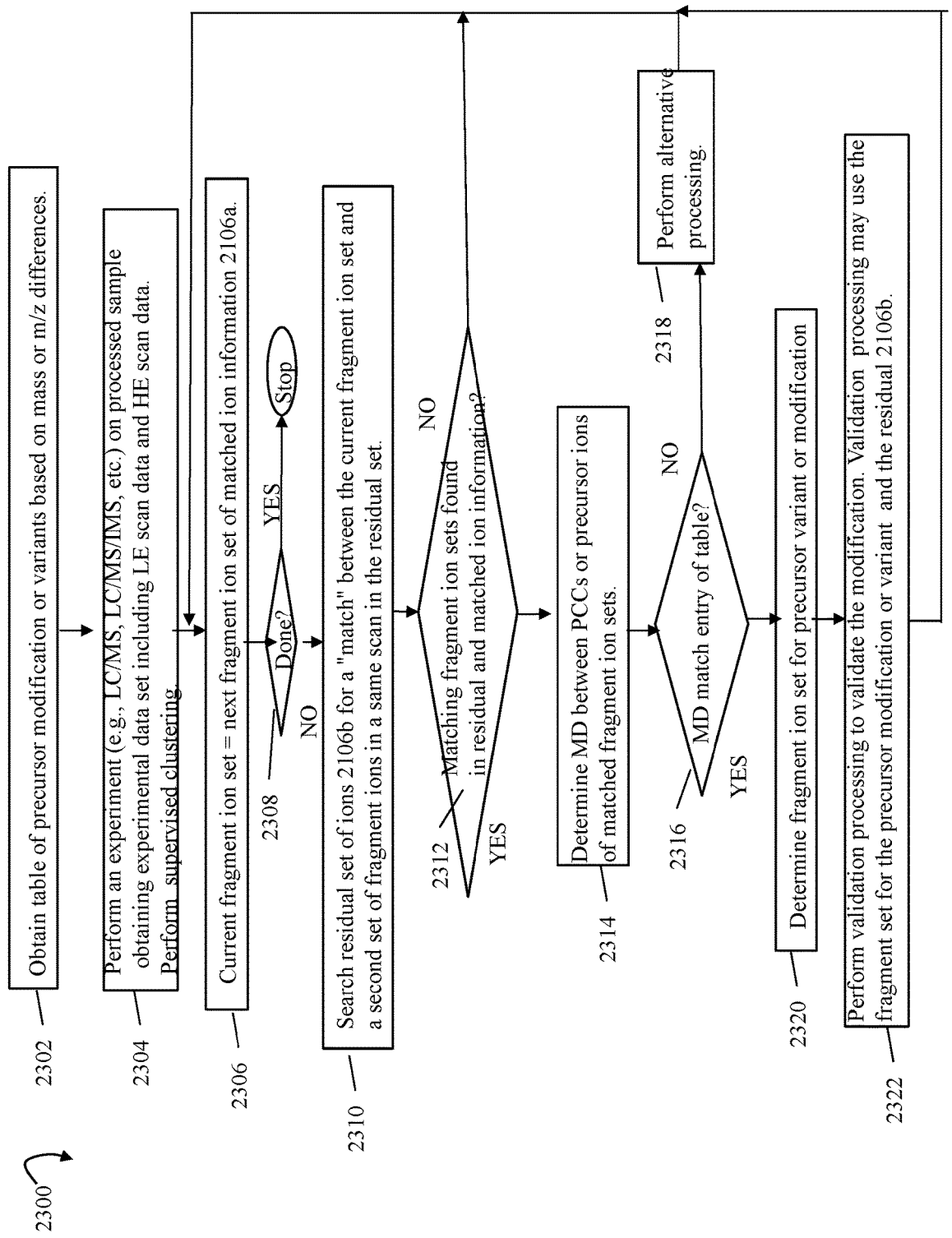

Referring to FIG. 24, shown is a flowchart 2300 of processing steps that may be performed in an embodiment in accordance with techniques herein. Flowchart 2300 summarizes processing as described above. At step 2302, a table of precursor modification or variants based on mass or m/z differences may be obtained. Table 2210 is an example of information that may be included in such a table. At step 2304, an experiment is performed on a processed sample and experimental data may be obtained. Supervised clustering may also be performed in step 2304 to obtain a set of matched ion information 2106*a* (e.g., experimental data matched to a target in the library) and a residual or remainder set of ion information 2106*b*. Processing begins at step 2306 to iterate through each fragment ion set of 2106*a* associated with a PCC or precursor ion matched to a corresponding PCC or precursor ion of the library 2107. At step 2306, current fragment ion set may be assigned the next fragment ion set of the matched ion information 2106*a*. A determination is made at step 2308 as to whether all fragment ion sets of the matched ion information 2106*a* have been processed. If so, processing stops. Otherwise, if step 2308 evaluates to yes, control proceeds to step 2310 to search the residual set of ion 2106*b* for a match between the current fragment ion set and a second set of fragment ions in a same scan in the residual set. For example, with reference to FIG. 22, step 2310 processing may result in determining a match between 2110*a* and 2112*a* as described above. At step 2312, a determination is made as to whether matching fragment ion sets are found in the residual 2106*b* and the matched ion information 2106*a*. If step 2312 evaluates to no, control proceeds to step 2306. If step 2312 evaluates to yes, control proceeds to step 2314 to determine the MD value with respect to the PCCs or precursor ions of the matched fragment ion sets. Step 2314 may, for example, determine the MD value with respect to P1 and P3 of FIG. 22. At step 2316, a determination is made as to whether a matching entry for the MD value is located in the table of precursor or modification variants. If step 2316 evaluates to yes, control proceeds to step 2320. At step 2320, the fragment ion set for the precursor variant or modification matched in step 2316 may be determined, for example, using the simulator as noted elsewhere herein. At step 2322, validation processing may be performed to validate or confirm the presence of the precursor variant or modification. For example, as described herein, such validation processing may use the simulated fragment ion set for the precursor modification or variant (as generated in step 2320) and also the residual 2106*b* to confirm that P3 is the precursor modification or variant. With reference to FIG. 22 and the example above, such validation processing may search for the presence of a modified fragment, such as F2" or F3", in the residual 2106*b*. Such validation processing may use, for example, AR1 and AR2 values for the ions P3 and associated fragment ions F1, F2" and F3". From step 2322, processing proceeds to step 2306.

If step 2316 evaluates to no, alternative processing may be performed. As described herein, such processing may include determining the MD values with respect to neighboring fragment ions included in 2110*a* for the matched precursor ion or PCC P1 in 2106*a*.

Figure 25:
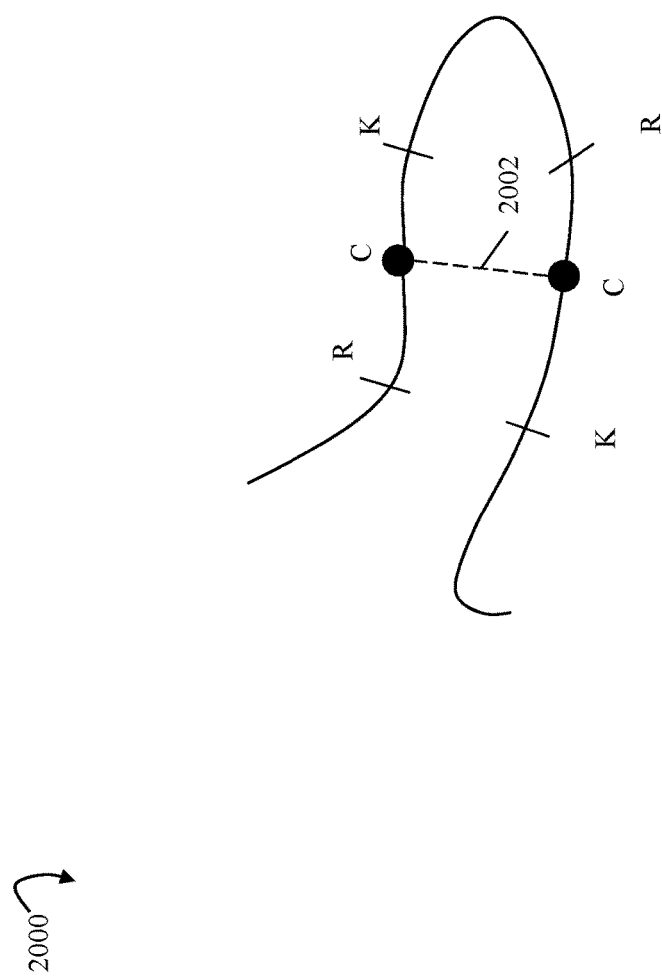
FIG. 25 is an example illustrating a disulfide bond formation.

Disulfide bonded peptides may be identified and validated using techniques herein. Prior to discussing such techniques, reference is first made to FIG. 25 illustrating an example of a protein as may be used in an embodiment in accordance with techniques herein. The protein may include various amino acids such as cysteines (denoted by the Cs), lysines (denoted by the Ks) and arginines (denoted by the Rs). Disulfide bonds attach to cysteines, such as indicated by element 2002. As part of sample preparation and processing for an experiment, the proteins in the sample may be subjected to various enzyme digestion (e.g., trypsin) and other processing which may cause peptide cleavage. Typical peptide cleavage sites may include, for example, the arginine and lysine sites.

For example, in-gel digestion may be performed as part of the sample preparation for the mass spectrometric identification of proteins during proteomic analysis. The in-gel digestion may include, for example, destaining, reduction and alkylation (R and A) of the cysteines in the protein, proteolytic cleavage of the protein and extraction of the generated peptides. The reduction and alkylation (R and A) of the cystines or cysteines potentially embodied in the protein, as may typically be performed as part of sample preparation processing, result in the disulfide bonds of the proteins (e.g., as illustrated by 2002) being irreversibly broken and the optimal unfolding of the tertiary structure of the protein as a linear amino acid string may be obtained. Performing such sample preparation may be performed, for example, in connection with various workflows described herein such as in connection with FIG. 21.

An embodiment in accordance with techniques herein may perform processing as described herein as part of verification of the PA protein structure to identify cysteine-containing peptides where the cysteine is not involved in a disulfide bond. In connection with such processing as described below in more detail, the sample being analyzed may be prepared, for example, using in-gel digestion whereby the sample preparation omits the reduction and alkylation (R and A). In this manner, any cysteines or cysteines in the sample remain intact for subsequent detection using techniques described herein. For example, supervised clustering techniques using a target PA library generated as described in connection with FIG. 21 may be used to find all peptides having a cysteine (which may function as a disulfide bond anchor) where such cysteines are also not involved in a disulfide bond.

An embodiment in accordance with techniques herein may performed processing to identify any disulfide bonded peptides in a sample. As described in more detail below, the presence of a cysteine residue in the target peptide may result in performing such processing. Disulfide bond localization may be performed using supervised clustering as described herein using a target library or database including the linear sequence of all cysteine containing peptides such as described in connection with FIG. 21. Processing described herein for disulfide bonded peptide detection and/or validation may include querying the target library or database and extracting the CPPISs of all cysteine containing peptides. The product ion spectra of each cysteine containing CPPIS may be screened in a manner similar to other peptides against all SSPPIS product ion spectra generated. If an appropriate number of SSPPISs spanning an acceptable chromatographic peak width are identified, a CPPIS is created. Correctly identified SSPPISs reflect, in time or scan number, an eluting peptide with their matched product ions and their intensity/areas illustrating the appropriate intensity distribution (increasing/decreasing) over the span. If a match is not found, processing moves to the next cysteine-containing CPPIS and the process is repeated. If a statistically significant number of product ions (e.g., such as specified threshold number) are matched, the algorithm next performs processing using a matrix or table of Δm/z values between any user-defined number of possible disulfide bonded peptides. Next the Δm/z between the matched peptide and the precursor ions' m/z is calculated and compared to the Δm/z values of the matrix. If a match is found, processing then proceeds with comparing the product ions of the companion peptide for validation and bond localization. If a statistically significant number of product ions are matched to the two peptides and their AR1 and AR2 ratios repeat across all the matched SSPPISs, a disulfide bonded CPPIS may be created.

An embodiment in accordance with techniques herein may use additional validation criteria for disulfide bonded peptides. Each linear sequence incorporated in a disulfide bond will be present at a retention and, if IMS is employed, drift time inconsistent with its experimental values. In the experiment, the therapeutic is reduced and alkylated, ensuring there is no cysteine bond formation. The movement in time of the set of consistent product ions significantly limit the identification as being a random event. Processing that may be performed in an embodiment in accordance with techniques for disulfide bonded peptide identification and/or validation is described in more detail in following paragraphs.

As a first part of processing in connection with techniques herein for detection and/or identification of a disulfide bonded peptides, steps may be performed to first validate the presence of the PA in the sample.

Figure 26:
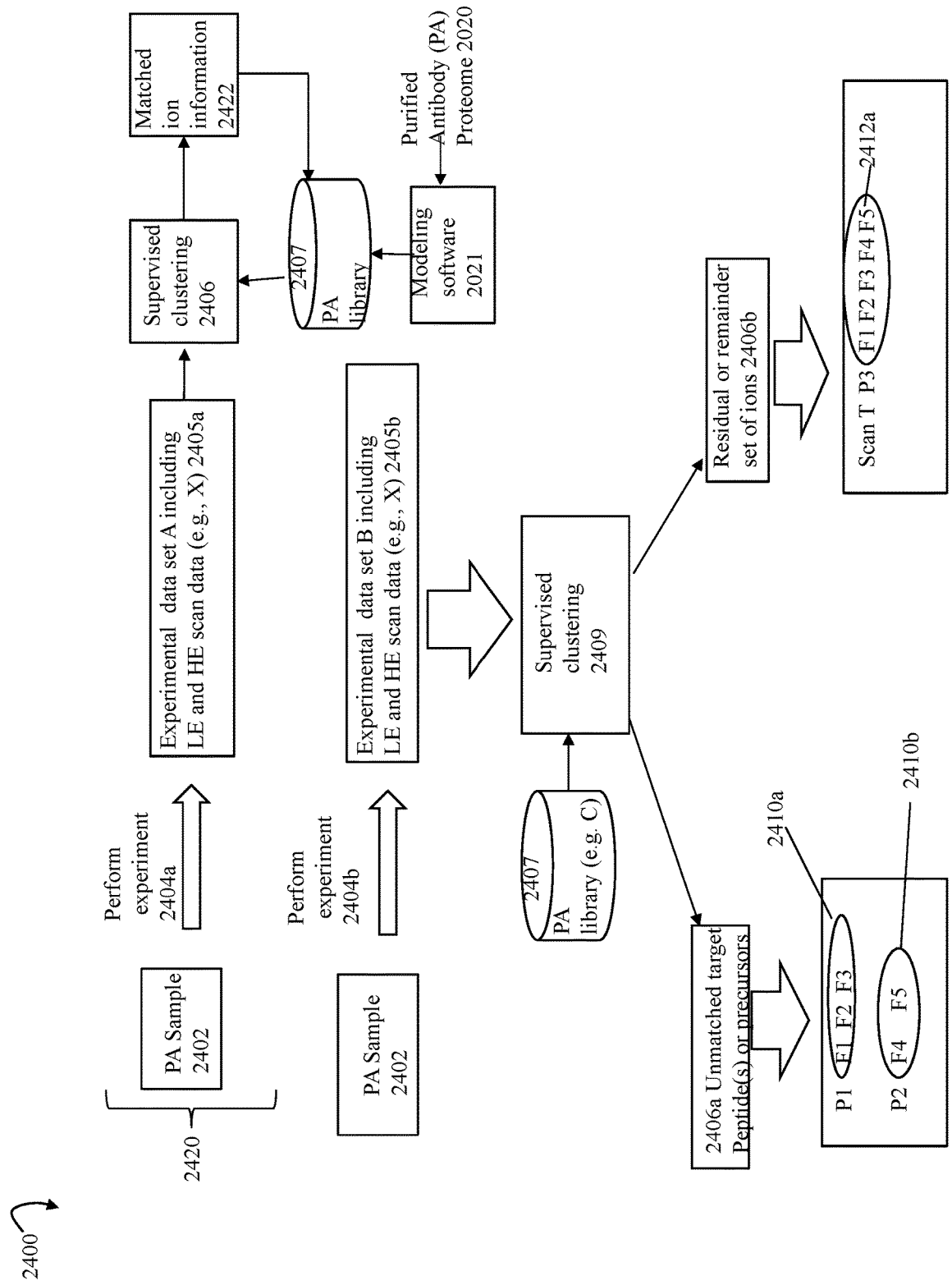

With reference to FIG. 26, shown are example workflows that may be performed in an embodiment in accordance with techniques herein. The first portion illustrated by 2420 may include performing steps similar to that as described elsewhere herein in connection with FIG. 21. Experiment 2404a may be a first such experiment performed with respect to a PA sample 2402. The experiment 2404a may include sample preparation processing performed for protein digestion and LC/MS or LC/IMS/MS analysis. In this first experiment 2404a, sample preparation includes performing reduction and alkylation whereby all cysteines in the sample are modified so that there are no disulfides (e.g. only tryptic peptides). LE and HE scan data 2405a may be obtained for the experiment 2404a. The LE and HE scan data 2405a may be further processed using the supervised clustering techniques 2406 described herein with the library for the PA protein 2407 used as the supervised clustering target library.

If the sample is prepared as described in 2404a, then all peptides in the PA library 2407 should be matched to corresponding ion information in the experimental data set 2405a. Thus, in one embodiment, the presence of the PA in the sample 2402 may be validated by matching all peptides in the library 2107 to ion information in the experimental data set as a result of performing supervised clustering 2406. As an alternative the presence of the PA in the sample 2402 may be validated by matching at least a specified number of peptides in the library 2407 to ion information in the experimental data set 2405a as a result of performing supervised clustering 2406. The foregoing first part of processing may also be referred to as peptide mapping which is an identity test for proteins including the chemical or enzymatic treatment of a protein resulting in the formation of peptide fragments followed by separation and identification of the fragments in a reproducible manner.

After performing the foregoing denoted by 2420, another portion of the same PA sample 2402 may be subjected to processing in a second experiment 2404b. The experiment 2404b, including sample preparation, may be the same as in experiment 2404a with the difference that the experiment 2404b includes sample preparation and omits performing reduction and alkylation. In this manner, sample processing omits the reduction and alkylation step so as not to break any existing disulfide bonds in the sample being analyzed via 2404b. Thus, if there are disulfide bonds existing in the sample, such disulfide bonds remain intact and are not broken in sample processing.

LE and HE scan data 2405b may be obtained for the second experiment 2404b. The LE and HE scan data 2405b may be further processed using the supervised clustering techniques 2409 (e.g., such as in FIG. 14A) described herein with the library for the PA protein 2407 used as the supervised clustering target library. It should be noted that the PA library 2407 may be generated as a result of performing the workflow of 2420.

As a result of performing supervised clustering in 2409, a first set of information 2406a may be obtained identifying those peptides or precursor ions (or PCCs) and associated fragment ions (e.g., CPPISs) of the library 2107 that were not matched to corresponding ion information in the experimental data set 2405b and where such peptides or precursors also contain cysteine. Additionally, as a result of 2409 processing, a second set of information 2406b may be obtained denoting the residual or remainder set of unmatched ions (e.g., unmatched PCCs and unmatched fragment ions) of the experimental data set 2405b. The residual or remainder set of unmatched ions 2406b may include sets of ions in each scan of the experiment data set B 2405b not matched to a peptide (e.g., PCC or precursor) of the library.

Thus, element 2406a denotes those peptides or precursors of the PA which were not identified or matched to corresponding ion information in the experimental data set 2405b and which also contain cysteine amino acid needed for formation of disulfide bonds (e.g. element 2406a denotes the unmatched targets of the PA library (e.g. those PCCs, peptides or precursor ions of the library 2407 which contain cysteine and which also were no matched to ion information in the experimental data set B 2405b)). From the unmatched, cysteine containing peptide or precursor targets of the PA library as identified in 2406a, we now have the product ion spectra (e.g. CPPIS) of each such unmatched cysteine containing peptide or precursor ion whereby the product ion spectra denotes the fragment ions expected to originate from fragmentation of the associated peptide or precursor ion. In this example, 2406a denotes that the library 2407 includes precursor or peptides P1 and P2 which were not matched by supervised clustering 2409 to corresponding precursor and fragment ion information in the experimental data set B 2405b. Additionally, 2406a indicates that the library also includes target fragment ion set 2410a for the target precursor P1 of the library, and that the library also includes target fragment ion set 2410a for the target precursor P2 of the library.

In accordance with techniques herein, processing may be performed to identify those precursors or peptides of 2406*a* each of which has a different retention time in 2405*a* as compared to 2405*b*. For example, processing may be performed to track a PCC of the precursor or peptide across different scans as described herein to determine the elution peak or profile across different scans (such as illustrated in FIG. 7) whereby the apex or scan in which the tracked precursor has a maximum intensity may be determined as its approximate retention time. It is expected that two the same tracked precursor or peptide will have the same retention time in 2405*a* and 2405*b* if the precursor is not a disulfide bonded peptide in the second experiment. Thus, if the precursor P1 is included in a disulfide bonded peptide, P1 is expected to have a different retention time in 2405*a* and 2405*b*. Similarly, if the precursor P2 is included in a disulfide bonded peptide, P2 is expected to have a different retention time in 2405*a* and 2405*b*. It should be noted that if IMS is utilized in the experiments 2404*a*, 2404*b*, then if a precursor, such as P1 or P2, is included in a disulfide bonded peptide in the second experiment 2404*b*, that precursor is expected to also have a different drift time or different or collisional cross section area ($CCSA^2$) in 2405*a* and 2405*b*.

For this example, assume that both P1 and P2 are unmatched cysteine containing target peptides or precursors of the library 2407 having such different retention times and drift times in 2405*a* and 2405*b*. Processing may be performed to search the residual 2406*b* to determine whether a threshold number of fragments ions associated with the combination of P1 and P2 appear in a same scan in the residual. For example, processing may be performed to form the set union of the fragment ion sets 2410*a* and 2410*b* which in this example is the combination fragment ion set (CFIS)={F1, F2 F3 F4 F5} and then search the residual 2406*b* for a match to at least a threshold number of the fragments of the CFIS in the same scan. For purposes of illustration in the example, it may be determined that scan T includes all fragment ions of the CFIS based on 2410*a* and 2410*b* thereby denoting two peptides P1 and P2 with cysteine appearing in the same scan T in the residual 2406*b*.

Processing may be performed to determine the theoretical mass of a new molecule, Mnew, including a disulfide bond between P1 and P2 which may be expressed as follows:

$$Mnew = M1 + M2 - (c*\text{mass of Hydrogen})$$

where
  M1 is the mass of P1 (e.g., may be the monoisotopic mass of P1);
  M2 is the mass of P2 (e.g., may be the monoisotopic mass of P2);
  c is an integer greater than 0 denoting the number of cysteine bonds or anchors between P1 and P2; and
  mass of Hydrogen denotes the atomic mass of hydrogen which is approximately 1.007 atomic mass units or amu's.

The simulator or modeling software 2021 may be used to determine the theoretical possible m/z's for Mnew. For example, Mnew may have multiple charge states such as +3, +5 and +7 that the simulator may determine. Then, the simulator may determine the theoretical m/z values for such multiple charge states at which Mnew may appear in an experimental data set such as 2405*b*. Each such m/z value therefore corresponds to an m/z of a PCC of Mnew.

Processing may now continue by searching the LE scan data of 2405*b* for an m/z matching one of the m/z values (as determined by the simulator) for Mnew. For example, assume that the simulator determines a first m/z value for Mnew which is matched to a corresponding m/z value in the LE scan data of 2405*b*. Assume the first m/z value denotes an m/z for PCC+3 of Mnew. The LE scan data of 2405*b* is searched to determine all scans which include the m/z for PCC+3 of Mnew. The existence or validation of the disulfide bonded peptide Mnew may be confirmed if the first m/z value for PCC+3 of Mnew appears in any scan of the LE scan data of 2405*b*.

Processing may now be performed to determine the fragment ions of 2405*b* associated with or originating from Mnew. The simulator may be used to calculate all theoretical fragment ions for the molecule Mnew which is the molecule of the disulfide bonded peptide pair P1 and P2. Such theoretical fragment ions for the molecule Mnew may be included in a new library L1 used as a target library for supervised clustering performed with respect to the experimental data set B 2405*b*. Consistent with description elsewhere herein, such supervised clustering results in generation of a CPPIS for Mnew, the disulfide bonded molecule or peptide Mnew including P1 and P2.

It should be noted that the foregoing example illustrates detection and identification of a molecule Mnew which is a peptide including a disulfide bonded pair P1 and P2 where P1 and P2 denote target peptides or precursor ions of the target library 2407 which were not matched by supervised clustering 2409 to corresponding precursor and fragment ion information in the experimental data set B 2405*b*. Thus, P1 and P2 may denote peptide or precursor candidates that may be included as a disulfide bonded peptide pair. Peptides or precursors which are candidates for a disulfide bonded peptide pair may also include "matched" target peptides or precursors of the library 2407 (e.g., peptides or precursors of 2407 which were matched by supervised clustering to corresponding precursor and fragment ion information in the experimental data set B 2405*b*) where such matched target peptides or precursors however exhibit other anomalous or unexpected behavior consistent with inclusion of such matched target peptides in a disulfide bonded pair. For example, assume P3 denotes a matched target precursor or peptide of the library 2407. P3 may exhibit intensity behavior which is different in 2405*a* and 2405*b*. Recall that experiments 2404*a* and 2404*b* may be considered replicates other than the difference in sample processing as described above (where 2404*a* includes sample processing to break any disulfide bonded pairs in 2402 and 2404*b* omits such sample processing and preserves any existing disulfide bonded pairs in 2402). Thus, the same peptide, precursor or PCC should exhibit similar behavior in both 2405*a* and 2405*b*. For example, it is expected that P3 has its maximum intensity at approximately the same scan and approximately the same drift time in both experiments if P3 is not involved in a disulfide bonded pair. P3 should also exhibit similar intensities in the same scan in both experiments. For example, for the same scan S1 in 2405*a* and 2405*b*, P3 should have approximately the same intensity in both experiments (within some tolerance). Similarly, fragments ions originating from P3 should also have similar intensities in the same scans in both experiments. Furthermore, AR2 values for P3 and its fragments should be consistent in both 2405*a* and 2405*b*. For example, a first AR2 value for P3 may be computed with respect to P3's intensity in two scans S1 and S2 of the LE scan data of experimental data set A 2405*a*, and a second AR2 value for P3 may be computed with respect to P3's intensity in the same two scans S1 and S2 of the LE scan data of experimental data set B 2405*b*, whereby the first AR2 value and the second AR2 value are expected to be approximately the same if P3 is not included in a disulfide bond in the second experiment having data set B 2405*b*. In a similar manner, AR2 values for fragment ions of P3 are also expected to be approximately the same if P3 is not included in a disulfide bond in the second experiment having data set B 2405*b*. Thus, comparison of such intensities and/or intensity ratios may be used to detect inconsistent or anomalous behavior of a matched target peptide or precursor P3 thereby denoting that P3 is also a candidate peptide or precursor to be considered along with unmatched target peptides or precursors of 2406*a*.

Figure 27:
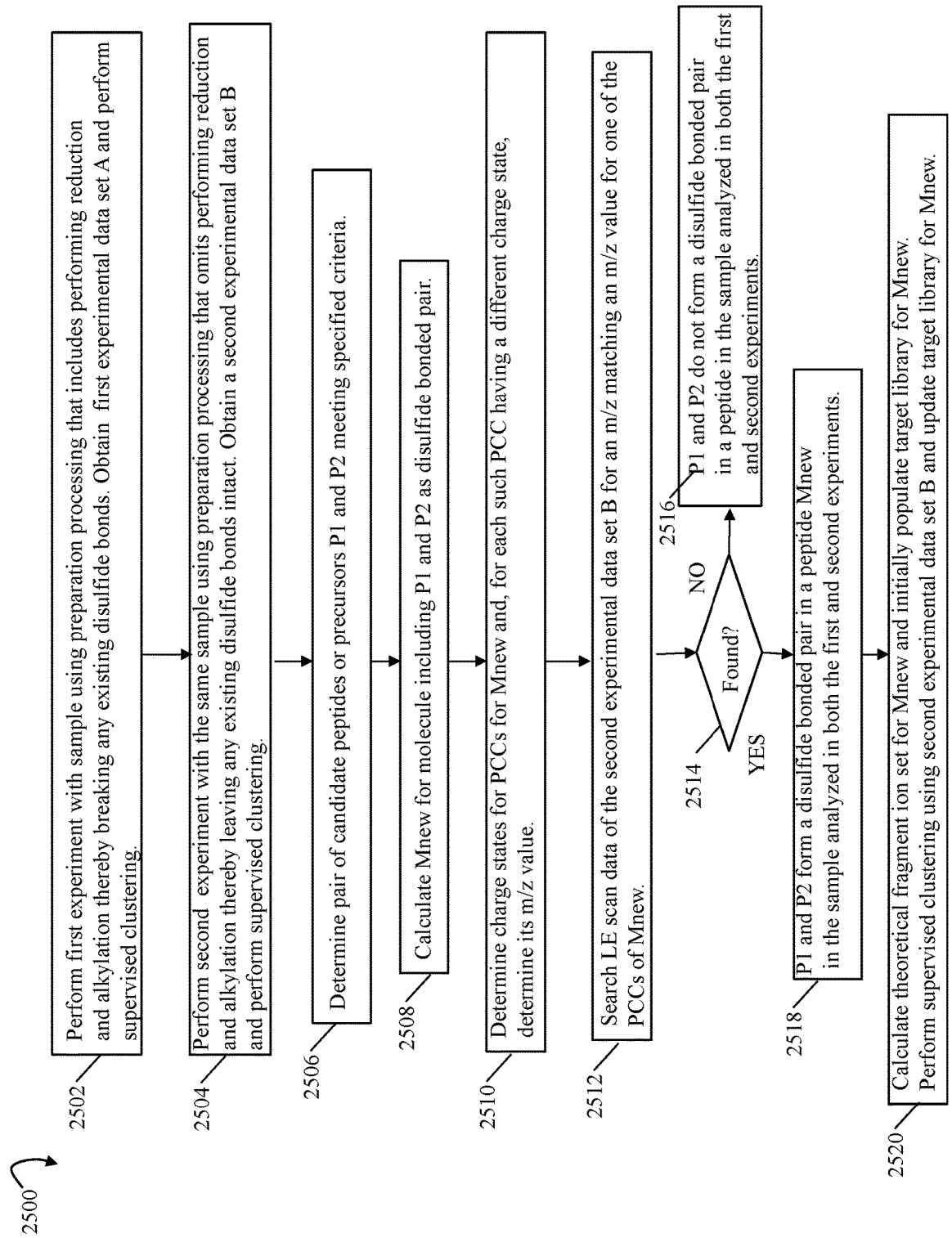

Referring to FIG. 27, shown is a flowchart of processing that may be performed in an embodiment in accordance with techniques herein to detect presence of disulfide bonded pairs in a sample. The flowchart 2500 summarizes processing described above.

At step 2502, a first experiment may be performed with a sample including the PA using preparation processing that includes performing reduction and alkylation thereby breaking any existing disulfide bonds. A first experimental data set A may be obtained for the first experiment and supervised clustering may be performed. The target library for the PA used in supervised clustering may be initially populated with theoretical fragment ion information such as using a simulator or modeling software mentioned elsewhere herein. Such supervised clustering may result in validating the sample includes the PA and also result in updating the target library with real experimental data from data set A.

At step 2504, a second experiment may be performed using the same sample and performing the same experiment as in step 2502 with the difference that preparation processing that omits performing reduction and alkylation thereby leaving any existing disulfide bonds intact. A second experimental data set B may be obtained for the second experiment and supervised clustering may be performed. The target library used in supervised clustering may be the updated target library for the PA as updated in step 2502 supervised clustering. As a result of supervised clustering in step 2504, the set 2406*a* of unmatched target precursors or peptides of the target PA library may be determined along with a residual or remainder set 2406*b* including scans of ions not matched to the target PA library in supervised clustering.

At step 2506, a pair of candidate peptides or precursors P1 and P2 may be determined meeting specified criteria. As described above, such criteria may include determining that each candidate contains at least one cysteine, determining that a threshold number of fragment ions for the pair appear in a single scan in the residual of the second experimental data set B, determining that each candidate has a different retention time (and different drift time if IMS is performed) in experimental data sets A and B (e.g., an associated maximum intensity in different scans of experimental data sets A and B), each candidate is either in the unmatched target precursor or peptide set 2406*a* or was otherwise matched to a target precursor of the library and also exhibits anomalous or inconsistent behavior. Such inconsistent behavior for the precursor or peptide candidate is inconsistent with respect to the candidate not being included in a disulfide bond in the sample.

At step 2508, Mnew for the molecule including P1 and P2 as a disulfide bonded pair may be calculated. At step 2510, simulator or modeling software may be used to determine the various charge states for PCCs at which Mnew may exist. For each such PCC having a different charge state, a corresponding m/z value may be determined. At step 2512, the LE scan data of second experimental data set B may be searched to locate an m/z in the LE scan data that matches an m/z value for one the PCCs of Mnew. At step 2514, a determination is made as to whether such a matching m/z has been located in the LE scan data of the second experimental data set B. If step 2514 evaluates to no, control proceeds to step 2516 where a determination is made the P1 and p2 do not form a disulfide bonded pair in a molecule or peptide in the sample analyzed in both the first and second experiments. If step 2514 evaluates to yes, control proceeds to step 2518 where a determination is made the P1 and p2 do form a disulfide bonded pair in a molecule or peptide Mnew in the sample analyzed in both the first and second experiments. Control proceeds to step 2520 to calculate the theoretical fragment ion set for Mnew, such as using the simulator or modeling software, and initially populate a target library for Mnew with such information. The Mnew target library may be used as the target library in supervised clustering performed with respect to the second experimental data set B to determine the CPPIS for Mnew. Thus, the Mnew target library may be updated with such CPPIS information.

It should be noted that steps beginning with step 2506 are illustrated in the flowchart 2500 with respect to a single pair of candidate peptides or precursors. Such processing may be repeated for each such pair of candidates.

An embodiment in accordance with techniques herein may also perform processing to detect and identify whether the sample includes any antibody drug conjugates (ADCs). Such techniques may include performing processing similar to that as described herein for identified disulfide bonded pairs. As known in the art, ADCs may be characterized as a class of highly potent biopharmaceutical drugs designed as a targeted therapy for the treatment of people with cancer. ADCs are complex molecules including an antibody linked, via a stable, chemical, linker with labile bonds, to a biological active cytotoxic (anticancer) payload or drug (also referred to herein as a cytotoxic agent or conjugate). Thus, the cytotoxic agent or conjugate may be attached or linked to the antibody at a particular amino acid (e.g., cysteine or other) of a peptide of the antibody.

In developing ADCs, an anticancer drug (e.g. a cell toxin or cytotoxin) is coupled to an antibody that specifically targets a certain tumor marker (e.g. a protein that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxic agent. After the ADC is internalized, the cytotoxic agent is released and kills the cancer. Due to this targeting, ideally the drug has lower side effects and gives a wider therapeutic window than other chemotherapeutic agents.

Figure 28:
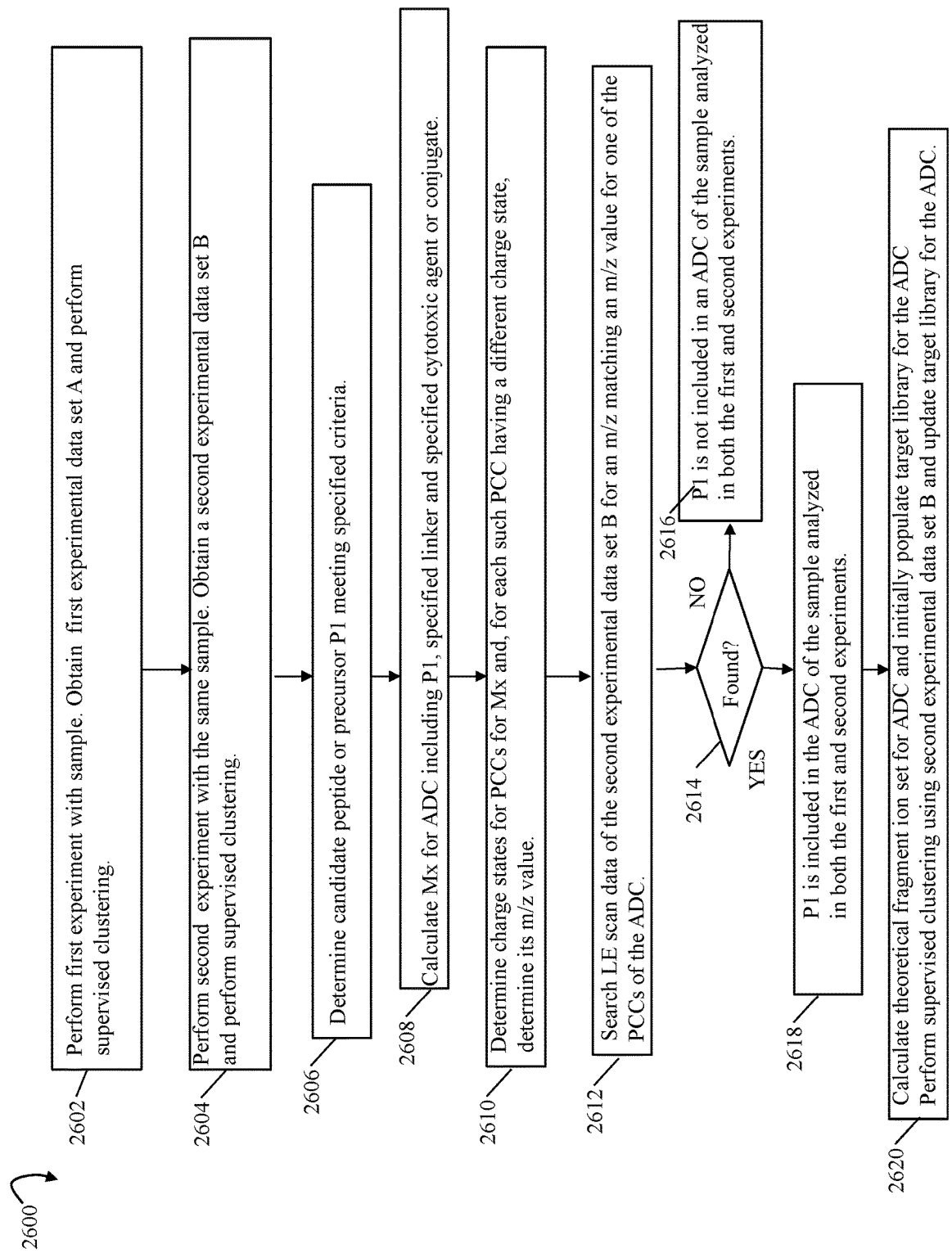

Referring to FIG. 28, shown is a flowchart 2600 of processing that may be performed in an embodiment in accordance with techniques herein to detect the presence of ADCs in a sample. For a particular ADC for which processing is performed in 2600 to determine whether the ADC is present in the sample, inputs may be provided including the target amino acid identifying the point at which the cytotoxic agent attaches to the antibody, the mass of the linker, and the mass of the cytotoxic agent or conjugate. In connection with processing such as described in subsequent steps, the conjugate or cytotoxic agent may attach to a cysteine amino acid. However, more generally, the conjugate or cytotoxic agent may attach to any amino acid of a peptide of the antibody.

It should be noted that steps 2602, 2604, 2606, 2608, 2610, 2612, 2614, 2616, 2618, and 2620 are respectively similar to steps 2502, 2504, 2506, 2508, 2510, 2512, 2514, 2516, 2518, and 2520 of FIG. 27.

At step 2602, a first experiment may be performed with a sample including the PA. The sample may be processed, for example, by performing protein digestion techniques known in the art. For example, such sample preparation processing may include performing reduction and alkylation. The prepared sample may then be analyzed by performing an experiment including chromatographic separation, mass spectrometry, IMS, and the like. A first experimental data set A may be obtained for the first experiment and supervised clustering may be performed. The target library for the PA used in supervised clustering may be initially populated with theoretical fragment ion information such as using a simulator or modeling software mentioned elsewhere herein. Such supervised clustering may result in validating the sample includes the PA and also result in updating the target library with real experimental data from data set A.

At step 2604, a second experiment may be performed using the same sample and performing the same experiment, and the same sample processing, as in step 2602. A second experimental data set B may be obtained for the second experiment and supervised clustering may be performed. The target library used in supervised clustering may be the updated target library for the PA as updated in step 2602 supervised clustering. As a result of supervised clustering in step 2604, a set (e.g., 2406a) of unmatched target precursors or peptides of the target PA library may be determined along with a residual or remainder set (e.g., 2406b) including scans of ions not matched to the target PA library in supervised clustering.

At step 2606, a candidate peptide or precursor P1 may be determined meeting specified criteria. It should be noted that 2506 determines a pair of candidates and step 2606 determines a single candidate. With an ADC, such criteria may include determining that the candidate contains at least one cysteine or other target amino acid to which the cytotoxic agent attaches. This is the target amino acid provided as an input for the particular ADC being detected or identified. Such criteria may include determining that a threshold number of fragment ions for the candidate P1 (where such fragment ions are specified in the target library for the PA) appear in a single scan in the residual of the second experimental data set B. Such criteria may include determining that the candidate P1 has a different retention time (and different drift time if IMS is performed) in experimental data sets A and B (e.g., an associated maximum intensity in different scans of experimental data sets A and B). Such criteria may include determining that the candidate P1 is either in the unmatched target precursor or peptide set 2406a or was otherwise matched to a target precursor of the library and also exhibits anomalous or inconsistent behavior. Such inconsistent behavior for the precursor or peptide candidate is inconsistent with respect to the candidate not being included in an ADC in the sample. Such inconsistencies are described in connection with disulfide bond detection and identification and may also be used in connection with processing described herein to determine a candidate P1 which may be a matched target precursor or peptide of the library exhibiting anomalous or inconsistent behavior such as with respect to differences between the first and second experiments.

At step 2608, Mx, denoting the mass for the ADC including P1, the specified linker, and specified cytotoxic agent or conjugate may be calculated. Mx may be calculated as the sum of the masses for each of the foregoing.

At step 2610, the simulator or modeling software may be used to determine the various charge states for PCCs at which Mx, the ADC, may exist. For each such PCC having a different charge state, a corresponding m/z value may be determined. At step 2612, the LE scan data of second experimental data set B may be searched to locate an m/z in the LE scan data that matches an m/z value for one the PCCs of Mx. At step 2614, a determination is made as to whether such a matching m/z has been located in the LE scan data of the second experimental data set B. If step 2614 evaluates to no, control proceeds to step 2516 where a determination is made that P1 is not included in an ADC of the sample analyzed in both the first and second experiments.

If step 2614 evaluates to yes, control proceeds to step 2618 where a determination is made that P1 is included in the ADC and the ADC is included in the sample analyzed in both the first and second experiments. Control proceeds to step 2620 to calculate (e.g., such as using the simulator or modeling software) the theoretical fragment ion set for the ADC having associate mass Mx. The theoretical fragment ion set for the ADC may be used to initially populate a target library for the ADC. The ADC target library may be used as the target library in supervised clustering performed with respect to the second experimental data set B to determine the CPPIS for the ADC. Thus, the ADC target library may be updated with such CPPIS information.

It should be noted that steps beginning with step 2606 are illustrated in the flowchart 2600 with respect to a single peptide or precursor candidate P1. Such processing may be repeated for other candidates.

What will now be described are techniques referred to herein as multi-mode acquisition (MMA). In one aspect, MMA may be characterized as including a combination of DDA and the Bateman technique or the high-low protocol data acquisition techniques described elsewhere herein. MMA may include performing mass spectrometry in combination with processing for one or more additional dimensions of separation. For example, MMA may include LC/MS analysis and may also include performing IMS. As described in more detail in following paragraphs, MMA provides for sequential isolation of variable size mass isolation windows (MIWs) whereby the width of the MIW (e.g. quadrupole of MS performing mass filtering or selection) is modulated across the elution time. In one embodiment, the elution time range may be partitioned into equal portions referred to herein as buckets or bins. The width of the MIW may be varied where the width is a function of the number of precursor ions in a particular time bucket or bin. Put another way, an embodiment in accordance with MMA techniques described herein may vary the MIW width across time, for example, so as to keep the number of precursor ions entering the first filtering quadrupole for subsequent fragmentation about the same. A goal of the foregoing is, within a single cycle, to have about the same number of precursor ions fragmented with each different sequential MIW utilized.

With MMA, a total range of m/z values, from a minimum m/z value to a maximum m/z value, may be specified. The total range of m/z values may be partitioned into multiple m/z intervals. Each m/z interval has an upper bound and a lower bound within the total range of m/z values. In some embodiments such as described in following paragraphs, the m/z intervals may overlap in terms of m/z ranges. Processing performed in connection with MMA techniques for each different m/z interval may be referred to herein as a different cycle. For example, the total m/z range of values may be partitioned into "n" m/z intervals whereby processing performed in connection with MMA for m/z interval "i", $1 \leq i \leq n$, may be referred to as cycle i.

The particular minimum and maximum m/z values of the total range of m/z values considered may vary with one or more factors such as, for example, the particular sample (e.g., is the sample a small molecule, single protein or antibody, complex mixture of multiple unknown proteins), the particular sample processing performed (e.g., what particular enzymes are used), and the like. For example, the inventors have performed simulations of experiments for a typical tryptic analysis of samples and have generally determined that roughly 50% of all ions in the simulated experiments have ions with m/z values that fall into the total m/z range from approximately 350 to 1350 for a typical tryptic analysis. It should be noted that the total m/z range may vary with the particular analysis and samples of interest being analyzed. Thus, based on such one or more factors that may vary with the sample, experiment, sample processing, and the like, a total range of m/z values may be specified for use with MMA techniques described in following paragraphs.

Figure 29:
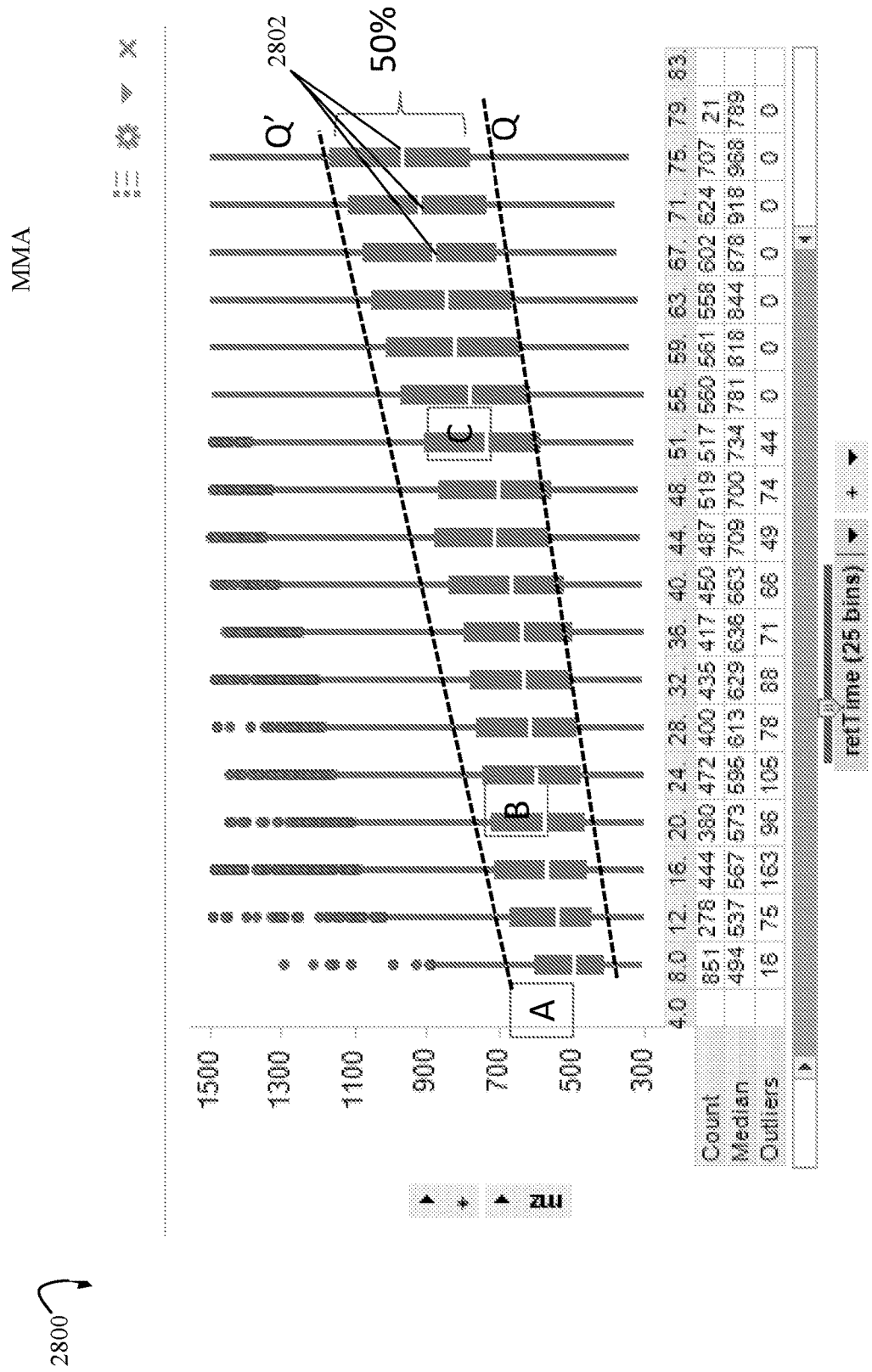
FIG. 29 is an example illustrating a frequency distribution of precursor ion m/z (mass to charge) values at various retention times that may be used in an embodiment in accordance with techniques herein.

Referring to FIG. 29, shown is an example illustrating a distribution of the frequency or count regarding the number of precursor ions over elution time. On the Y axis is m/z and on the X axis is retention time (RT). The thickness of the rectangles or spots on the graph denote the frequency or number of precursor ions in a particular RT bin or range having a particular m/z value. The larger the rectangle or spot at a point on the graph, the greater the number or frequency of ions associated with the particular m/z values and RTs at that point on the graph. For example, the boxes or rectangles between dashed lines Q and Q' indicate that roughly 50% of the precursor ions fall in the total m/z range from about 350 to 1350. The white bisecting lines between various rectangles on the graph denote the median values in each RT bin. Element 2802 identifies 3 such lines each denoting a median value in one of the RT bins.

It should be noted that the minimum and maximum m/z values of the total range, the distribution regarding the frequency of ions having the different m/z values, and the like, as described in following paragraphs may be obtained in any suitable manner. For example, an embodiment may obtain such information through running actual experiments on various samples, through simulation, and the like. For example, information illustrated in FIG. 29 regarding the distribution of the frequency of m/z values of precursor ions over elution time may be obtained using a simulator or modeling software such as discussed elsewhere herein.

For purposes of illustration, the total m/z range of 350-1350 divided into "n" m/z intervals or partitions may be used in connection with subsequent examples and explanations to illustrate use of MMA techniques. However, it should be noted that the total m/z range may be generally any range of m/z values desired.

Information regarding the distribution of the frequency or count of the number of precursor ions having the various m/z values may be used in MMA techniques to vary the width or size of the MIW. As described in following paragraphs, the size or width of the MIW may be selected so that the number of precursor ions selected and allowed to pass through for subsequent fragmentation is approximately the same across the elution time or RT bins in the cycle.

Illustrated in FIG. 29 are 3 of the "n" m/z intervals denoted as cycles A, B and C on the graph. Cycle A may have the m/z interval from 350-550. Cycle B may have the m/z interval from 475-700. Cycle C may have the m/z interval from 525-750. Thus, in the illustrated example, the m/z ranges of the different m/z intervals or cycles overlap.

It should be noted that the particular amount of overlap between m/z intervals, if any, may be specified as an input in connection with processing described herein. For example, as a first option, an embodiment may indicate that there is to be no overlap between m/z intervals associated with the n cycles. As a second option, an embodiment may indicate a fixed amount of overlap to occur between each two consecutive cycles. Such an overlap may be indicated, for example, by indicating an absolute amount or number of m/z values (e.g., 25). As another option, an embodiment may vary the amount of overlap between two consecutive cycles such as based on a function, equation, and the like.

Figure 30:
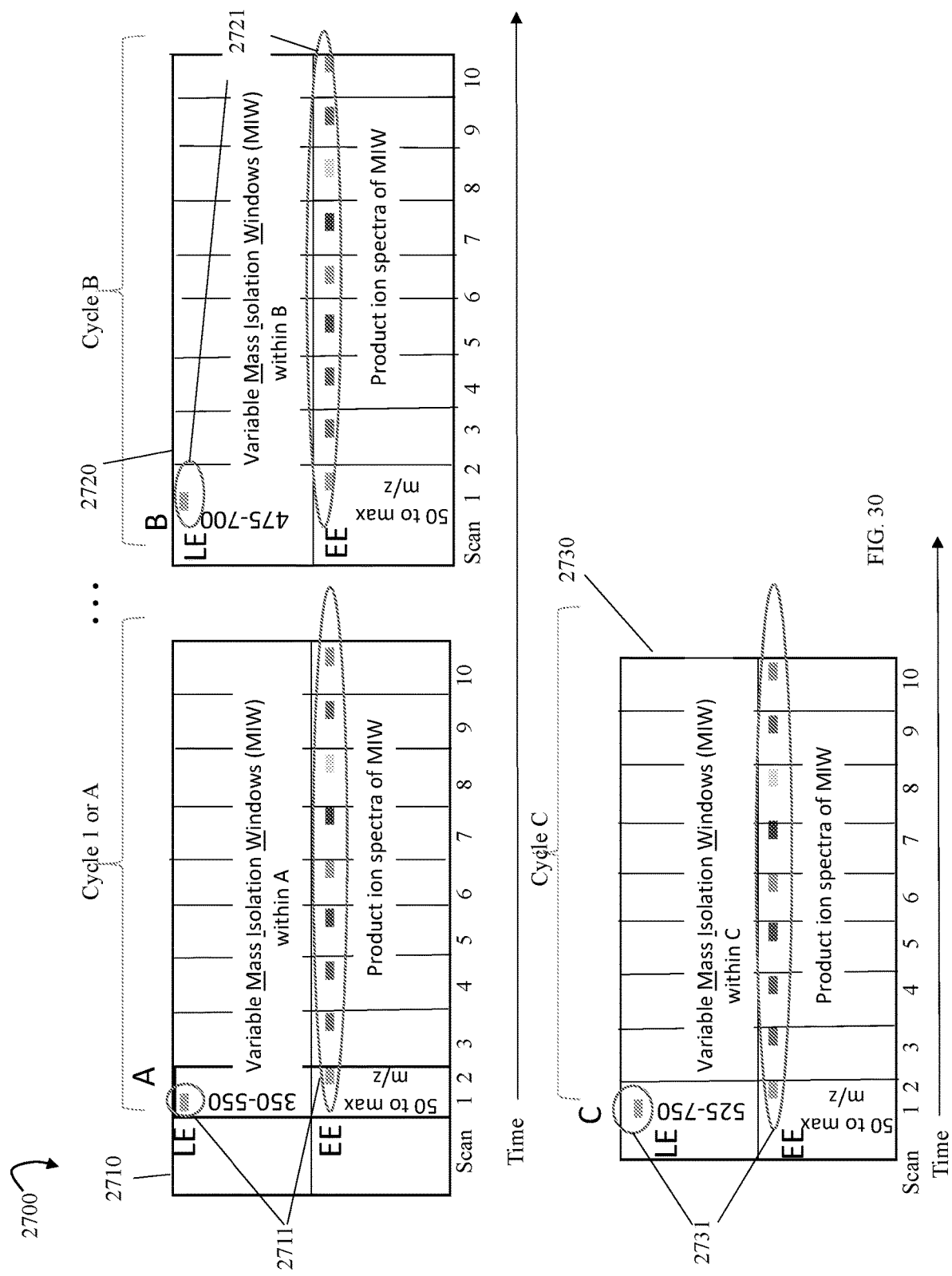
FIG. 30 is an example illustrating variable mass isolation windows (MIWs) and data acquisitions in different scans of cycles in accordance with an embodiment performing multi-mode acquisition (MMA) techniques described herein.

Referring to FIG. 30, shown is an example illustrating in more detail the MIWs that may be used in connection with cycles A, B and C in an embodiment in accordance with techniques herein.

In the example 2700, generally illustrated are the different MIWs within each of the cycles A, B and C. Each cycle in this example includes 10 scans—1 low-energy/survey scan, 1 elevated-energy scan covering the initial MIW as illustrated in 2711 and 8 elevated energy scans according to the scheduled varying size MIW's for that cycle (e.g., such as per 2930 of FIG. 31). An embodiment in accordance with techniques herein may use the Bateman technique or the high-low protocol data acquisition technique described elsewhere herein for the $1^{st}$ and $2^{nd}$ scans for each cycle to obtain precursor and associated fragment data for the initial MIW for each cycle (e.g., initial MIW being the entire m/z interval for the cycle). Each subsequent scan (3-10) reflect the product ion spectra of only those precursor ions within the scheduled MIW window for that scan of that cycle.

With reference to cycle 1 or A, illustrated in 2710 are 2 time lines LE and EE representing the variation in the quadrupole's precursor ion MIW (LE) and the elevated energy (EE) or high energy (HE) performed over elution time while varying the MIW width and, for each MIW width, also varying the associated m/z range within cycle A. In a similar manner, with reference to cycle B, illustrated in 2720 are 2 time lines LE and EE representing the variation in the quadrupole's precursor ion MIW (LE) and the elevated energy performed over elution time while varying the MIW width and, for each MIW width, also varying the associated m/z range within cycle B. Additionally, in connection with cycle C, illustrated in 2720 are 2 time lines LE and EE representing the variation in the quadrupole's precursor ion MIW (LE) and the elevated energy performed over elution time while varying the MIW width and, for each MIW width, also varying the associated m/z range within cycle C.

In this example, for each cycle, the first scan, denoted scan 1, uses a MIW corresponding to the entire m/z interval associated with the cycle. For example, for cycle A, element 2710 identifies 10 scans with scan 1 denoting the entire m/z range 350-550 for the m/z interval associated with cycle A. Scan 2 reflects the product ion spectra of the initial MIW (m/z=350-550) The remaining 8 scans numbered 3-10 each reflect the set of fragment ions emanating from the precursor ions within the scheduled MIW window for that scan as illustrated in 2930.

In a manner similar to that as described for cycle A, for cycle B, element 2720 identifies 10 scans with scan 1 denoting the entire m/z range 475-700, and scan 2 the fragment ions from the initial MIW for the m/z interval associated with cycle B. The remaining 8 scans 3-10 reflect the product ion spectra of those precursor ion within the scheduled MIW having a width and associated m/z range or window that both vary across subsequent or sequential scans.

In a manner similar to that as described for cycle B, for cycle C, element 2730 identifies 10 scans with scan 1 denoting the entire m/z range 525-750, and scan 2 the fragment ions from the initial MIW for the m/z interval associated with cycle C. The remaining 8 scans 3-10 reflect the product ion spectra of those precursor ion within the scheduled MIW having a width and associated m/z range or window that both vary across subsequent or sequential scans.

In an embodiment in accordance with techniques herein, for cycle A, scan 1, LE scan data may be obtained for m/z range 350-550 and HE scan data may be obtained for m/z range 50 amu to a maximum m/z where the maximum m/z is a function of the highest m/z and z for that MIW at that time, and if IMS is employed, drift. For scans 3-10 of cycle A, no LE scan data is obtained. Rather, the quadrupole is varied to only transmit the scheduled MIW for each such scan. In each scan 3-10, the MIW may be specified narrower or wider depending on what part of the initial MIW for that cycle is being sampled as illustrated in 2930. Varying the MIW widths are described in more detail below. For scans 3-10 of cycle A, HE scan data is obtained using the particular varying MIW width for the particular scan.

Techniques that may be used in determining the varying MIW width and also the varying m/z ranges associated with each MIW in such scans 3-10 of cycles A, B and C are described in more detail in following paragraphs. It should be noted that the width of MIWs may be set in an embodiment in a manner similar to how DDA creates a switch list. Alternatively, the width of the MIWs may be preprogrammed, such as using the simulator or other software controlling the instrumentation. Additionally, the range or window of m/z values associated with each MIW may be programmed to change with each scan.

Thus, with reference to FIG. 30, each of the rectangles or bars in a cycle denotes a data acquisition that may be made in an embodiment in accordance with techniques herein. For example, in cycle A, element 2711 represents the various LE and HE data sets acquired within a single execution of cycle A. Element 2711 includes a single LE scan data set for scan 1, and 9 HE data sets for scans 2-10 as may be acquired within a single execution of cycle A. In cycle B, element 2721 represents the various LE and HE data sets acquired within a single execution of cycle B. Element 2721 includes a single LE scan data set for scan 1, and 9 HE data sets for scans 2-10 as may be acquired within a single execution of cycle B. In cycle C, element 2731 represents the various LE and HE data sets acquired within a single execution of cycle C. Element 2731 includes a single LE scan data set for scan 1, and 9 HE data sets for scans 2-10 as may be acquired within a single execution of cycle C.

In an embodiment in accordance with techniques herein, processing associated with a single cycle may be repeated for a time period before continuing processing using the next cycle. For example, consider the following. An experiment has a total elution time or total amount of time for the experimental run of 100 minutes. The number of m/z intervals, "n", specified may be 20 whereby each m/z interval or cycle may be executed for 5 minutes (e.g., 100/20=5). The MS scan rate may be 10 scans/second or 600 scans/minute. Thus, 3,000 scans of data may be acquired in 5 minutes for each cycle. In this example, processing associated with cycle A may be repeated for 5 minutes. Once cycle A has run for the 5 minute time period, the next subsequent cycle may be performed for 5 minutes, and so on, until all 20=n cycles have each had their associated processing performed.

Generally, as will be described in more detail in following paragraphs, as the frequency or count of the number of ions within an m/z interval increases, the width of the MIW decreases with the goal of selecting or allowing approximately the same number of ions to pass through the mass filter for subsequent fragmentation over time. Thus, the attributes of width and m/z window or range of the MIW at each scan may be characterized as a function of the distribution of the frequency of precursor ions at different m/z values.

Figure 31:
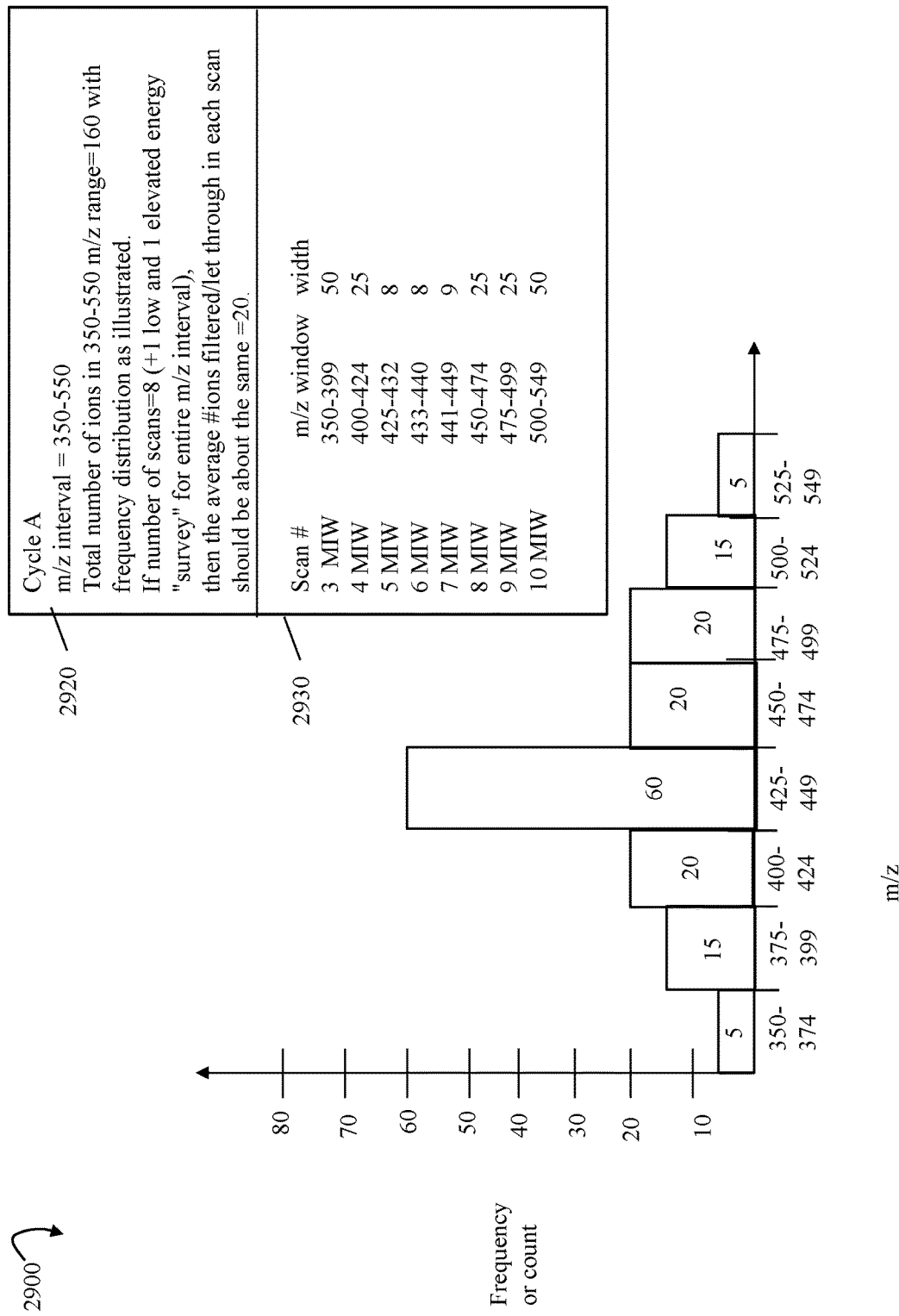
FIG. 31 is an example of a frequency distribution histogram of different m/z bins or intervals that may be used in an embodiment of the MMA technique described herein.

Referring to FIG. 31, shown is an example illustrating a frequency distribution of the m/z values for cycle A that may be used in an embodiment in accordance with techniques herein. The example 2900 graphically illustrates a distribution for cycle A having an associated m/z interval of 350-550. As mentioned elsewhere herein, the distribution of 2900 may be obtain in any suitable manner. For example, the distribution may be simulated or theoretically determined using a simulator or modeling software, may be obtained as a result of running real experiments, and the like.

The example 2900 illustrates 8 m/z bins or buckets where each m/z bin is 25 m/z units. It should be noted that the m/z interval for cycle A is 350-550 whereby the m/z interval includes 350 but does not include the endpoint 550 in this example (e.g., denotes the m/z interval 350≤m/z<550). FIG. 31 specifies inclusive m/z values for each m/z bin denoted. For example, the first bin has an inclusive m/z range of 350-374 with a frequency of 5 precursor ions falling into the m/z range. The second bin has an inclusive m/z range of 375-399 with a frequency of 15 precursor ions falling into the m/z range. The fourth bin having the inclusive m/z range of 425-449 has the highest frequency of 60 of all illustrated m/z bins. As the frequency or count denoting the number of precursor ions in an m/z bin or interval increases the width of the MIW decreases.

Element 2920 lists some properties associated with the distribution for cycle A having the m/z interval 350-550. In this example, the m/z interval 350-550 has a total number of ions of 160 (e.g., sum of all frequencies in 2900). If the number of scans over which the MIW is varied=8 (e.g. as in scans 3-10 in FIG. 30), then the average number of precursor ions filtered or allowed to pass through in each scan should be about 20. Based on this, code may be executed to determine, for each scan in the cycle A, the varying MIW width and its associated m/z window or range. In this example, a scan of cycle A may have an MIW with an associated m/z window that does not overlap with the m/z window of a previous scan in the same cycle A. The m/z windows of all the MIWs across all scans 3-10 may cover the entire m/z interval. A next scan has an associated m/z window for its MIW that starts where the previous scan's m/z window ended (e.g., scan 4 has an associated m/z window for its MIW that starts with m/z=400 where the previous scan 3 has an associated m/z window ending at m/z=399). Thus, within a cycle such as A, processing may set the MIW to have an associated m/z window that incrementally steps through the entire m/z interval for that cycle A.

Element 2930 lists the varying widths and m/z windows for each scan number 3-10 that may be determined and used in connection with processing for a single execution of cycle A.

Figure 32:
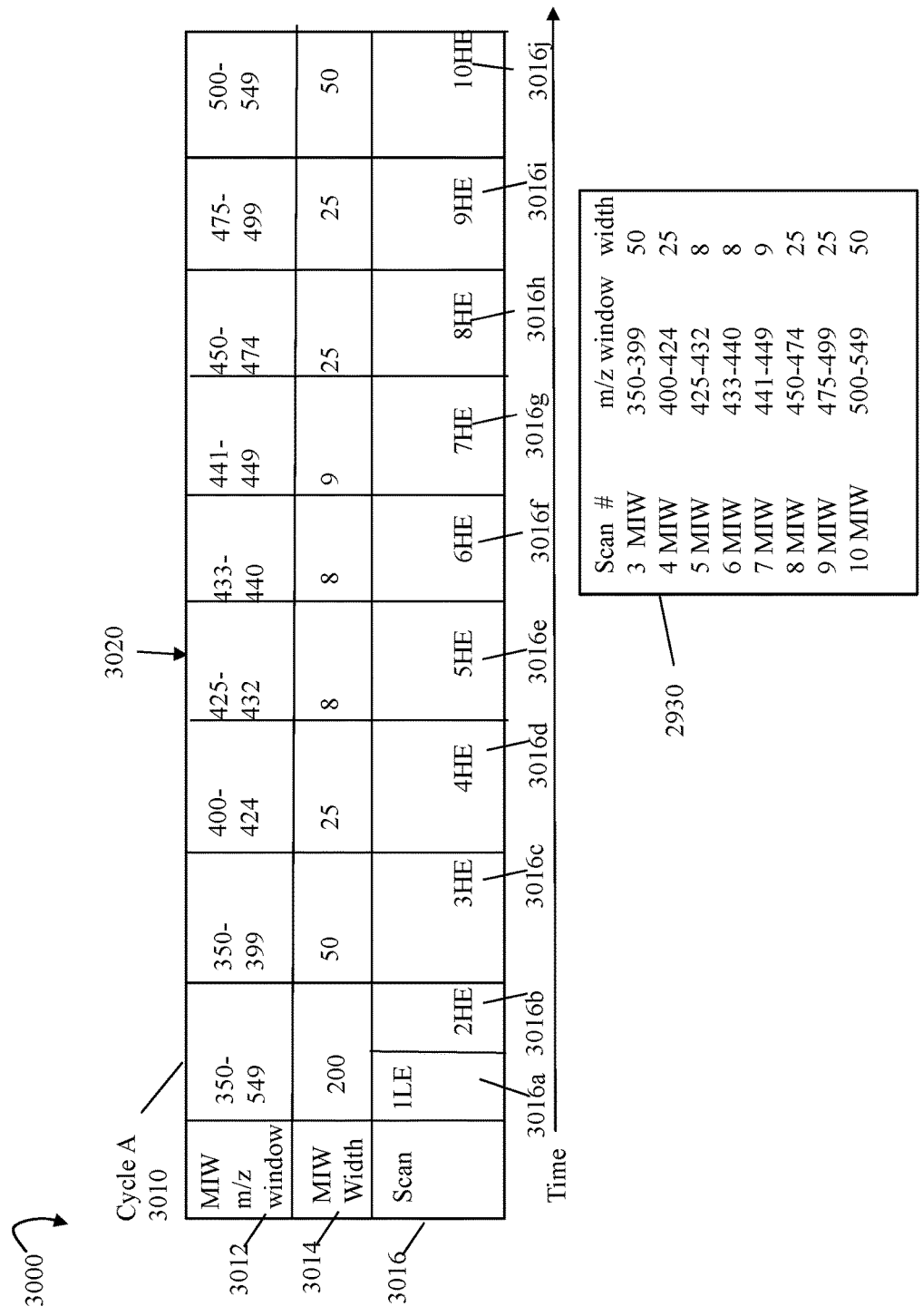
FIG. 32 is an example illustrating MIW settings include varying m/z window and varying width in a single cycle that may be used in an embodiment in accordance with techniques herein.

With reference to FIG. 32, shown is a further illustration of the varying MIW widths and m/z windows that may be used in the various scans in an embodiment in accordance with techniques herein for a single execution of cycle A. The example 3000 includes the information from table 2930 reprinted for ease of examination. Additionally, the example 3000 includes table 3010 identifying, for each scan in a single execution of cycle A, the associated MIW m/z windows and MIW widths. Row 3012 denotes the different MIW m/z windows for each scan. Row 3014 denotes the different MIW widths for each scan. Row 3016 denotes the particular scan by number along with an indication as to whether it is a low energy or high energy scan.

As mentioned elsewhere herein, cycle A includes 10 scans sets each corresponding to one cell in row 3016. For scan "X", where X is an integer in the inclusive range from 1 through 10, specifying "XLE" denotes that scan X is an LE scan, and specifying "XHE" denotes that scan X is an HE scan. Thus, each cell in row 3016 may denote either a single low energy scan or single high energy scan.

As mentioned above and elsewhere herein, in scan 1 3016a (denoted 1LE), a data set is acquired for the LE "survey" scan using an MIW that is the entire m/z interval for the cycle. Scan 2 3016b (denoted 2HE) is the high energy scan including fragment ions generated by precursor ions using the MIW from scan 1. In scans 3-10, processing may be performed to set and use the specified MIW (having width and m/z window as indicated by rows 3012 and 3014 for each such scan) and then perform an HE scan data acquisition (as denoted by 3HE through 10HE) for precursor ions within the specified MIW for that scan. For example, element 3016a is a single cell of table 3010 denoting the first scan in which a set of LE scan data is obtained for the MIW set to the entire m/z interval from 350-549, inclusively, having a MIW width of 200. Cell 3016b denotes the Second scan in which a set of HE scan data is acquired through fragmentation of precursor ions having an m/z value for the specified MIW width of 200 for the m/z window 350-549, inclusively. Similarly, cells 3016c-3016j denote setting the MIW width and m/z window to the particular settings indicated in rows 3012 and 3014 for remaining scans 3-10 (e.g., in each of scans 3-10, an HE data acquisition is performed for fragment ions generated from precursor ions having an m/z falling in the particular MIW's m/z window specified for that scan).

Based on the distribution in FIG. 31, using the MIW widths and m/z windows as in the table 3010 of FIG. 32 results in varying MIW widths and m/z windows so that approximately the same number of 20 precursor ions are filtered or selected and allowed to pass through for subsequent fragmentation.

It should be noted that the foregoing example in connection with FIGS. 31 and 32 illustrate use of a frequency distribution that is a function of m/z values such as in an LC/MS experiment. An experiment may also use IMS in combination with LC/MS thereby adding another dimension of separation that is draft time or collisional cross section area ($CCSA^2$). Thus, in such an embodiment also using IMS, the buckets or bins on the X axis as illustrated in FIG. 31 may be a function of both m/z and drift time or $CCSA^2$.

Figure 33:
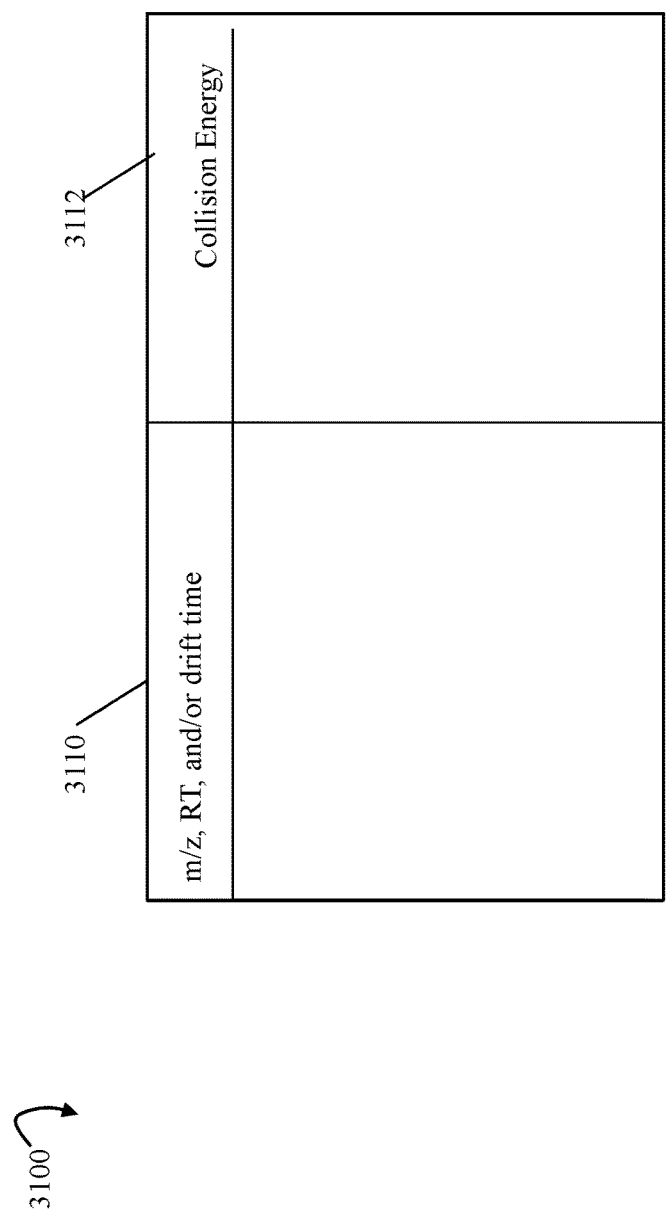
FIG. 33 is an example of a table of various predetermined collision energy values that may be used in an embodiment in accordance with techniques herein.

Additionally, an embodiment in accordance with techniques herein may also select a collision energy in each scan that may vary with one or more of the particular MIW m/z window, retention time (RT), and/or drift time or $CCSA^2$. For example, reference is made to FIG. 33 where a 3100 table is illustrated that may be used in an embodiment in accordance with techniques herein.

The table 3100 may be a lookup table of predetermined collision energy values. The table 3100 may be indexed by any one or more of m/z, RT and drift time or $CCSA^2$ as indicated by column 3110. Column 3112 may provide different collision energies used for different values of for m/z, RT and drift time or $CCSA^2$. Each row of table 3100 may identify, for a particular set of one or more values specified for m/z, RT and drift time or $CCSA^2$, a corresponding collision energy value or range of values that are recommended for use. Thus, an embodiment in accordance with techniques herein may use the table 3100 to vary or select a collision energy in each HE scan based on the particular MIW m/z window associated with that particular HE scan. For example, reference is made back to element 3020 of FIG. 32 for scan 5 with an m/z window of 425-432. For a particular execution of cycle A processing, the RT or elution time and drift time may be determined and used along with the m/z window of 425-432 to select a matching entry of 3110. From the row of the table 3100 including the matching entry 3110, a collision energy value may be retrieved from column 3112 and used as the selected collision energy for the precursor fragmentation or HE scan 5HE. Thus, during the execution of cycle A processing, the collision energy may be set to the retrieved collision energy value in cycle 5HE.

In one embodiment in accordance with techniques herein, as noted above, a simulator or modeling software may be used to determine theoretical distributions used in determining the MIW widths and m/z ranges for the various cycles. In such an embodiment, the software may be provided with a set of inputs. Such inputs may include the total elution time, number of m/z intervals, one or more parameters characterizing the sample and sample preparation, acquisition time (e.g., length of time of a single scan), one or more parameters characterizing the overlap between m/z intervals, whether IMS is performed, whether to use a constant collision energy, and whether to vary or set a collision energy in the HE scans using the lookup table such as described in connection with FIG. 33 (e.g., in accordance with m/z, RT, and/or drift time or $CSSA^2$). The foregoing inputs are described in more detail elsewhere herein. Based on the inputs, the simulator or modeling software may determine MIW having varying widths and m/z windows as described above for the various cycles.

As described herein, an "SSPPIS" is a Single-Scan Precursor-Product Ion Spectra including data from an LE scan and its corresponding HE scan. As described herein, such LE and HE scan data sets may be obtained in connection with various acquisition methods some of which are described herein. For example, the Bateman technique or the high-low protocol techniques may be used. Additionally, an embodiment may use other acquisition techniques such as DDA and MMA as just described. With respect to DDA and MMA acquisitions, a SSPPIS may be constructed on every PCC within the mass isolation window of the selected precursor ions from each survey scan. In connection with MMA, the "survey scan" may be the first scan of each cycle in which the mass or m/z filtering selects all m/z's in the m/z interval for a cycle (e.g., see 3016a of FIG. 32) thereby allowing precursor ions of all such m/z's to pass through for fragmentation.

Each individual PCC regardless of acquisition method, may be initially assigned its companion product ion spectra. This includes all precursor ions within a MIW, such as in an MMA or DDA acquisition, or within the LE scan such as in connection with the Bateman technique or the high-low protocol techniques. If the data was acquired with IMS activated, the initial precursor and product ion alignment may be accomplished by matching drift times within a defined tolerance.

Figure 33B:
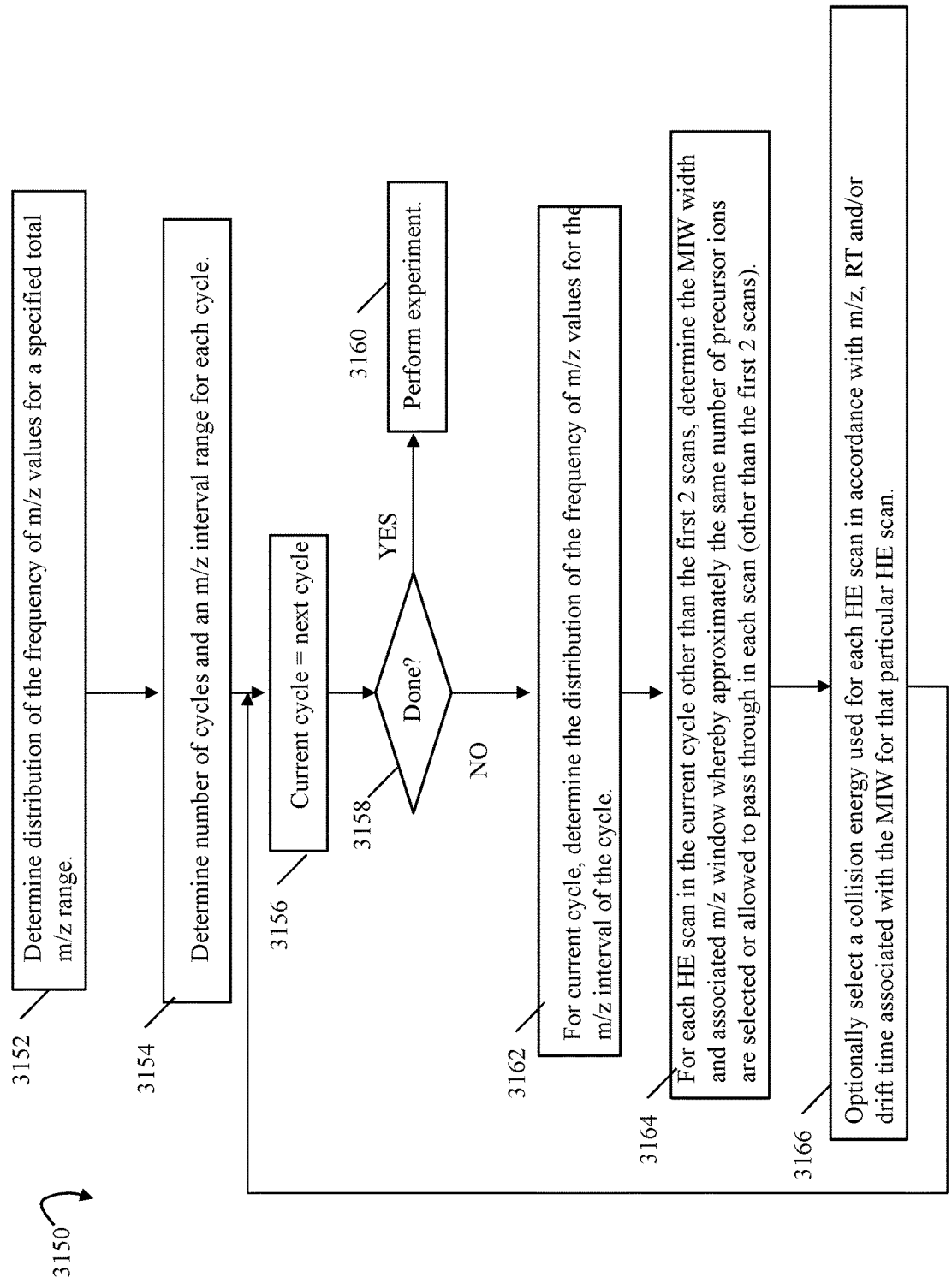

Referring to FIG. 33B, shown is a flowchart of processing steps that may be performed in an embodiment in accordance with MMA techniques. The flowchart 3150 summarized processing described above. In step 3152, a distribution of the frequency of m/z values for a specified total m/z range is determined. In step 3154, a number of cycles for the experiment is determined and, for each cycle, a corresponding m/z interval range is determined. In step 3156, current cycle may be assigned the next cycle for which processing is performed in subsequent steps. At step 3158, a determination is made as to whether processing has completed for all "n" cycles. If so, control proceeds to step 3160 where the experiment may be performed using the various MIWs determined for scans of the "n" cycles. If step 3158 evaluates to no, control proceeds to step 3162. For the current cycle, the distribution of the frequency of m/z values for the m/z interval of the current cycle is determined. For example, FIG. 31 illustrates such processing that may be performed in connection with step 3158 for the current cycle. At step 3164, processing is performed for each scan of the current cycle other than the first 2 scans. For each such scan other than the first 2 scans, determine the MIW width and associated m/z window whereby approximately the same number of precursor ions are selected or allowed to pass through in each scan (other than the first 2 scans). For example, step 3164 determines the information as illustrated in table 2930 of FIG. 32. At step 3166, processing may optionally be performed to select a collision energy used when performing each HE scan in accordance with the m/z window of the MIW associated with the HE scan, and RT and/or drift time associated with the particular HE scan. Control proceeds to step 3156.

Thus, flowchart 3150 performs processing to determine a schedule of the particular MIW widths and associated m/z windows for the "n" scans, along with any optionally determined collision energies in step 3166, and then proceeds with performing the data acquisition in connection with step 3160 using the foregoing.

Figure 34:
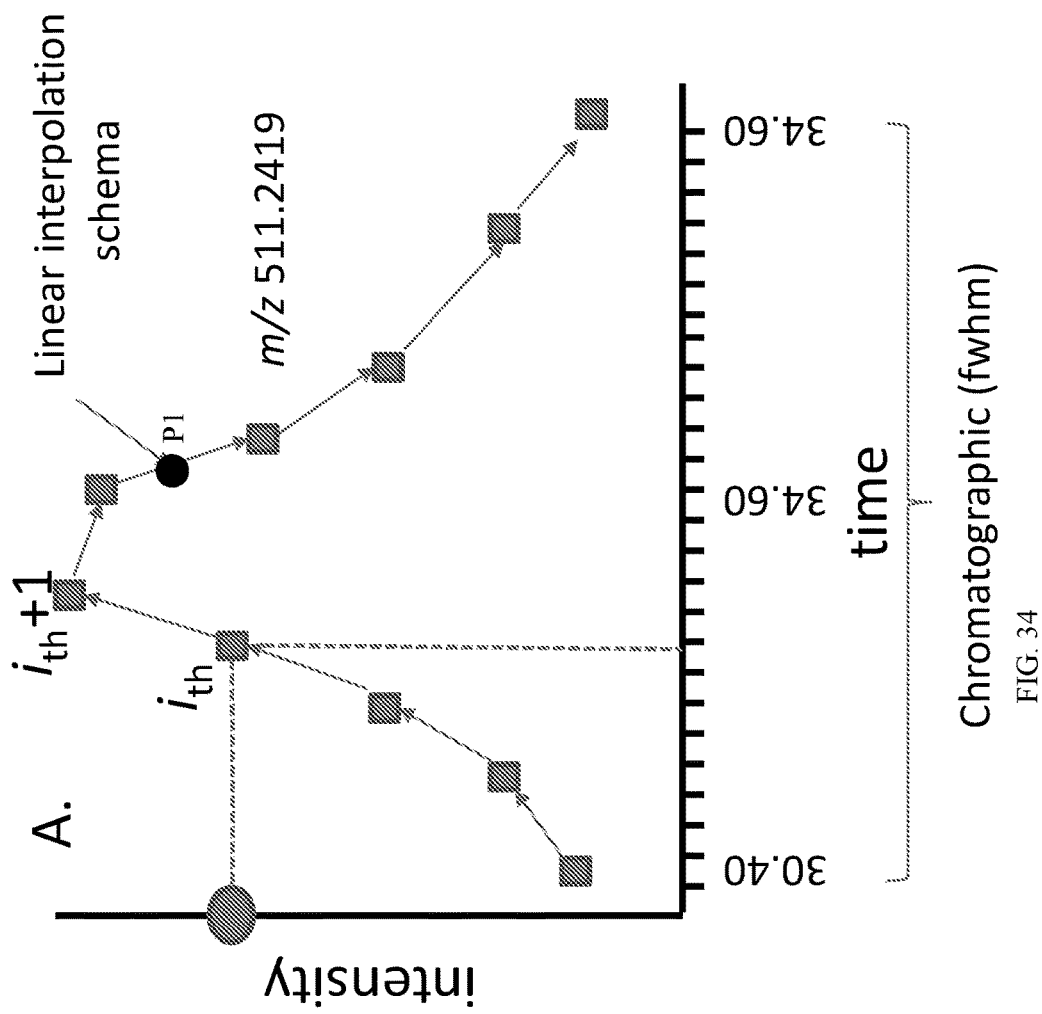
FIG. 34 is an example illustrating determining a precursor ion or PCC intensity using interpolation such as may be performed in connection with various data acquisition techniques in an embodiment in accordance with techniques herein.

With reference to FIG. 34, processing that may be performed in an embodiment in accordance with techniques herein to determine an intensity for a PCC in an MMA or DDA acquisition is described. For a particular PCC having an associated m/z, the intensity of the PCC in various scans may be tracked. For DDA, such scans may include the survey scans. For MMA, such scans may include the first scan in a cycle (e.g., element 3016a of FIG. 32). Given that the intensity of the PCC or precursor ion is known in the survey scans and the fact the MS/MS acquisitions are sequential in time, the intensity of the precursor ion in the survey scan and fragmentation will differ. ARi is the ratio of a product ion to a parent precursor when fragmented. If there are five precursor ions or PCCs within the MIW, each precursor ion is producing its own product ion or MS/MS spectra. The product ions in the MS/MS spectra represent the composite spectra from all the precursors. With this being the case the composite product ions are shared with all five precursors, filtered by m/z and area or intensity. The product ion intensities can't be larger in m/z or intensity, as well as a minimum intensity $\frac{1}{250}^{th}$ to that of their precursors. In accordance with techniques herein, processing may be performed to determine the PCCs intensity at the time of fragmentation. FIG. 34 illustrates how this may be accomplished. At each survey scan, the PCC's intensity value may be recorded and a linear regression or interpolation may be performed to determine any desired intensity value between survey scans. Illustrated in FIG. 34 are 10 points corresponding to 10 scans at which the intensity of the same PCC is known and tracked across time to form the illustrated curve. For example, such 10 points may correspond to 10 survey scans or times when the PCC's m/z is selected. Fragmentation of the PCC may occur, for example, at point P1 which may be between two survey scans. An intensity for the PCC at point P1 may be determined using linear interpolation or any other suitable technique known in the art.

In proteomics studies, it is generally accepted that depth of coverage and dynamic range is limited in DDA acquisitions. The serial nature of the method limits both sensitivity and the number of precursor ions that can be sampled. To that end, a number of data-independent acquisition (DIA) strategies, some of which are described herein, have been introduced with these methods, for the most part, immune to the sampling issue and with some having limitations with respect to sensitivity. One major limitation with DIA approaches is interference, i.e., MS/MS spectra are highly chimeric and often incapable of being identified using conventional database search engines. In at least one embodiment of techniques herein utilizing each available dimension of separation prior to ion detection, a particular implementation and workflow of the MMA strategy described in following paragraphs may be utilized. The MMA strategy and workflow in following paragraphs that may be used in an embodiment includes multiplexing both narrowband and wideband DIA acquisitions in a single analytical workflow. Some embodiments of techniques herein may perform MMA having an iterative nature whereby the MMA workflow limits the adverse effects of interference with minimal loss in sensitivity. Qualitative identification can be performed by Selected Ion Chromatograms (SIC) or conventional database search strategies.

High-resolution DIA acquisition strategies have been highlighted as emerging technologies, showing increased popularity in the arenas of qualitative and quantitative "targeted analysis." It has also become widely accepted that higher-resolution Q-Tof and Orbitrap mass analyzers are "ripe for adoption" in the arena of targeted quantification in complex matrices. Higher resolution mass analyzers reduce assay development time by eliminating the necessity for researchers to determine, upfront, the best transitions to each peptide. The ability to accurately quantify peptides in complex mixtures may be predicated on the applied analytical workflow's ability to measure the physicochemical attributes of each ion independent of the surrounding matrix. Higher resolving power, in terms of m/z, chromatographic, and drift peak widths are paramount in reducing the adverse effects of ion interference. Data processing tools, such as may be used in connection with techniques herein, may calculate an Ion Purity Score (IPS), a metric reflecting how well each ion's area has been measured. An IPS is calculated by comparing the half-heights; m/z, time, and drift to their respective experimental means. For evaluating the measured m/z, the resolution of the lock mass channel is used for comparison whereby for ICR's, mass resolution is a function of the transient measurement time and m/z, knowing the measurement transient time and m/z provides the means to calculate the theoretical mass resolution for comparison. As for chromatographic and drift peaks widths, each respective width is compared against the median of all calculated values across the entire gradient elution for each.

An increase in resolution, in any of the employed separation space, does not come without consequence. In connection with analytical techniques, the relationship between selectivity and resolution follows a standard S-curve. Resolution settings that exceed the inflexion point often have deleterious effects on other aspects of the experiment, for example a loss of sensitivity. Sensitivity is a function of ion flux (ions/unit time). Narrower chromatographic peaks result in, higher ion flux. Narrower chromatographic peaks require faster scan times to maintain duty-cycle. If an increase in scan speed does not lead to a concurrent increase in the number of product ion spectra per unit time, there is no net gain in either duty-cycle or sensitivity. Ion flux may be generally defined as a rate at which ions are output from an MS detector per unit of time (e.g., number of ions/unit of time and how they are distributed across an m/z range). Ion flux is similar to the frequency distribution of different m/z values over time such as described elsewhere herein (e.g., FIG. 31 in connection with description regarding MIW selection size and range with MMA).

Mass resolution in trapping instruments is a function of m/z and the transient measurement time, with narrow peaks requiring faster sampling speeds, the concurrent increase in the transient measurement time reduces the experimental mass resolution proportionally. For the Q-Tof geometries, resolution is independent of measurement time, with sensitivity governed by the duty-cycle and transmission of the time-of-flight analyzer. By increasing the number of co-orthogonal separations the stress on mass and chromatographic resolution can be alleviated allowing each to operate below their respective inflexion points. The ability of an applied analytical workflow to accurately identify and quantify the greatest number of peptides in complex mixtures, across the widest dynamic range, with the highest accuracy and precision, may be characterized as a direct consequence of the number and resolving power of all separation techniques employed prior to ion detection.

The $MS^E$ DIA workflow acquires MS full-scan data in an alternating fashion with the collision moving cell between a low and an elevated energy state. As known in the art and described elsewhere herein, $MS^E$ (also referred to herein as the Bateman technique or high-low protocol) refers to a method for tandem mass spectrometry data acquisition using alternating low-energy collision-induced dissociation and high-energy collision-induced dissociation where the former is used to obtain precursor ion accurate mass and intensity data for quantification and the latter is used to obtain product ion accurate mass. With $MS^E$ (e.g., the Bateman technique or high-low protocol) there is no precursor ion selection, with all precursor ions fragmented simultaneously. In such an embodiment, the collision energy may be ramped from a low to elevated energy state across the elevated energy acquisition time to provide for a more complete fragmentation across all charge-states. Product ions are aligned to their parent precursors by similarities in peak shape and apex retention time (also sometimes referred to herein as RT or $t_r$). Depth of coverage, the number of peptide identifications, may be comparable to the more traditional DDA acquisition strategies of the time. However, identification within these highly chimeric product ion spectra requires a specialized database search engine. The inability to process and search the $MS^E$ DIA data using both commercial and open-source data processing and search tools has been a limitation. The selectivity of this method was improved, for example, with the introduction of Traveling Wave Ion Mobility Spectrometry (TWIMS). The TWIMS geometry separates ions in two-dimensions (IMS drift and m/z) prior to detection. The addition of IMS increases peak capacity and reduces chimericy with little reduction in sensitivity. For IMS-enhanced datasets, precursor and product ions are aligned by their respective peak shapes, and apex retention and drift times ($t_d$ is also used herein to refer to drift time or drift time bin). These high-definition $MS^E$ ($HDMS^E$) IM (ion mobility)-DIA precursor and product ion spectra reflect higher selectivity allowing for greater depth of coverage, and dynamic range. Though selectivity is increased and hence product ion spectral quality improved, the $HDMS^E$ IM-DIA product ion spectra are still highly chimeric and still, to a large extent, require special DIA data processing tools. Despite this improved selectivity, the ability to identify a similar number of peptides compared to the more recent, higher scan rate, DDA instruments is challenging.

It has been suggested that DIA product ion spectra may be too complex to be identified using conventional database search tools based on reasoning that qualitative identification is best accomplished by screening the product ion spectra against spectral libraries using Selected Ion Chromatograms (SIC). To that end, a number of alternative DIA strategies have been introduced utilizing the SIC approach (e.g., including: FT-ARM, SWATH (Sequential Window Acquisition of all THeoretical Mass Spectra) Acquisition, and MSX (multiplexed DIA) acquisition). Though similar to $MS^E$ DIA in that there is no precursor ion selection, the m/z scale is sampled serially using user-defined m/z intervals. The narrowing of the m/z scale limits the number co-fragmenting peptides reducing chimericy in the product ion spectra. In these DIA workflows, a user-defined mass isolation width is either stepped across a predetermined mass scale (SWATH) or is randomly positioned within it (MSX). As an example, with the MSX approach, a series of 4-Th wide mass isolation windows are randomly sampled across a predefined mass range of 500-900 m/z. Consistent with discussion in following paragraphs and elsewhere herein regarding modeling and simulation, this portion of the m/z domain (e.g., 500-900 m/z) reflects the greatest density of precursor ion flux over the entire time domain. The assumption is that product ion spectra generated from narrower (but still wider than DDA) mass isolation windows will be less chimeric and more amenable to identification via the SIC approach. The method can also be enhanced and chimericy reduced by de-multiplexing overlapping product ion spectra and segregating product ions into groups. Matched product ions are assigned to the over lapping regions, leaving those unique to each in their respective m/z bin. Given, the ion density of the selected m/z window (500-900 Th) and the lower mass resolving power of higher scan rate $MS^2$ (e.g. MS/MS) acquisitions, the ability for two or more co-fragmenting precursors to produce product ions of a similar m/z, within the mass resolution, is high. Depleting these ions may limit selectivity instead of increasing it.

Modes of DIA may not by themselves overcome existing limitations of DDA. Duty-cycle is still a function of scan speed and higher scan speeds are detrimental to sensitivity. In order to maintain some semblance of duty cycle with SWATH or MSX, the width of the m/z domain needs to be reduced in order to set an acquisition time that does not completely sacrifice sensitivity. Though product ion spectra are acquired on all eluting peptides, the highly restricted sampling of the m/z space means that large regions of the m/z are left un-sampled. Sampling of the entire m/z scale would require; even faster scan speeds, wider m/z isolation windows or multiple injections. Having to acquire multiple injections does not increase duty-cycle nor does it have any effect on experimental peak capacity or ion interference.

An embodiment using techniques described herein may be characterized as having improved selectivity available with DIA techniques without losing sensitivity. To this end, described in following paragraphs is one embodiment in accordance with techniques herein with an MMA acquisition strategy which utilizes ion flux, m/z and drift to set the width of the MIW for each DIA acquisition. In such an embodiment, elution time may be segmented into scan cycles, and the number of scan cycles may be a function of the mean chromatographic (FWHM) of all eluting components. A lower limit of five scan cycles may be enforced, given that accurate AUC (area under the curve) quantification requires a minimum of five data points across a chromatogram peak's FWHM. In at least one embodiment as described below, each scan cycle may include 17 separate DIA acquisitions— One low-energy, two wideband (50 Th<MIW<500 Th), and fourteen narrowband (1 Th<MIW<50 Th) $HDMS^E$ IM-DIA (high definition $MS^E$ ion mobility) acquisitions (e.g., $HDMS^E$ denoting performing IMS in combination with $MS^E$ which is the Bateman technique or the high-low protocol for data acquisition). As described below and consistent with other description herein each of the wideband and narrowband acquisitions may use a MIW having a size or width and an associated m/z range that may vary with each scan cycle. Each MIW may specify an m/z range denoting a range of m/z values allowed to pass through a low energy scan for subsequent fragmentation. Thus, use of the MIW with an m/z range provides for selectively allowing precursor ions or ions in the low energy scan having an m/z within the m/z range to be fragmented to limit the amount of generated fragment ions originating from one of the precursor ions. Other than the repeating low-energy $HDMS^E$ IM-DIA full-scan acquisitions, in at least one embodiment, the center m/z value for each wideband and narrowband $HDMS^E$ IM-DIA acquisition changes with scan cycle. In at least one embodiment, processing may be performed to select MIW windows in the wid and narrowband MIWs to step through the entire m/z range while also allowing for overlap between MIWs in subsequent scans. The dynamic movement of the center m/z between scan cycles allows for multiple sampling of each precursor as a component of varying MIWs. Using a demultiplexing schema, techniques described herein produce highly discriminate product ion spectra with little compromise in sensitivity.

The highly selective product ion spectra can be searched using traditional database search engines or matched using known SIC techniques. Identified spectra may be deposited in the putative section of Molecular Ion Repository (MIR). Such putative identifications (e.g., precursors, and for each precursor its associated fragment ions) for an eluting molecule or component may be presumed or believed to be correct but have not yet been validated. In at least one embodiment, once a minimum of fifty putative identifications have been deposited, a validation algorithm internal to the MIR is activated. Operating in the background, the validation algorithm may continually select a random sampling of thirty putatively identified product ion spectra and perform processing to determine correlations and statistical significance between such spectra. For example, an embodiment may apply both dot-product spectral correlations and Pearson Product-Moment Correlation Coefficients known in the art to determine significance. For example, dot-product spectral correlations is described in Toprak, U. H., Gillet, L. C., Maiolica, A., Navarro, P., Leitner, A., & Aebersold, R. (2014). Conserved peptide fragmentation as a benchmarking tool for mass spectrometers and a discriminating feature for targeted proteomics. Molecular & Cellular Proteomics, 13(8), 2056-2071, which is incorporated by reference herein, and Pearson Product-Moment Correlation Coefficients is described in Morreel, K., Saeys, Y., Dima, O., Lu, F., Van de Peer, Y., Vanholme, R., . . . & Boerjan, W. (2014). Systematic structural characterization of metabolites in Arabidopsis via candidate substrate-product pair networks. The Plant Cell, 26(3), 929-945, which is incorporated by reference herein. If a positive correlation is found, a composite product ion spectrum (described elsewhere herein) is produced and the molecular ion signature of that peptide may be stored in the MIR.

What will now be described are materials and methods used in one embodiment with techniques herein described in following paragraphs.

In sample preparation, yeast strain W303 MATα (ATCC: 24657) (Blue Sky BioServices, Worcester, Mass.) was grown in YPD medium until early- to mid-log phase. Cells were harvested by centrifugation at 4,000 g for 5 min at 4° C. The pellet was suspended in 100 mM Tris pH 7.6 containing 100 mM dithiothreitol (DTT) and 5% sodium dodecyl sulfate (SDS). Unless stated otherwise, all chemicals were from Sigma-Aldrich (St. Louis, Mo.). The resulting lysates were heated to 95° C. for 5 min, followed by sonication using a Bioruptor sonicator (Diagenode, Liege, Belgium) at 20 kHz, 320 W, 60 s cycles for 30 min. After complete lysis, the supernatant was centrifuged at 16,000 g for 5 min to clarify the protein extract.

Further in connection with sample preparation, approximately 50 µg of each sample was lyophilized and dissolved in 0.05% (w/v) RapiGest (Waters Corporation, Milford, USA) in 50 mM ammonium bicarbonate. The samples were reduced in the presence of 10 mM DTT at 60° C. for 30 min and alkylated in the presence of 50 mM iodoacetamide (IAA) at ambient temperature in the dark for a further 30 min. Proteolytic digestion was initiated by adding sequencing grade TMPK-treated trypsin (Promega, Madison, Mich.) at a 1:10 (w/w) ratio and incubated overnight at 37° C. TFA was added to a final concentration of 0.5% (v/v) in order to hydrolyze the RapiGest and the solutions incubated at 37° C. for 20 min before being vortexed and centrifuged for 30 min at 13,000 rpm. Concentrated stocks were diluted to 100 ng/µl prior to sample analysis.

What will be described is an LC-MS configuration that may be used in connection with analyzing the foregoing sample. 1D nanoscale LC separation of tryptic peptides was performed with a nanoAcquity system (Waters Corporation), equipped with a BEH C18 1.7 µm, 20 cm×75 µm analytical RP column (Waters Corporation). One microliter of sample was loaded on column. Mobile phase A was water containing 0.1% (v/v) formic acid, whilst mobile phase B was acetonitrile containing 0.1% (v/v) formic acid. Peptides were eluted from the analytical column and separated with a gradient of 5-35% mobile phase B over 90 min at a flow rate of 300 nl/min, followed by a 10 min column rinse with 90% mobile phase B. The column was re-equilibrated at initial conditions for 20 min. The column temperature was maintained at 35° C. The lock mass compound, [$Glu^1$]-Fibrinopeptide B (50 nM), was delivered by the auxiliary pump of the LC system at 250 nl/min to the reference sprayer of the NanoLockSpray source of the mass spectrometer.

Mass spectrometric analysis of tryptic peptides was performed using both a Synapt G2-Si and Xevo G2-XS QTof mass spectrometer (Waters Corporation, Wilmslow, United Kingdom). Both instruments were operated in resolution mode with nominal mass resolution settings of 20,000 and 25,000 respectively. All experiments were performed in positive electrospray ionization mode and the ion source block temperature and capillary voltage were set to 80° C. and 2.5 kV, respectively. The time of flight analyzers (ToF)

were externally calibrated with a NaCsI mixture from m/z 50 to 1990. Data were lock mass corrected post acquisition, using the doubly charged monoisotopic ion of [Glu$^1$]-Fibrinopeptide B. The reference sprayer was sampled with a frequency of 30 s. Accurate mass LC-MS data were collected in a data independent (HDMS$^E$ IM-DIA) mode of acquisition on the Synapt G2-Si and data independent (MS$^E$ DIA) on the Xevo G2-XS QTof. All acquisitions were acquired for 0.1 seconds with a 0.025 second interscan delay. In low energy MS mode, data were collected at a constant collision energy of 4 eV per unit charge. In elevated energy mode, the collision energy was ramped from an initial to final value using a lookup table similar to those used in DDA acquisitions.

Figure 35:
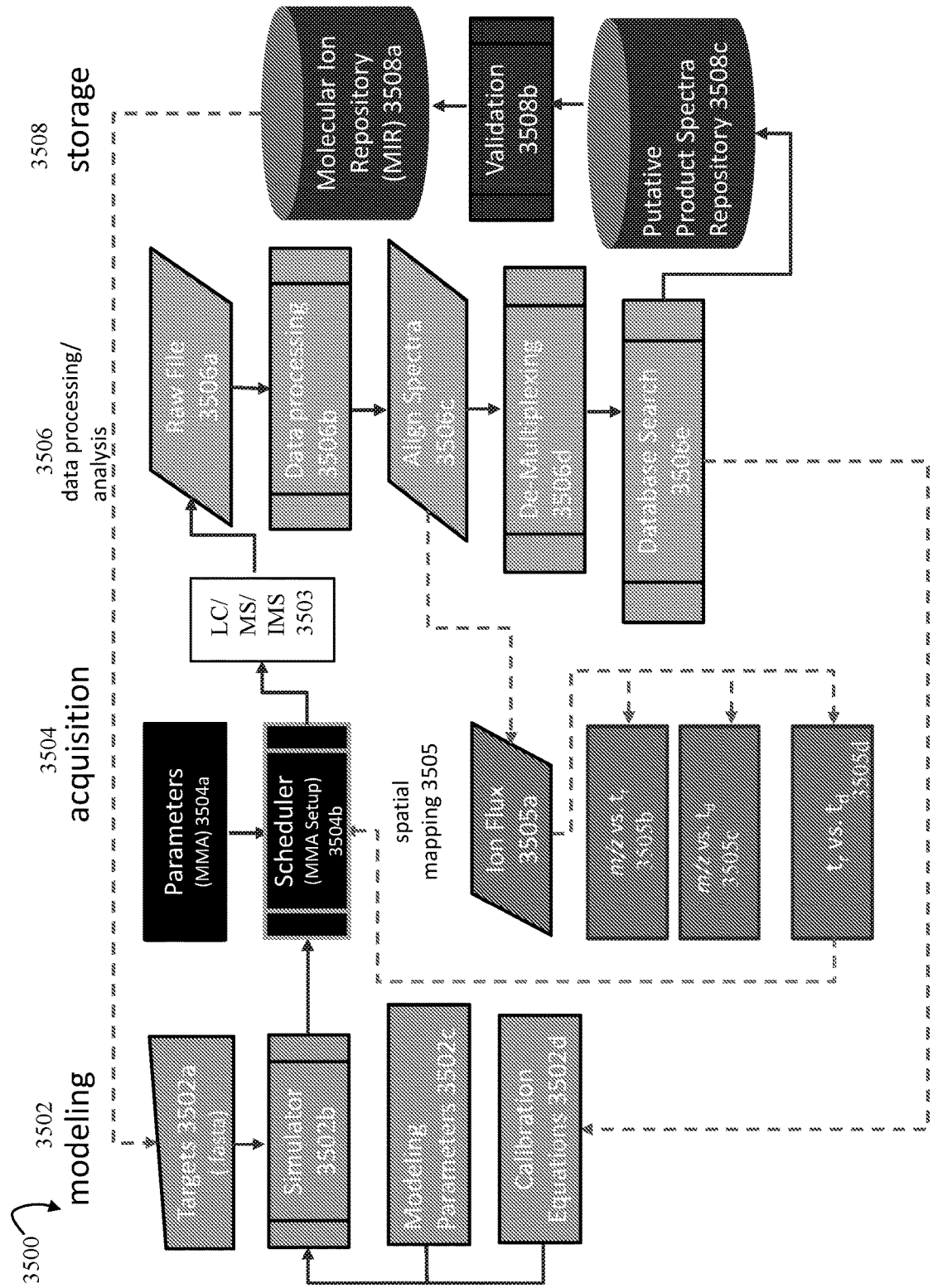
FIG. 35 is an example illustrating a workflow that may be used in an embodiment in accordance with techniques herein.

Referring to FIG. 35, shown is an example 3500 illustrating a workflow that may be performed in an embodiment in accordance with techniques herein. The workflow 3500 may be performed in connection with the above-mentioned sample for which an experiment is performed.

Element 3502 denotes a workflow modeling phase including targets 3502a, simulator 3502b, modeling parameters 3502c, and calibration equations 3502d. Element 3504 denotes a workflow acquisition phase including the scheduler 3504b, scheduling parameters 3504a, and instrumentation and equipment 3503 used to performed the experiment. In at least one embodiment, element 3503 may generally denote scientific instrument systems that perform chromatography (e.g., LC), mass spectrometry and (optionally) ion mobility spectrometry for sample analysis, such as for analysis of the prepared yeast sample described above. In at least one embodiment, the scheduler may determine a schedule used to control a mass spectrometer when performing data acquisitions for experiments and sample analysis. Consistent with discussion elsewhere herein, one or more additional instruments besides the mass spectrometer may also be used in connection with performing sample analysis although an embodiment of the scheduler as described herein may only affect processing performed by the mass spectrometer. Element 3506 denotes a general workflow data processing or data analysis phase including raw file 3506a, data processing 3506b, align spectra processing 3506c, demultiplexing 3506d and database searching 3506e. Element 3508 denotes a storage workflow phase including MIR 3508a, validation processing 3508b, and putative product ion spectra repository 3508c. Element 3505 denotes a spatial mapping phase that generates outputs regarding ion flux 3505a, m/z vs. $t_r$ 3505b, m/z vs. $t_d$ 3505c and $t_r$ vs. $t_d$ 3505d.

Generally, the workflow 3500 illustrates two major workflow paths where a first pathway is defined by solid connectors and arrows and a second pathway is defined by dashed arrows and connectors. The first pathway denotes flow using the simulator. Flow denoted by the second pathway may be used in an iterative manner such as, for example, for each run or injection performed as well as iteratively across multiple runs or injections as noted elsewhere herein.

A file denoting the simulation or modeling targets 3502a is input to the simulator 3502b. In connection with the yeast sample noted above, the targets 3502a may include the possible peptides, proteins, or an entire proteome that may be in the sample under testing and analysis. Generally, targets 3502a identifies the set of molecules to be simulated by the simulator 3502b. Thus, the targets 3502a may vary with the particular sample being analyzed. For example, if the sample included small molecules, pesticides, and the like, the targets 3502a would identify such molecules that may occur in the sample under analysis using the workflow 3500. The simulator 3502b simulates the attributes or physiochemical properties of the molecules identified in the targets 3502a. For example, the modeled attributes determined by the simulator 3502b for the target molecules 3502a may include expected, modeled or simulated attribute values for retention time, drift time, fragmentation pattern information (e.g., precursor and associated fragment ions generated as a result of fragmenting the precursor ion), m/z for precursor and fragment ions, and the like. The modeled attributes may generally include modeled values for any attributes described herein and also known in the art.

The modeled or simulated attributes (e.g., modeled physical and chemical properties for the target molecules of 3502a) are input to the scheduler 3504a which uses the modeled inputs to set up/determine an MMA schedule. The data acquisition parameters 3540a are described in more detail elsewhere herein and generally vary with the particular experiment and data analysis performed. For example, the scheduler 3504b is able to determine the order in which eluting molecules or components are expected in connection with acquisition such as based on the simulated retention times. The scheduler 3504b sets parameters 3504a affecting the acquisition timeline such as, for example, the number of scan cycles/chromatographic FWHM, scan time, wideband and narrowband m/z isolation widths (MIWs), and collision energy table. The parameters 3504a may also include user defined information such as any user-defined minimums or match tolerances.

Sample analysis is performed by the instruments 3503 which include a mass spectrometer operating in accordance with the MMA setup or schedule generated by the scheduler 3504b. As a result of the experimental run or injection, raw data 3506a is produced which is then processed in data processing 3506b. Data processing 3506b includes data processing as described below and elsewhere herein. For example, data processing 3506b may include single scan processing, processing to construct a charge cluster group or PCC, and processing to determine a charge state or potential/candidate charge state, of a PCC. Alignment processing 3506c may include aligning precursor and product or fragment ions in each scan (e.g., forming SSPPISs for single scans), and also combining PCCs in time by m/z (e.g., to form a curve denoting an ion or PCC eluting over time). Thus, alignment processing of 3506c may include forming SSPPISs for single scans and combining SSPPISs for the same PCC over time (e.g., form profile or envelope of the same PCC eluting over time). The aligned product and precursors or SSPPISs are then input to de-multiplexing 3506d.

Generally, the de-multiplexing 3506d may be characterized as a further refinement of the particular product ions associated with a particular precursor ion or PCC (e.g., to selectively refine, filter, or limit the product ions in the experimental data determined as generated through fragmentation of the PCC or precursor ion of the experimental data). Demultiplexing may include, for example, using various criteria as described herein to further filter, exclude or remove fragments ions associated with PCCs (e.g., criteria may use AR1 and AR2 values and other as described herein) to determining the best identifying product ion spectra for each eluting component (e.g., determine best fragment ions included in a CPPIS for an eluting component where the fragment ions may be used to identify the precursor ions of the eluting component).

At the end of demultiplexing, a CPPIS may be constructed for an eluting component or molecule (e.g., combining SSPPISs for the same eluting component or molecule) such as in connection with unsupervised or non-supervised clustering. With unsupervised clustering, processing 3506e may include adding the CPPIS to the putative repository 3508c for further validation in 3508b. Once validated, a CPPIS may be included in the MIR 3508a.

With supervised clustering, step 3506e may include extracting a target CPPIS from the repository 3508c and querying (e.g., based on m/z, retention time and drift time (if IMS is used)) across the time line of SSPPISs from the experimental data. SSPPISs in the experimental data matching (e.g., matching precursor or PCC m/z) the target CPPIS may be combined into an experimental CPPIS and then added to the repository 3508c. Subsequent validation 3508b may perform processing to further validate the experimental CPPIS which may replace or supplement an existing CPPIS for an eluting component or molecule in the MIR 3508a.

Results from an experiment performed may be transmitted from 3506c back to the scheduler 3504b in the form of spatial mappings 3505 (e.g., via the flow path from 3506c, to 3505a, 3505b, 3505c, 3505d and then to the scheduler 3504b). Based on the experimental data that feeds back into 3504b through 3506c, the scheduler 3504b may modify or revise the schedule or MMA setup and also further revise the parameters (e.g., may revised the collision voltage or energy, change the MIWs, and the like). In at least one embodiment, the MMA schedule and parameters may be revised to now identify, or target to produce experimental data with a next sample injection or run, those molecules which have not been previously identified (e.g., those molecules for which experimental data has not yet been acquired in a prior injection run or experiment). For example, in a first run, the scheduler 3504b may determined an acquisition schedule and associated parameters 3504a based on simulated information such as simulated attributes or properties of the molecules in target 3502a. After this first run, experimental data may be obtained for some first portion of the molecules in 3502a. In a second run, the scheduler may select an an acquisition schedule and parameters 3504a with a goal of obtaining experimental data for other molecules of 3502a not in the first portion.

Database search 3506e may include supervised clustering as described herein where a target eluting component's CPPIS may be selected from 3508c to determine whether the target eluting component's CPPIS matches SSPPISs of the experimental data. If so, additional attributes regarding the matching target eluting component may be obtained from the repository 3508c and provided as an input to the simulator 3502b in the form of calibration equations and/or modeling parameters 3502d (e.g., what collision energy should be used, what is the retention time for the eluting component, what are the drift times for the different PCCs or precursors of this eluting component, what are the fragmentation patterns (precursors and, for each precursor, its associated fragment ions) for the eluting component).

In one embodiment, the simulator 3502b may be initially used to predict, simulate or model physical and chemical properties of all molecules in the targets 3502a such as by generating simulated theoretical fragment patterns (e.g., each precursor and associated fragment ions originating from each precursor via fragmentation) for all targets 3502a. For example, assume targets 3502a has 1000 molecules. The simulator 3502b may initially generate such simulated attribute information for the 1000 molecules to determine an initial MMA schedule and paramters 3504a used when performing a first experimental run. Now, the first experiment is performed based on the initial MMA schedule and parameter to acquire experimental data including attributes or properties for 200 of these eluting molecules. The attributes for the 200 molecules obtained through the first experimental run may then form a feedback now input into the simulator. However, the simulator 3502b may continue to simulate information for the remaining 800 molecules of the target set for which no experimental data has yet been acquired. In a similar manner, the simulator 3502b may also be updated with information from the MIR 3508a (arrow from 3508a to 3502a) where the simulator 3502b may use inputs from the MIR 3508a and simulate remaining eluting molecule information. For example, for a first eluting molecule, the MIR includes attributes/physical properties such as RT, drift time, precursor and product ion spectra for precursors of the eluting molecule, etc. However, for a second eluting molecule, the MIR may not include any information. Thus, the simulator may use and output the information from the MIR for the first eluting molecule. However for the second eluting continue, the simulator will continue to output and to use simulated attribute information (e.g., theoretical fragmentation pattern denoting what product ions are expected for which precursors for the second eluting molecule). In at least one embodiment, the MMA schedule (also referred to herein as a schedule or acquisition schedule) and parameters may be revised to now identify with a next sample injection or run those molecules of targets 3502a which have not been previously identified (e.g., modify MMA setup or schedule 3504b and parameters 3504a to target obtaining real experimental data for those molecules of 3502a for which the simulator is still generating simulated attribute information).

Further detail regarding the various items and processing steps in 3500 is provided in following paragraphs and figures.

In connection with modeling 3502, the ability to accurately model and simulate the perturbative effects of stress on a biological system, requires sound knowledge and understanding of the system(s) being simulated. Both the elemental composition and linear sequence of amino acids of a peptide are known, therefore the m/z and z of all possible precursor and product ions to that peptide can be calculated. This is the general modus operandi for all open source and commercially available peptide database search engines. The number of isotopes a precursor can generate is directly related to its elemental composition and concentration. The following paragraphs further describe the individual components of the modeling phase or process 3502.

In connection with the particular experiment regarding the yeast sample noted above, a target file 3502a may be provided. In order to properly simulate how the ions from a cellular lysate would be distributed in a LC-MS workflow, reflecting a given peak capacity, the input protein list must be ordered, as close as possible by concentration. To accomplish this goal, over 100 raw and processed yeast cellular lysate data sets were obtained, for example, from publicly available sources such as on the internet. Raw data files were processed using Mascot Distiller and MaxQuant known in the art and also described in, for example, Cox, J., & Mann, M. (2008). MaxQuant enables high peptide identification rates, individualized ppb-range mass accuracies and proteome-wide protein quantification. Nature biotechnology, 26(12), 1367-1372, which is incorporated by reference herein. All product ion spectra were searched against the UniProt *S. cerevisiae* (Jul. 3, 2014; 6752 entries) fasta database using Mascot, X! Tandem and *Andromeda* known in the art as described, for example, in Cox, J., Neuhauser, N., Michalski, A., Scheltema, R. A., Olsen, J. V., & Mann, M. (2011), *Andromeda*: a peptide search engine integrated into the MaxQuant environment. Journal of proteome research, 10(4), 1794-1805, which is incorporated by reference herein. For each search result, the protein scores were normalized by dividing each score by the sum of all scores. Assuming that a proteins' concentration is a direct consequent of its normalized score the results were combined, re-normalized and sorted in descending order. This constitutes how the ordered database is constructed. The yeast ordered database served as the input (e.g., targets 3502*a*) into the simulator 3502*b*. In addition to the ordered database, the user inputs modeling parameters 3502*c* and calibration equations 3502*d* for the on column loading, gradient and IMS calibration files, as well as the resolutions for drift, chromatographic, and m/z. Using the Hi3 quantitation strategy, the on-column load is distributed across the simulated proteins establishing each proteins molar concentration. Hi3 quantitation strategy is known in the art such as described in, for example, Silva, J. C., Gorenstein, M. V., Li, G. Z., Vissers, J. P., & Geromanos, S. J. (2006), Absolute quantification of proteins by LCMSE a virtue of parallel MS acquisition. Molecular & Cellular Proteomics, 5(1), 144-156, which is incorporated by reference herein.

Figure 36A:
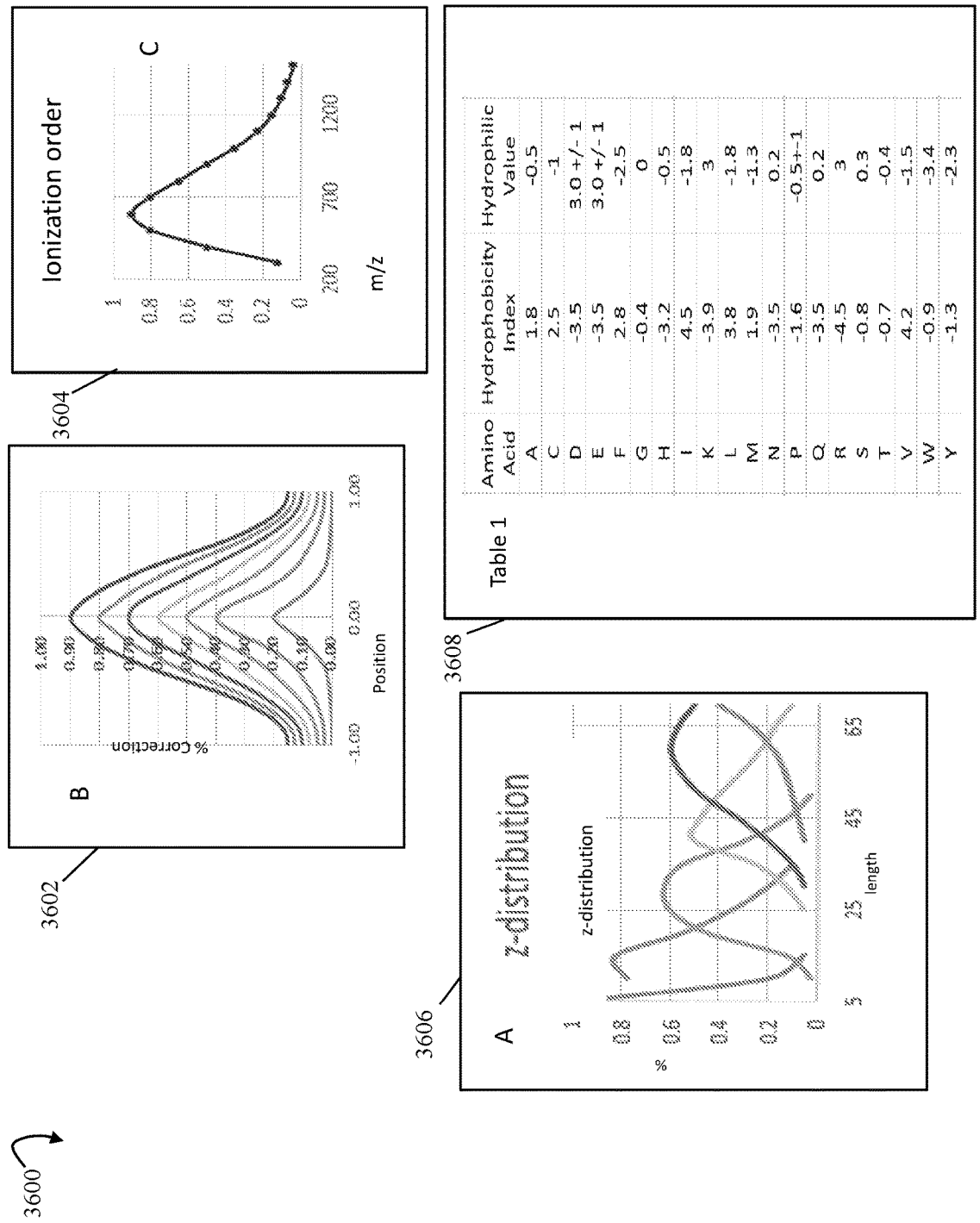
FIGS. 36A and 36B are examples of simulator inputs that may be used in an embodiment in accordance with techniques herein.
Figure 36B:
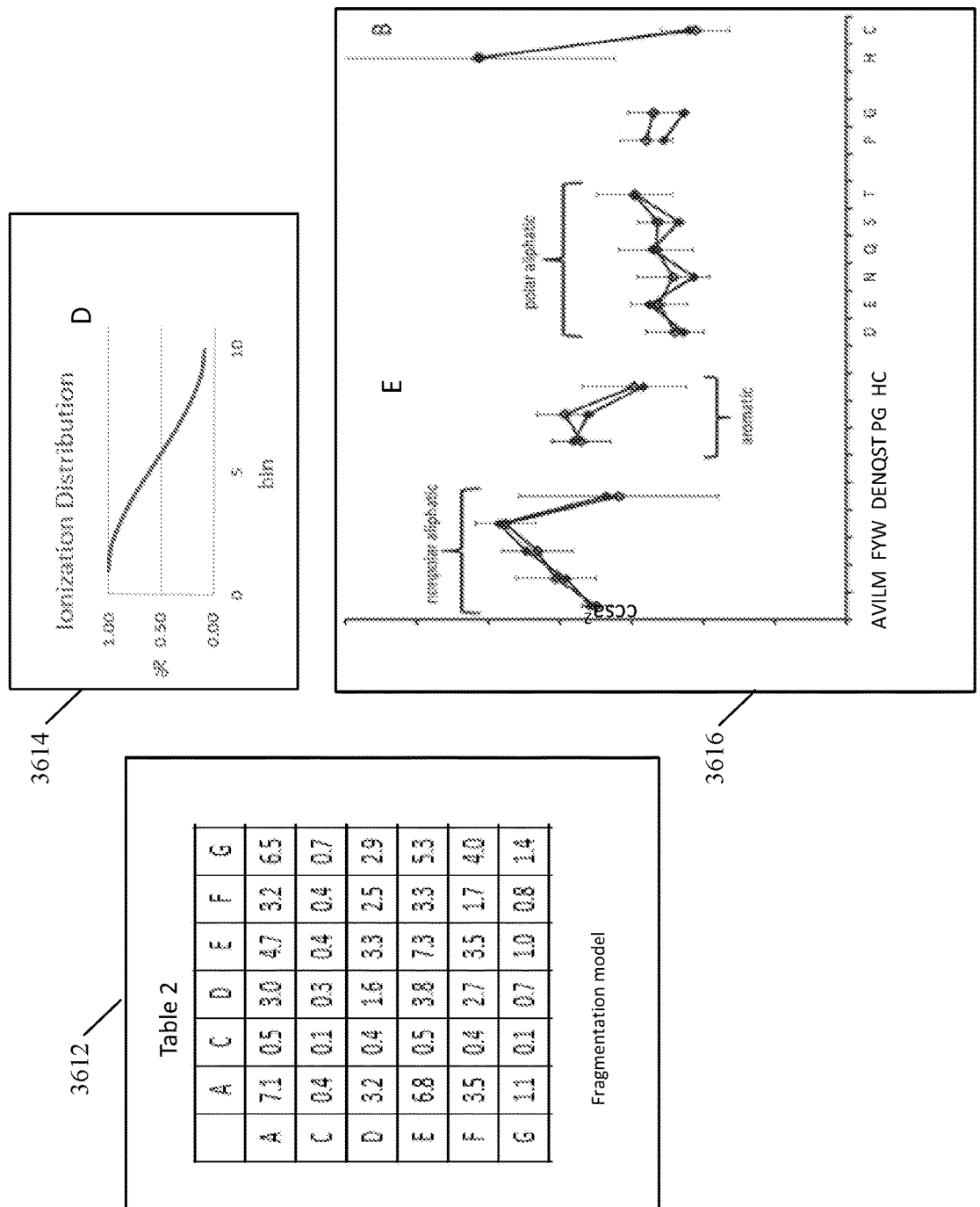

Referring to FIGS. 36A and 36B, shown are examples 3600 and 3601 further illustrating different inputs that may be provided to the simulator 3502*b*. Collectively, the elements of 3600 and 3601 may denote a sampling of information included in the modeling parameters 3502*c* and calibration equations 3502*d*. In particular the tables and models of 3600 and 3601 illustrate a sampling of the tables and models used by the simulator to estimate the precursor and product ion flux from an input set of peptides, proteins or an entire proteome. Panel A 3606 reflects the distribution of z based on peptide sequence length. Panel B 3602 depicts a table of adjustment (%) to be applied given the positioning of chargeable residues (K, R, H) relative to the n- and c-termini. Panel C 3604 determines the ionization order (highest-to-lowest) by m/z. The m/z of each charge state of each peptide is placed on the curve with the y-axis intercept defining the ionization order. The curve in panel D 3614 defines which percentage of the area of a peptide is assigned to each z. Panel E 3616 and Table 1 3608 illustrate the CCSA and hydrophobicity values of each amino acid, respectively. The simulator utilizes these values for calculating each peptide's retention time and each charge state's CCSA. Table 2 3612 reflects a frequency value for each di-peptide bond. The residual difference, defined as the difference in precursor ion intensity in low-energy minus residual intensity in elevated-energy, is multiplied by the calculated value to set the fragment ion intensity. The assigned intensity (multiplied by 1000) is distributed across isotopes.

When electrosprayed into a mass analyzer, peptides can take on multiple charge states. Panel A 3606 and panel B 3602 respectively reflect the distribution of z as a function of peptide length and the position of certain chargeable residues. Proteins, in as far as amino acid composition is concerned, are quite similar. The curve reflected in Panel C 3604 assigns ionization order. Each peptide is assigned a m/z or series of m/z values based on the number of theoretical charge states it can take on. Where each m/z value lands on the curve is reflected in its rank from 0-1 with one being the best ionizing. Given the similarity in composition, the number of best-to-least ionizing peptides per protein is a direct function of length. How those peptides are distributed is illustrated in panel D 3614. Assuming a similarity in composition the number of peptides occupying each bin in 3614 is also a function of length. With this being the case the peptides to a protein are distributed across the ten bins of 3614. Which peptides reside in which bin is a function of where their m/z values lie on the curve illustrated in panel C 3604. Briefly, a 10 kDa (Dalton) protein would result in one peptide per bin, whereby a 100 kDa protein would result in ten. Once order has been defined, the intensity of the best ionizing peptide is assigned given the proteins molar amount and calculated or defined response factor (cts/mole), and all others are assigned by multiplying the intensity of the best ionizing peptide to where they lie on the curve. Once each precursor m/z receives its intensity, it is distributed using an isotopic modeling algorithm.

Modeling algorithms for physicochemical attributes, retention time, drift time, and collisional cross sectional area are known in the art, for example, in Krokhin, Oleg V., and Vic Spicer, "Predicting peptide retention times for proteomics", Current Protocols in Bioinformatics (2010): 13-14; Petritis, Konstantinos, et al., "Improved peptide elution time prediction for reversed-phase liquid chromatography-MS by incorporating peptide sequence information", Analytical chemistry 78.14 (2006): 5026-5039; and Meek, James L. "Prediction of peptide retention times in high-pressure liquid chromatography on the basis of amino acid composition", Proceedings of the National Academy of Sciences 77.3 (1980): 1632-1636; Moruz, Luminita, et al., "Chromatographic retention time prediction for post-translationally modified peptides", Proteomics 12.8 (2012): 1151-1159; Valentine, Stephen J., et al. "Using ion mobility data to improve peptide identification: intrinsic amino acid size parameters", Journal of proteome research 10.5 (2011): 2318-2329; and Knapman, Tom W., et al. "Considerations in experimental and theoretical collision cross-section measurements of small molecules using travelling wave ion mobility spectrometry-mass spectrometry", International Journal of Mass Spectrometry 298.1 (2010): 17-23, which are all incorporated by reference herein.

Panel E 3616 and Table 1 3608, respectively, illustrate each amino acid's collisional cross sectional area and hydrophobicity index (HI) value. Knowing elemental composition, linear sequence, length, and z, an elution and drift time can be predicted for a given column type, gradient profile, flow rate, column temperature, gas density and field strength. The simulator 3502*b* utilizes these values and estimates the elution and drift order of the modeled peptides and their respective charge cluster groups. Variability between the experimental and predicted values is a function of how well the models for each measurable attribute have been defined.

Peptide fragmentation is independent of the instrument platform/geometry provided. A similar method of fragmentation (e.g. low-energy CID/collision cell) and the instrument is operated under similar gas pressure and collision energy. Table 2 3612 illustrates a section of a one of the three fragmentation tables utilized by the simulator. Each table reflects a matrix of all possible binary pairs (AA, AC, AD, etc.) of amino acids. Similar to the construction of the ordered input fasta databases, each matched product ion intensity is normalized to the sum intensity of all the matched product ions to that peptide. The first table reflects the normalized intensity for each of the 400 possible binary pairs. The second, reflects the normalized frequency of each possible binary pair (sequences) with the third representing the frequency of the identified pairs. For each binary pair, a ratio frequency is calculated between how often the pair was identified relative to how often the pair was identified. Next, the normalized intensity ratio values are divided by the normalized frequency (present/detected) with the result normalized to the total sum of all the binary pairs. The three models are used to assign a fractional value to each theoretical product ion. The product ion intensity is calculated by multiplying its fractional value to the intensity value for the charge cluster group of the peptide. The assigned intensity is then distributed into the appropriate number of isotopes. A more detailed description of a fragmentation modeling process may be found, for example, in "Conserved peptide fragmentation as a benchmarking tool for mass spectrometers and a discriminating feature for targeted proteomics", Molecular & Cellular Proteomics, 13(8), 2056-2071, which is incorporated by reference herein.

In at least one embodiment, the MMA overall workflow of 3500 may be under complete user control or run as an automated process. The schematic of the workflow 3500 can be applied to single sample or executed iteratively for recursive and/or exhaustive analysis of technical or biological replicates. As noted above, the solid line arrows and connectors form a first pathway illustrating the use of the simulated ion flux for initial MMA schedule setup and parameter construction whereas the dashed arrows and connectors forming a second pathway reflects the iterative workflow where the acquisition timeline of an acquisition scheduled (generated by the scheduler 3504*b*) is based on the ion flux of the previous injection.

In batch analysis mode, post-acquisition processing may correct for any variation in retention and/or drift time between injections using the highest scoring peptides as molecular markers for least squares fits. In addition, in connection with the scheduler 3504*b* and the MMA schedule in one embodiment, the center m/z for each narrowband and wideband acquisition is excluded in the next scan in the same cycle. The exclusion list is cumulative, continually limiting what parts of the m/z scale are to be narrowly sampled per unit time. The constant changing of the center m/z ensures the acquisition of differential product ion spectra which, when processed by the de-multiplexing algorithm, produces product ion spectra of continually increasing selectivity. Once the entire m/z domain of the low energy scan has been sampled multiple times within multiple isolation windows, the process repeats until all injections of a single mixture, replicates, or members of a cohort of biological samples have been exhausted. The grey stippled boundary lines D1 in the example 3700 discussed below in more detail illustrate multiple samplings of the same m/z space. This iterative approach allows for the creation of highly specific product ion spectra for each eluting peptide. Included are all the measured physicochemical attributes for every ion of every spectrum across all injections. The MMA strategy significantly increases the number and selectivity of product ion spectra with very little effect on sensitivity. The resultant cleanliness of each product ion spectra makes the workflow ideal for traditional database searches as well as for SIC targeting.

Figure 37:
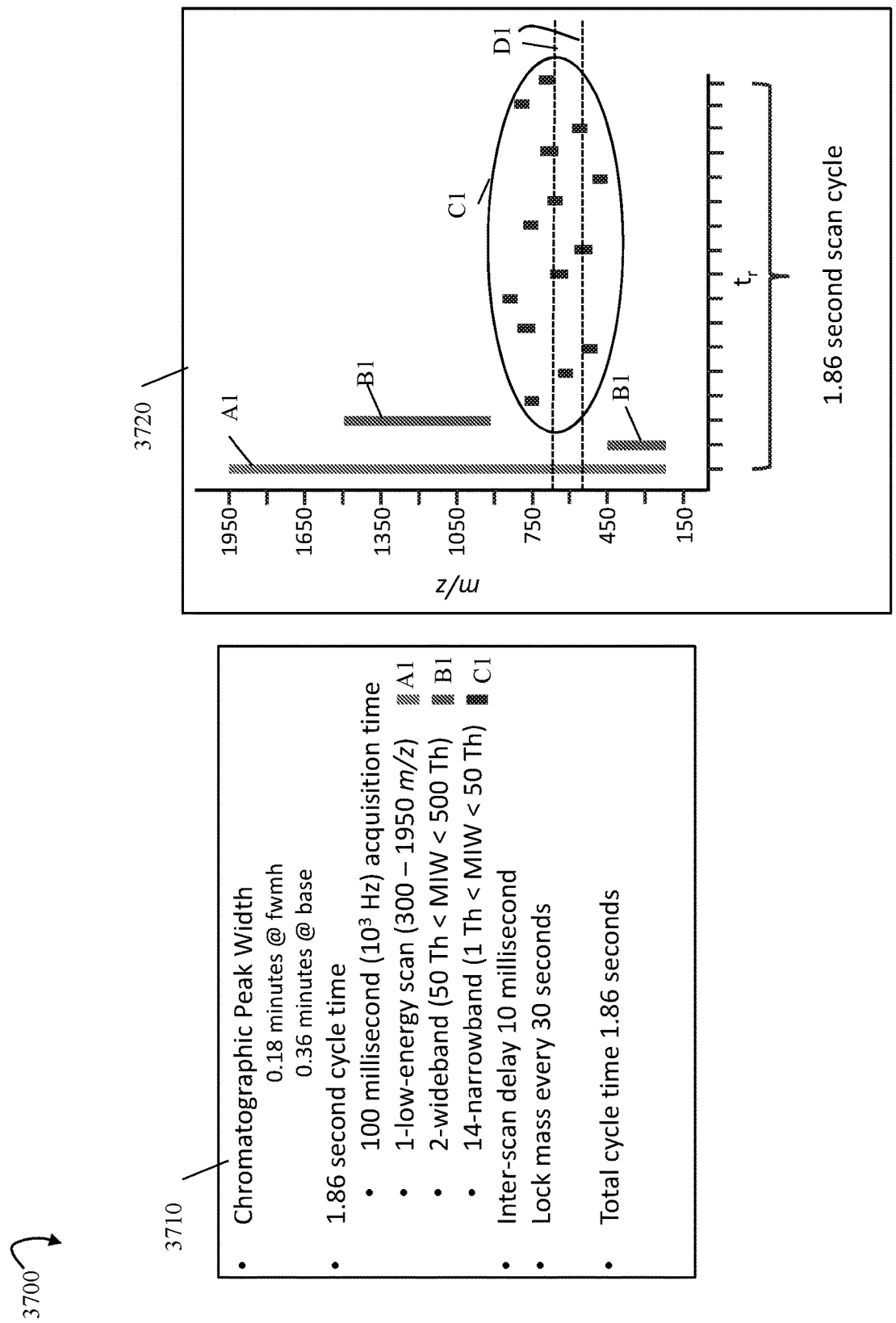
FIG. 37 is an example of inputs and outputs associated with a schedule in an embodiment performing the workflow of FIG. 35.

In connection with cycle time determination by the scheduler 3504*b*, reference is made to FIG. 37. In order to maintain the capacity to perform highly accurate AUC quantification on label-free, isobaric and isotopically labeled samples, a minimum of five data points are required across an eluting peptide's FWHM of its peak (e.g., need 5 data points/5 spectra between two half height points of a chromatographic peak such as between points H1 and H2 in FIG. 7). To that end, the starting metric for determining the appropriate scan cycle time, acquisition speed, and number of acquisitions per scan cycle is the median chromatographic FWHM. The scheduler 3504*b* may perform processing using an algorithm that constructs the MMA timelines that uses inputs, such as, the dynamic range (e.g., range of counts denoting a signal intensity for detected ion), measure of the detection range of a detector, instrument response factor (in counts/mole injected) and LOD. The response factor may be user-defined or determined experimentally such as described, for example, in Silva, J. C., Gorenstein, M. V., Li, G. Z., Vissers, J. P., & Geromanos, S. J. (2006). Absolute quantification of proteins by LCMSE a virtue of parallel MS acquisition. Molecular & Cellular Proteomics, 5(1), 144-156, which is incorporated by reference herein.

Element 3710 summarizes information used in determining the scan cycle time in one illustrative embodiment. The acquisition speed is proportion to five times the LOD (the MS accumulation time that will generate a usable signal on the lowest expected ion), but never to exceed the fastest scan rate (50 ms). In manual mode all parameters including scan speed, acquisition time, response factor and dynamic range may be user-defined. The number of acquisitions per scan cycle is determined using the calculated acquisition speed, instrument inter-scan delay time and acquisition frequency of a reference (lock) mass. In connection with determining scan cycle time, the median peak width, and thus median FWHM, is known from an experimental run. In this example 3710, assume the FWHM is 0.18 minutes or 10.8 seconds. In at least one embodiment as described herein, a minimum of 5 points, and thus 5 spectra or scans, within the 10.8 second interval is desired. Therefore, a maximum scan cycle time of 2.16 seconds/scan cycle may be used to ensure the minimum 5. In this particular example, a 1.86 second cycle time is used with the MM workflow 3500 (e.g., 10.8/6=1.8 seconds) with approximately 6 cycles/FWMH.

Figure 38:
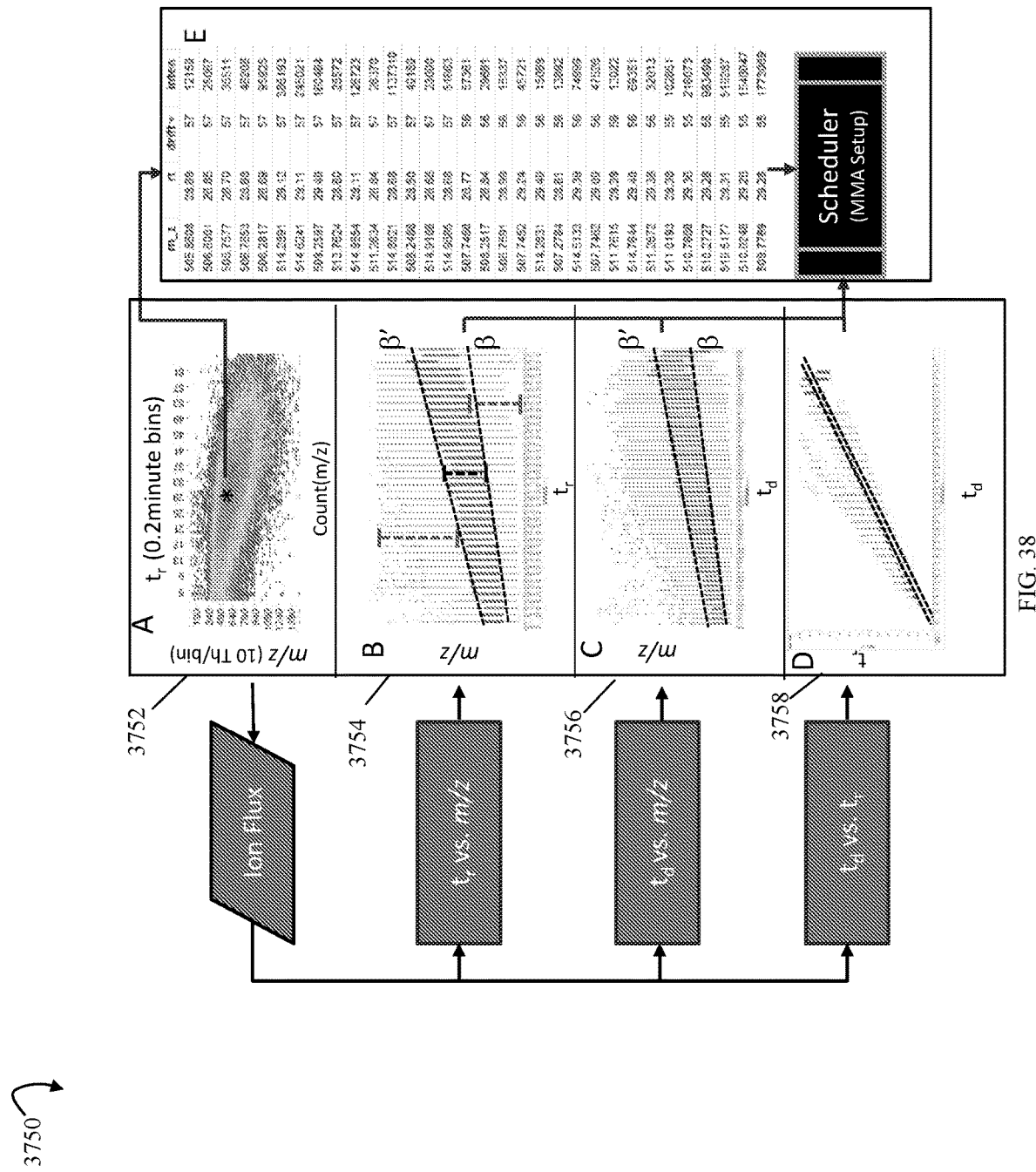
FIG. 38 is an example of spatial mapping that may be used in the workflow of FIG. 35 in an embodiment in accordance with techniques herein.

With reference to 3720, for a first scan cycle of 1.86 seconds, an embodiment may perform 17 data acquisitions or experiments and thus 17*6=102 experiments or acquisitions across a single peak without loss of sensitivity (with 100 millisecond acquisition time). The 17 data acquisitions include 1 low energy scan A1, 2 wide band scans B1 and 14 narrow band scans C1. Element A1 denotes a single low energy (LE) scan where all precursor ions in the 300-1950 m/z range are allowed through. Different MIWs in terms of the wide-band MIWs B1 and narrow band MIWs C1 may utilized for selective precursor ion fragmentation. Two wide band MIWs B1 may be selected each having a range or width between 50 and 500 m/z values. Fourteen narrow band MIWs C1 may be selected each having a range or width between 1 and 50 m/z values. Generally, different MIWs may be selected—medium or narrow width—depending on the density of the number of precursor ions within a particular m/z range. For example, in regions of the m/z range A1 having lower ion flux, medium MIWs may be used. In regions of the m/z range A1 higher/highest ion flux, narrow band MIWs may be used. Thus, narrower MIWs may be used in the portions of the m/z range having the higher/highest ion flux in order to minimize ion interference and spatially resolve or separate the ions (e.g., generated fragments from precursors) in such regions of higher/highest ion flux. In one embodiment, in subsequent scan cycles, 2 wide MIWs and 14 narrow MIWs may be selected each with a different center point than in a previous scan cycle in order to shift the m/z subrange associated with each MIW on subsequent scans. The size of each MIW may be determined based on a desired maximum number of precursor ions within any defined m/z bin corresponding to some continuous number of m/z values (e.g., no more than 10 precursor ions per m/z bin). This is further described below in more detail with reference to FIG. 38 illustrating various distributions from a previous injection.

In connection with determining MIWs, there is a limited amount of m/z sufficient space that can be occupied in any product ion spectra. Thus the number of product ions capable of populating that space with minimal chimeric interference is a function of the precursor population and their aggregate product ions present in the collision cell per unit time. In the example 3750 of FIG. 38, shown are examples illustrating the spatial mappings 3505 that may be generated from experimental data and used in providing inputs to the MMA scheduler 3504b such as to determine the MIWs used in particular scans of a cycle time in an embodiment in accordance with techniques herein. Panel A 3752 represents an ion flux heat map illustrating precursor ions grouped into two-dimensional m/z vs. $t_r$ bins. Each m/z vs. $t_r$ bin is 10 Th wide and 0.2 min wide. Panel B 3754 reflects the distribution of m/z vs. retention time. Panel C 3756 reflects the distribution of m/z vs. drift. Panel D 3758 reflects the distribution of retention time $t_r$ vs. drift time $t_d$. Densely populated portions of the m/z range having the highest ion flux are denoted by the "*" in 3752 and also the densely populated m/z range between boundary lines β and β' in 3754 and 3756. Thus, for example, the m/z range between boundary lines β and β' in 3754 and 3756 may denote an m/z range where the narrow MIWs are used with wide MIWs used in m/z ranges above boundary lines β ' and below β (outside of the area bounded by boundary lines β and β').

At a scan speed of 100 ms and inter-scan delay time of 10 ms as illustrated in 3710, each scan cycle may contain approximately 108 spectra, each treated as its own experiment. An example of how these spectra are distributed across a median chromatographic FWHM of 1.86 seconds is illustrated in 3720 of FIG. 37. In 3720, the first acquisition of every scan cycle is a low-energy precursor ion scan followed by two wideband elevated-energy scans B1 having associated m/z ranges outside the upper and lower boundary lines β and β' (as reflected in panel B 3754). The width of the wideband MIW acquisitions may be defined by a limit of ten precursor ions per drift bin. As a first instance in connection with narrowband MIWs, the scheduler selects a calculated number of precursor ions reflecting the highest normalized intensity within the boundary lines β and β' for each scan cycle. The m/z values for such precursor ions may be used in determining a starting m/z range for narrowband MIWs. Using the selected m/z values, the width for each narrowband acquisition may be calculated similarly with a maximum of 10 precursor ions per drift bin. In this manner, as described elsewhere herein, the m/z range and width associated with each MIW may vary with the goal of tuning the MIW width based on including the maximum number of 10 precursor ions per drift time bin. As a variation, the mass isolation widths associated with wide and/or narrowband MIWs may also be user-defined. Portions of the same space in time, drift and m/z may be re-sampled within a same scan cycle as long as the center precursor m/z of the MIW is unique. With the median chromatographic FWHM defining the number of scan cycles, each precursor has the opportunity to be sampled more than once across its elution in a single scan cycle. The process repeats until all precursor ions have been sampled in either a narrowband or wideband MIW in the current scan cycle. The scheduler keeps track of which regions of the multi-dimensional space have yet to be narrowly sampled. Operated in batch acquisition mode, the cumulative exclusion of center m/z values ensures that the m/z, time and drift space within the boundary lines β and β' illustrated in panels B 3754, C 3756 and D 3758 may be completely sampled (e.g., obtain elevated energy scan data for the entire bounded multi-dimensional space) before the process repeats.

The foregoing processing of ensuring that the defined range of the multi-dimensional bounded region (e.g., denoted by the boundary lines β and β' in panels B 3754, C 3756 and D 3758) is sampled prior to repeating again for the defined range may generally occur within a single injection or run, or may span multiple injections or runs. In the case of spanning multiple injections, the same sample or different samples may be used in each injection or run so long as the samples using include a same or common set of molecule(s) (e.g., all samples include molecules as defined in targets 3502a) for which analysis is performed. When spanning multiple injections, information, such as experimental data (e.g., ion flux, covered or sampled m/z ranges, etc.) related to a first injection or run may be used by the scheduler to automatically determine the schedule of the second next injection or run (e.g., m/z ranges of wide and/or narrow MIWs for each scan and scan cycle of the next second injection and run) to ensure complete sampling of the entire multi-dimensional bounded region. More generally, the foregoing illustrates the iterative nature and feedback of the workflow processing that may span across multiple injections, across cycles and scan cycles of the same injection, and the like. The scheduler 3504b is generally provided with information regarding what portion(s) of the multi-dimensional bounded region have already been sampled at a current point in time so that the scheduler may perform processing to sample those remaining portions of the multi-dimensional bounded region that have not yet been sampled (e.g., determine schedule for sampling and operation of the mass spectrometer and/or ion mobility spectrometer subsequent to the current point in time to ensure the entire multi-dimensional bounded region has been sampled prior to possibly repeating for the multi-dimensional bounded region). As described herein, the information providing the feedback noted above to the scheduler between injections may include experimental data such as ion flux and other data (e.g., see example 3750 of FIG. 38).

Generally, the width of the wideband and narrowband MIWs may be determined algorithmically or may be user-defined, as noted above. The scheduler, acknowledging the timeline of a previous acquisition, sets the new acquisition timeline such that the center m/z for each wideband and narrowband acquisition is excluded. MMA time line construction may be performed, utilizing either, a user-defined chromatographic FWHM or the median value of a prior experiment, where in this example the scheduler sets the number of scan cycles to six. In auto-mode in this example, the acquisition order is set to execute one low-energy full scan, two wideband (50 Th<MIW<500 Th) scans, and n narrowband (1 Th<MIW<50 Th) scans, where n is a function of user-defined or algorithmically determined LOD (moles). The scheduler requires inter-scan delay time and a response factor (cts/mole) as minimum input. The response factor (RF) can be calculated from a reference mass or user-defined. In addition to the inter-scan delay time, the LOD/RF algorithm determines acquisition time. Dividing the scan cycle time by the acquisition time sets the number of acquisitions, with the number (n) of narrowband acquisitions equal to the total number of scans in the cycle, minus three.

In addition to setting cycle time, acquisition speed, number of acquisitions, and the widths of the MIWs, when operated in auto mode, the scheduler 3504b also monitors and if necessary may adjust the applied collision energy for each MIW. As with many of the parameters 3504a in the MMA workflow, a collision energy table can be user-defined, or the resident table can be optimized using the fragmentation efficiency data from a previous injection. As described elsewhere herein in connection with data processing 3506b, a fragmentation efficiency may be calculated for each eluting peptide. In two-dimensional data (time and m/z) precursor ions from the same peptide, regardless of z, fragment simultaneously. To efficiently fragment each z, the collision energy is toggled between the optimal values for each across the acquisition time. In three-dimensional data, precursor ions are separated by m/z and z as such the optimal collision energy for efficient fragmentation is applied as a function of drift time. The scheduler calculates a series of fragmentation profiles (m/z vs. z) from the input data to optimize the resident collision energy table. Similar to the dynamic selection and exclusion of precursor ions and mass isolation windows, in batch analysis mode, the iterative nature of the process provides for continually optimization of the collision energy table.

What will now be described in more detail is the data processing and analysis phase 3506. Consistent with discussion herein, single scan processing is performed. Considering the example MMA scenario illustrated in 3700 (e.g., with a chromatographic separation space of 60 min, 1.86 s cycle times, 100 ms acquisitions and an inter-scan delay of 10 ms), approximately 2,000 low-energy $HDMS^E$ IM-DIA all ion scans or spectra are acquired, approximately 4,000 varying mass isolation width wideband (50 Th<MIW<500 Th) scans or spectra are acquired, and approximately 24,000 narrowband (1 Th<MIW<50 Th) scans or spectra are collected. The MMA data processing algorithms of 3506 treat each scan as its own independent experiment. Processing starts by accessing information from the reference (lock) mass channel. Analysis of this channel provides two important pieces of information; namely, mass resolution of the oa-TOF analyzer and the stability of the m/z calibration over the complete elution time. The acquisition channels are processed scan-by-scan in time order. For each scan, the m/z (2D) and m/z, drift (3D) vectors are centered using a single-scan centering algorithm. During the centering process, the FWHM is calculated for each ion in all dimensions ($t_r$, $t_d$ and m/z). These values, in conjunction with the reference mass data, are used to calculate a purity score, a metric utilized by to determine whether an ion's area is unique or a composite due to interference (e.g., its ion signal or area has a contribution from another interfering ion).

Data processing 3506b may include performing processing using information, such including information of FIGS. 39 and 40 described below, in connection with forming candidate isotopic clusters of ions in the same scan (e.g., thereby forming a PCC), assigning a charge z to the PCC, and correcting for ion interference. Such techniques for forming a PCC and assigning it a charge state as described below may be performed in connection with other processing described herein. For example, forming a PCC and assigning it a charge state may be performed in connection with unsupervised/non-supervised clustering described elsewhere herein. In at least one embodiment, once the ion purity score, centered m/z, drift and area values has been calculated for a precursor ion, the m/z value of each precursor ion is decomposed into two distinct values, it's nominal integral m/z and its fractional m/z. For example, for a precursor ion in a single scan having an m/z of 680.33, the nominal m/z=680 and the fractional m/z=0.33.

Figure 39:
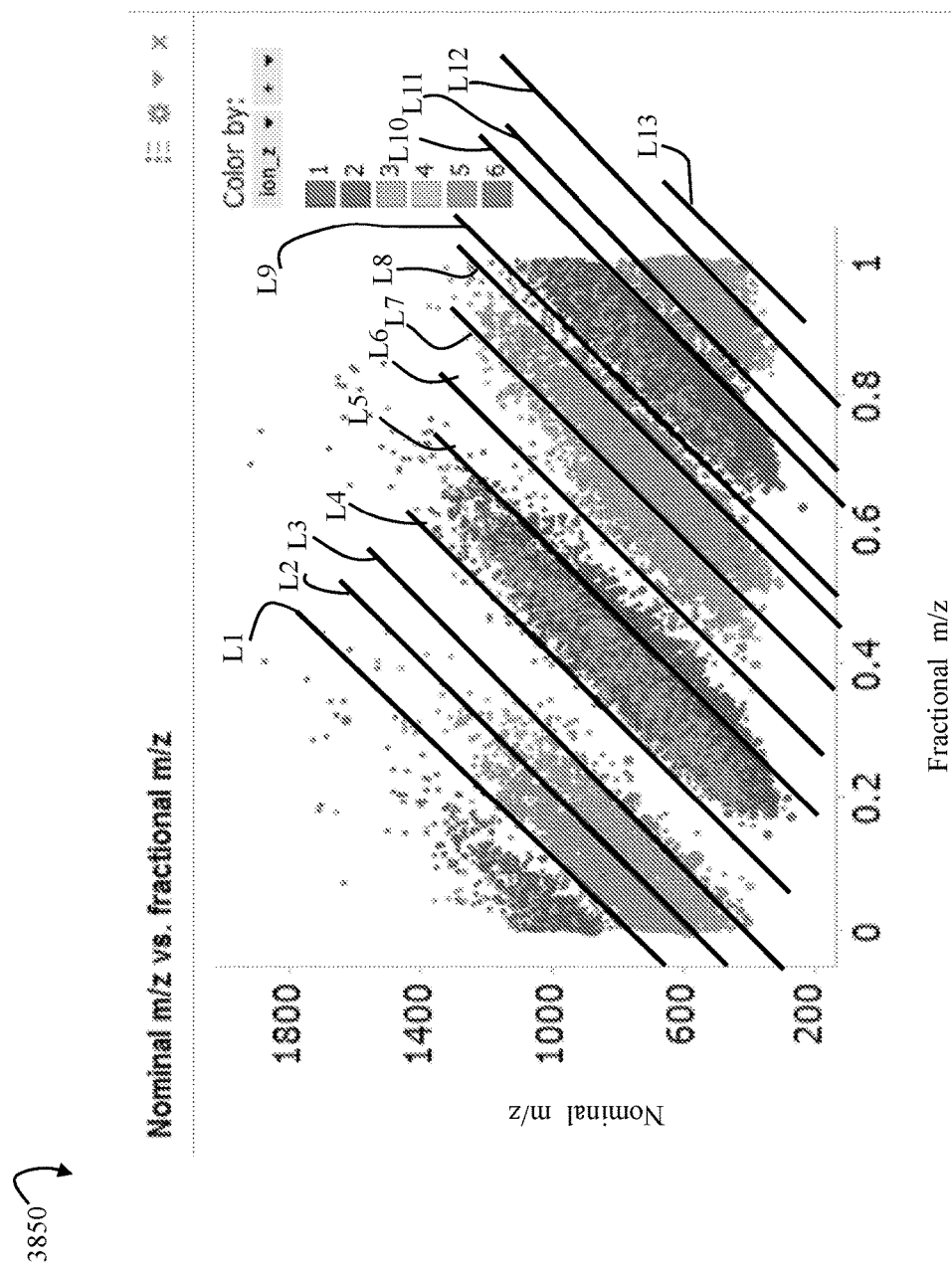
FIG. 39 is an example illustrating charge state vectors that may be used in an embodiment in accordance with techniques herein.

With reference to FIG. 39, shown is an example illustrating a plot of nominal m/z vs. fractional m/z values for different ion charge states. In this example 3850, there may be a maximum of 6 possible charge states based on the resolution power of the particular instrument and the graph in 3850 illustrates a distribution of the nominal m/z vs. fractional m/z for ions. The information used to populate 3850 may be constructed using known ion data determined using any suitable manner. As seen by the example 3850, charge vectors are formed which include vectors unique to a particular charge state as well as vectors where the same m/z may take on multiple z values. For example, the following may be charge state vectors unique to a particular charge state: between lines L1 and L2 includes primarily 3+(e.g., z=3) charge state ions, between lines L2 and L3 includes primarily 4+ charge state ions, between lines L3 and L4 includes primarily 5+ charge state ions, between lines L5 and L6 includes primarily 1+ charge state ions, between lines L6 and L7 includes primarily 4+ charge state ions, between lines L7 and L8 includes primarily 3+ charge state ions, between lines L10 and L11 includes primarily 5+ charge state ions, between lines L11 and L12 includes primarily 3+ charge state ions, and between lines L12 and L13 includes primarily 4+ charge state ions. The following may be characterized as multilane charge state vectors including multiple charge states: between lines L4 and L5 (e.g., includes multiple charge state ions such as 1+, 2+, 3+ and 4+), and between lines L9 and L10 (e.g., includes multiple charge state ions such as 2+ and 4+). Where the additional IMS drift time dimension is available, a plot may be similarly formed of drift time vs. the fractional m/z portion, where the plot illustrates both unique charge state vectors and multi-lane charge state vectors.

The foregoing are examples of distributions that may include both unique and multi-lane charge state vectors offering different views of separation within the fractional m/z space. The modality of m/z may be observed as it relates to charge z whereby the distribution of fractional m/z may be characterized as multi-modal with respect to certain charge states. For example, z=4 ions can interdigitate with z=2 ions, and z=6 ions can interdigitate with z=3 ions. However, some fractional m/z values are unique to a given charge state. There are some fractional m/z values for charge state z=4 that cannot/do not exist for ions of charge state z=2. The same is true with respect to charges states z=6 and z=3. Additionally, certain pairs of charge states like 2+ and 4+, or 3+ and 6+, are both multi-modal and additionally reflect the characteristics of a harmonic series. Using z=3 as an example, the expected fractional m/z difference between isotopes would be equal to ⅔, ⅓ and ⅔. There will always be inter-digitation of fractional m/z in harmonic charge states like $2^+$ and $4^+$, or $3^+$ and $6^+$. However, two $2^+$ isotope series cannot be interdigitated to mimic the isotopic distribution of a $4^+$ series. Nor can two $3^+$ isotope series mimic that of a $6^+$ series. Correctly assigning z to an ion mapped to one of multi-lane charge state vectors may be determined as a function of modular arithmetic, where z=the modulus. In at least one embodiment, information such as one or more distribution plots based on fractional m/z may provide some indication of charge state separation whereby charge state vectors uniquely associated with one charge state along with multi-lane charge state vectors associated with multiple charge states. Such plots (e.g., such as in FIG. 39) may be used to perform an initial or candidate charge state assignment to each ion. In some cases, the initial charge state assignment may be a set including multiple possible charge states. It should be noted that adding an additional IMS dimension of drift time may be used to obtain an additional plot, for example, of drift time vs. fractional m/z allowing for improved segregation of ions into different charge state groupings. Subsequent to such initial charge state assignment where possible, additional processing may be performed to form candidate isotopic clusters or PCCs using chaining as described below.

Figure 40:
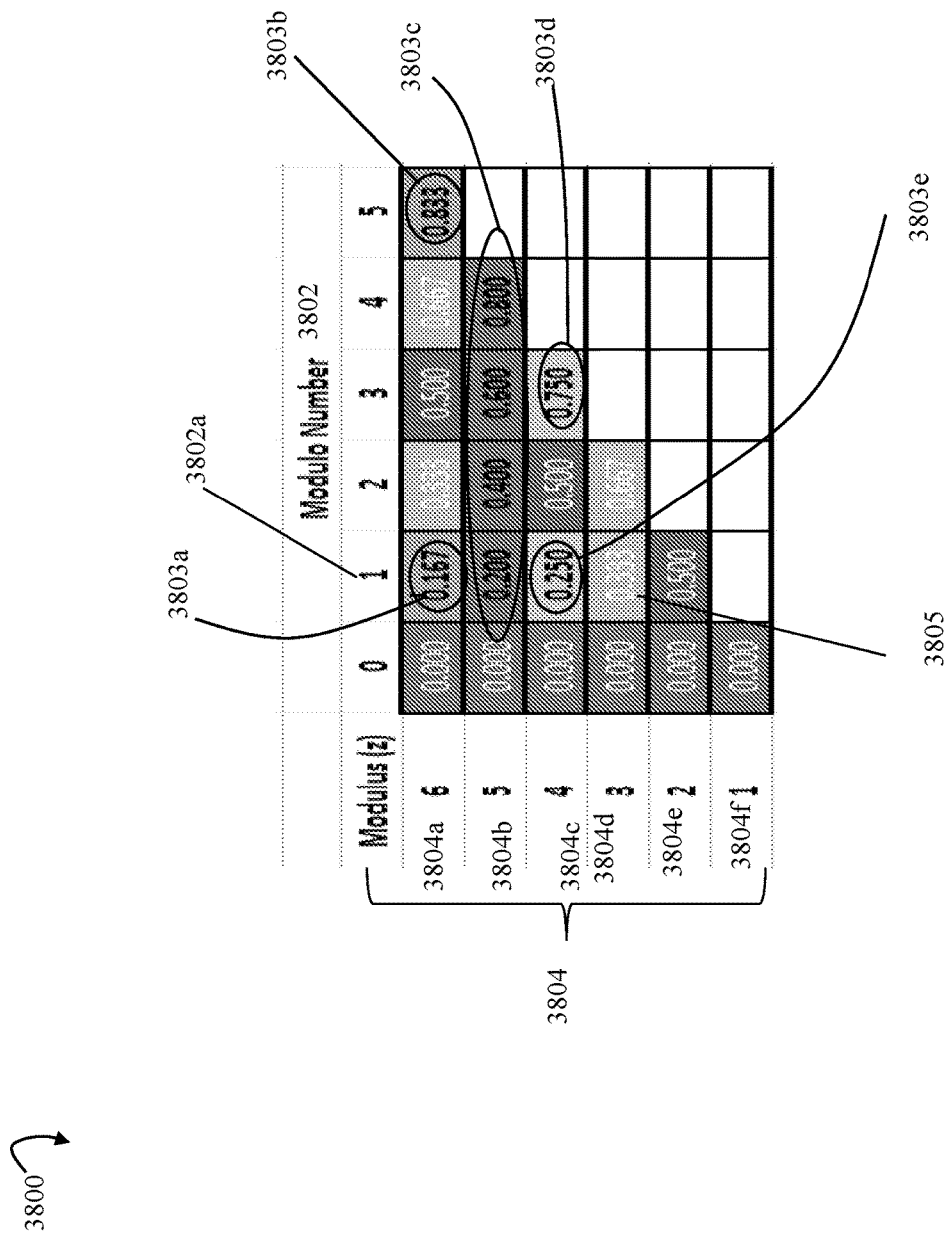
FIG. 40 is an example of a table that may be used in connection with assigning charge state to precursor charge clusters in an embodiment in accordance with techniques herein.

To further illustrate, reference is now made to FIG. 40 which includes a table that may be used in an embodiment in accordance with techniques herein. The table 3800 reflects modular arithmetic where the modulus is equal to z and the modulo numbers are equal to the maximum number of isotopes in a series before the fractional m/z wraps and re-starts at zero. The fractional values represented in each cell reflect the ratio theoretical isotope/z or modulus. The information in table 3800 may be used in chaining isotopes together into PCCs as will now be described. The table 3800 includes a row for each possible charge state and a column for each possible isotope. There are 6 possible charge states in this example where the modulus is z as denoted by the row values 1-6 in 3804. Additionally, up to 6 isotopes may be included depending on the charge state. Each column corresponds to a particular one of the possible isotopes $A_0$ through A5, where "An" more generally denotes the particular isotope, "n" being an non-negative integer, and "n" for the particular isotope denotes the column in table 3800 associated with that particular isotope. The values for "n" corresponding to the different isotopes denote the modulo numbers 3802. An entry in the table denotes a step or delta distance in terms of m/z that a particular isotope A1-A5 is with respect to the isotope $A_0$ within a single scan. Each entry in the table may be identified by a pair of values (X, Y) where X denotes the "z" or modulus row identifier and Y denotes the column identifier "n" associated with a particular An isotope. The value of the entry in the table is equal to the isotope number "n" (e.g., Y) for that entry divided by the charge state (e.g., X) for that entry. More generally, the value of each entry in the table=Y/X, where the entry is identified by (X, Y) as just described.

Using z=3 with reference to row 3804d, the expected fractional m/z difference between isotopes are equal to ⅔, ⅓ or 0.33 and ⅔ or 0.67. Using z=6 with reference to row 3804a, the expected fractional m/z difference between isotopes is denote are equal to %, ⅙ or 0.167, ⅔ or 0.33, ⅜ or 0.5, ⅘ or 0.667, and ⅝ or 0.833. Thus, there is inter-digitation of fractional m/z in harmonic charge states like $3^+$ and $6^+$ because the delta m/z between two consecutive isotopes for charge state 3 is a multiple of the delta m/z between two consecutive isotopes for charge state 6 (e.g., 0.333 delta m/z between any two consecutive isotopes such as $A_0$ and $A_1$, or $A_1$ and $A_2$ for charge state 3 is a multiple of (two times) the 0.167 delta m/z between any two consecutive isotopes such as $A_0$ and $A_1$ for charge state 6). However, there are particular entries in the table where such inter-digitation does not occur whereby the particular delta m/z distance from the $A_0$ isotope (e.g. value stored in a table entry) only appears in a single entry of the table. For example, entries of the table 3800 denoted by 3803a-3803e are unique entries in the table and therefore denote instances when a charge z may be assigned to an ion.

Furthermore, the table 3800 may be used in chaining or connecting together different isotopes in a same scan to form a candidate PCC as will now be described. Processing begins by selecting the lowest m/z ion in the low energy scan (e.g., lowest m/z precursor ion in the scan) to ensure that the initial link is an $A_0$ isotope. Knowing all possible charge states, processing then starts at the highest theoretical charge state to deal with the harmonic modality effects of 2+ and 4+, or 3+ and 6+ ions. For example, processing start with column 1 3802a and traverses the column downward, in sequential order, from the highest charge state z=6 (row 1) to the lowest charge state z=1 (row 6). For each entry in the column having a value D (denoting a delta m/z), the m/z values in the scan are queried to determine whether there is an m/z in the scan equal to the sum of $A_0$'s m/z+D. For example, assume $A_0$ in scan S1 has an m/z of 600.0. For entry 3803a=0.167, is there an m/z in scan S1 equal to 600.167 (e.g., 600.0+0.167)? If so, then this matching m/z is assumed to be the A1 isotope. As described elsewhere herein, such m/z matches may be made within some specified level of tolerance or acceptable error. Isotope chaining then continues using the same delta m/z of 0.167 to chain together other isotopes. Searching of the scan S1 continues to locate locate remaining isotopes of the same PCC where the distance between each consecutive pair of ions/isotopes located have an m/z difference or distance of 0.167. Continuing with the above example, in scan S1 processing may locate 4 additional matching m/z ions having m/z values of 600.333, 600.50, 600.667 and 600.833. In connection with the foregoing example, 6 ions are determined as a candidate PCC having a charge state of 6+ since the m/z of the presumed $A_1$ isotope was located an m/z distance of 0.167 from the m/z of the $A_0$ (e.g. 0.167 is located in row 1 for charge state 6). Chaining for the current PCC stops when no further ions in the scan are located an m/z distance of 0.167 from the most recent matching isotope's m/z. For example, no ion was located in scan S1 having an m/z of 601.

As a variation to the foregoing, assume that there was no m/z in scan S1 equal to 600.167. In this case, processing continues down the column 3802a to use the delta m/z=0.200 as specified in the row 3804b for the next highest charge state of 5. The same query is made to determine whether there is an m/z in the scan equal to 600.200, the sum of $A_0$'s m/z, 600, added to 0.200. If so, the matching m/z is presumed to be that of the A1 isotope and the delta m/z of 0.200 is further used to chain to other subsequent isotopes of the same PCC as described above where the distance between each consecutive pair of ions/isotopes located have an m/z difference or distance of 0.200. The PCC is presumed in this case to have a charge state of 5 and chaining continues to locate additional ions until no further ions in the scan are located an m/z distance of 0.200 from the most recent matching isotope's m/z. If there is no m/z in scan S1 equal to 600.20, processing further continues to sequential traverse the column 3803a and use the next delta m/z value=0.250 for the next highest charge state 4 in row 3804c.

The foregoing traversal down column 3803 (from highest to lowest charge state) continues until either 1) a matching ion is located which has an m/z equal to 600 plus one of the m/z delta values in column 3803a, or 2) all entries in the column have been processed and no matching ion has been located. Once all entries in 3802a have been processed while considering a candidate $A_0$ having an m/z of 600, the next lowest m/z in the low energy scan may also be similarly processed. For example, assume that the next lowest m/z in scan S1 is 602.5, processing may performed for this ion with m/z=602.5 in a manner similar to that as described above for m/z=600 based on the presumption that the ion with m/z=602.5 is an $A_0$ isotope in an attempt to form an isotopic cluster or PCC.

Figure 41:
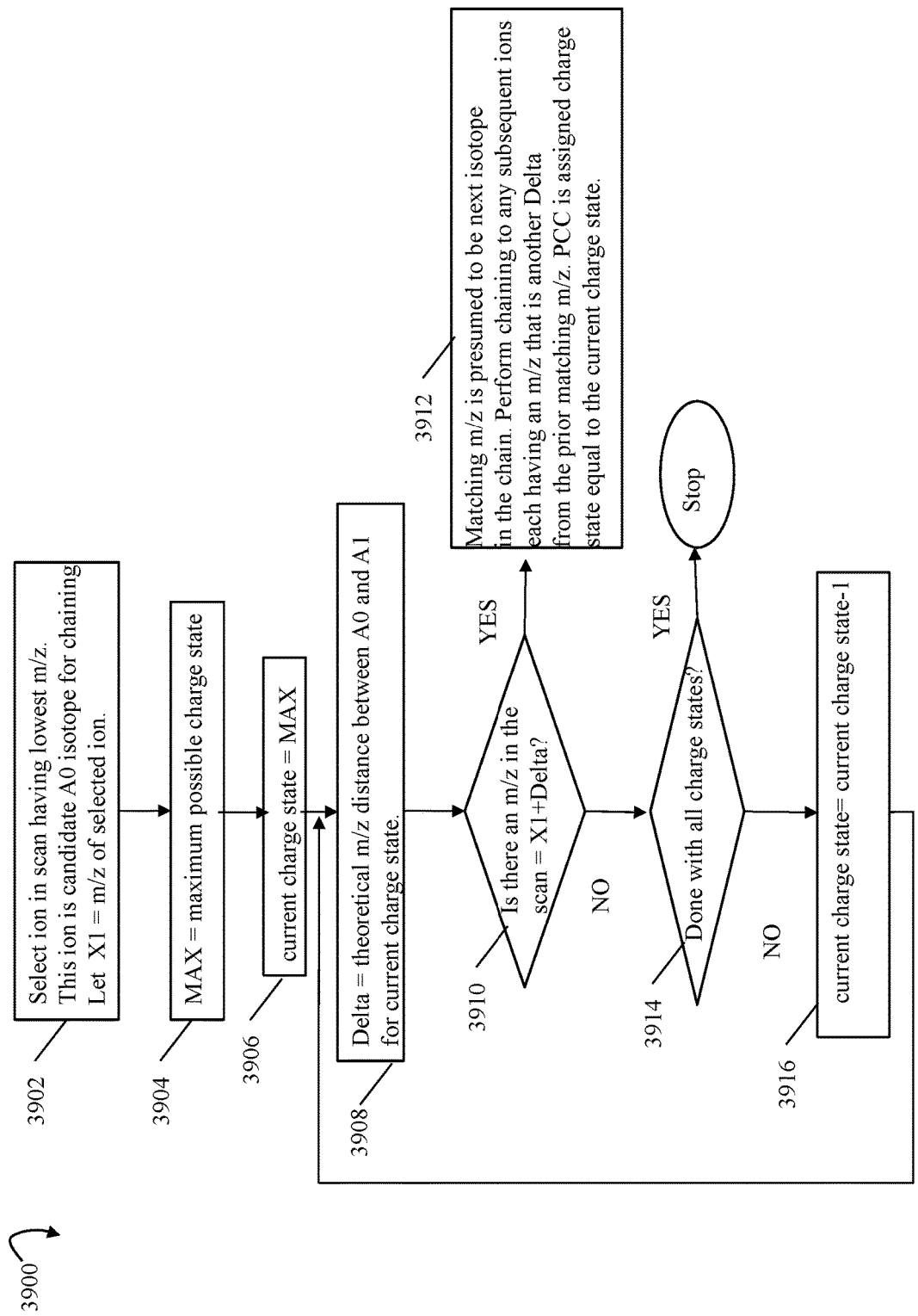
FIGS. 41, 46A 46B are flowcharts of processing steps that may be performed in an embodiment in accordance with techniques herein.

Referring to FIG. 41, shown is a flowchart of processing steps that may be performed in an embodiment in accordance with techniques herein. The flowchart 3800 summarizes processing described above in connection with performing chaining using the table 3800 to form a candidate PCC of isotopes in an embodiment in accordance with techniques. At step 3902, an ion in a current scan is selected where the ion selected has the lowest m/z in the scan. The scan is a low energy scan of precursor ions. The ion selected is a candidate $A_0$ isotope for chaining to other ions to form a PCC. Let X1=the m/z of the selected ion having the lowest m/z of all ions in the scan. At step 3904, MAX is assigned the maximum possible charge state, such as 6. At step 3906, current charge state is assigned MAX. At step 3908, Delta is associated the theoretical m/z distance between $A_0$ and $A_1$ for the current charge state. More generally, as noted above, Delta represents the m/z distance between each pair of consecutive isotopes in the isotopic cluster having a charge state equal to the current charge state. Delta denotes a value of an entry of the table 3800. For example, when current charge state=6, Delta is set to 0.167 based on entry 3803*a*. Processing is performed for the current Delta in the loop commencing with step 3908.

At step 3910, a determination is made as to whether there is an m/z in the current scan equal to X1+ Delta. If step 3910 evaluates to yes, control proceeds to step 3912 where the matching m/z is presumed to be that of the next isotope in the chain. Step 3912 includes performing chaining to any subsequent ions in the scan where each such subsequent ion has an m/z that is another Delta from the prior matching m/z. Chaining stops when no additional is located having an m/z that is Delta more than the last matching m/z. The PCC or isotopic cluster formed via the chaining is assigned a charge state equal to the current charge state. If step 3910 evaluates to no, control proceeds to step 3914 where a determination is performed as to whether processing is complete for all charge states. If so, processing stops. Otherwise if step 3914 evaluates to no, control proceeds to step 3916 where the current charge state is decremented by 1 and processing continues with step 3908 with the next entry in the table 3800 such as the next entry in column 3802*a*.

It should be noted that processing described above used to form candidate PCCs and assign it a charge state may perform the processing with respect to delta m/z values for selected charge states. For example, prior to performing flowchart 3900 processing, a subset of one or more possible charges states may have been determined for the candidate $A_0$ ion selected in step 3902. For example, using other means, such as that graph 3850 of FIG. 39 and/or other information, the number of 6 possible charge states may be further reduced. For example, the candidate $A_0$ ion may have an m/z that places it in one of the multi-lane charge vectors between lines L9 and L10 and may be assigned a possible charge state of 2+ or 4+. In this case, processing of flowchart 3900 may be reduced whereby only delta m/z values of 0.250 and 0.50 for these charge states need to be evaluated.

After the candidate PCC has been constructed, processing may be performed to validate the PCC. For example, the area or ion signal intensity of each isotope in the PCC is validated and/or adjusted by the isotopic model. The isotopic model uses the elemental composition of an averagine to calculate both the theoretical isotopic distribution (e.g., of ion signal areas, intensities or counts) and the predicted number of isotopes above the LOD for a theoretical peptide of that m/z and z. Generating an isotopic model of an averagine is known in the art and described, for example, in Valkenborg, D., Jansen, I., & Burzykowski, T. (2008), "A model-based method for the prediction of the isotopic distribution of peptides", *Journal of the American Society for Mass Spectrometry*, 19(5), 703-712, which is incorporated by reference herein.

Figure 42:
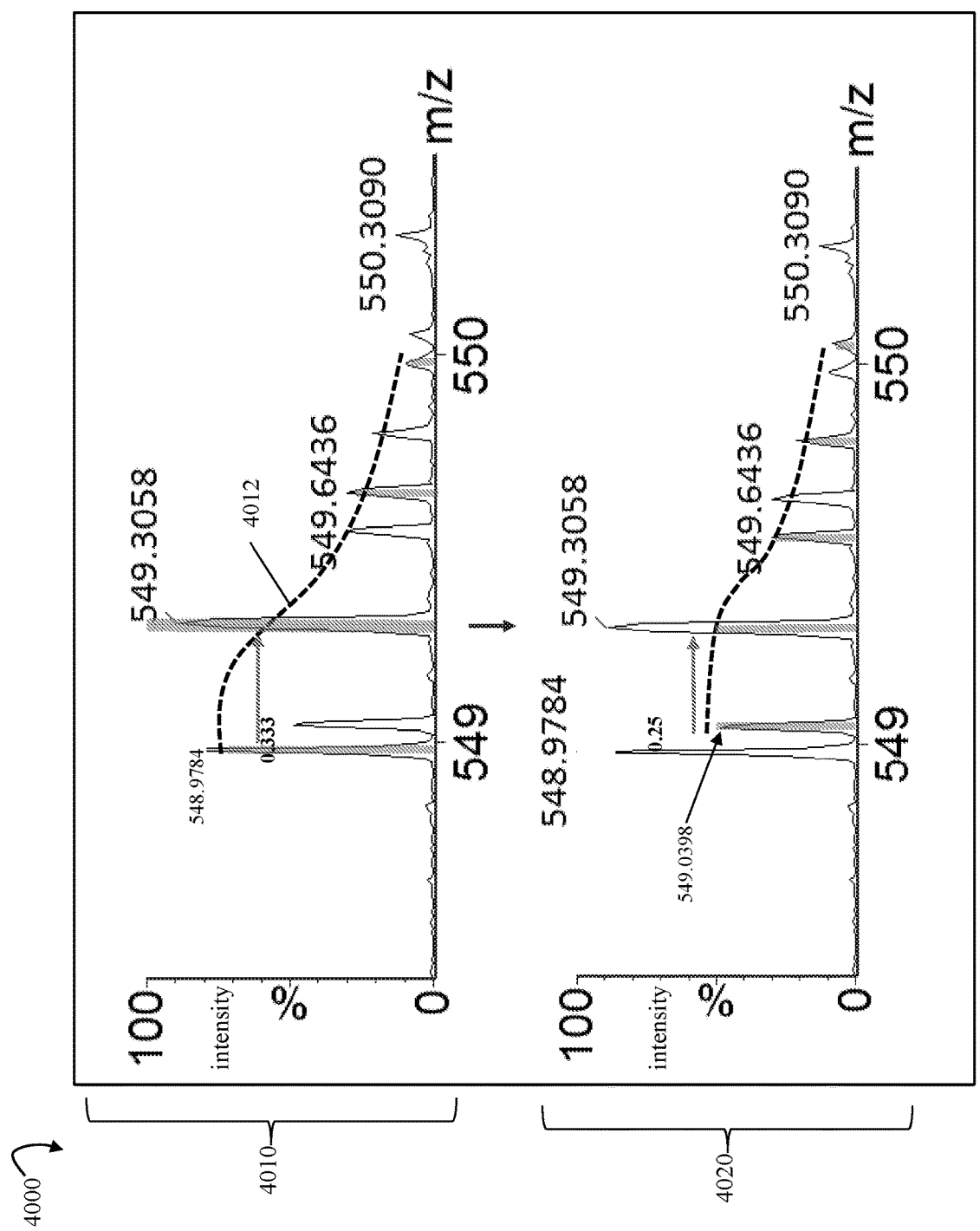
FIGS. 42, 43 and 44 are graphical illustrations of various techniques that may be performed in an embodiment in accordance with techniques herein.

To further illustrate, reference is made to FIG. 42. Each ion may be assigned a series of measured or calculated attributes. In at least one embodiment, these attributes may include: m/z, area (e.g., measure of intensity of the ion), theoretical charge state(s), and purity score(s) for m/z and in the instance of three-dimensional data m/z and drift. Referring to the example 4000, processing may be performed as described above in connection with FIGS. 40 and 41 where the chaining processing starts with selecting the lowest m/z ion from the two dimensional scan, ensuring that the initial link is an $A_0$. The ion with the lowest m/z in 4010 is 548.9784. Previous processing may, for example, have initially assigned the ion a possible $3^+$ or $6^+$ charge state. Starting at the highest charge state, $6^+$, 0.1667 Th (1/z) (e.g., table entry 3803*a*) is added to the lowest m/z of 548.9784 whereby the foregoing sum is queried against the complete ion list of that scan for a match. In this example, no match is found in the scan illustrated in 4010 and it is determined there is no $6^+$ companion $A_1$ ion. Processing then considers the next theoretical charge state, $3^+$, where 0.333 Th (1/z) (e.g., from entry 3805) is added to the the lowest m/z of 548.9784 whereby the foregoing sum is queried against the complete ion list of that scan for a match. In this case, a matching m/z ion is found at 549.3058 where the foregoing m/z at 549.3058 is the candidate $A_1$ isotope. In at least one embodiment, the mass match tolerance (used in determining matching m/z values) may be automatically set to ±3 times the measured mass precision from the preceding reference mass calibration.

In this example, the $A_1$ isotope with m/z=549.3058 may have a lower ion purity score than expected (e.g., may be lower relative to other scores or a threshold level). Additionally, there may be a mass error. Mass error is described elsewhere herein in following paragraphs. The foregoing mass error may be interpreted as suggesting the presence of an interfering ion of slightly lower m/z than the predicted value for the $A_1$ isotope, 549.3117 Th (±3 times the measured mass precision). The search for additional isotopes $A_2$ and $A_3$ is repeated and the number of isotopic relations extended to a total of four (e.g., $A_0$ m/z=548.9784, A1 m/z=549.3058, A2 m/z=550.0, A4 m/z=5503090). The suspected interference may be confirmed or validated since the mass error between links 2 and 3, and links 3 and 4 are proportional with that of the preceding calibration.

The dashed curve 4012 in 4010 of FIG. 42 illustrates the predicted isotopic distribution of the $3^+$ charge cluster. The calculated isotopic model is matched against the experimental data of 4010. The intensities of the chained ions reflecting a unique z, or validated z assignment, and high purity scores, may be used as anchors to correct for composite ion areas like that of an $A_1$ isotope. For example, if one of the ions chained (denoting an isotope of the candidate PCC just formed) has a high purity score and is included in unique charge state vector mapping the ion to a single charge state, properties (e.g., intensity, mass, charge state) of that ion may be used as an anchor with isotopic modeling to determine, predict or model other isotopes of the PCC and also model attributes of such other isotopes in the PC. For example, the A2 ion with m/z=549.646 may be such an anchor ion whereby A2's attributes (e.g., m/z, intensity or area, retention time, drift time (if any)) may be used to model expected theoretical attributes (e.g., signal intensity or area) regarding the A1 ion of the same PCC. Such modeled attributes for the experimental A1 ion m/z=549.3058 may be compared to the modeled attributes to make corrections or adjustments to the experimental data and may also be used to detect ion interference. For example, the modeled intensity of the A1 ion may be used to correct or adjust A1's experimental data intensity from that illustrated in 4010 to the result illustrated in 4020. Additionally, the model isotopic distribution illustrated by 4012 indicates an interference at the A1 ion and a further corrective action may be taken with respect to the experimental data. In order to address any variation between the real elemental composition and that of the averagine used to model the isotopic distribution, processing may allow for a 20% variation before performing any corrective action such as creating a "virtual ion". The virtual ion may be assigned the remaining ion area as well as all the other attributes assigned to the associated parent in the experimental data scan. For example, as illustrated in 4020, a virtual ion with the corrected ion area may be created for the A1 ion with m/z=549.3058 thereby allowing the same ion with m/z=549.3058 to be accurately assigned as both the $3^+$ $A_1$ isotope of the current PCC under consideration and also be associated with another second PCC with charge state=$4^+$ having an $A_0$ ion with an m/z=549.0398. Thus, element 4010 and 4020 illustrate how the areas of a non-conforming (e.g., low IPS, high area) A1 isotope with m/z=549.3058 are corrected and a "virtual" ion is created. The virtual ion may be used in connection with subsequent chaining processing performed to create other candidate PCCs such as another PCC with a charge state of 4 using m/z=549.3058 as the $A_0$ ion as noted above.

After processing of the low-energy precursor ion scans to form PCCs with assigned charge states as described above, PCCs may be combined across time based on their m/z values, and with 3-dimensional data (e.g., including IMS), drift time. Generally, this may be characterized as another type of chaining or linking performed at a higher level than that as described above where individual PCCs are formed. Now, processing is performed to combine the individual PCCs, each in a different scan, to form the chromatographic peak, also known as an elution profile or envelope for a single PCC (e.g., form the peak or envelope over time for the same PCC such as illustrated in FIG. 7).

Figure 43:
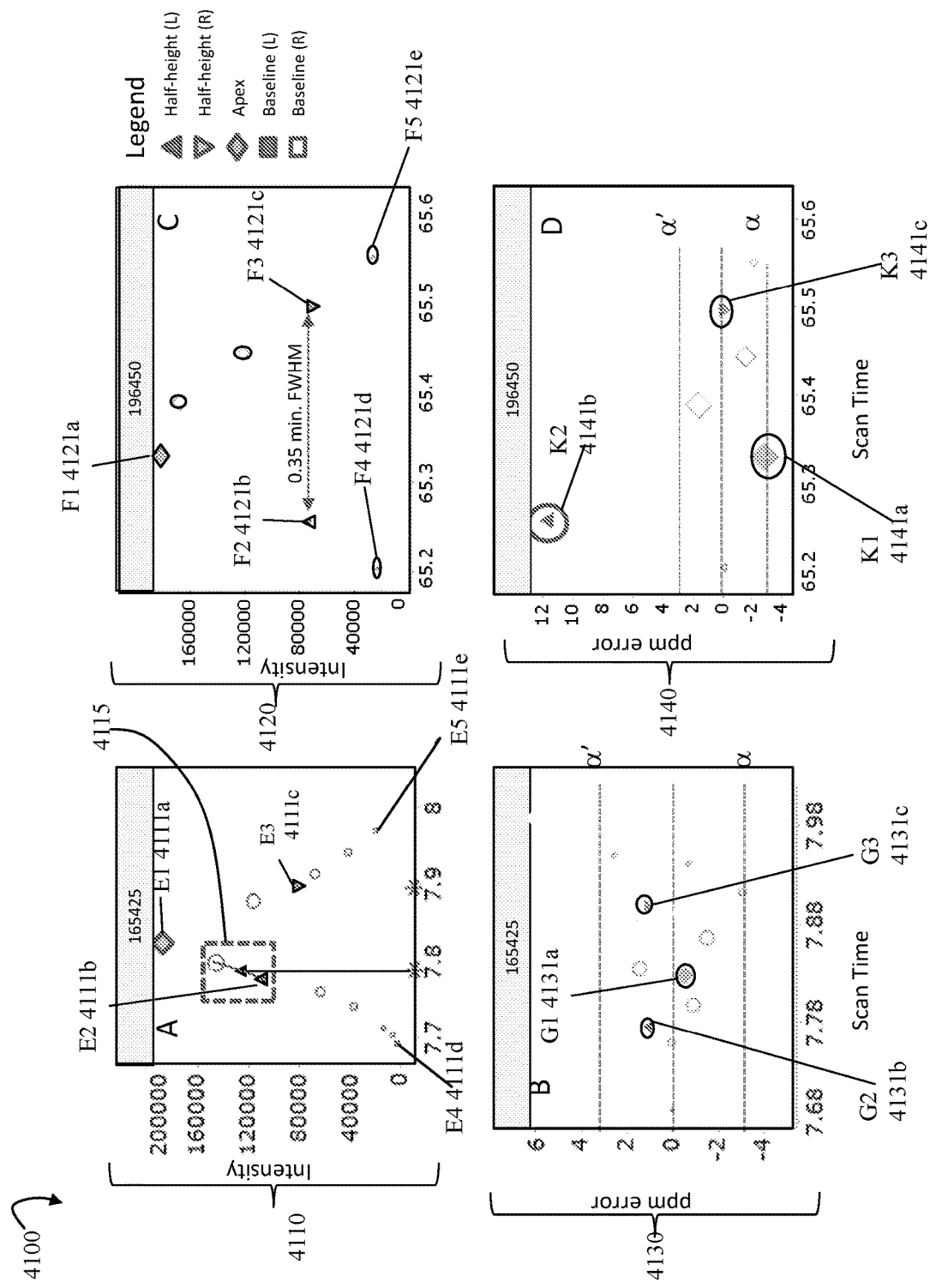

To further illustrate, reference is now made to FIG. 43 wherein panels A 4110 and C 4120 illustrate the processing performed to combine PCCs across time by their m/z values and thus track the same PCC at different points in time to form an eluting profile or envelope for the PCC. In at least one embodiment, the m/z used for each PCC may be the m/z of the $A_0$ isotope. Panel A 4110 illustrates plotting of a first PCC having a first m/z at different scan times in the experimental data and Panel C 4120 illustrates plotting of a second different PCC having a second m/z at different scan times in the experimental data. Panels A 4110 and C 4120 are graphical displays of each PCC's intensity vs. scan time. In 4110 for the first tracked PCC, element 4111a E1 denotes the apex (e.g., point H of FIG. 7), elements 4111b-c E2 and E3 denote the peak half height points (e.g., H1 and H2 of FIG. 7), and elements 4111d-e E4 and E5 denote the peak baseline points (e.g., where the peak profile for the PCC is determined to start and end). In 4120 for the second tracked PCC, element 4121a F1 denotes the apex (e.g., point H of FIG. 7), elements 4121b-c F2 and F3 denote the peak half height points (e.g., H1 and H2 of FIG. 7), and elements 4121d-e F4 and F5 denote the peak baseline points (e.g., where the peak profile for the PCC is determined to start and end).

In addition, for the two tracked PCCs of 4110 and 4120, associated error plots may be determined. Element 4130 illustrates a first error plot for the first PCC tracked or chained across time in 4110. Element 4140 illustrates a second error plot for the second PCC tracked or chained across time in 4120. In 4130 and 4140, the error is an m/z error in parts per million (ppm). The m/z (ppm) error may be calculated by comparing the preceding $A_0$ m/z value to that of the next linked PCC in the chain. Thus, for a first point $P_n$ and a second point $P_{n+1}$ in the plot 4110, the mass error or m/z error for $P_{n+1}$ denotes a delta or difference in m/z values between points $P_n$ and $P_{n+1}$ where Pn is a point used in forming the peak that is immediately prior to $P_{n+1}$ (e.g., mass error $P_{n+1}$=m/z $P_{n+1}$−m/z $P_n$). In 4130 and 4140, the lower and upper boundary lines a and a' reflect the calculated mass precision from the previous lock mass calibration which in the example +/−3 ppm (e.g., α at −3 ppm and α' at +3 ppm). In 4130, G1 4131a denotes the mass error for the peak or apex point E1 4111a, G2 4131b denotes the mass error for the half height point E2 4111b, and G3 4131c denotes the mass error for the half height point E3 4111c. In 4140, K1 4141a denotes the mass error for the peak or apex point F1 4121a, K2 4141b denotes the mass error for the half height point F2 4121b, and K3 4141c denotes the mass error for the half height point F3 4121c.

A visual comparison of the FWHM between 4110 and 4120 illustrate the curve or profile of the points in 4120 to be much wider than that formed by the points of 4110 indicating a possible interference in 4120. Through analysis, the interference in 4120 may be validated based on information of mass errors in panel D 4140 between points K1 4141b and K2 4141a. In particular, point K2 4141b at a first point in time denotes a significant deviation in measured mass error from the acceptable mass error range (denoted by boundaries α and α') thereby denoting the interference. Subsequent points in time, such as K1 4141a and K3 4141c denote mass errors within the acceptable mass error range thereby indicating that the interference of the interfering ion(s) remains. Therefore every point or scan after K2 4141b may be determined as having interference. Thus, the eluting peak 4120 is actually be a composite or collective peak of ion intensities for multiple different PCCs (e.g., two or more precursor ions which overlap to produce the combined elution profile of 4120) whereby such interference commences at F2 4121b and remains for the remainder of the scans at subsequent points in 4120. If it were the case that the interference no longer occurred from a scan time such as 65.4, then at scan time 65.4 there would be a corresponding negative mass error detected that may be characterized as the complement or reverse of the +12 ppm mass error denoted by K2 4141b. In other words, if the interference no longer occurred from scan time 65.4 forward, then at scan time 65.4 there would be a mass error value of approximately −12 ppm.

It should be noted that no interference may be determined for any of the scans or spectra for points in 41110 since no mass errors for such scans or spectra exceeded the acceptable mass error range.

Figure 44:
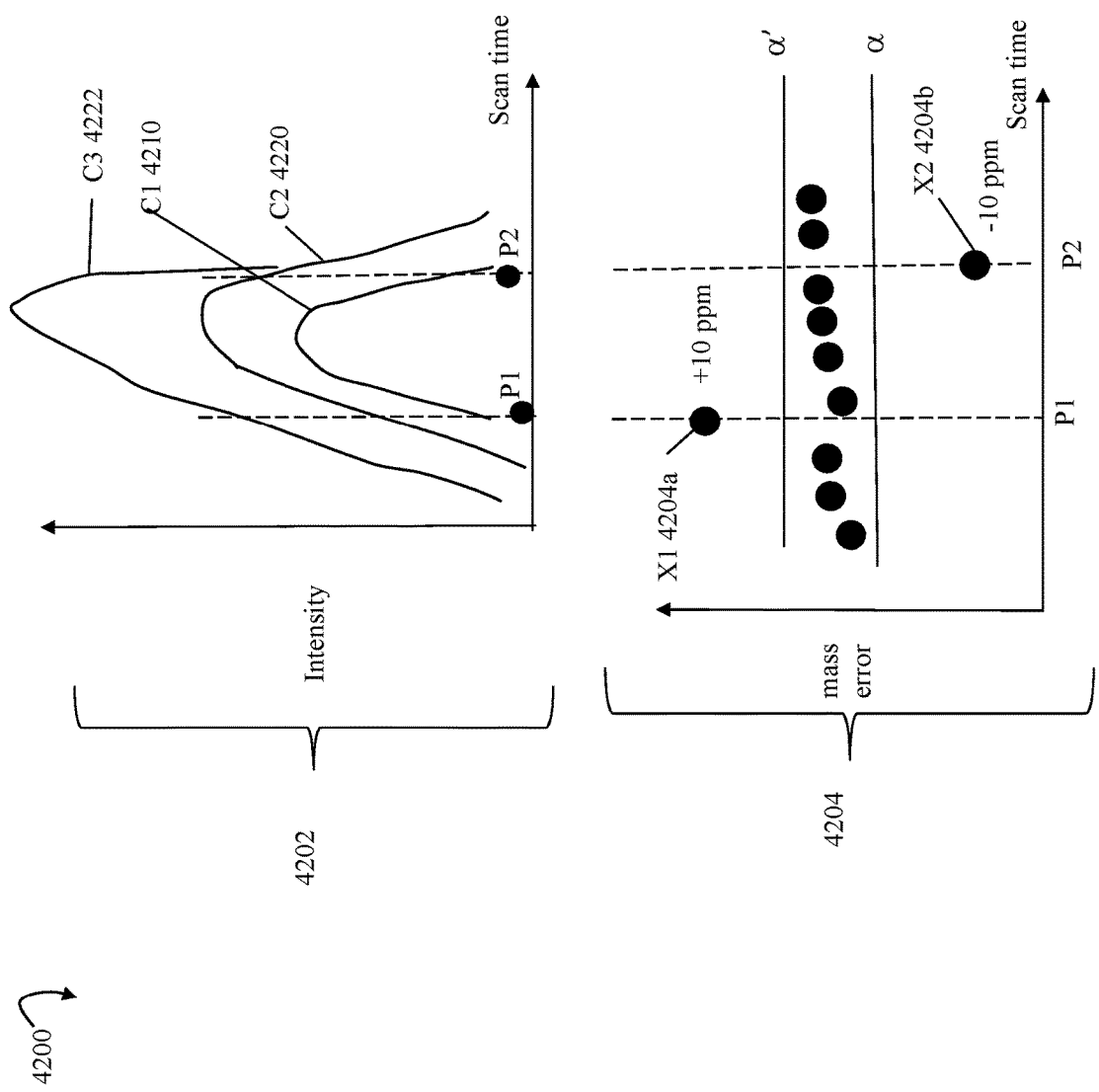

As another example in connection with interference, reference is made to 4200 of FIG. 44. The example 4200 includes element 4202 illustrating two chromatographic peaks C1 4210 and C2 4220 for two different PCCs which interfere with one another. Element 4202 illustrates intensity vs. scan time. The composite or resulting peak C3 4222 actually seen may be the sum combination of 4210 and 4220. One goal is to detect the fact that the composite peak C3 4222 viewed is actually contributed to by multiple ions such as 4210 and 4220 and then try to deconvolve or decompose the composite peak C3 into its components such as 4210 and 4220. At a first point or scan time P1, a first mass error may be determined that is outside of the acceptable mass error range and thereby denotes the beginning scan of the interference. In a similar manner, a subsequent next occurrence of a second mass error at a second point in time P2 may be obtained where the second mass error is outside of the acceptable mass error range thereby denoting the ending of the interference detected at the first point P1. The mass error for points between the foregoing first and second points P1 and P2 may be within the acceptable mass error range. Element 4204 illustrates mass error vs. scan time denoting mass error values that may be obtained for corresponding scans at different points in 4202. In particular X1 4204*a* and X2 4204*b* may denote mass errors that exceed the acceptable mass error range, respectively, at points P1 and P2. The remaining error values of 4204 may all be within the acceptable mass error range. In this manner, X1 and X2 may be used as points denoting possible interference boundaries. Scans taken at times where interference is suspected may be excluded from consideration in connection with forming a CPPIS for the tracked precursor ion or PCC. As an alternative, an action may be taken to correct or further refine information extracted from experimental data of the interfering scans as described below in more detail.

In this example 4200, once mass errors X1 and X2 exceeding the acceptable mass error range are detected, further processing may be performed. Since the mass error at X1 is 10 ppm and the mass error at X2 is −10 ppm, it may be determined that the interference begins at scan time P1 and ends with scan time P2. When selecting scans or spectra for inclusion in a CPPIS, an embodiment may choose to exclude the interfering scans. As an alternative, an embodiment may take another action such as by examining fragmentation patterns. In particular, fragment ions in scans while the interference occurs from P1 to P2 may originate from any of the multiple interfering ions. However, a fragment ion frag1 appearing in a scan prior to P1 or after P2 but not in a scan from P1 to P2, inclusively, may be determined as originating from the tracked precursor ion or PCC. In a similar manner, a fragment ion frag2 unique to interfering scans from P1 to P2, inclusively (e.g., frag 2 appears in one or more scans from P1 to P2, inclusively, but not prior to P1 and not after P2 may be determined as originating from an interfering precursor ion and not originating from the tracked precursor ion or PCC.

An embodiment may further exclude scans or spectra used in connection with CPPIS formation and further analysis based on the average detected ion peak width W1. For example, an embodiment may exclude scans which are included in tailed left and right ends of the detected peak. In at least one embodiment, only scans within the average peak width W1+/−two standard deviations may be used for CPPIS formation.

In at least one embodiment, at least two scans or spectra between the two left and right half height points of a peak may be used in forming the CPPIS for a tracked PCC or precursor ion. In an alternative embodiment, only a single scan or spectra between the two left and right half height points may be selected. The particular scan(s) selected (and thus the particular fragment or product ions of such selected scan(s) used in forming the CPPIS for the associated precursor ion) may be in accordance with one or more criteria as described herein used to exclude and/or refine information based on experimental data. For example, an embodiment may choose to exclude any scan for which interference is suspected where such interference may be determined using one or more mass errors which are outside of the acceptable mass error range. An embodiment may select a scan for use in forming the CPPIS where the scan is between the two left and right half height points and where the PCC or precursor ion tracked has a maximum intensity of all scans between such points. An embodiment may select a scan for use in forming the CPPIS where the scan is between the two left and right half height points and where the PCC or precursor ion tracked has a maximum ion current of all scans between such points. Ion current for an ion in a scan may be defined as the relative intensity of that ion to the sum intensity of all ions in the scan. Thus, the scan in which a precursor ion has the maximum ion current is the scan in which the precursor ion has the largest intensity relative to the total intensity of all ions in the scan. For example, in scan S1, precursor ion prec1 may have an intensity of 10 and the total intensity of all ions in the scan may be 20 so that prec1 has an ion current of 10/20=50% in S1. In scan S2, precursor ion prec1 may have an intensity of 10 and the total intensity of all ions in the scan may be 200 so that prec1 has an ion current of 10/200=5% in S2. In such a case, S2 may be selected to characterize prec1 and S1 may be excluded since prec1 has its maximum ion intensity in S2.

In the absence of interference, at least one embodiment may select one or two scans between the two half height points in a peak where the selected one or two scans have the maximum ion current of all candidate scans that may possibly be selected. It should be noted that the scan having the maximum ion current of all candidate scans may not be the scan having the highest or maximum intensity of all such candidate scans.

In the presence of suspected or detected interference (such as based on one or more mass errors exceeding the acceptable mass error range), an embodiment may choose to exclude any scans having interference. Alternatively, an embodiment may select a combination of interfering and non-interfering scans such as to further refine the particular fragment ions determined as originated from the tracked PCC or precursor ion (e.g. thus refine the fragment ions included in the CPPIS and the putative identification of the precursor ion). For example, a first interfering scan S1 may be selected and a second non-interfering scan S2 may be selected. A first set R1 of fragment ions unique to S2 (in S2 but not in S1) may be determined where such fragment ions in R1 are determined as originating from the tracked PCC or precursor ion and the remaining fragment ions in S2 may be ignored/not used in identifying the precursor ion. A second set R2 of fragment ions common to both S1 and S2 may be determined where such fragment ions in R2 are determined as not originating from the tracked PCC or precursor ion and rather determined as originating from an interfering ion.

Figure 46A:
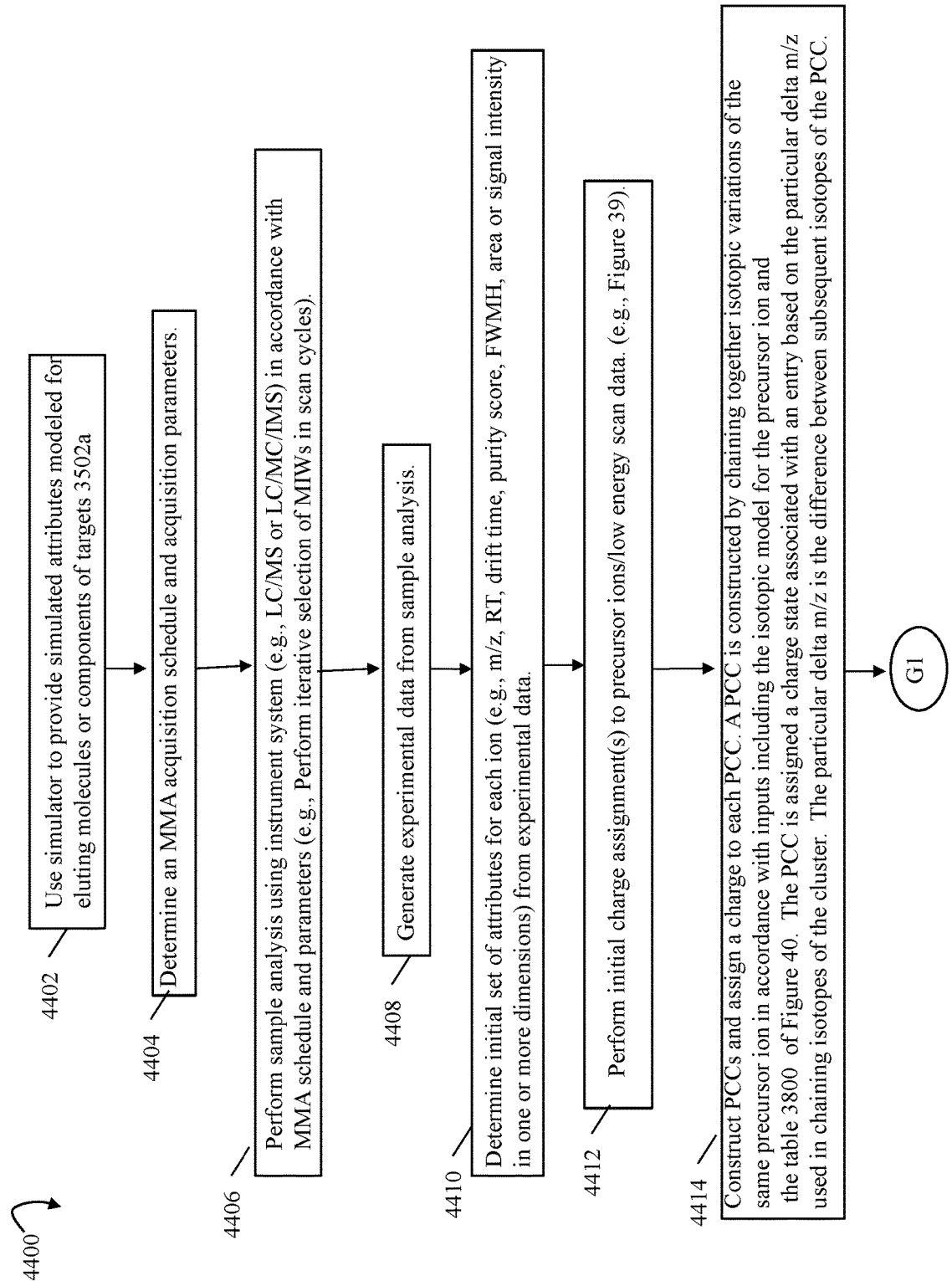
Figure 46B:
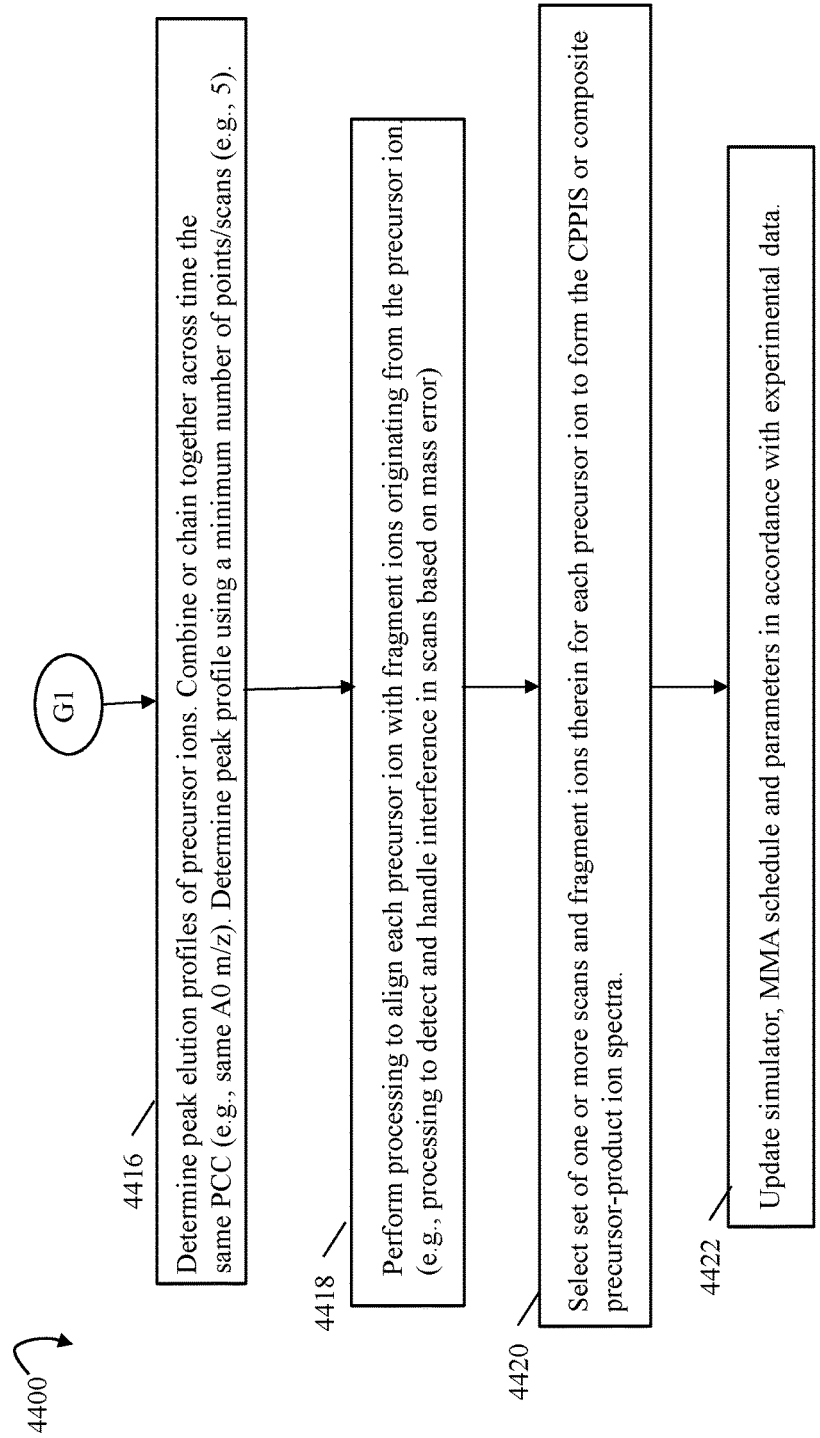

Referring to FIGS. 46A and 46B, shown are flowcharts 4400 and 4401 that may be performed in an embodiment in accordance with techniques herein. The flowcharts 4400 and 4401 summarize processing that may be performed based on one particular workflow as illustrated in FIG. 35. At step 4402, the simulator may be used to provide simulated attributes modeled for eluting molecules or components as identified in the targets 3502*a* of FIG. 35. At step 4404, the MMA scheduled may perform processing to determine an MMA acquisition scheduled and parameters. At step 4406, sample analysis may be performed using an instrument system including an MS and/or MS and IMS. The sample analysis may be performed through data acquisition techniques and scheduling in accordance with the MMA schedule and parameters. Step 4406 may include iterative selection of different MIWs in multiple scan cycles in accordance with the MMA schedule. At step 4408, experimental data may be generated from the sample analysis. Subsequent steps outline different data processing steps that may be performed using the experimental data obtained in step 4408. It should be noted that, consistent with other discussion herein, an embodiment may perform additional steps than those as included in the flowcharts 4400 and 4401. At step 4410, an initial set of attributes may be determined for each ion from the experimental data. Such attributes may include, for example, m/z, RT, drift time, purity score, FWMH, area or signal intensity in one or more dimensions, and the like. At step 4412, an initial assignment of one or more charge states may be made to precursor ions or ions in the low energy scans. Step 4412 may include performing processing using information such as described herein in connection with FIG. 39. At step 4414, PCCs may be constructed and each assigned a charge state. A PCC may be constructed, for example, by chaining together isotopic variations of the same precursor ion in accordance with inputs including the isotopic model for the precursor ion and also using the table 3800 of FIG. 40. The PCC is assigned a charge state associated with an entry of the table 3800 selected for use in chaining. The entry denotes the particular delta m/z used in chaining together isotopes of the cluster. The particular delta m/z is the difference between consecutive isotopes chained together to form the PCC. At step 4416, peak elution profiles or envelopes (e.g., chromatographic peaks) are determined for precursor ions. Step 4416 may include combining or chaining together across time the same PCC (e.g., based on matching $A_0$ m/z). The peak profiles may each be determined using a minimum number of points or scans. At step 4418, processing may be performed to align each precursor ion with fragment ions originating from the precursor ion. Step 4418 may include, for example, performing processing to detect and handle interference in scans based on mass error. At step 4420, processing may be performed to select one or more scans, and fragment ions therein, for each precursor ion to form a CPPIS or composite precursor product ion spectrum. At step 4422, the simulator, MMA schedule and parameters may be updated in accordance with the experimental data. Although not illustrated, the processing may also include storing putative CPPISs in the repository 3508c such as in connection with unsupervised/non-supervised clustering.

Given that each scan is treated as its own independent experiment, all product ions may be initially assigned to each precursor ion within the MS mass isolation window of the narrowband. A fragmentation efficiency is calculated for each precursor by comparing its intensity to that of any residual (leftover) intensity found in the product ion spectra. At the moment of fragmentation, a precursor ion's intensity is a function of its acquisition time relative to that of the initial link in the charge cluster chain. Element 4110 illustrates the change in precursor ion intensity between any two scan cycles. The asterisks illustrate the time a precursor ion was selected for fragmentation. The alignment processing may interpolate the pre-fragmentation intensity using a linear regression, as denoted in 4115, connecting the two links bounding the selected precursor. The up arrow infers the intersection.

A direct relationship exists between fragmentation efficiency and the number and dynamic range of product ions that a precursor ion can generate. A properly fragmented precursor will produce more product ions relative to its length than one that is either over or under fragmented. The dynamic range of product ions to a parent precursor is inversely proportional to the parent's fragmentation efficiency. Over- and under-fragmented precursors generally produce lower numbers of product ions relative to their precursor length, although they generally reflect a wider dynamic range. In iterative batch processing, these efficiencies are used to optimize the collision energy table between injections. FIG. 44 illustrates two linear regression lines defining the dynamic range of product ion area, represented as a percent of the parent precursor ion's intensity, vs. fragmentation efficiency. Product ion assignment is not only limited by dynamic range but also m/z and z. Given that an ion's molecular mass is a direct reflection of its elemental composition the nominal integral mass versus fractional m/z plots can also be used for determining a product ion's charge. For instruments employing collision-induced dissociation (CID) as the mechanism of fragmentation, a precursor ion of charge z can only produce product ions reflecting a maximum charge of z−1. The single exception to this rule occurs with precursor ions of z=1. Singly charged precursor ions can only produce singly charged product ions. For this reason, any product ion or chained isotope of a product ion, not residing in a charge vector commensurate to its parent precursor ion's z, is immediately eliminated from the product ion spectra. Similarly, in an attempt to reduce distraction, the user could elect to align product ions of z>1 to precursor ions of z>2.

Through the precursor ion chaining process (e.g., as described in connection with FIG. 43 to produce the precursor ion's chromatographic peak or elution profile), de-multiplexing processing may determine when, and in what scans, a precursor ion has undergone fragmentation By controlling the center of the MIW for each wideband and narrowband acquisition as described above in connection with MMA, within and across scan cycles, as well as cumulatively excluding those m/z values for subsequent selection in any following injection, the de-multiplexing processing is afforded the opportunity to continually increase the selectivity of any product ion spectrum. Following each iteration, post-acquisition processing corrects for any variations in retention or drift times between any two injections. Continual refinement of the relative positioning in retention and drift times between injections allows the de-multiplexing algorithm to access the additional overlapping product ion spectra.

Additionally, the de-multiplexing processing also has access to all metadata such as actual or interpolated precursor ion intensities, mass calibration error, actual or corrected product ion intensities, and purity scores relating to every ion in each and every scan. Utilizing this metadata, the de-multiplexing algorithm significantly reduces the chimeric effects of wider mass isolation windows by limiting product ions to only those that have the same m/z within the defined mass error, and exhibit a change in relative abundance proportionate to that of its putative precursor. Both m/z and intensity ratio match tolerances can be determined either algorithmically, based on previous reference mass calibration, by ion purity scores, or can be user-defined. Generally, the permitted area ratio tolerance is much wider than the actual m/z. In other words, the matched product ion intensity must be greater where the precursor ion intensity is greater, and smaller in instances where the precursor ion intensity is smaller. At the conclusion of all the filtering in at least one embodiment, each product ion spectrum may be written in either the industry standard mzML or mgf file formats for subsequent database searching. Identifications can also be made by querying, simulated product ions spectra or composite product ion spectra from the MIR such as described herein in connection with supervised clustering.

Referring back to FIG. 35, product ion spectra of peptides reflecting a score in excess of the search engines calculated 95% confidence interval may be deposited into 3508c as putative identifications. To create a unique or global identifier for a peptide, the peptide sequence may be concatenated with its m/z and if the sequence contains a modification the position of the modification relative to the n-terminus is also included. Techniques that may be used identifying such modifications are described elsewhere herein. In addition to identified peptides, the un-matched product ion spectra are also deposited, albeit, in place of a peptide unique identifier they are assigned a global identifier. The global identifier is used similar to a UPC (universal product code) in that it consists of the rounded (1 decimal place) precursor ion m/z concatenated to its calculated CCSA (also sometime referred to herein as CCS ($Å^2$) for the collisional cross sectional area). Once a minimum number (e.g., 50) of putative identifications (e.g., peptide sequences or global identifiers) have been deposited into 3508c, validation processing 3508b may be performed operating in the background. The validation algorithm of 3508b may continually attempt to create CPPISs by randomly selecting a minimum of thirty of the matched or identified product ion spectra. Validation processing may used, for example, dot-product spectral correlations and the Pearson Product-Moment Correlation Coefficient (r) to first determine significance. For the Pearson product-moment correlation coefficient r to reflect a positive correlation, a set of null correlations is required to compare against. These null correlations are created from peptides of similar m/z and z but different linear sequences. In general a correlation may be considered valid if $r>=0.75$.

In summary, DDA may be believed to lack the speed and sensitivity necessary to maximize qualitative depth-of-cover and quantitative accuracy across the widest experimental dynamic range. DIA strategies like MSX and SWATH have been developed to address the sampling limitation of serial DDA analyses, but sensitivity with these DIA approaches may still have deficiencies or drawback. Other DIA methods, like the Bateman technique or the high-low protocol for data acquisition, are not limited by sensitivity, but produce highly chimeric product ion spectra. There is a fixed amount of mass sufficient space that can be occupied in an MS/MS spectrum. In higher resolving power mass analyzers, the accessible m/z space in a product ion spectrum, is limited by the number, elemental composition, and concentration of the product ions contained within it. Though the linear sequence of peptide's contained within the MIW is different, they all sample the same amino acid distribution of the proteome. When acquiring product ion spectra within a mass isolation window, the isolation window in and of itself ensures that all the co-fragmenting precursors are of similar m/z. With respect to concentration the number and area distribution of isotopes to a product ion, is a direct function of its elemental composition and concentration. As illustrated in the charge vectors (e.g., FIG. 39), different isotopes from different product ions can share the same m/z. Assuming two orders of magnitude in dynamic range for peptides within a MIW, it is highly possible that one isotope from one product ion interferes with another from a second product ion.

In order to maximize precursor ion sampling, maintain sensitivity, and limit product ion interference, an optimal acquisition method as described herein may be used to control the number of precursor ions entering the collision cell per MS/MS acquisition. How many, is a function of the composite resolving power of all the in-line orthogonal separation techniques employed prior to ion detection. Selectivity, with regard to the number of accurate peptide identifications that can be made in a single experiment, is not a function of scan speed and/or MIW. Rather, selectivity, is a function of interference. Even in the most complex mixture, the ability to measure the physicochemical attributes of a larger complement of precursor and product ions can be achieved if the applied analytical workflow employs sufficient orthogonality, i.e., IMS, higher mass resolving power, narrow chromatographic peaks, varying MIW windows, modeling and multiplexing to measure the attributes of each ion independently from the surrounding matrix.

Quantitative accuracy, whether it be on isotopically or isobarically labeled peptides, is also a consequence of interference. With respect to iTRAQ and TMT labeling, each reported ion area is compromised if more than one peptide is present in the collision cell during disassociation. With respect to label free or absolute quantification by AUC analysis, if either area is a composite, the calculated relative or absolute abundance will be compromised. Analytical workflows impoverished by a limited number of pre-ion detection separation techniques, generally rely upon very narrow mass isolation widths and mass resolution in an attempt to minimize chimericy. Although narrowing the MIW to <1 Th reduces the possibility of co-fragmentation, it does not eliminate it. Narrow mass isolation widths inevitably compromise duty-cycle because very fast scan speeds are required to ensure an adequate sampling rate. Sensitivity is further compromised given that the switch in intensity from MS to MS/MS is generally set to the apex intensity of the least intense ion of interest. Setting the switch in intensity at such a level all but ensures that a precursor is never sampled at its apex intensity. For workflows that rely on narrow MIW, higher acquisition speeds are necessary to maintain duty-cycle; however, higher scan speeds adversely affect mass resolution, especially in MS/MS acquisitions.

To increase the sampling rate, without incurring the detrimental effects of chimeric product ion spectra, requires an analytical workflow, such as the MMA worklflow of FIG. 35, capable of handling sample complexity in an intelligent manner. Taking benefit of maximal peak capacity requires a thorough understanding of the available separation space, resolving power (in the m/z, chromatographic, and drift dimensions), accessible dynamic range; and, most importantly, the complexity of the sample under study. The acquisition scheduler 3504b included in an embodiment in accordance with tehcniques herein may utilize this information and create a "composite resolution". Generally, resolution is related to m/z, however when acquiring data in multi-dimensional space, resolution/peak capacity is a composite. In the MMA workflow, experimental resolution/peak capacity is multiplicative in that it is the product of the resolving powers of each of the pre-ion detection separation techniques employed. In one example described herein, the distribution of m/z by drift as illustrated in 3756 of FIG. 38 is strikingly similar to the distribution of m/z by time in 3754 of FIG. 38 in that 50% of all ions are within a narrow 30 drift bin portion of the entire drift space. An embodiment of the data processing algorithm described herein centers m/z and drift on a scan-by-scan basis, resulting in a drift resolution of ±1 drift bin; hence, the peak capacity of any single scan is increased ~10 fold with IMS enabled. Further, the precursor ion chaining, as illustrated in FIG. 43 allows for the service of an area ratio filter in the de-multiplexing algorithm. Within the MMA workflow, the scheduler can intelligently govern the ion flux through the collision cell guided by the prior knowledge obtained from highly accurate models or previously processed data.

The data shown in FIG. 3752 of FIG. 38 reflects the density of ions in 10 Th by 0.2 min bins. In at least one embodiment, these may be the default settings when the MMA is operated in fixed MIW mode. The MIW may be user-definable. In auto mode, the scheduler may set the MIW to an algorithmically determined maximum. For example, for two-dimensional acquisitions, the MIW may be set to limit the number of precursor ions to ten. In three-dimensional data, the MIW may be set such that the maximum number precursor ions per drift bin is less than ten. With regard to three-dimensional acquisitions, the distribution of m/z as a function of drift defines the maximum number of co-fragmenting precursors per acquisition. Element 3754 of FIG. 38 illustrates that 50% of all precursor ions exist within a 250 Th (±50 Th) MIW with the median m/z steadily increasing with time. The second and third quartiles are bound over time by the two linear regression lines β and β'. β and β' are divergent, illustrating a widening in m/z with time. Element 3756 of FIG. 38 illustrates a similar pattern reflecting m/z versus drift. This allows the MMA workflow to increase the MIW from narrowband to wideband acquisitions in regions of m/z above and below the boundary lines β and β'. To accurately determine a peptide's concentration or relative abundance using AUC quantification, a minimum of five data points must be acquired across its peak FWHM. The data shown in FIG. 37, for example, illustrates how the number of scan cycles, narrowband and wideband acquisitions, and scan times may be calculated based upon the mean chromatographic peak width.

Figure 45:
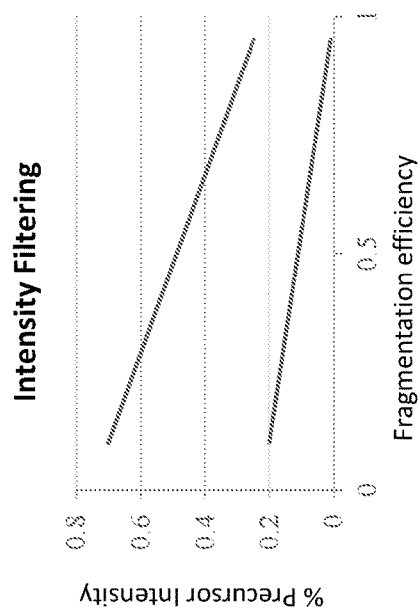
FIG. 45 is a graphical representation of intensity filtering in an embodiment in accordance with techniques herein.

In at least one embodiment in accordance with techniques herein, the de-multiplexing processing may include comparing the product ion spectra from all narrowband acquisition in which the defined m/z range was sampled. Product ions may be matched by m/z, drift and area ratio using match tolerances of ±3× the preceding reference mass precision (ppm), ±1 drift bins and ±2.5× the calculated area ratio for each $A_0$ isotopes resident with the defined m/z range. In the instances where more than one precursor ion is present, the product ion spectrum may be further filtered utilizing the precursor ion z and its calculated fragmentation efficiency (e.g., FIGS. 40 and 45). Wideband product ion spectra may be handled similarly. In embodiments in accordance with techniques herein such as implementing the workflow of FIG. 35, it is the iterative nature of the automated workflow, the constant movement of the center m/z for all narrowband and wideband acquisitions that provides the opportunity for the de-multiplexing and validation algorithms to continually improve the selectivity of the product ion spectra.

In at least one embodiment using techniques herein, identified product ion spectra exceeding a 95% confidence along with all other un-matched product ion spectra may be deposited into the putative section 3508c of the MIR. Associated with each is all metadata for all ions, both precursor and product. In such an embodiment, once a minimum of fifty putative peptide identifications or matched global identifiers have been deposited, the validation algorithm 3508b attempts to create CCPISss for each. The validation algorithm may utilize, for example, Pearson Product Moment Correlations and ANOVAs to test for significance. Provided a valid correlation, CPPISs, including error bars reflecting the acceptable variation in each product ions normalized intensity are created and moved into the validated section of the MIR 3508a.

Clarity and depth-of-coverage, as they relate to the accurate qualitative and quantitative analysis of complex proteomics samples, is a direct function of peak capacity. The peak capacity of any analytical workflow can be defined as the product of all resolving powers from each orthogonal separation technique applied prior to ion detection. As with all analytical techniques, the degree to which selectivity increases with specificity follows a standard s-curve. The rate of change, is initially shallow, migrates into the linear region, hits an inflexion point, and then rapidly approaches an asymptotic limit. Any increase beyond the asymptote can have detrimental effects on data quality. It is obvious that employing additional orthogonal separations both in- and off-line prior to ion detection, will have a positive impact on maximizing peak capacity. As more dimensions of separation are added, the stress applied to each is eased allowing each to work at or near their inflexion point. The orthogonal separation techniques that may be employed in the MMA in an embodiment may include, but are not limited to 1D and 2D UPLC, mass resolution, IMS, multiplexing, area ratio, and fractional m/z.

By maximizing peak capacity, the data processing as described herein is capable of correcting for many of the ion interferences associated with DIA analysis of complex mixtures. Using each ions' measured FWHM (m/z, $t_r$, $t_d$) a purity score is assigned reflecting how well its area has been measured. The $A_0$ isotope for each charge state of a peptide and its associated products is accurately identified using the charge vectors, isotope modeling and ion chaining. Isotopes are clustered into charge groups and the number and area distribution of each validated or corrected. If an interference has been determined a virtual ion is created and made available for subsequent clustering. Analyzing the data scan-by-scan, provides the data processing and de-multiplexing algorithm the means to compared m/z, area rates of change, and continuity between like product ion spectra within and between injections. Using the processed data of the previous injection to define the MMA workflow of the current, provides the method the ability to interrogated regions of m/z not previously sampled as narrowband DIA acquisitions.

By constantly adjusting the center m/z value of each wideband and narrowband acquisition the product ion spectra from a prior scan cycle or injection can be used to filter another. Depositing the resulting metadata for all product ion spectra including that of the parent precursor into the putative portion of the MIR allows for product ion spectra, regardless of identification status, to be compared. Composite product ion spectra are created from dot product spectral, and Pearson product-moment, correlations. These composite product ion spectra can then be queried against the processed, non-clustered ion detections.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A method of processing mass spectral data comprising:
performing an experiment using a sample, said experiment including performing mass analysis using a mass spectrometer;
acquiring precursor ion data and fragment ion data as a result of performing the experiment;
determining one or more precursor charge clusters included in the precursor ion data;
performing peak detection for a first of the precursor charge clusters wherein the first precursor charge cluster is tracked across a plurality of scans forming a detected peak for the first precursor charge cluster; and
determining, in accordance with validation criteria, a first set of fragment ions identified in the fragment ion data associated with the first precursor charge cluster.

2. The method of claim 1, wherein the method includes using the validation criteria to filter or refine an initial set of fragment ions, and determine a revised set of fragment ions.

3. The method of claim 1, wherein said mass spectrometer switches between a low energy mode generating primarily precursor ions and an elevated energy mode generating primarily fragment ions of the precursor ions, said switching being in accordance with a protocol that alternates application of the low energy mode and the elevated energy mode with a sufficient frequency whereby each of the low energy mode and the elevated energy mode is applied a plurality of times during a chromatographic peak width, wherein said precursor ion data is mass spectral data acquired when in the low energy mode and wherein said fragment ion data is mass spectral data acquired when in the elevated energy mode.

4. The method of claim 1, wherein each of the precursor charge clusters identifies a precursor ion at a single charge state.

5. The method of claim 1, wherein the validation criteria includes one or more intensity ratios of any of the first precursor charge cluster and a fragment ion of the first set of fragment ions.

6. The method of claim 5, wherein an apex scan is a scan at which the intensity of the first precursor charge cluster is at a maximum in the plurality of scans, and wherein said determining, in accordance with validation criteria, a first set of fragment ions identified in the fragment ion data associated with the first precursor charge cluster includes:
   determining a first intensity ratio of the first precursor charge cluster in a first of the plurality of scans to the apex scan;
   determining a second intensity ratio of a first fragment ion of the first set in the first scan to the apex scan; and
   determining that the first intensity ratio and the second intensity ratio are approximately the same.

7. The method of claim 1, wherein the precursor ion data and fragment ion data is acquired from more than one mass isolation window across the plurality of scans.

8. An apparatus comprising:
   a processor; and
   a memory comprising code stored thereon that, when executed, performs a method of processing mass spectral data comprising:
      performing an experiment using a sample, said experiment including performing mass analysis using a mass spectrometer;
      acquiring precursor ion data and fragment ion data as a result of performing the experiment;
      determining one or more precursor charge clusters included in the precursor ion data;
      performing peak detection for a first of the precursor charge clusters wherein the first precursor charge cluster is tracked across a plurality of scans forming a detected peak for the first precursor charge cluster; and
      determining, in accordance with validation criteria, a first set of fragment ions identified in the fragment ion data associated with the first precursor charge cluster.

9. The apparatus of claim 8, wherein the method includes using the validation criteria to filter or refine an initial set of fragment ions and determine a revised set of fragment ions.

10. The apparatus of claim 8, wherein said mass spectrometer switches between a low energy mode generating primarily precursor ions and an elevated energy mode generating primarily fragment ions of the precursor ions, said switching being in accordance with a protocol that alternates application of the low energy mode and the elevated energy mode with a sufficient frequency whereby each of the low energy mode and the elevated energy mode is applied a plurality of times during a chromatographic peak width, wherein said precursor ion data is mass spectral data acquired when in the low energy mode and wherein said fragment ion data is mass spectral data acquired when in the elevated energy mode.

11. The apparatus of claim 8, wherein each of the precursor charge clusters identifies a precursor ion at a single charge state.

12. The apparatus of claim 8, wherein the validation criteria includes one or more intensity ratios of any of the first precursor charge cluster and a fragment ion of the first set of fragment ions.

13. The apparatus of claim 12, wherein an apex scan is a scan at which the intensity of the first precursor charge cluster is at a maximum in the plurality of scans, and wherein said determining, in accordance with validation criteria, a first set of fragment ions identified in the fragment ion data associated with the first precursor charge cluster includes:
   determining a first intensity ratio of the first precursor charge cluster in a first of the plurality of scans to the apex scan;
   determining a second intensity ratio of a first fragment ion of the first set in the first scan to the apex scan; and
   determining that the first intensity ratio and the second intensity ratio are approximately the same.

14. The apparatus of claim 8, wherein the precursor ion data and fragment ion data is acquired from more than one mass isolation window across the plurality of scans.

15. A method of processing mass spectral data comprising:
   performing an experiment using a sample, said experiment including performing mass analysis using a mass spectrometer, wherein said mass spectrometer operates in accordance with a schedule for a plurality of scans;
   acquiring, during a scan, precursor ion data within a mass isolation window;
   determining one or more precursor charge clusters using the precursor ion data;
   adjusting the mass isolation window for a subsequent scan using the precursor ion data; and
   determining a peak profile for a first precursor ion by chaining together a portion of the precursor charge clusters.

16. The method of claim 15, wherein said acquiring includes iteratively using different mass isolation windows in elevated energy scans.

17. The method of claim 15, including determining a bounded region having a plurality of dimensions including m/z and retention time; and iteratively using different mass isolation windows in elevated energy scans until fragmentation has been performed for the bounded region.

18. The system of claim 15, wherein said mass spectrometer switches between a low energy mode generating primarily precursor ions and an elevated energy mode generating primarily fragment ions of the precursor ions, said switching being in accordance with a protocol that alternates application of the low energy mode and the elevated energy mode with a sufficient frequency whereby each of the low energy mode and the elevated energy mode is applied a plurality of times during a chromatographic peak width, wherein said precursor ion data is mass spectral data acquired when in the low energy mode and wherein said fragment ion data is mass spectral data acquired when in the elevated energy mode.

19. The method of claim 15, wherein each of the precursor charge clusters identifies a precursor ion at a single charge state.

20. The method of claim 15, wherein at least a first portion of the mass isolation windows have sizes and associated m/z ranges determined in accordance with selecting approximately a same number of precursor ions for fragmentation.

* * * * *